United States Patent
Gros et al.

(10) Patent No.: US 9,278,086 B2
(45) Date of Patent: *Mar. 8, 2016

(54) COMBINATION THERAPY AND USES THEREOF FOR TREATMENT AND PREVENTION OF PARASITIC INFECTION AND DISEASE

(71) Applicant: The Royal Institution for the Advancement of Learning/McGill University, Montreal (CA)

(72) Inventors: Philippe Gros, St-Lambert, CA (US); Gundula Min-Oo, San Francisco, CA (US); Anny Fortin, Montreal (CA)

(73) Assignee: The Royal Institution for the Advancement of Learning/McGill University, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/332,829

(22) Filed: Jul. 16, 2014

(65) Prior Publication Data
US 2014/0329894 A1 Nov. 6, 2014

Related U.S. Application Data

(63) Continuation of application No. 13/277,942, filed on Oct. 20, 2011, now Pat. No. 8,815,942.

(60) Provisional application No. 61/394,958, filed on Oct. 20, 2010.

(51) Int. Cl.
| | | |
|---|---|---|
| A61K 31/365 | (2006.01) | |
| A61K 31/145 | (2006.01) | |
| A61K 31/357 | (2006.01) | |
| A61K 31/35 | (2006.01) | |
| A61J 1/00 | (2006.01) | |

(52) U.S. Cl.
CPC ............... *A61K 31/357* (2013.01); *A61J 1/00* (2013.01); *A61K 31/145* (2013.01); *A61K 31/35* (2013.01); *A61K 2300/00* (2013.01)

(58) Field of Classification Search
CPC ..................... A61K 31/365; A61K 31/145
USPC .................................................. 514/468, 665
See application file for complete search history.

(56) References Cited

U.S. PATENT DOCUMENTS

| | | | |
|---|---|---|---|
| 4,868,116 A | 9/1989 | Morgan et al. | |
| 4,980,286 A | 12/1990 | Morgan et al. | |
| 5,166,320 A | 11/1992 | Wu et al. | |
| 5,399,346 A | 3/1995 | Anderson et al. | |
| 5,554,655 A | 9/1996 | Thoene | |
| 5,714,519 A | 2/1998 | Cincotta et al. | |
| 6,340,746 B1 | 1/2002 | Roberts et al. | |
| 6,468,522 B1 | 10/2002 | Stein et al. | |
| 6,521,266 B1 | 2/2003 | Mann | |
| 8,815,942 B2 * | 8/2014 | Gros et al. ............. 514/468 | |
| 2009/0082426 A1 | 3/2009 | Commercon et al. | |
| 2009/0298881 A1 | 12/2009 | Li et al. | |

FOREIGN PATENT DOCUMENTS

| | | |
|---|---|---|
| WO | WO 89/02468 | 3/1989 |
| WO | WO 89/05345 | 6/1989 |
| WO | WO 89/07136 | 8/1989 |
| WO | WO 91/14689 | 10/1991 |
| WO | WO 92/07573 | 5/1992 |
| WO | WO 95/05452 | 2/1995 |
| WO | WO 99/65914 | 12/1999 |
| WO | WO/00/04024 | 1/2000 |
| WO | WO 00/04025 | 1/2000 |
| WO | WO/00/42046 | 7/2000 |
| WO | WO 03/076446 | 9/2003 |
| WO | WO 2007/009388 | 1/2007 |
| WO | WO 2007/083228 | 7/2007 |
| WO | WO 2007/089670 | 8/2007 |
| WO | WO 2007/116135 | 10/2007 |
| WO | WO 2008/046109 | 4/2008 |
| WO | WO 2008/092262 | 8/2008 |
| WO | WO 2008/127381 | 10/2008 |

OTHER PUBLICATIONS

"The Use of Artemisinin & Its Derivatives as Anti-Malarial Drugs," World Health Organization, Malaria Unit, Report of Joint CTD/DMP/TDR, Informal Consultation, Geneva, Jun. 10-12, 1998, pp. 1-33.

Dias et al., "Evaluation and intermethod comparison of the Bio-Rad high-performance liquid chromatographic method for plasma total homocysteine," *Clin Chem*, 44: 2199-2201, 1998.

Dunay et al., "Artemisone and artemiside control acute and reactivated toxoplasmosis in a murine model," *Antimicrob Agents Chemother*, 53: 4450-4456, 2009.

Eastman et al., "Artemisinin-based combination therapies: a vital tool in efforts to eliminate malaria," *Nature*, 7: 864-847, 2009.

Fidler et al., "Pharmacokinetics of cysteamine bitartrate following gastrointestinal infusion," *Br J Clin Pharmacol*, 63: 36-40, 2007.

Fortin et al. "Identification of a new malaria susceptibility locus (Char4) in recombinant congenic strains of mice," *Proc Natl Acad Sci USA*, 98: 10793-10798, 2001.

Fortin et al., "Complex genetic control of susceptibility to malaria in mice," *Genes and Immunity* 3: 177-186, 2002.

(Continued)

*Primary Examiner* — Andrew D Kosar
*Assistant Examiner* — Raymond Covington
(74) *Attorney, Agent, or Firm* — Klarquist Sparkman, LLP

(57) ABSTRACT

The invention relates to compounds, methods, uses, compositions, combinations, kits and packages for the prevention and/or treatment of parasite infection (e.g., *Plasmodium* parasites) and/or disease (e.g., malaria) based on uses of (a) cystamine, cysteamine, and analogs, derivatives, prodrugs, precursors thereof; an agent capable of inducing their production; and/or salts thereof, and (b) artemisinin and functional derivative, analog, conjugate, metabolite, prodrug or precursor thereof, and/or salts thereof.

43 Claims, 43 Drawing Sheets

(56) References Cited

OTHER PUBLICATIONS

Fortin et al., "Recombinant congenic strains derived from A/J and C57BL/6J: A tool for genetic dissection of complex traits," *Genomics*, 74: 21-35, 2001.

Hunt et al., "Immunopathogenesis of cerebral malaria," International Journal for Parasitology, 36: 569-582, 2006.

Keiser et al., "Artemisinins and synthetic trioxolanes in the treatment of helminth infections," *Curr Opin Infect Dis*, 20: 605-612, 2007.

Kleta et al., "Pharmacological treatment of nephropathic cystinosis with cysteamine," *Expert Opin. Pharmacother.* 5(11): 2255-2262, 2004.

Lebo et al., "Inactivation of Human y-Glutamylcysteine Synthetase by Cystamine," *Journal of Biol Chem*, 253(8): 2615-2623, 1978.

Li et al., "Artemisinin derivatives bearing Mannich base group: synthesis and antimalarial activity," *Bioorganic & Medicinal Chemistry*, 11(20): 4363-4368, 2003.

Li et al., "Synthesis and antimalarial activity of artemisinin derivatives containing an amino group," *J. Med. Chem*, 43(8): 1635-1640, 2000.

Lüersen et al., "Plasmodium falciparum-infected red blood cells depend on a functional glutathione de novo synthesis attributable to an enhanced loss of glutathione," *Biochem J*, 346: 545-552, 2000.

Min-Oo et al., "Complex genetic control of susceptibility to malaria: positional cloning of the Char9 locus," *The Journ of Exp. Medicine*, 204(3): 511-524, 2007.

Min-Oo et al., "Cysteamine, the molecule used to treat cystinosis, potentiates the antimalarial efficacy of artemisinin," *Antimicrobial Agents and Chemotherapy*, 54(8): 3262-3270, 2010.

Min-Oo et al., "Genetic analysis in mice identifies cysteamine as a novel partner for artemisinin in the treatment of malaria," *Mamm Genome*, 22: 486-494, 2011.

Patel et al., "The association of the glycophorin C exon 3 deletion with ovalocytosis and malaria susceptibility in the Wosera, Papua New Guinea," *Blood*, 98: 3489-3491, 2001.

Penet et al., "Protection against cerebral malaria by the low-molecular-weight thiol pantethine," *PNAS*, 105(4):1321-1326, 2008.

Ploypradith, "Development of artemisinin and its structurally simplified trioxane derivatives as antimalarial drugs," *Acta Trop*, 89: 329-342, 2004.

Posner et al., "Orally active, hydrolytically stable, semisynthetic, antimalarial trioxanes in the artemisinin family," *J. Med. Chem*, 42(2): 300-304, 1999.

Sissoko et al., "Efficacy of Artesunate + Sulfamethoxypyrazine/ Pyrimethamine versus Praziquantel in the Treatment of *Schistosoma haematobium* in Children," *PLoS One* 4(10): e6732, 2009.

Tallarida, "Drug synergism: its detection and applications," *J Pharmacol Exp Ther*, 298: 865-872, 2001.

\* cited by examiner

Mus musculus vanin 1 (Vnn1) nucleotide sequence (SEQ ID NO:1)
gi|6755978|ref|NM_011704.1
Coding Sequence = 22-1560

```
   1 ttgctgtcgt tggacttcag catgggcacg tcttggtggc tggcgtgtgc tgcagcgttt
  61 tctgccctct gtgtcttaaa agccagctcg ctggatactt tcctcgcggc tgtttacgag
 121 catgctgtga tcctgcctaa ggacaccctg ttgccagtgt ctcacggtga ggctctggca
 181 ttaatgaacc agaatctgga ccttctggaa ggagcgatcg tatctgcagc gaagcaggt
 241 gcgcacatta ttgtgactcc agaagatggc atatacggtg tgcgtttcac cagggatacg
 301 atctaccat acctggagga gatcccagac cctcaagtaa actggatacc ctgtgataac
 361 cctaaaagat ttggctctac cccggtgcag gagagactca gctgcttggc caagaacaac
 421 tccatctatg ttgtggcgaa catgggagac aagaagccgt gtaacaccag cgactctcac
 481 tgtccacctg acggcagatt ccagtacaac actgatgtgg tgtttgattc ccagggtaaa
 541 ctggttgcga gataccataa gcaaaacatt ttcatgggag aagatcagtt caatgtcccc
 601 atggagcctg agtttgtgac tttcgacacc cccttggaa agtttggcgt cttcacctgt
 661 ttcgatattc tcttccatga tccccgctgt acccctgtga cagaattcca ggtggacacc
 721 atactgttcc caaccgcctg gatgacgtcc cttcctcatt tggcagccat tgaattccac
 781 tcagcttggg ctatggcat ggggtcaat ttcctagcag ctaatctaca taatccctcg
 841 aggagaatga caggaagtgg tatctatgca cccgattctc aagggtctt tcactacgac
 901 aggaagaccc aagaaggaaa actcctcttc gctcagctga atcccaccc aattcactcc
 961 ccggtgaact ggacttccta gctagcagt gtagaatcaa ccccaaccaa aacccaggaa
1021 tttcagagta ttgtcttttt tgatgagttt acctttgtgg agctcaaagg gatcaaagga
1081 aattacactg tttgccagaa tgacctctgc tgtcacctaa gctaccagat gtctgagaag
1141 cgagcagatg aggtttatgc ctttggagcc tttgatgggc tgcacaccgt ggaagggcag
1201 tactacctac agatctgcat cctgctaaaa tgtaaaacta ccaatttacg cacctgtggt
1261 agttcagtgg acacggcttt taccaggttt gaaatgttct cgctcagcgg cacttttgga
1321 accggtatg tcttccctga agtgttgctg agtgaggtca agctcgcacc tggggagttt
1381 caggtgtcaa gtgatgggcg cctggttagc ctgaagccaa cctcgggacc tgtgttaacc
1441 atcgggctct ttggaggtt gtatgggaag gactgggcat ccaatgcttc ctcagacttc
1501 atagcacact cgctgataat aatgctgatt gtgacgccta ttatacatta cttgtgctga
1561 tggaattttt acatttttta ttttatttag aaaatttaaa attggtggat gcagaaaaaa
1621 taactgtttg tcaacagtgg actcgggtgt aagcaaataa agtgcctctt ctttagaaaa
1681 acatatgtac accagataca tttcaggaaa attaataaaa ctttgagcat tggaacgaga
1741 tggagggcca agtaaaggtc gcatgtgttt tattcagaag aaataaaat tacagttaaa
1801 aggcacttca aaccatcata agatagattt acaagaggtg taaatctatt atacatctta
1861 ctcagttatg cttagaattt ccaatgtgtt tgttcatttg ggctattaag tatttatctc
1921 aacatttccg ttctctcatg gaccagatcc tgtagtttta attcttcagt tcaagtccca
1981 gttcccacaa cctcagaacg tgactgcctt ggtgtctttg caatgaaga cataagaggc
2041 atcattagca tggactttaa ttcaatatga ctgatctcct cagaagaaat caggacaaag
2101 acttgcatca agtgaagccc ttgtgaacac aggaaaagat ggtcatgtac aacaagaaaa
2161 ggggcctcag gagaacgcaa acctgctaac gtgtcaaact tccaggtctc cagaatcatg
2221 aggcaataaa tttctgtttt aaatgaaaaa aaaaa
```

Mus musculus vanin 3 (Vnn3) nucleotide sequence (SEQ ID NO:3)
gi|6755980|ref|NM_011979.1
Coding sequence = 113-1615

```
   1 atatattcac aggcagctgg ctggcatcac gacttgcgtc tgaatatttt ttttccccac
  61 tgagatacag tagaagaacc ttctgatttt cagagatcag tctattttaa ttatggcttc
 121 attacatttt cctcaatggg cagtgagttt tgtcttcttt gcccaggctg tgggttcaat
 181 ggacactttt attgctgctg tgtatgaaca tgctgtttata ctgccaaaca aaactgaaag
 241 tcctgttttcc actgaagagg ctttgctcct gataaacaag aacatagaca ttttggagag
 301 tgcaatcaag ctggcagcca gacagggtgc acatatcatt gtgacgccag aagatggaat
 361 ctatggttgg atcttcacca gggagaccat ttacccctac ctagaggata taccagaccc
 421 tgaagtgaac tggattccct gtagagaccc taggagggttt ggctacacac cagtacagga
 481 gagactgagc tgccttgcca aggagaactc tatctatatt atggcaaata ttggggacaa
 541 gaagccatgc aatgctactg atcctcattg tccccggat ggccgttacc aatataatac
 601 caatgtggtc ttcgattcta agggtaggct aacagcccgc taccataagt acaatctttt
 661 tgaaccagag attcagtttg atttccccaa agattcagag ctggtgacct tgacaccccc
 721 gtttgggaag tttggcatct tcacttgctt tgacattttc tcttatgacc agctgtggt
 781 ggttgtgaag gacacccagg tcgacagtgt tctcttaccc acggcgtggt acaacaccct
 841 gcccctgctt tcagcagttc cattccattc ggtgtgggcc agagccatgg gggtcaacgt
```

FIG. 7A

```
 901 gcttgctgca aacacccaca acaccagcat gcatatgaca gggagtggaa tctacagccc
 961 ggaagctgtc cgagtgtacc actatgacat ggagacagag agtggccaac tgctgctttc
1021 agagctgagg tctcggcctc gccagcacgc caccctgca gaggttaact ggagcgctta 1081 tgccaggact gtgaagccgt tctcatcggg gcaggcagac ttcccaggaa agatttattt
1141 tgacgaattt agcttcacca agcttacagg aagtgctggc aattacacag tttgccaaaa
1201 ggacctgtgc tgtcacctga cttacaagat gtctgaaagc cgaatggacg aggtgtatgt
1261 tctgggtgcc tttgatggac tccatacagg ggaaggccag tattacctac agatatgtac
1321 attgctgaag tgtcaaacca ccaactcgag aacttgtggg gaacccgtgg ggtcagcttt
1381 tacaaagttt gaagaattct ctctcagtgg cacctttcgg acaaaatatg ttttcccaca
1441 gatcgtgcta agtgggagtc aacttgccct ggaaagatat tatgaagtct caagagatgg
1501 acgtctgagg agtcgaggtg gagccccttt gcctatctta gtgatggccc tgtatggaag
1561 agtgtttgag agagaccctc cgcgcttagg gcagggacct gggaagctgc agtgatccct
1621 tcattgggga ccccacccgc ctgccctgac aagggggcg gggtctgcac aggattagcc
1681 tggcagagag cggggctcta agagcaagaa caaggagctg cagggttcca ttaggagata
1741 cgatgtaagc tgctgaaaag gcaaagcaag tgagaggaaa caataaagta aaaaagcaaa
1801 aaaaaaaaaa aaaaaaaa
```

Homo sapiens vanin 1 (VNN1) nucleotide sequence (SEQ ID NO:5)
gi|4759311|ref|NM_004666.1
Coding Sequence = 15-1556

```
   1 cattggactt cagcatgact actcagttgc cagcttacgt ggcaattttg cttttctatg
  61 tctcaagagc cagctgccag gacactttca ttgcagctgt ttatgagcat gcagcgatat
 121 tgcccaatgc caccctaaca ccagtgtctc gtgaggaggc tttggcatta atgaatcgga
 181 atctggacat tttggaagga gcgatcacat cagcagcaga tcagggtgcg catattattg
 241 tgactccaga agatgctatt tatggctgga acttcaacag ggactctctc tacccatatt
 301 tggaggacat cccagaccct gaagtaaact ggatcccctg taataatcgt aacagatttg
 361 gccagacccc agtacaagaa agactcagct gcctggccaa gacaactct atctatgttg
 421 tggcaaatat tggggacaag aagccatgcg ataccagtga tcctcagtgt ccccctgatg
 481 gccgttacca atacaacact gatgtggtat ttgattctca aggaaaactg gtggcacgct
 541 accataagca aaaccttttc atgggtgaaa atcaattcaa tgtacccaag agcctgaga
 601 ttgtgacttt caataccacc tttggaagtt ttggcatttt cacatgcttt gatatactct
 661 tccatgatcc tgctgttacc ttggtgaaag atttccacgt ggacaccata gtattcccaa
 721 cagcttggat gaatgttttg ccacatttgt cagctgttga attccactca gcttgggcta
 781 tgggcatgag ggtcaatttc cttgcatcca acatacatta cccctcaaag aaaatgacag
 841 gaagtggcat ctatgcaccc aattcttcaa gagcatttca ttatgatatg aagacagaag
 901 aggaaaaact cctcctctcg caactggatt cccacccatc ccattctgca gtggtgaact
 961 ggacttccta tgccagcagt atagaagcgc tctcatcagg aaacaaggaa tttaaaggca
1021 ctgtcttttt cgatgaattc acttttgtga agctcacagg agttgcagga aattatacag
1081 tttgtcagaa agatctctgc tgtcatttaa gctacaaaat gtctgagaac ataccaaatg
1141 aagtgtacgc tctagggca tttgacggac tgcacactgt ggaagggcgc tattatctac
1201 agatttgtac cctgttgaaa tgtaaaacga ctaatttaaa cacttgcggt gactcagctg
1261 aaacagcttc taccaggttt gaaatgttct ccctcagtgg cactttcgga acccagtatg
1321 tctttcctga ggtgttgctg agtgaaaatc agcttgcacc tggagaattt caggtgtcaa
1381 ctgacggacg cttgttagt ctgaagccaa catccggacc tgtcttaaca gtaactctgt
1441 ttgggaggtt gtatgagaag gactgggcat caaatgcttc atcaggcctc acagcacaag
1501 caagaataat aatgctaata gttatagcac ctattgtatg ctcattaagt ggtagaata
1561 ttgactttt ctctttttta tttgggataa tttaaaaaat gatggatgag aaaagaaaga
1621 ttggtccggg ttaatattat cctctagtat aagtgaatta ctagtttctc tttatttaga
1681 caaacacaca cacaccagat aatataaact taataaatta tctgttaatg tagattttat
1741 ttaaaaaact atatttgaac attggtcttt cttggacgtg agctaattat atcaaataag
1801 tatcacaaat cttttacgca gaagaaataa aaactacggg tagaaaacat aagaactatc
1861 ataaaattta cttacaagga ggctgctctt gttaccactt ttattatatt acgtatcact
1921 tattcagctc tgctgaaaat ttccaatgac tttgtttgtt tgctcttttg gttttttacc
1981 taaacaatac attttgattc tctgtgggt tgataatgtc tccccaaaat ttacatgttg
2041 aagcacctca gaatgtgact gtatttggag acagggtctt taagaggta aaataaggtc
2101 attaggatag accctaattc aatatgactg atgatcataa agaagaggc gagtagggca
2161 caacaggcac aagggagac cataaggaga cacagaggaa ggacaactct ttacaagcta
2221 agaagagagg gcctcagaag aaaccaaccc tgccaacacc ttgatcttgg acttccagcc
```

FIG. 7B

```
2281 tccaaaacta tgagaaataa atttctattg tttaagtcac ccagtccatg gtactttgtt
2341 aggcagccct ggcaaatgaa tcaaagaccc attcctgttc ctctccccac cactactgtt
2401 ttctactgta atctgaagct tcaacaaaag gcttacctgg taagaatatt cagctggtct
2461 gggtcctcaa gactccaata gacactctta aagaaggatt gctgatggat tgatagtgaa
2521 accattagat cattgaattc ctctggaatt agaaaaccag agagtcccat tttaagaaat
2581 tagatatttta atatagcatt gtgtgttcta ttttagtaac agcagaatct cttgacatta
2641 cacaactcag tgaaacaaca tcatttaagc caaaatatct cccaactgac tgatagactc
2701 tgagcactaa tatcatagtg ctgtgatgat ggacaattac atagtaccga taacagccat
2761 gcactgtgca aagcatgccc ttctgcacag gagagcaagg cacttgcagt agtgatctat
2821 gccagcaaaa catcatttg agacaaacat ttttgtggca gatgttttc ctaaaagta
2881 ctatatcatc caagaaatat ttgagtaaaa tcccttgttc ttttgggtga cattaactga
2941 catttgcttt ttttcaagac ctaatagaaa ataagaaagc ccataatgta tttagaaaca
3001 ggaatcctca gagcaattct ctgtattctc atataatttc aatgtaaaac agaaaacata
3061 ttgatgtgtt ggtgataggc ttgaattatt aaaaacttca aaaacaaaa
```

Homo sapiens vanin 2 (VNN2), transcript variant 1, nucleotide sequence (SEQ ID NO:7)
gi|17865813|ref|NM_004665.2
Coding Sequence = 12-1574

```
   1 aaaccttggc catggtcact tcctcttttc caatctctgt ggcagttttt gccctaataa
  61 ccctgcaggt tgtactcag gacagtttta tagctgcagt gtatgaacat gctgtcattt
 121 tgccaaataa aacagaaaca ccagtttctc aggaggatgc cttgaatctc atgaacgaga
 181 atatagacat tctggagaca gcgatcaagc aggcagctga gcaggtgct cgaatcattg
 241 tgactccaga agatgcactt tatggatgga aatttaccag ggaaactgtt ttcccttatc
 301 tggaggatat cccagaccct caggtgaact ggattccgtg tcaagaccc cacagatttg
 361 gtcacacacc agtacaagca agactcagct gcctggccaa ggacaactct atctatgtct
 421 tggcaaattt ggggacaaa aagccatga attccgtga ctccacatgt cctctaatgt
 481 gctacttttca atacaataca aatgtggtgt ataatacaga aggaaactc gtggcacgtt
 541 accataagta ccacctgtac tctgagcctc agtttaatgt ccctgaaaag ccggagttgg
 601 tgactttcaa caccgcattt ggaaggttg gcattttcac gtgctttgat atattcttct
 661 atgatcctgg tgttaccctg gtgaaagatt ccatgtggg caccatactg tttcccacag
 721 cttggatgaa cgttttgccc cttttgacag ctattgaatt ccattcagct tgggcaatgg
 781 gaatgggagt taatcttctt gtggccaaat cagcctaaat atgacaggaa
 841 gtggtattta tgcaccaaat ggtcccaaag tgtatcatta tgacatgaag acagagttgg
 901 gaaaacttct cctttcagag gtggattcac atcccctatc ctcgcttgcc tacccaacag
 961 ctgttaattg gaatgcctac gccaccacca tcaaaccatt tccagtacag aaaaacactt
1021 tcagggatt tatttccagg gatgggttca acttcacaga acttttgaa aatgcaggaa
1081 accttacagt ctgtcaaaag gagctttgct gtcatttaag ctacagaatg ttacaaaaag
1141 aagagaatga agtatacgtt ctaggagctt ttacaggatt acatggccga aggagaagag
1201 agtactggca ggtctgcaca atgctggaagt gcaaaactac taatttgaca acttgtggac
1261 ggccagtaga aactgcttct acaagatttc aaatgttctc cctcagtggc acatttggac
1321 cagagtatgt ttttcctgaa gtgctactta ccgaaattca tctgtcacct ggaaaatttg
1381 aggtgctgaa agatgggcgt ttggtaaaca agaatggatc atctgggcct atactaacag
1441 tgtcactctt tgggaggtgg tacacaaaagg actcacttta cagctcatgt gggaccagca
1501 attcagcaat aacttacctg ctaatattca tattattaat gatcatagct ttgcaaaata
1561 ttgtaatgtt atagggcgtc tctttatcac tcagcttctg catcatatgc ttggctgaat
1621 gtgtttatcg gcttcccaag tttactaaga aacttgaag ggctatttca gtagtataga
1681 ccagtgagtc ctaaatattt ttctcatca ataattattt ttaagtatt atgataatgt
1741 tgtccatttt tttggctact ctgaaatgtt gcagtgtgga acaatggaaa gagctgggt
1801 gtttgggtca gataaatgaa gatcaaactc cagctccagc ctcatttgct tgagactttg
1861 tgtgtatggg ggacttgtat gtatgggagt gaggagtttc agggccattg caaacatagc
1921 tgtgcccttg aagagaatag taatgatggg aatttagagg tttatgactg aattccctt
1981 gacattaaag actatttgaa ttcaaaaaaa aaaaaaaaaa aaaaaaaaa aaaa
```

Homo sapiens vanin 2 (VNN2), transcript variant 2, nucleotide sequence (SEQ ID NO:9)
gi|17865815|ref|NM_078488.1
Coding Sequence = 113-1516

```
   1 gactggagga gcacaggcct tggaaaggaa agcagctgag atccagagga gtggaaggct
```

FIG. 7C

```
  61 cccccttgac taaagctaaa caccagtttc tcaggaggat gccttgaatc tcatgaacga
 121 gaatatagac attctggaga cagcgatcaa gcaggcagct gagcagggtg ctcgaatcat
 181 tgtgactcca gaagatgcac tttatggatg gaatttttac agggaaactg ttttcccttta
 241 tctggaggat atcccagacc ctcaggtgaa ctgattccg tgtcaagacc cccacagatt
 301 tggtcacaca ccagtacaag caagactcag ctgcctggcc aaggacaact ctatctatgt
 361 cttggcaaat ttgggggaca aaaagccatg taattcccgt gactccacat gtcctcctaa
 421 tggctacttt caatacaata ccaatgtggt gtataataca gaaggaaaac tcgtggcacg
 481 ttaccataag taccacctgt actctgagcc tcagtttaat gtccctgaaa agccggagtt
 541 ggtgactttc aacaccgcat ttggaaggtt tggcattttg acgtgctttg atatattctt
 601 ctatgatcct ggtgttaccc tggtgaaaga tttccatgtg gacaccatac tgtttcccac
 661 agcttggatg aacgttttgc cctttgac agctattgaa ttccattcag cttgggcaat
 721 gggaatggga gttaatcttc ttgtggccaa cacacatcat gtcagcctaa atatgacagg
 781 aagtggtatt tatgcaccaa atggtcccaa agtgtatcat tatgacatga agacagagtt
 841 gggaaaactt ctccttttcag aggtggattc acatcccta tcctcgcttg cctacccaac
 901 agctgttaat tggaatgcct acgccaccac catcaaacca tttccagtac agaaaaacac
 961 tttcagggga tttatttcca gggatgggtt caacttcaca gaacttttg aaaatgcagg
1021 aaaccttaca gtctgtcaaa aggagctttg ctgtcattta agctacagaa tgttacaaaa
1081 agaagagaat gaagtatacg ttctaggagc ttttacagga ttacatggcc gaaggagaag
1141 agagtactgg caggtctgca caatgctgaa gtgcaaaact actaatttga caacttgtgg
1201 acggccagta gaaactgctt ctacaagatt tgaaatgttc tccctcagtg gcacatttgg
1261 aacagagtat gttttttcctg aagtgctact taccgaaatt catctgtcac ctggaaaatt
1321 tgaggtgctg aaagatgggc gtttggtaaa caagaatgga tcatctgggc ctatactaac
1381 agtgtcactc tttgggaggt ggtacacaaa ggactcactt tacagctcat gtgggaccag
1441 caattcagca ataacttacc tgctaatatt catattatta atgatcatag ctttgcaaaa
1501 tattgtaatg ttatagggcg tctctttatc actcagcttc tgcatcatat gcttggctga
1561 atgtgtttat cggcttccca agttttactaa gaaactttga agggctattc cagtagtata
1621 gaccagtgag tcctaaatat ttttttctcat caataattat ttttaagta ttatgataat
1681 gttgtccatt ttttggcta ctctgaaatg ttgcagtgtg gaacaatgga aagagcctgg
1741 gtgttgggt cagataaatg aagatcaaac tccsgctcca gcctcatttg cttgagactt
1801 tgtgtgtatg ggggacttgt atgtatggga gtgaggagtt tcagggccat tgcaaacata
1861 gctgtgccct tgaagagaat agtaatgatg ggaatttaga ggtttatgac tgaattccct
1921 ttgacattaa agactatttg aattcaaaaa aaaaaaaaaa aaaaaaaaaa aaaaaa
```

Homo sapiens vanin 3 (VNN3), transcript variant 1, nucleotide sequence (SEQ ID NO:11)
gi|66932887|ref|NM_018399.3
Coding Sequence = 73-897

```
   1 atgtaaagtt tttccagtga aacaaaacgt aagaatctga gtttgttttc caaagatcac
  61 taaattttag ttatgattat atcacatttt ccaaatgtg tggcagtttt tgccctcctt
 121 gctctgagtg ttggtgcact ggacacttttt attgctgcag tatatgaactg tgcggtgata
 181 ttaccaaaca gaacagaaac acctgtttca aaagaagaag ctttgctcct gatgaacaag
 241 aacatagatg ttttggagaa agcagttaag ctggcagcga agcaggtgc acatatcatt
 301 gtgacccag aagatggaat ctatggttgg atcttcacca gggagagcat ttaccctat
 361 ctagaggata taccagaccc tggagtgaac tggattccat gtagagaccc ctggagattc
 421 ggcaacacac cagtgcaaca aagactcagc tgcctggcca aggacaactc tatctatgct
 481 gtggctaata ttggggacaa gaagccatgc aatgccagtg actctcagtg tcccctcgat
 541 ggccgttacc aatacaacac tgatgtggtg tttgattctc agggaaaact gttggcacgc
 601 taccataagt acaatctttt tgcacctgaa attcagtttg attttcccaa ggattcagaa
 661 cttgtgactt tgacactcc ctttgggaag tttggcattt ttacttgctt tgacattttt
 721 tctcatgacc cagctgtggt ggtggtggat gagtttcaat tgacagcatt ctctacccca
 781 cagcatgtta caacacgctg ccccctcctct cggctgcttc cttccattca gcatgggcca
 841 aggccatggg agtcaatcta cttgctgcaa ataccacaa caccagcat cacatgacag
 901 ggagtggaat ctacgcccca gaagcagtca aggtgtacca ctatgacatg gaaacagaga
 961 gtggtcagct gttgctatca gaactgaagt ctcggcccg ccgtgagccc acctaccctg
1021 cagctgttga ctgcatgcg tatgccagca gtgtcaagcc attttcctct gaacagtcag
1081 attttctggg gatgatttat tttgatgagt ttaccttcac caagcttaag agaaatacag
1141 gaaattacac agcttgccag aaagatctgt gttgtcactt aactacaag atgtctgaga
1201 agcgaacaga cgagatctat gccctaggtg cttttgatgg actgcacaca gtagaaggcc
1261 aatattactt acagatatgt gcattactga agtgtcaaac cactgacctg gaaacgtgtg
1321 gagaacctgt ggggtcagct tttaccaagt ttgaagactt ctccctcagt ggcacatttg
1381 gaacgcgtta tgttttccca cagatcattc taagtgggag tcagcttgcc cctgaaagac
```

FIG. 7D

```
1441 attatgagat tcaagagat ggacgcttga ggagccgaag tggagccct ttgcctgtct
1501 tagttatggc cctgtatgga agagtgtttg agaaggaccc tccacgctta gggcagggat
1561 ctgggaaatt ccagtgatct cctttagcag agcccttta ggattagcct ggctaagaaa
1621 ggaagaaaaa aaagagatcc gttagtgtct gtttagaaaa gatgttataa acttacagaa
1681 acaaatataa taaactgaag cagatttgaa aagcaaaaaa aaaaaaaaa aaa
```

Homo sapiens vanin 3 (VNN3), transcript variant 2, nucleotide sequence (SEQ ID NO:13)
gi|66932886|ref|NM_078625.2
Coding Sequence = 73-516

```
   1 atgtaaagtt tttccagtga acaaaacgt aagaatctga gtttgttttt caaagatcac
  61 taaattttag ttatgattat atcacatttt ccaaaatgtg tggcagtttt tgccctcctt
 121 gctctgagtg ttggtgcact ggacactttt attgctgcag tatatgagca tgcgtgata
 181 ttaccaaaca gaacagaaac acctgtttca aaagaagaag ctttgctcct gatgaacaag
 241 aacatagatg ttttggagaa agcagttaag ctggcagcga agcagggtgc acatatcatt
 301 gtgaccccag aagatggaat ctatggttgg atcttcacca gggagagcat ttacccctat
 361 ctagaggata taccagaccc tggagtgaac tggattccat gtagagaccc ctggaggaag
 421 agtaaaaaga tgaatgagcc tgttttccaaa gagctttgct atcactgtca ttcagaatgc
 481 aatcaatatg gccatggaa attgtatagg acttgaaaaa ggaagcccta cttctgggac
 541 cacatttac gaccacctag ctgagtgata atcactaaa atatagtaag tttgaggaaa
 601 tgtctattga attagattcg gcaacacacc agtgcaacaa agactcagct gcctggccaa
 661 ggacaactct atctatgtcg tggctaatat tggggacaag aagccatgca atgccagtga
 721 ctctcagtgt cccctgatg gccgttacca atacaacact gatgtgtgt ttgattctca
 781 gggaaaactg ttggcacgct accataagta caatctttt gcacctgaaa ttcagtttga
 841 ttccccaag gattcagaac ttgtgactt tgacactccc tttgggaagt tggcatttt
 901 tacttgcttt gacatttttt ctcatgaccc agctgtggtg gtggtggatg agtttcaatt
 961 gacagcattc tctaccccac agcatggtac aacacgctgc ccctctctc ggctgttccc
1021 ttccattcag catgggccaa ggccatggga gtcaatctac ttgctgcaaa tacccacaac
1081 accagcatgc acatgacagg gagtggaatc tacgcccag aagcagtcaa ggtgtaccac
1141 tatgacatgg aaacagagag tggtcagctg ttgctatcag aactgaagtc tcggccccgc
1201 cgtgagccca cctaccctgc agctgttgac tggcatgcgt atgccagcag tgtcaagcca
1261 tttccctctg aacagtcaga ttttctgggg atgatttatt ttgatgagtt taccttcacc
1321 aagcttaaga gaaatacagg aaattacaca gcttgccaga aagatctgtg ttgtcactta
1381 acttacaaga tgtctcagaa gcgaacagac gagatctatg cctagtgtgc ttttgatgga
1441 ctgcacacag tagaaggcca atattactta cagatatgtg cattactgaa gtgtcaaacc
1501 actgacctgg aaacgtgtgg agaacctgtg gggtcagctt ttaccaagtt tgaagacttc
1561 tccctcagtg gcacatttgg aacgcgttat gttttcccac agatcattct aagtgggagt
1621 cagcttgccc ctgaaagaca ttatgagatt tcaagagatg gacgcttgag gagccgaagt
1681 ggagcccctt tgcctgtctt agttatggca ctgtatggaa gagtgtttga gaaggaccct
1741 ccacgcttag ggcagggatc tgggaaattc cagtgatctc ctttagcaga gccctttag
1801 gattagcctg gctaagaaag gaagaaaaaa aagagatccg ttagtgtctg tttagaaaag
1861 atgttataa cttacagaaa caaatataat aaactgaagc agatttgaaa agcaaaaaa
1921 aaaaaaaaaa aa
```

Homo sapiens vanin 3 (VNN3), transcript variant 3, nucleotide sequence (SEQ ID NO:15)
gi| 66932889|ref|NM_001024460
Coding Sequence = 73-426

```
   1 atgtaaagtt tttccagtga acaaaacgt aagaatctga gtttgttttt caaagatcac
  61 taaattttag ttatgattat atcacatttt ccaaaatgtg tggcagtttt tgccctcctt
 121 gctctgagtg ttggtgcact ggacactttt attgctgcag tatatgagca tgcgtgata
 181 ttaccaaaca gaacagaaac acctgtttca aaagaagaag ctttgctcct gatgaacaag
 241 aacatagatg ttttggagaa agcagttaag ctggcagcga agcagggtgc acatatcatt
 301 gtgaccccag aagatggaat ctatggttgg atcttcacca gggagagcat ttacccctat
 361 ctagaggata taccagaccc tggagtgaac tggattccat gtagagaccc ctggaggaaat
 421 cactaaaata tagtaagttt gaggaaatgt ctattgaatt agattcggca acaccagt
 481 gcaacaagga ctcagctgcc tggccaagga caactctatc tatgtcgtgg ctaatattgg
 541 ggacaagaag ccatgcaatg ccagtgactc tcagtgtccc ctgatggcc gttaccaata
 601 caacactgat gtggtgtttg attctcaggg aaaactgttg gcacgctacc ataagtacaa
 661 tctttttgca cctgaaattc agttttgaa ccctgaaatt cagtttgatt ccccaaggat tcagaacttg tgacttttga
 721 cactcctttt gggaagtttg gcattttac ttgctttgac attttttctc atgacccagc
 781 tgtggtggtg gtggatgagt tcaattgac agctctc acccacagc atggtacaac
```

FIG. 7E

```
 841 acgctgcccc tcctctggc tgttccttc cattcagcat gggccaaggc catgggagtc
 901 aatctacttg ctgcaaatac ccacaaccac agcatgcaca tgacagggag tggaatctac
 961 gccccagaag cagtcaaggt gtaccactat gacatggaaa cagagagtgg tcagctgttg
1021 ctatcagaac tgaagtctcg gccccgccgt gagcccacct accctgcagc tgtttgactgg
1081 catgcgtatg ccagcagtgt caagccattt tcctctgaac agtcagattt tctggggatg
1141 atttattttg atgagtttac cttcaccaag cttaagagaa atacaggaaa ttacacagct
1201 tgccagaaag atctgtgttg tcacttaact tacaagatgt ctgagaagcg aacagacgag
1261 atctatgccc taggtgcttt tgatggactg cacacagtag aaggccaata ttacttacag
1321 atatgtgcat tactgaagtg tcaaaccact gacctggaaa cgtgtggaga acctgtgggg
1381 tcagctttta ccaagtttga agacttctcc ctcagtggca catttggaac gcgttatgtt
1441 ttcccacaga tcattctaag tgggagtcag cttgccctg aaagacatta tgagatttca
1501 agagatggac gcttgaggag ccgaagtgga gcccctttgc ctgtcttagt tatggccctg
1561 tatggaagag tgtttgagaa ggaccctcca cgcttagggc agggatctgg gaaattccag
1621 tgatctcctt tagcagagcc cttttaggat tagcctggct aagaaggaa gaaaaaaaag
1681 agatccgtta gtgtctgttt agaaaagatg ttataaactt acagaaacaa atataataaa
1741 ctgaagcaga tttgaaaagc aaaaaaaaaa aaaaaaaaa
```

Homo sapiens vanin 1 (VNN1) gene, complete cds (SEQ ID NO:17)
gi|68248545|gb|DQ100297.1
Coding Sequence = join (1959..2168, 4155..4278, 21806..22005, 22680..22971, 23411..23772, 31490..31660, 32673..32855)

```
   1 gttcccttgg caattgcaga ataaatgcat tatagttact aaagtaaaaa attagatatg
  61 cctgtttgca gattgaacta taaaaatacc attcaaagac aaatagatct aaaaataaaa
 121 tggaaaaaca taaacactaa ttctgtaaat attatactta atgcacaact gaaacaaaat
 181 ttgccagctt actcaatatc aaaatctatg aacagttttt ctattttata taatttccct
 241 ctcctctctc tggatctcgc tccccagctc attttttctt tttttgtc tgattcttta
 301 tacacctctg ttgcctctgt gataagcagc ttccaagatg gttcctaatg ctttattgga
 361 tagaatacaa caaaagcgat gaggtgttgc ttccccaatt acattacgaa gcatccgtgg
 421 cttccatctc cagtgggttc acttgctgtc tggctctaag ggaatccaga taccataatg
 481 cgggctgccc tatggtgagg tttgcatcac taggaactca tgtctctggg caacaaccaa
 541 tgaggtcttg atccctgccg tcagcacat gagggagctt ggagctcgga agtgaatcct
 601 cctgagtca agccttgata tagctagcc tggacgtcag ttgactgcag ccttgtgaaa
 661 gagaccttgg gccagaggca ccagctaaac tgccccctgga ttcctgaccc agagaaagtg
 721 ggagatgatg tatttttgct ttttgaagct gctgaatttg gggataattt gttatatagc
 781 aatagaaaat gagtaactct tttgtattcc tctttgtcct ggcttcccca ttttgaggaa
 841 aataaagtaa atcaaagtgt agagctgaaa tattcacatg aaaataataa taaagtttta
 901 aaattattg aatgtcttgt gttgacattc caaaatatat gaattccaaa aatttatatg
 961 ttgaagtcct aactgtcagt atcttagaat gtaactttt tggaaaaggg gtcatttcag
1021 atctaattag ttaagatgaa gttatactgg agtacagtgg gcactaaatc gaattggtcc
1081 tatgattgag tctcagtctt tcagtgagcc tgtaccctg ggtttatgac cttcagttgg
1141 ctttttttctt ctgcccttat ttggcataaa aacaagcag gtggatcacc tgaggtcagc
1201 aatttgagac cagcctgcc aacacggcga aaccctgtct ctactaaaaa tacaaaaaat
1261 tagcctggcg tggtggcggg cgcctgtaat cccagctact ggggaggctg aggcaggaga
1321 atcacatgaa cccgagaggc ggaggttgca gtgagccaag attccgccac tgcactctag
1381 cctgggtgac aagagtgaaa ctccatctca aacaacaaca acaataaaca aacaacaacg
1441 atgacaaaaa aagctagagc tgggatttc cctttccctg tgttaaagat tagagtggtg
1501 tcctcacaaa aaggaaaac ttggatacag gcacacacat gggagaata gcatatgaag
1561 agacacaggg agaaggcagc catctatggg tcaaggagag aggcctgaa cacatctttc
1621 cttcaccgcc ctcaggagga accaactctg ctgacaccttt catctgggac tcccaccctc
1681 cagaactgca aagcaataaa tttttttatttt ttacaccac ccagtttatt gtattttgtt
1741 aggcagccct agcgaactaa tgtacataga gtcttgagt taatcttcac aaattactgc
1801 aataagggag ggtctttttgt tatgtaacaa tgctatgaaa tcatagcgtt ttctraatta
1861 acttccgtag tttaaggtac taagtcctgg acaccacgtg tcttcttct ataaatacca
1921 ggacatgctc tgttttcag cactcattgg acttcagcat gactactcag ttgccagctt
1981 acgtggcaat tttgcttttc tatgtctcaa gagccagctg ccaggacact ttcattgcag
2041 ctgtttatga gcatgcagcg atattgccca atgccaccct aacacacgtg tctcgtgagg
2101 aggctttggc attaatgaat cggaatctgc acatttggga aggagcgatc acatcagcag
2161 cagatcaggt accatctcta ccatctctcc agtgtactgg attctatgag aaagcagggg
2221 gtcctaggag acagggcac tgtcaggtc agttacactt ttagatgata tatgtatcag
2281 agtagccaag aacctttatt ttacagttag aattctactt tcctctcaaa attagagcaa
2341 ggacttccct aaaagtaaga acaaagttaa gaaagaacaa atttgctcat tatcaagaag
```

FIG. 7F

```
2401 cagcagacct tgaggaact ggccataaat tcaacatctt tgttccctt ttctggtaca
2461 gatggaggat ggaggataaa tgggtcaggg actaggtgct attttcagag tattagtggc
2521 cttcatgtac tcatgtgcta ttaaggcttt gcaggttttc gaataaattt ataatctgaa
2581 aacaaattta agttttcaat tccttgccag catgcattat atacttcaca cttcattcta
2641 attacaagat aaaagtatat gtaatgcatt gtgagtcctt aagtttagtg aaggtttcag
2701 tttgaaghta atcatacagt ataaattgtg gttacacaa atattatttt aaaagctatt
2761 gatcgattag gtgtagacca ggaatacatg aagtgtgata aaagtcatgg ataaatgtgt
2821 attacatata tctataaata tatattcttt tgtgttgttg agttaaggtc tcactctgtc
2881 acccaggatg gagtatagtg gtgtgatcac gtctcactgc agccttgact tcccgggctc
2941 aggtgattct cccactacag tctccagagt agctgggacc acagatgcat gccaccgtgc
3001 ccagctaagt tttgtatttt ttgtagagat gggattttgc catgttgccc acgctggact
3061 tgaactcctg acctcaggtg atccacctgc cttgggctcc caaagtgctg ggattacagg
3121 catgagctac cgtgactgcc ctatattctt atatatacta atatttaaaa ggttatcagg
3181 agttctgatg ttcttttttca tccttagtcc aactatttcc ttgaaggtca cagagctttt
3241 taaggtgact ctctaattgg aaggtgccca ggttagctca ggcagtactt gtaggcatgg
3301 gacagttcaa gtaaccagtt tgtggctcct cttttttctga gaagcaggaa tcatgtttgc
3361 aggggaaagc tagggcagag gaggaaataa acagaatatt taagttatta atcagtcttg
3421 acacaggcac agtcatcagc gaaagttcaa ggagaggctt ggttccagga taagctaggt
3481 ttatagttaa cgactgccat aggaaacaac aatggcagga ttagaaaatt aaaatgcttg
3541 actaagccag gtgcggtggc tcatgtctgt aattccaaca ctttgggagg ctgaagcagg
3601 cggatcacct gaggttggga gttcaagacc atcctgacca atatggagaa accccatctc
3661 tactaaaaat acaaaaatta gccaggcgtg gtggcagatg cctgtgatcc tagctactta
3721 tgaggctgag gcggagaat cgcttgaacc cggaggtgg agattgtgt aagcgagat
3781 ctagccattg cactccagcc tgggcagcag agcgaaactc catctgaaaa aaaaaaaaa
3841 gagagaaaaa aaaatgcttg actagaagcc caaacctcac cattatgtaa catatccatg
3901 caacaaacct gcatttgtac cctttgaatc taaaattaga aataasgaaa agaaagaaa
3961 aagaaaaaga agtgacagtg cactgaaaaa aaggaaatt aaaatgcttt ggaaaagaaa
4021 ataaattata aaaatataga aaacaaaata agatttaagg ggtgtgggg aagcccaaat
4081 agttgttact cagccactca gctcctcagc tcctcttgca ggcccccctt tggattaagt
4141 tgcattttta acagggtgcg catattattg tgactccaga agatgctatt tatggctgga
4201 acttcaacag ggactctctc tacccatatt tggaggacat cccagaccct gaagtaaact
4261 ggatccctg taataatcgt aacaggtaaa gaaacaactt gtgaaaaatt cactagtaaa
4321 catcaacttg atttacctgg gaaaactttg ttgatgatca ttgcatagat ccacgatcaa
4381 ttcttaagtt tcagtatagc ttattttca tctactatgg gtatatttac tgggagagca
4441 aatatgaatt atgaagtcac agaaatcaga gctagaaagt agcttagaaa tcatcacatt
4501 cagtgtgaac atctctggtc tctgactcct caccagtgaa cagaaaaata tttccctgtg
4561 taggtctgtg atttgaaaac tatatgagta aatggcaaaa gagagtcaca tcagtttaag
4621 attaatagtt ttcctttctc attgctaaga tagctgatga ggttaatgta gtaaaagtcc
4681 ttaaagtgta agctgattgt aatctaagag gtgatatggc aggattttaa gtggtttaag
4741 tcaggtctcg gctacagaga tattaagtgt ggtgaaagca gcactattaa ttttaatgta
4801 aggaaaccaa tatcttatac acctaagaaa atcatgtcga ttcacatact tctttctgaa
4861 tacacatggc taaaattatt ttaggaattc ctctttggga actattctca aaaccgcaca
4921 acgccagtta gaatggtgat cattaaaaag tcaggaaaca acagatgctg gagaggatgt
4981 ggagaaaggg gaactctttt acactgttgg tgggagtata aattagttca accattgtgg
5041 aagacagtgt ggtgattcct caaggatcta gaaccagaaa taccatttga cccaccaatc
5101 ccattactgg gtatatacca aaggatcata aatcatttta ctataaagac acatgcatgc
5161 atatgtttat tgcagcactg ttcacaatag caaagacttg gaaccaaccc aaatacccat
5221 caatggtaga ctggataaag aaaatgtggc acatatatac acagaacac tacacagctg
5281 taaaaaggga taagttcatg tcctttgcag ggacatggat aaagctggaa accatcatc
5341 tcagcaaact aacacaggaa cagaaaacaa aacactgcat gttctcgctc ataagtggga
5401 gttgaacaac gagaatacat ggacacaagg agggaacat cacacaccgg ggcctgtcgg
5461 ggagtcgggg gctaagggag ggatgcatt aggagaaata cctaatgtag atgatgggtt
5521 ggtggtgca gcaaccacc atggcacgtg tataccatg taacaagcct gcatgttctg
5581 cacatgtatc tcagaactta agtataata ataataatac taaaattaaa aatcccacag
5641 aaactggctg ggtgtggtga ctcatgcctg taattccaac actttgggag gccgaggcag
5701 gaggatcacc tgaggtcagg agtttgagac cagcctggcc aatttgcaa aaccccatct
5761 ctactaaaaa tacaaaaatt agtggggcgt ggtggtgca acctataatc ccagctactt
5821 ggaaggctga ggcagggaga actgcttgaa cctgggaggc agaggttgca gtgagccaag
5881 atagtgacac tgcactccag cctgggtaac agagctagac tctgtctcaa aaacaaacaa
5941 acaaacaaac ccacaaaaac tacttacaga gacacttga ttttgacaag gtggattttg
6001 ataaattcca gtgttattta tcgtaatcat ttactctatt cttatttaat tgtaccataa
6061 ttatttctta tttaatcatg tcatatgtca gtgcttcagt ttctaaaagg caagcactct
6121 attatcactt ccactatgaa ttgaattgac ttatttctga atggcctttc cctagaacct
```

FIG. 7G

```
6181 catctccaag ggcctcctga acatccccac aaggatgtcc cattcacttc atttcaagga
6241 acacggttgc ccatttatgt tttccatcaa ctaatgatgt ctgaatgtct tgccttaatt
6301 ctctctgtct ctctctctct tttttttttt ttgagagag agactctgtg tcgcccaagc
6361 tggagtgcag tggcgtgatc tcagctcact gcacctcta tccccaggt ccaagcaatt
6421 cttgtgcctc agcctcccga agatgacaag tgtgagccac aacaccagc tagttttttg
6481 tattttcagt agagatgggt ttcaccatgt tggccaggct ggtcttgaac tcctggcctc
6541 aagtgatcca cctgctcggc ctcccaaagt gctgggatta caggtatgag tcatcacgcc
6601 cagctgcctt aatttattaa ctctgcaaat ttttttgag tacctattat gtctaaacat
6661 tgttctgggc aatgaagtga acaaaacaga ttaaaaattc ctgtcccctt gaaatttata
6721 ttctagtgtg gggaggtaat aaatgtttta aaagataat tatctatcta tctatcatct
6781 atctatcatc tatctattat ctatctacct atctttatat aggtatcttt catctgtcta
6841 cctatctatg atatgaggtg aagtaaatg ttatggaaaa aataaagtgg ggaaggtgaa
6901 tagggtggca agcgtgggc tgaaatttta tgaaggtcgtc tgagggcatc acagtgagat
6961 ttcagcaaag acctgaaaga aatgaggcaa tagatcatgt gagtatctga aaaaagtgca
7021 ttccaggctg aaggaattct aaattccaag atcctgtggt cagagtatgt gtctaaccta
7081 tggaacagaa aaagggttag tgtggttaca gtgatgtgac agaagaggag aaaagtagga
7141 aatggaggca gaagggcagg aggagcgcaa tgttgagaat agactccagg gtataggtca
7201 ccaaagaagc agagggcagt tcaaaagctg ttgtgatcat tatggcatag agatgatggg
7261 tctgagacca agaaatggta gaagtttagg tattgagaag tggacagatt ccgaataaag
7321 tttgaaagta gcactggcag gttttgttga aagactggat gtaggatgtg agagaaaagg
7381 aggactcaat atccttccct gctctcatag aatcagatct catcttattg agtatgtttg
7441 aagtatgcac atagttgatt gctttctctt ctcatattca ccaaactttt gggacctaca
7501 tcacctctta gactgagcgt taaaggaaca ggctctcatc acttttcttt ttattttaat
7561 ttatttagca tttatatgtc atatcgttcc agaaggattt gaagtttcta attatatcta
7621 atataattaa aaataggata cttcagttct aacaacaaac tagaacccat atgaatagag
7681 gaagcagttg ttatgaggca tcatggtaaa gagctgctca ttacaactgg atgttaagta
7741 tagttctaag agtttctgag cagctaagag aagtacaatt ttgttcagac acttgattg
7801 catcatagaa gaaagcttgc atatttcttc agagacaaac tatgtctaat aacctaactt
7861 aaagatgaat ttacttattc aactgttttt gttaattatt ttattttaa ctttcatggg
7921 tacatagtag atgtatatat ttataggta catgagatgt tttgatgttt gtacacaagc
7981 atgcaatggt aacaatcaca tcatgaagaa tggggttttcc atccctcaa gcatttatcc
8041 tttgtattac aaaccattca attatgctct tttaggtatt taaaaatgta caattaagtt
8101 attattgatt atagtcaccc tgttgtgcta ttgaatacta gaccttattc attcattcta
8161 actattttt tgtacccatt aatctcctca ctttctcccc actcctcccc taactaccct
8221 tcccagcctc tggtaaccat cttctattc tctatctcta tctccatgag ttcaattgtt
8281 ttgatttca gatcccacaa ataagtgaga acatgtgatg tttgccttt tgtgcctaac
8341 ttacgttatt tcacataacc taatgatctc cagttccatt catattgttg caaatgactg
8401 gatctcattc tttttgtagc tgaatagtac tttattgtgt acatgtacca cacggttgtt
8461 tccaaatttt ggctattgt aacagagttg caataaacat gaaagtgcag atatcttttc
8521 tatatactga ttttctttt gaggagtata tacccagcag tgggattgct ggatcgtatg
8581 gtggctctat tttagtttt ttgagaaacc ttcaaactgt tctctacagt gactgtacta
8641 atttgcattc ccactaacag tgtatgaggg ttcccttttc tccacatcct caccagcatt
8701 tgttataagt cattttaaca ggtgtgagat gatataattg tacttttgat ttgcttttt
8761 ttttttttga gacagagcct ccctcttgtt gcccaggctg aagtgcaatg gtgccatctt
8821 ggctcactgc aacctctgcc tcctgggttc aagcaattct cctgcctcag cctcacgagt
8881 agctgggatt acaggtgcct gccactacac ccagctattt ttgtatttt ggtagagacg
8941 gggttccacc atgttgtcca ggctgatctc aaactcctga ctcaggtga tcctcttgcc
9001 tcagcctcca gaaatgctgg gattacaggt gtgaatcacc atgcccggtt gatttgcagt
9061 tttctgatga tcagtgatgt tgagcaactc ttcacatgcc tgtttgccat ttgtataact
9121 tcttttgaga aatgtctgtt caaatctttt gccattttt ggattggatt attagatttt
9181 ttttcctata gagttgtttg gacttcttac atattccggt tatgaatccc ttataagatg
9241 gatagtttgc acatatttta tcccaatctg tgggttgtct cttcactttc ttgatagttt
9301 ccctgctgt gcagaagctt tttaccttca tgtgattcca tttgtccatt ttgctttgg
9361 ttgcctgtgc ctgtgggta ttactcaaga aatctttgtc cagaccaatg tcctggagag
9421 ttccccaaa gtttttctttt agtagtttca tagtttgagg tcaaatattt aagtatataa
9481 ttcattttta ttgattttt gtatatggtg agagataggg gtctactttc atcttccgc
9541 atatggtat ctggttttcc cagcaccatt tattgaaaaa actgtcctt ccccaatata
9601 tgctcttggc atctttgttg aagacgagtt cactgtagat atttgggttt atttctgggt
9661 tctctcttct gtttcattgg tctatgtgtc tgttttatg ccagtaccat gcagttttgg
9721 ttactagagc tctgtagtat aatttaaagt caggtaagt gatttctcca gtttttttc
9781 tttttgctta ggaggggctc tggatctcac gtaaatttca gaatcttttt
9841 ttctatgtct gtgaagaatg acattggtat tttgatggag attgcattga atctgtagaa
9901 tgctttggat agtatgggca ttttaaacaat attgattctt ccaatctatg aacatggaat
```

FIG. 7H

```
 9961 atctttccat gttttgtgtc ctcttcaatt tcttacatca atgttttaca gacttcattg
10021 tagagagctt tctcttcttt ggataaatta attcctaggt attgtatttt atttatagct
10081 ataacaaatg ctattccttt cttgatttct ttttcagatt gcttgctgtt ggcacagaaa
10141 tgctactgat tttttatgtt gattttgtat cctgcaactt tactgaattt gtttgtcagt
10201 tctattagtt ttttggtgga gtctttaggg ttttccaagt ataagataat aacatctgca
10261 aacaaaaata attttcctcc tttccaattt ggatgcattt tatttctttc tcttgtctga
10321 ttacttttagt gagaacctcc actactatgt tgaataatag tggtgaaaat ggacattctt
10381 gtcttttcta gatcttagag aaaagctttc agttttccct cattcagtat gataccagcc
10441 atgggtctgt cataaatggc tattattgtg ttgaggtatg ttccttctat atccagtcat
10501 tgagggtttt tattatgaag gaatgttgaa ttttaccaaa tatttttttca gtgtcaattg
10561 aaatgaccat ttggtttttg ttcttcattc tgttgatata atgtgccaca tcaattgatt
10621 tgtgcatgtt gaaccatcct tgcacccttg ggataaatcc gacttggtca tgatgaataa
10681 tttttttaatg tgtcgttgca tttggtttgc tagtattttg ttgaggtttt tttgcatcaa
10741 tgttcatcag ggatgttggg ctgtagtttt ctttttatg tgtctttgcc tggttttggt
10801 atagtataat actagcctca ttgaatgagt ttggaagcat tcctttctct attttttgga
10861 atagtttgaa taggatttgt attagttctt taattgtttg gtaaaattca gcactgaagc
10921 ctttaagtcc tgggcttttt tttgctggga gatcttttat tacagcttca atcttattat
10981 ttgttatctg tctattcagg ttttggatttt cttttgtggtt caatcttggt aggctgtatg
11041 tgtctaggaa tttattcatg tctttaggt tttccaattt atcggcatgt agttgctcat
11101 agtaatctct aatgatcttt tgaatttctg cagtattggt tataatgtct catttttcat
11161 ctctgagttt attttttcttc tatcttttttc tcttagctc actaaaagtc aatttttatct
11221 tttcaaaaag aaactttta gtttttttg gatgttttttt atttcaatct catttatttc
11281 tgttcagatg tttattattt ttcttctact aatttcaggt ttggtttgct cttccttttc
11341 tagtttaaaa aaatatatca ttaggctgtt tacttgaagg ttttcttctt tgttagtgta
11401 ggcacttata gctataaact ttcctcttag aacgatttttg ctgtatccca taagtttttga
11461 tatgttgcat atccatttttc atttgtttca ataaaaattt taaatttctt cttaatttct
11521 tcattaacct gctggtaatt caggagcaca ttgtttaaat tctgtatgtt tgtatagttt
11581 tcaaaattcc ctttgctatt gatttctagt actattccac tgtggtcaga gaagatactt
11641 gatatgatct caatttttttt taatgtttta agatttgttt tgtgacctaa catatggtct
11701 ctccttgaga atgatccatg tgctggggag aagaatgttt attctgtagc cattggatga
11761 aattttctgt aactatctat taagcccact tggtctgtaa tgcagattaa gtccaatgtt
11821 tctttatttt ttttttcctt ctggatgatc tgtccaatgc tgaaagtagg atgttgaaat
11881 ctccagctat tattgcattg ggatctatct ctctctttag ctctagtaat atgtccttta
11941 tatatctgtg tgctcaagtg ttagcacact tgtgtgctca attgttatat cctctgacag
12001 aattgacctc tttatcatta tataattaat ttctttgtct ccttttatgg tttttgtcct
12061 gaaatctatt ctgtctgata aaatatagc taccctgct cttttgttt tccattttgca
12121 tggaaatctt tgctatccct ttattttctg tctgtctgtg tctttataag tgaagtgtgt
12181 ttcttgtaca caatcgacca ttgccattga ttttttttttct ttttatcca tttagccact
12241 ctatgtcttt tgattggaga gtttagacca tttacattca atgtttattt gttaagtaag
12301 gacatactcc tgccattttg ttttttttgtt ttctggttgt tttgtggtgt tgtcttcctt
12361 tcttcctgtc ttccttttttg tgaaggtgtt tttctctgat ggtatgtttt aattttttgct
12421 tttcatttttt tgtgtatctg ttgtaggttt tttgatttga tgttatgcag cttgtaaata
12481 acaacttata gttcattatt ttaaagtgat gacaacttaa cattgattgt ataaactaac
12541 aagcaaagag aaagctaata aaagcttcat acttttaactt catcccccat acttttaatt
12601 tttaatactt tctatttata tcttatactg tctatgtctt aaaaagcttt tataattatt
12661 attttttgatt ggttcatctt ttagttttttc tactcaagat atgagaagtt tacaccacaa
12721 ttacagagtt ataacactcc atgtttgtct gtgtacttac tagtgagttt tgtaccttaa
12781 gatgctttct tattggttat tgatgtcttt ttcttcaga ttgaagaaat ttcttagca
12841 tttcttataa gagaaggcag tgggttcttt tctggctcag ggtgggtcta gaaatgccat
12901 ccaggagcta agtcctggaa ttgaggactt taggagtctg cttggtgctt catgttactg
12961 tggctaagtt ggtacccaat ttgtaagaca aagtccttttt actcttcect ctcctttcct
13021 ccccatgcct ccccatggct acaacagctg ggaatgtgct gggtcacacc tgaaaccagc
13081 atggtactgg gtcccaccca agcctcgtgg tgagtactgc ctggctatca ctgatgttta
13141 ttcaaagccc aagggctctt tagttagcag gtgatgattc ttgccaggac tgggtccttc
13201 catttaaggc aagaagttcc cttatagcct agtgtatgtc tagaaatatc atcagggagc
13261 tagggcctgg gttggggat tcagtactct acttggtgct ttatttact gtggttgagc
13321 tgttatccaa gttgcaagac aaagtcctct ttatgctcct gtctcctttc ttaaggcaga
13381 gggacggagt ctctcaaagc tgtgagctgt gctgctgga gttggaggag ggttgatgca
13441 accactcctt tgactactcc agctggtgtc tcactaggtt atgtgcgctc caaggctact
13501 ggttctgagc tcagtacagc actaggactt gcctaggaat tgtagtcctt gtggcctaaa
13561 tcagctgtcc ccaacgtttt tggcaccagg gactggtttt gtggaagaca atttttttaat
13621 ggacagggtg gagtatgctt tctggataaa actgttccac cttagatcat caggcattag
```

FIG. 7I

```
13681 ttaaattctc ataaggaaca tgcaacctag attcctcaga tgcacagttc acaacaggct
13741 tccattccta tgagaatcta atgctgcaac tgatctgaca ggaggcagag ctcaggcagt
13801 aatgtcactc atctcctact gtgcagccag tttctaacag gccatggact ggtactgccg
13861 tgcagcccaa ttcctaacag gccacagtcc atggcatagg gattgggaac ccctggccta
13921 gactgccttt caagtttatt tagaacccca gagaacttta tcccacattg gtgatccttg
13981 gtagaactca ggttctgact gctgggtagg acaattcctc tctgacaaga gctgttctaa
14041 atgtgccctc tgtgggcact ggctgaattc tgtgccatgt tgctttctgc tgttacatgg
14101 caacactgac ttccaatgta aagtcccaca atcactgtac tttccttccc ccaagggcac
14161 aaatttttctc tccacaccat gtggtaacct ggaggatggg ggagagtggt attggcaatt
14221 aaagactttc tttcttacct ccttcagtgc ctctttcctt gatatgattt taaaacaagg
14281 tactgtgatt actcttctga ttttttggttc ttatgaaggt tcattcttgt tgtggatggt
14341 tgttcagttt ggtgatcctg caggaagaca attgctggaa ggttctattt ggccatcttc
14401 ctctgcttcc tcctcatctt ttatttcttc ctcttgcctg attgctctgg ctaggacttc
14461 cagtatgatg ttgaatagaa gtggtgaagg tgggcttcct tgtcttgtta cagttcttag
14521 aacaaaggct ttcagctttt cccattcca taggatgtta gctgtaggtg ctgacatata
14581 cgccatctat agcctttatt atgttgaggt atattccttc tgtataataa agtgcacatg
14641 tctgaattat atattacttg ccttgagggt gccaagaaac tatttatact gcctagaata
14701 ttaacctttta ttatgcctaa agagttcatt agtcaaatgt tggttttgat gtagacctca
14761 tagtttaaaa tttaacattt aaattaaatg ggttataatt tttaatacca cctaaataca
14821 atatattgat ccaatataga aagttagatc aatgttagaa ataaagagtc acagtgtacc
14881 tttccagact tgtcattagc atttcatatt tatagtttta gctttgattt gaatgtctca
14941 cagatgaact taaatcaaca cataattcca ccatagcata atagtaatta ggcagtttcc
15001 ctaaatttga gaacattgcc ttaatgtagt tgtgatgttt tgaggcttca tagcttaaat
15061 ccartataccc attatggaat ctatagagca gggctatgga gaaaggcttc agagaagttt
15121 ttttgctac tataacctta tttaaagaaa caaacagaaa aaaacccaaa cgtatttgaa
15181 gtctgcttaa atattactgt taaatgtgaa gtgtttatat ctaacattca taatcatatg
15241 aatgtcaaca tttagtttcg agtagaaaaa gataaatcat tactgtgagt taagaaattt
15301 aaatggagat gtgtgaggga gcatgtccat ttcatcctc ccatctccac cctcccaga
15361 gtttcatccc cagggtgccc ttcttggttt ccagcctctg tgttctgct tggggtcttg
15421 acttcttccc atgccactca ggctcagccc cagactagaa cagggtttgg gaagcagtgg
15481 ggatagccaa gatgggtgtc agtgggtggc ccagcagttt ctgtcccagg agtggccaca
15541 ggccagggggt agtggtggct gtgcatgtgg ccagcctgct gccattgtcc catccttgtc
15601 agggccctct ctttcacctt acagcatctg aggggcagag ctctagagtg tttgggcaga
15661 caatgcctct gaaaattttt ttttaaataa aatttagatg acaagtatat atcatatatg
15721 cagtgaccaa gcatataact actttacagt catctaactg ctgtagcaat gatatgtaac
15781 tacagtgtca aaacaccctg acagttttca gaaacccaat gtggagacca tctgccatat
15841 cttacttttt ctttaggtac aatattcaaa ttcatattga ttttgcttac atatgaatag
15901 tttcaaattt gttcacatat ggtttaaact tttttgtccct attgtcttac tcaggcttgt
15961 gtaacttaaa atgagcctga gcatggtct acacacagca agatgtgtaa taaaaacaca
16021 attttagtgc tactttcaaa attcatgcta ttaagaaaga tgctgttttc aaagctgaaa
16081 agatcatgaa atggctaact tacatatcag aggttggata attccttact attgaggtgt
16141 tatattttct gtgtagtaaa tgccttcaaa tattaactga aagatcagtg aagtcatttt
16201 cccttttgtg attccaactt cattttgttt atttttgaaga taattaatat tttaattgca
16261 aagaaaaatt atagcattgg aaaattttct gtatatgag aataacaatg aaccaaattt
16321 accaattagg gaaccatttc aggaattgtt ggatggtgaa ttttttcttca gtaactatgc
16381 tttagttgca atgcagtatg cccagaaaca atccatttca acttctgaat gtttgatttg
16441 gaacatttgt ttgatgagta ttcagttaaa cacttggata caaactcttt ccagaaggtc
16501 acatctctac catttatctt ggaatgtttc tgaagacatt ctactcattt tattaactgt
16561 atacacttct gttttggat ctccaatatg attatagaca atatcaacat agaaggcttt
16621 gatttagact ccaagtttta gagcatttga tcttgacatg ccttaaattg ggcttccagt
16681 caaaattgag gccacttctc ctttcaaatg gcaagttctc ttgaatgagt gaatagtgga
16741 gttgtagaaa ttgaaggca gtagtagctt tcacttaca ttacaacttc tccaatgcaa
16801 tctttttccat tctcatcaag tctgaaaccg tgaacctata ttcacctatt tggaacacat
16861 cagttgccaa tgggacatcc ctttcctctt ctattgattt tacagccgaa tagaagaagc
16921 tcagttcaac acatccaagg tgcttgggct gcaccttcat ttaacacagg aatctgtcca
16981 gtaaattcac agagaaaatg cctttgtgtt aaagccaaag aactgaatta gactaacatc
17041 ttgtacttca aagtcctgta gccttgcagt cattctgagg ctattgtcta tcatgtgcaa
17101 actcaattag tctcaaacca cagatcttta actgacatct agacttcagt tccaacaagg
17161 cattcagctg gtgtagcagt ttctgacagt caggtttcag tacctctatc atcttgatag
17221 tgattgagcc tcagtggtaa ccacccttct tgggcctgca ctcacctcac cccacgaaat
17281 ccaatctcag aggcctagga aacaaagcaa acagagaggc ccaggagggg gaagccttcc
17341 tgggtggatg tctctgcaga gccaccaaga tcatattgcc ctcatcaggg tcagcttgga
```

FIG. 7J

```
17401 gctgaagggc tgaaaaggca ttttgatatt tgattgcata ttatttcata ctgttatttc
17461 agagttttgt gtgcacacat tgtttcttca gtaagcctaa tgctttataa gcatagcaac
17521 cacatctgac atttctatgt ctctcacatt gtatgcttgg acagctctgc ctggaatatt
17581 cttccccag ttgcccacat gtccaatata gtgctttgtg ttgtgtcaaa acctaatgca
17641 tatttgttga atattttaaca tgtgatgatt ttagattagt aaatatcttt ccgataattg
17701 atgattttg ttatacctaa agattgaaca ctttgaaagc agccttagaa aatgcatttc
17761 aattattctc tttcacctcc tccttctgtg cccagggcaa aactctgcat ggattaagga
17821 ctcagcaaat atcatggatg aagcaacagg cagatttcag gcaccataag caaactgaat
17881 ttttaaaccc taaattagga catgtggtct aattttggag cattttatgt gtacgccaaa
17941 cagcctgaga aatgtagctt gaattgaaat atattagaat acatgaagac taatagagtc
18001 agtaggaaaa tatgtttgtc atcagaactg tttcagaaat ccaaacacc aacctactta
18061 ttccaccact taaggtgatc caaaaagact gggggtaaac atgtttcaag tggttcaatg
18121 tgttgtaatt tatatctatg catttcagat atcaattgaa gcaaggtgg gttaaactat
18181 tgaacggttg ttctttctta caaacacatt gaaataataa ttttctatat gtattattat
18241 atccttttcc aatcttttc aaggatatgt tttatagatg attgctatgg ctttccttat
18301 attcattata caaatttgtt tgtagatcta gtagccaata tttgatgtca ccaaatttt
18361 attcatacaa cagttatctc agccttctca gctattcttc aataaccatt tatcatttca
18421 gagttgtgca atagaggata aatatagcaa tatgttaaat attatttca aaattgtatt
18481 ttaattgctt tactgggaca attattggta acttttgtaaa agaataaaaa aatcaggcat
18541 taacaaatgc tccaggattt ccattgtttc atactagctg gtactgccct agccaatcct
18601 tgttacctct tatttgaaca atggcaacag cttcctaatg aatccctgc atttagtctc
18661 tcactgttcc agtacattct acactccgtg ttctatttat ctttatgaag aaaattttga
18721 ccaggttgct tctgtcttca aaggctttaa tagtacctat ttattactaa atttggaaca
18781 aatcttagcc tcttgtgcaa agctcaatat ccatccttcc ttccttcctt cctccctgcc
18841 tcccttcttc cttcttttt ttaaaatatt tttaaacttt ttattttttc gagacagagt
18901 ctcactctgt cacccaggct ggagtgcagg ggcgcaatct cagctcactg caagctccac
18961 ctcccgagtt cacgccattc tgctgcctca gcctcctgag tagctggaac tacaggcacc
19021 tgccaccacg cctggctaat ttttttgtatt tttagtggag acgggttc accgtgttag
19081 ccaggatggt ctcgatctcc tgacctcagg tgttccactg gcctcagtct tgcaaagtgc
19141 taggattaca ggcgtgagcc actgtgccct ctcctctcct ctcctcccct cccctcctct
19201 cccctcccct ccttctctc tttcctttct tctcaaatct gagaatgtct tcatttctcc
19261 ctcccttttg aagggcagtt ctgatggata tagaattctt ggttgtcaga ttttttttc
19321 tttcagtact ttaaatatat cagctcaatg ctttgtggtc tccaaagtta ttgatgagaa
19381 atctgccgat aatcttattg gggatccctt gtatgtatga gtcacttctg tcttgctgct
19441 ttcaagattc tcatttgtc tttgctctc tacaatttga ttatagtgtg tcttagtgtg
19501 agtctctttg aattcattcc cttggagttt gttgagcttc ttggatcttt atattcatat
19561 ctttcttcaa gtttgggaag tttcagcca ttattcttc aaataatctc tcttctcctt
19621 ctgagactcc cacagtgcat gtgttggaca ctcaatggtg ttcctaaggc tctgttcaat
19681 tttcttaat atttttgtt gttgttctgc agactcaata atttcaatgg tcctgtcttc
19741 cagttcactg ttctttttt ctacatgcct gaattggtct tcgaatcctc ctataaaata
19801 ttcatttcag ttattgtaat tttcagctcc agattctttt taggttttct atcttttat
19861 tgatatttct actttgtttt gttttttgat tttctccaca tcttcctta ttttcttaag
19921 cttctgtaaa accattgttt taaagtctgt gtttagtagg tctgtcatgt ggtccttttc
19981 agggatgatt ttcgttggtt tattttcct ttcttttgag tgagtcatac tttcctgttt
20041 ctttgtatga tttgatttt tttggttga taactagaca tttgagtactt atcacatggt
20101 tactctggga atcagattct ctgggttgc tatgtttgtt tgtttgtttg ttttgttgtt
20161 gtaggatgtt tgtgttgagg atcagcttga gatgtaaatt taaggtcttc ttagaccttt
20221 tatgagtctg tacctttccc tgggcatgta tggcgacttt ctaaatttcc ctgtatattt
20281 aattgcttat tccttaaatg tctcactatc caaggagaa aaagagaaaa taaataaata
20341 aataagacac tggttctta aatctcctgg aagccacttc agccagaaag agggcctgca
20401 aaatggtgt gtctgtatgt atacacaaca atagctgctt gcctttgcat ttgtacctcc
20461 atgatcagaa gcaacaatta gtgatcagaa tgcagatctc gtatatttga aagacaaggt
20521 cattattgtc caccctgctc ccataagctg cctgcaagct gcttaggaa cacagacatg
20581 gcagcctgtc acagggacag gggatgagga attggtaacc actattgagc taagagctaa
20641 aatgactga aattaactgt aagttacctt ccaagcattc ttctggaagt tgcaagcact
20701 agagctccaa aatagtaata ttagacagat tccaacagtg caattgttat ctaggtgggg
20761 agaaaaattc cctgctctgc tatcttccca gcatccctct acctctaaat ttttgttaac
20821 tcattcaaaa aaattttttt ttgagatgga gtctcactct tgttgcctag gatggagtgc
20881 aatggcatga tctcagctca ccacaacctc tgcctccaa gatcaagcaa ttctcccacc
20941 tcagcctctt gagtagctgg gattatagcc gcacgccacc aggcccagct aattttgtat
21001 ttttagtaga gacgggttt cttcatgttg gtctggctgg tctcgaactc ctgacctcag
21061 ctgatccacc cacctcggcc tcccaaaatg ttgggattac aggcatgagc taccacacct
```

FIG. 7K

```
21121 ggcccccccaa aatttgttttt ttgagacagg gttttgctct gttgcccagg ttggaatgca
21181 gtggaactca ctgtagcctc aaaatcccaa gttcaagcaa tcatcccacc tcagtctccc
21241 aaatatctga gactacaggc acacaccact atgcctggct attttttttt ttttcattt
21301 tttgtagaga gacagtcttg ctttgttgcc caggctggtc tcaaactcct gggctcaagc
21361 aatccttcct ccttggactc ccaaagtgct ggaattacag gcatgagcaa ccacacccac
21421 cccaagatat tttttaatgc ctctcttctg ttagacataa ttttagtaaa cgggatatgt
21481 aagtcattga tctatgatat ccacaggatg ctgcagacat tataagacaa acacgtaagt
21541 gaaatatga ctatagatta cgataaatgc tatgaagaaa aaatacgtgg tctggaatct
21601 tatcctacag taggttccta caaccaattt tactcaagca tgggcttcct ctgaactcct
21661 ttcttgtctt aatacttctc ttctaattat tgttatttag aatttacttt tgcatatatc
21721 aaataatagg tttaggcaac tatcattcag gattttgttg agagttaaga ttgatttaca
21781 aagattttt tcctccaata aacatgtatc agatttggcc agaccccagt acaagaaaga
21841 ctcagctgcc tggccaagaa caactctatc tatgttgtgg caaatattgg ggacaagaag
21901 ccatgcgata ccagtgatcc tcagtgtccc cctgatggcc gttaccaata caacactgat
21961 gtggtatttg attctcaagg aaaactggtg gcacgctacc ataaggtaaa attaatttgc
22021 aaataatcca attagttaat gcctaatgaa ataaagtggg caaggagaaa aatatgttat
22081 tgataatgat aagcacactt tagaaatcga gtaggggcaa agcatagaaa gtaatgataa
22141 agtgtggaaa gctcctataa agaggcttaa ggggttccgt gtacatataa gaacacagga
22201 gtgtgttttc aggagtgtgt agcagtcaga aagtgccgca tgcattatgt tgcctaatgt
22261 tgcctttttgg actttgtcct tttaaaggca taccctgaca atgggtcaag gctagaatga
22321 aaaactgctt accacatag ctctgtcttg aggagaatgg aacaaacaaa gttccttgcc
22381 aaggaaaaca gttaagtcta cttggcaaac agaagtaatc tattttatgt cttataagat
22441 tccagtgggt ctttatagat aaagataccc atgtacatat ttgtaatgtg gagactgaac
22501 taaaggccca atttagctag aatggcctct gattctctaa agcaaactca tttcccatga
22561 aaacactgat catagatgaa attggcacta agatgtgagc ttgtacttttt tcccacactg
22621 tgatgtccag atcaacttcc taaataatt ttttctctt tatcttctgt ttattgcagc
22681 aaaaccttt catgggtgaa aatcaattca atgtacccaa ggagcctgag attgtgactt
22741 tcaataccac ctttggaagt tttggcattt tcacatgctt tgatatactc ttccatgatc
22801 ctgctgttac cttggtgaaa gatttccacg tggacaccat agtattccca acagcttgga
22861 tgaatgtttt gccacatttg tcagctgttg aattccactc agcttgggct atgggcatga
22921 gggtcaattt ccttgcatcc aacatacatt accccctcaaa gaaaatgaca ggtaatgtgt
22981 gatcttaaag atatgcaggc tgatgtaatc agaaaagaaa agaaaaaaaa aacatgtttt
23041 tctagctaac gcatactcct taatacaatg tttttccagct cttaattttt gaacatctag
23101 ctgttaatat gctatagaat caatctcagt ctaaattgtt ttgtagattt atttggtttt
23161 atttaacttg attttttttt caaaatatat gacttcttac atacaactct cccttcttgg
23221 cttcttggtt tcatacttta attgatttcc tctcacttct ctgtctttat cagcatgttt
23281 tactgaaatt aataaaacat ataacttaga gagagtaaaa tgtgaatatg aggttaaaat
23341 agtaataaca attatgaaat cccttttac tttccaattt caaatgatgt tttcaactta
23401 ttacttccag gaagtggcat ctatgcaccc aattctcaa gagcatttca ttatgatatg
23461 aagacagaag agggaaaact cctcctctcg caactggatt cccacccatc ccattctgca
23521 gtggtgaact ggacttccta tgccagcagt atagaagcgc tctcatcagg aaacaaggaa
23581 tttaaaggca ctgtcttttt cgatgaattc actttttgtga agctcacagg agttgcagga
23641 aattatacag tttgtcagaa agatctctgc tgtcatttaa gctacaaaat gtctgagaac
23701 ataccaaatg aagtgtacgc tctagggca tttgacggac tgcacactgt ggaagggcgc
23761 tattatctac aggtaatatt ttgatgtcag aagagttact ggataaaata aagacactca
23821 gttaaatata cagtttagat aaatatgaa tgattttttta gtataagat atcacacttt
23881 tgggattta tgtatgctaa aaattttgtt gtttatttga aattcaactt tagctgggaa
23941 gcctacaaat acaggctaaa tttatttgct aaatctttt ttttttttt tgagacagag
24001 tctcactctg tagcccaagc tggagtgcag tggtgcatca gctcactgca agcctgcct
24061 cctcggccaa gcaattctca cgcctcagcc tccaagtag ctgggactac aggcgagtgc
24121 caccacgcct ggctaatttt tttgttgttg ttgtatttta gtagagacag agtttcacca
24181 tattggccag ggtggtctca actccccga gctcaggtga tccgcccacc tcagcctccc
24241 aaagtgttga gattataggc atgagccacc gtgcctgcc tatttgctaa accttgaaac
24301 cttgatgtc agttcaattt taagctgatt gggaaaggc aggacattta cttgcagtag
24361 cagtattaaa aataaatatt caaattacag atcattataa caggagttca ttgaaaaccc
24421 attttatttc ctgcctgaac aaattaagcc attttcctta tatgttcaca aatgcctatc
24481 ttgctttata aagagtttga cactaagtat atcctggata tgaatggggt tgaccaccaa
24541 gatagttcaa tggaatggtt tattgctgca aagatccaat ctctcattgc tcgcaagtgg
24601 cctccaggc cctccattc ttctcttctc ttcctggtc tggccccat ctttatctcac
24661 ttaacaggg ttcctattga cagtctgaca atctcagctc catccagtca gttctccata
24721 ttgtagttac agaaatcaca aaaagctgtt tttgattata atactgtctg gcttaaaatt
24781 cttcactgac ttctaattga caaatcaaat ttcttaacat gaaagacaca caaagtctag
```

FIG. 7L

```
24841 atgtgtggtc ccttcctatt ctctatcctc taatctcact tctacttaca aatatcctgg
24901 gcttctgcaa tattgaaata ttttcccatc tcctatttgc tagcatatgc agaacctcaa
24961 ggtgtttgca cagattgttt ggtcctttat ccgtggcgag ccccacctac taatctttca
25021 tagcactttt ctggtgttat cgtcaccaag aggggttcct ggatatttcc cacagagcta
25081 ctcctacctc tccagatgag ttaagtacat cctttatgtg ctcccaggac accctatgct
25141 tagctttatc aaagacatat tatgtcatag tattcactta cttatttgag actgagaacc
25201 ccttgagtgc tgaaattatg ccaactgcac agtattttgt ttgctctatg ataactaccc
25261 taacaatact ttttcgtttt agcaaatgaa ggctactat atgccaggta tttatttagt
25321 gttaatgata tgaagataaa taagcataga tcctcctctt gaagaattca gtcttagta
25381 atggagaaag acatttgaac agataatttc agcataggtt ggcatgtgat tgtccgtaga
25441 atgcacattt tgctggagga gtactaaaga gctactatta gattaatttg tgaacgcagg
25501 gaagtttctg gagctgatgc tattatccag gtgaaaaaga gtaggagggg attctttgtg
25561 gtgtgaagag catgaacaag ggtgtggatg caggcaggag cagggtctgc agggaacagc
25621 aacaggtcag tgctactaag gcaactgagg catggcttgc gaagctgggt ttggtgggaa
25681 ataagcctgg aagcaacatc ctgtcctgca ggatcttacc tagcacactt aagattcagc
25741 ctttattctg tgggtgatgg tcagctggtg gaagtggtcc agtgaaggaa tgatgtggtc
25801 agatctacct ttgaatatat catttttact actctgtaga tgatggagca aagacccaaa
25861 agactagatt attaaaatag tcttattaag ggtctggacc aagactgtgt tgttggaat
25921 aaaagcaggg catggagtct agacatattt agaaaatgga actcagtggc caatttgatg
25981 tggaacagga aacggaatg gagagtccag aatgtggcag atttctggca agaatggctg
26041 ggtgggtgag atgcatctga cagatcagga ggcaagagag gagcagactc actgacagtg
26101 ggtagaggct gagttcagtt atagatgtgc tggttttgaa gtagttatga gacattcagc
26161 tggacccagc cagttgtctg ttgaatactt tggtctgatg cttaagggag atactagaat
26221 tagaaatatt gtttcaaaaa tcagcaagat acaaggggca attaagcaaa caacagtgaa
26281 tgatacgaca aaggagactg tactgacagt aaagaactat tgacaaagta gaacctttgg
26341 gagcttcggt atttggggca ggaaaggaca gaggacaaga aacctgcaaa tacaattaag
26401 aaataaagga aaatttaaaa agagaacatc tggtagatgc caaggaagta gagactcttg
26461 gaggaaagaa atcatgaggt gtattaacac aatacgttga ccattattag cattttttgag
26521 tataattttg gcagaatttt ctgagctcat aatgatagga tgatgggcag attatattgg
26581 gttgaaaagt caaagggaag tgaatgcact tttttcccca agaaatctta tctgagacaa
26641 gaagaagaga agcaagacaa tggtttaaca gagactcatg gtcaggagaa atgtgtgtgt
26701 atgtgtgtat gtgtgtgtgt gtgtttctca acaaacgaga gagccttgat tgccttgta
26761 ggtctaagag aaagagctac aaaaggaaaa aatacataaa atatgagagg aatcaggtcc
26821 agtgcagtgg cctgtaatcc cagcactttg ggaggtcaag gcgggcagat catctgagat
26881 caggagtttg tgaccctgt ccaacatggt gaaaccgtc tctactaaaa atacaaaaat
26941 tagccaggca tggtggcagg cgctgcaat cccagctact tggaaggctg agacaggaga
27001 attgcttgat cctgggagat agaggttgca gtgagctgaa attgtgccac tgcactccag
27061 cctaggcaac agagtgagac tctgtctcaa aataaaataa aatatacaag gaatcattac
27121 tcctactcag tgttccaagg tgctggagga aagagggaaa aatagtatca tgaacacagg
27181 tacaaaatgt ccaacaactg gaaattaaat gaatcatatt gtagaagaac atttattgcc
27241 ataaaattat taccatatac catatgttat attaacatat atagccttat atatgtgaca
27301 ttcatatggt attatattgc tatataaatt tttaaaatta aatataaat tgtgatgtat
27361 tattttttaag ttaaaaaaag ttggtcacaa aacaagagag taatctctta gctcttcttc
27421 cctccttttc cttcctgcct cctcaatctt ttcctacctt tttacctcct ccagagtctt
27481 ggctctacct aaagagagtt gtgggaagtt ctttcttagt gttgtgaggt aggttagctt
27541 tgtcaagtaa aaccaagctt tctgtttatc ttgctagacg gtgatatttc atctaaacga
27601 ttggtaccag atatgttttg gaatcttcct atttaaagat aataatacat attacttgat
27661 attaccagca gagtctggga aaataccag aatcaaacat attaatatat ctattggaaa
27721 acatgggatt attcacctta aatagcttga ataaaaatgt tatagcctta tgttaattca
27781 agttaggtct taatgccaat gtgccagtgg gttacaaaaa tccttttattt tcagaagatt
27841 ttggattttt gtattgaaga taaggaattt tggtataata ttatatttat aatttttcat
27901 agtctaactg tgatgatata ttatgcttga aaaatctcga ttatcaccaa aagctacctc
27961 caaaccaagg gaagagacac aaagagaggt aaaagtgaaa tasaccccta tcttgccaca
28021 cagatttttcc aagcatttta tagcaaatat gcataatttt gtttatatca gtatgtcatt
28081 gcaaacatca ctcagagttt tgctttata gttttctttt gtttttccta aagttattaa
28141 ttgccttatt ttttaaatt tcgttaatct tctttgactt tttgttaaaa cccatatct
28201 tccaacagca tctcagaata attttccac aatatatttt tcataatttt atctggagct
28261 aaaaataata acctttctct gcactggttt ccctctagtc attctgcaca gttgtcatat
28321 tgagatttcc tttactgtca tcctaggaat gctctcttag ctatttcctt gttttaggtt
28381 ctctgttttt ctccttctac ctttatttgc tcctttgttc tgttgtagtc aacgctgtct
28441 agtcacattg ctctaatctg aactggctgc tctccatgcc ttgtatacga taggagtcat
28501 cctggaatct ccctttatcc tcatggctgaa gatttttctt taccacttcc ctgtgtggat
```

FIG. 7M

```
28561 ttcctgtttt ctgttcccg tcttccttgt tttgggcttg tgccctcttt cttgttgtta
28621 acagtttccg gaaagagagt gatcgggatg caagatttt gagactcact ggtctgaaac
28681 tgcctttcct cttaaattta gttaagtatt tccctgggca tggaattcaa aggtggttat
28741 gactttcttt caggattgtg aatgtattta tatcctccca tcttacgttg ctattgagaa
28801 ttctgaagtt cttctgattc ctgattcttt gtatgtgtat tcctcattcc acaccttccc
28861 cagaatgcat gcagaattc ttcctttcta ttttcttttc tcttttctg aaactcttat
28921 tattgggatc ttctgcctct tggattaggg ctctaatttt ccgacatttt ctctgctatt
28981 ttttactact ttattttct cctctactt ctgagagat tcctcctctt gatcttccaa
29041 atcttgtact gaatcttta tttttgttaa catgttctta atttccaaga actcttttt
29101 cttgtcttcg gagtttcaac acttattgtt gttttgtgca tgtattattt ttcttctct
29161 ctctgaggct atttaggaaa ttttttattg aagctcctcc ccctgcttc cttcaagttg
29221 cttttatctg cttttttatt tgcttttca tgcaataagt ttttctcaca tgtctggtaa
29281 ctcttgggga ttaccaaaaa ctcatagaaa attctgacca tgtgagtaac acttgccaat
29341 tttgagcttc atgatagaat gatctagctg gacctttgc tgcgggaaa tcggaggtaa
29401 gtgtctttgg agacttcctc ttgggatggt caggtctccc aggtttcaag attcttctaa
29461 tttccttctt gaatcagttg cctaatttag gaaataaaaa tacaggatct ccaggtaaat
29521 ttgaagttca gataaacttt gttttttttg agagagtctc tttctgttgc caaggctgga
29581 gtgcagtggc atgattccg ctcactgcaa ccctgcctc ccgggttcaa gcaattctcc
29641 tgcctcagcc tcccgagtag ctggattac aggttcatgc caccactcc agctaatttt
29701 ttatatttt ggtacagatg gggtttccc atgttggcca ggctggtctc gaactcctga
29761 cctcaagtga tccgcctgcc tcggcctccc aaagtgctgg gattacaggt gggagccact
29821 gctccgacgcc cagataaaca ttttttaa aaagtgtaag tatgtcccat tcaatattta
29881 agacatactt atactaaaaa attatttgtt gtgtatctga acttcacatt taactgggag
29941 tcttgtcctg tgttttacct ggcaaccta ttcctgaaag ataaatcctt gctgacagca
30001 ttagggatcc aagtgaggaa aatggccttg caaggtgtgg gtggggtgg agggggaacg
30061 ttttcaacat tcagtgttat ttattcaggt aatcccttc aactatgtct cttaaactt
30121 catctaaaga ccatccactt tacctctct ggaaacattc tccgttattt actggagtag
30181 gggaggatca gttatctggt tttttggagg acttagtatc caaggcatcc ttcacaactt
30241 tctgctcatt tattttcctt tgactgccac aactttactc ctagctctag gtatagagca
30301 gtccagtga ttaatttgag tgctttgcag tgtagatagg gattcttggc tctttctact
30361 gctagtttag gacctggttt tcttgggtct gctgaatcaa ttactacttt ttgtatcaac
30421 atcctagttt ttaaaactgt gttgtggtct ttcctcctat tttcctacct ttgtgggtta
30481 aaaaaatag tgttcttttg aaggattgta ggaaataaaa ttgaagcata tgttcattct
30541 acctttacct gaaagttact tctatcccat cttaatacac ttgcactgaa gtgattactt
30601 tccacctgca aagtggaaac aataagacca gttagcggct gctgctttag tcaagcaaga
30661 gatgaaggtg acttggaata tgctgtacag atggcattaa atgaatatgg atctcctttt
30721 ggaaacttt catctgcatg gtgagatgac tcacatactt agatttata ttcaaatagc
30781 tacgtactat agtggaagaa aaacttaatg gagaagtgtt tcagttcttg cgcagtatag
30841 aggatatgac ttttccagat tacaggggtt gcctctaggt caactctagg gctcattaca
30901 actctgaagc tcttttattg tgtgaaacag gcaataagat atgatttaca caggtgccta
30961 aattaaacct ttaaacacat tttaaattct tgataattaa aatcattagt aacttgagaa
31021 caatgaagat atagctgttc atggctatag gccaaggatc tgattgcttt tacaggcta
31081 atcttttga cagtgaattg caggaggcac tggggcttaa agccctttat ttttattatt
31141 agttgtatta attattcagt gataaactgg atgactctaa tgaagaagta acattatttt
31201 accaaataaa gtggcatagg cattttctta gatcaagaga gtatttcagt tgactttctc
31261 atgtttttt tttaagagca tctagcagtt tatttaatta ttttattcta tttttatct
31321 ttaaaattta tcctagcttt attgtcatta acaaatgaaa attgtatatc tttacagtgt
31381 atgatgtgac gttttgatat gtgtacacac cgtgaaatga ttaaatcaag caaattcaca
31441 tatcccacat gactttctta tgacttactg gttttcatga cttcctaga tttgtaccct
31501 gttgaaatgt aaaacgacta atttaaacac ttgcggtgac tcagctgaaa cagcttctac
31561 caggtttgaa atgttctccc tcagtggcac tttcggaacc cagtatgtct ttcctgaggt
31621 gttgctgagt gaaaatcagc tgcacctgg agaatttcag gtaagaatct tcgaatattg
31681 ccaattagtt tcatgtaaga ggaagcactt tttgatataa aaatctgtc aagtgcttac
31741 aaatatcata aaatttccat ttagaaaggt taagattatc cttgggatc atgaaggaca
31801 ttgagcaggc tgcatttctt gtctggaaat tcttaacata ataattactg tgtccttcag
31861 aataaaaaaa tatatatctt attttgggga ttataggag tttaaagtct tccaagtaga
31921 aagaagattc aacgagagta gtttcagaac cagtgccatt ggagcccctt aggaccactg
31981 gggagtgatg gcctagggaa gttgaaagga gtccctctcg tcgagtgagt caaggctctg
32041 tgtgatggta gaaggaaaag agacaaggaa aagctgaaga agagagaatt tgacagtggc
32101 ggatgttagc aaaaaagcaa aaacttttta aagttcagaa ataatccctt gcttcacatg
32161 tgctctgccc agccacattc tttcgctgac ttcctgcaag ttctcctccc actcccgtt
32221 cctggtagaa accactgctg gggtgtggga ggacaatgga atggtgagga ggttgtggtg
32281 agcaagagac aggagatgac agatgctcag ttcaaatccc tgttagtcaa ttgcttcggg
```

FIG. 7N

```
32341  ccattgtggg gagtctttat cttgtctgag aggactaggt ttctcttctg tatactgcca
32401  aatccactgg tttgtgttta ttaactctta cggcgcttcc acaggtaagt aaattagaag
32461  acattgatta cgggcatctc actaataaat gaatcagtgc cagtttcata gctccaattt
32521  ttcttgtact tggcaacatt tcaaattttt ctgatagaat ggaatttggc cagtattttt
32581  gtttcttcat tctgttatag taaatttttaa aagtgattta tgggattgta aaacttgaag
32641  gtagcctttg cctactttt tgttttaatc aggtgtcaac tgacgacgc ttgtttagtc
32701  tgaagccaac atccggacct gtcttaacag taactctgtt tgggaggttg tatgagaagg
32761  actgggcatc aaatgcttca tcaggcctca cagcacaagc aagaataata atgctaatag
32821  ttatagcacc tattgtatgc tcattaagtt ggtagaatat tgacttttc tctttttat
32881  ttgggataat ttaaaaaatg atggatgaga aagaaagat tggtccgggt taatattatc
32941  ctctagtata agtgaattac tagtttctct ttatttagac aaacacacac acaccagata
33001  atataaactt aataaattat ctgttaatgt agatttatt taaaaaacta tatttgaaca
33061  ttggtctttc ttggacgtga gctaattata tcaaataagt atcacaaatc ttttacgcag
33121  aagaaataaa aactacgggt agaaaacata agaactatca taaaatttac ttacaaggag
33181  gctgctcttg ttaccacttt tattatatta cgtatcactt attcagctct gctgaaaatt
33241  tccaatgact ttgtttgttt gctcttttg ttttttacct aaacaataca ttttgattct
33301  cttgtgggtt gataatgtct ccccaaaatt tacatgttga agcacctcag aatgtgactg
33361  tatttggaga cagggtcttt aaagaggtaa aataaggtca ttaggataga ccctaattca
33421  atatgactga tgatcataaa agaagaggcg agtagggcac aacaggcaca aagggagacc
33481  ataaggagac acagaggaag gacaactctt tacaagctaa gaagagaggg cctcagaaga
33541  aaccaaccct gccaacacct tgatcttgga cttccagcct ccaaaactat gagaaataaa
33601  tttctattgt ttaagtcacc cagtccatgg tactttgtta ggcagccctg gcaaatgaat
33661  caaagaccca ttcctgttcc tctcccacc actactgttt tctactgtaa tctgaagctt
33721  caacaaaagg cttacctggt aagaatattc agctggtctg ggtcctcaag actccaatag
33781  acactcttag agaaggattg ctgatggatt gatagtgaaa ccattagatc attgaattcc
33841  tctggaatta gaaaaccaga gagtcccatt ttaagaaatt agatatttaa tatagcattg
33901  tgtgttctat tttagtaaca gcagaatctc ttgacattac acaactcagt gaaacaacat
33961  catttaagcc aaaatatctc ccaactgact gatagactct gagcactaat atcatagtgc
34021  tgtgatgatg gacaattaca tagtaccgat aacagccatg cactgtgcaa agcatgccct
34081  tctgcacagg agagcaaggc acttgcagta gtgatctatg ccagcaaaac atcatttgaa
34141  gacaaacatt tttgtggcag atgtttttcc taaaaagtac tatatcatcc aagaaatatt
34201  tgagtaaaat cccttgttct tttgggtgac attaactgac atttgctttt tttcaagacc
34261  taatagaaaa taagaaagcc cataatgtat ttagaaacag gaatcctcag agcaattctc
34321  tgtattctca tataatttca atgtaaaaca gaaaacatat tgatgtgtta gtgataggct
34381  tgaattatta aaaacttcaa aaacatccta agtgtttctt ttttgctcaa cgttgtcaac
34441  tatagtaggt ctccttgtg gtgtaatgaa ttgcccccaa actattatct taaaacaaca
34501  aacatttatt atcttatagc atttctgagg gtcaggatct gggactggct tagtggagtt
34561  gttctggatc agggcctttg gaaagttgta gttaacttgt ccccaggct gccatcatct
34621  caaggctcgg gtggggctgg agaaaatctg cttctcagct cactcacggc ggttgccagg
34681  cctccattct ttaggatgct agaaaaactt tcataaaatg tcatctggct tctcctagag
34741  caatgatact gagagagaaa gcacatgaga gaaagagcga gggaacttgg atgtaagcca
34801  cagtctttga aaacctaatc acagaagtga catctcttct tccacatgat gttggtcaca
34861  tggaccaaca atggcacaac gtggacagaa tcaaacagag ttgagaatat caggaggtgg
34921  ggcttcatgg gggccatttt ggatgctatc atagtgaata tatgtattta tatttatatc
34981  tgtatatatt gcaatgtaat ttaaaaaata ggattgtttt cctttctttt ttgctatatg
35041  tgatatgtat ttcaaaatac actcccaata gttacgtctg aaaagcacta cactaaaaaa
35101  ctttctatac attgaataat taaattaaat aatctaataa tctctacttt tggtccatag
35161  taaatttaag ttaactgttt gccttaacta cagttgtgg caaaaccatc tccttttaat
35221  atacacaagg gacttttttt ttttttttg agacggagtt ttgctcttgt tgcccaggct
35281  ggaatgcgat ggtgtgatct cagctcactg caacctctgt ctcctgggtt taagcgattc
35341  tcctgccaga gcctcctgtg tagctggat tacaggctgg gattacaggc atgcgccacc
35401  atgcctgcct aatttgtat ttttagtaga gatggggttc ctccatgttg gtcaggttgg
35461  tctcgaaacc cgagctcagg tgatccaccc gtctaggcct cccaaagtgc tgggattaca
35521  ggcgtgagcc accatgcccg gccgtggga cttttgcatt catttttcag aagcttactt
35581  tgtaggggaa catacattaa aggtaacaa aataaacagc ataagttcca gaattattaa
35641  ttcatgaagt gcaaccacta ggaaaagggg tcttaaaaac atcaccctct ttactggatt
35701  cttgaagaa accaagattt tttcctaat aatctgtttt atacacaata tataccaaaa
35761  atatataaat ataagtat ataacaaaag tgaaagaaac tgactcttaa tcacaatgtt
35821  ctgaatagca agaggaatac taaaaaagtc aactagaaag tcatgtcaac gtcaaaatct
35881  gttctgaaac acatcacttt gattttatac tgaaagccga tacctcgaat ttcctctgct
35941  tgctgtcct gtggttgtac tgggcatgtt ccaaatgtat cacttttatt tttatttcaa
36001  taatttcaag tgttatttta gattcaggag gcccatgtgc aggtttgtta catgggtata
```

FIG. 7O

```
36061 ttcagtaatg ctgaggtttg gggtacaaat gatcctgtca cccaggtgat aagcataata
36121 cccaaaaggt agttttcagc ccttccccc tccctgtttc ccagctgtag tagccgctag
36181 tgtctgttgt taccatcttt atatctatgt gtaccaaatg tttagcttcc atttaaaagt
36241 gagaatatgc agtatttggt ttctgttcc tgccttaact tgcttaggat aatggcctcc
36301 agctgcatcc atgttgctgc aaaagacatg attttgttct ttttatggc tctgtggtat
36361 tctatggtg
```

Homo sapiens vanin 2 (VNN2) gene, complete cds (SEQ ID NO:18)
gi|82399141|gb|DQ249347.1|[82399141]
Coding Sequence = join (2009..2221, 2346..2476, 3857..4049, 7144..7432, 8375..8748, 10028..10198, 15403..15594)

```
    1 atactaacag tctattatac aatctgctaa aaattcataa aaatatctat ccctttacat
   61 tttccacaaa agggcttgac cattttcct gaattatttt tagttttctg ctctatagag
  121 ataagaaaag ttattccttt aatagaaact tctattcaaa gcagaaaata tgagcagatc
  181 ttatttatag cccctaggcc ccattcttaa caaaacattt atctcagtaa gaaggaaagc
  241 acagaataaa ctttgtttaa tcgtacctac tcttctatgc tgtctaaaag catttccgtg
  301 acttttacca aagggctgga taaaaataaa acaaatcctt tatttggcag gattgggcct
  361 ggggaaggga gaatatgaat gtcctaagaa ggcatctgag atcacatcct gtatttgttg
  421 ttattattgt tttttttttt tttttttctt ttgagacgga gtttcgctct gtcgcccagc
  481 ctggagcgca atggtgtgat ctcagctcac tgcagcctct gcctcctggg ttccagcgat
  541 tctcctgcct cagcctcccg agtagctggg attacaggcg cccaccacca cgaccagcta
  601 cttttgtgt ttttggtaga gatgggggt tccactatgt tggccaggc ggtcttgaac
  661 tcctgacctc aagtgatctg cctgcctcgg cctcccaaag tgctaggatt acaggcatga
  721 gccactgcac ctggcctgtt agcattgttt taaactcat tgttgttatt tgctgctaac
  781 aaaaatgtaa gttacatctt ctccttacta caacacagat gatctttatc accaatcctg
  841 gactcttccc cttccctggc atcttcctcc aaagcagggg gtggggaggg aggaaaaaga
  901 aggaggagaa ggagtaggag gagaaggaga agtaggggga ggatggggag ggaagggtga
  961 aagagagaaa gaaggaaaga agcggagtat cctgagcgct gggccccct gagctgagat
 1021 tcctcctctg gcctaggtgc ctcggggtat tgttgctgta ggcactaact atacagagt
 1081 gaacaaacca gacacaaat cctgctttc tggagcacat gttttcagtc cttaatagca
 1141 ataagtaagt cagagtgtag atttgggtaa attttgttat caatattgtc ctgtgttaca
 1201 ttttcttagt agtaagtatt taatatttc ccccccgtct aaaaataaac acaatgtaag
 1261 tgactcaaca gaaccaaaaa aattgttgtc aattttaaa tttaataaat gagatatttg
 1321 ttgggatgtg atttttttac acgagagtta gttatgagtt tctattaaca aaagctggaa
 1381 ttgttctata tttgaattcg ggtgtcttt ggaaataaa tattaaatct tagtactaat
 1441 agtacatgct gttcaatccc tgtaatactt tctgattgtc ttaaatggac tgcaacttt
 1501 cttctcttaa aagtggtcag atatattgcg ttcttaagat tataaagtag gccaagtgca
 1561 gtggctcacg cctgtaatcc cagcactttg agaggctgag gtggatggat cacaagatca
 1621 ggagtttgag accagcctgg ccaatatgt gaaacccat ctctactaaa aatacaaaaa
 1681 ttagctggac gtggtggcgc gcacctgtag tcctagctgt ttcagaggct gaagaaggac
 1741 aatcgcttga acctgggagg tggaagttgt agtgagctga gcttgcgcca ctgcattcca
 1801 gcctgggtga cagagcaaac tccgcctcaa aaaaaaaaa aaaaaaaaaa aagagaaga
 1861 agaagaagaa gaagaagaag aagaagaaga aaaaagatga taaagtaaaa ggccagtaac
 1921 tggcagccac atgttatgca aacattctcc cctctgtaaa tactacatga atgttatttt
 1981 tgctttcaga aatcactaaa ccttggccat ggtcacttcc tcttttccaa tctctgtggc
 2041 agttttgcc ctaataaccc tgcaggtgg tactcaggac agttttatag ctgcagtgta
 2101 tgaacatgct gtcatttgc caaataaaac agaaacacca gtttctcagg aggatgcctt
 2161 gaatctcatg aacgagaata tagacattct ggagacgagg atcaagagc cagctgagca
 2221 ggtatctct tatttctgtt aatcataatg tacacgaggg gcatgggagc tggtggaaga
 2281 cgagagagct gaattgtctg tgttgtacat ggaaaaatca tttttattt gcttgttttg
 2341 aacagggtgc tcgaatcatt gtgactccag aagatgcact ttatggatgg aaatttacca
 2401 gggaaactgt tttcccttat ctggaggata tccagaccc tcaggtgaac tggattccgt
 2461 gtcaagaccc ccacaggtat tttaactatc ttagtctttt gtgcaaaagt aactctctaa
 2521 aatgcgcacg ttcaccaaag caaatgatt gctcttgaat taccatatat gtggtatatg
 2581 ttatggttat atttatctca acatttgtca gatttaaaa aattgtactt agatactatt
 2641 taacaatctt ttgtgattga aaatctttat taaattttga gaaaatgtgt aaatagggta
 2701 ttcctgcaag aaaactaag ggaagagatc tcatagatac aagtagtaac ttaatttctg
 2761 aagtagacag tggattgtgt taggaataca ttccaaagcc tctgctgaag ggacacccctt
 2821 tcaatgttat agagtctctc cattccagag ttgcttctta ggcagaaaga cttcaccatg
 2881 tattttcaag tgaatcataa gaccttatgc tttgaaactg cattttccta ggctcacaaa
 2941 tctaattttc ctgggaaaag gttatctaga aaccttctaa tatatattaa aaatctgggt
```

FIG. 7P

```
3001 cctactgtca tcctggaggt gtcaacgtgg cagttgcatg gacaagtctg gcatgaaaag
3061 acaaaattat atctggagat agaaaatcaa atgtcagcat atagatggtg ttaaacacca
3121 tgatgagttc acctgtggag tgagttagag aagagtttag gtataaggct tgagcactag
3181 gaaattctag tgtttagact cggaagaaaa cgaggaatca gcagaagagt cgaagaagag
3241 caaccaataa ataggaaaat gagagggtgg gtccagaaga gaagtgaggt gtttccagaa
3301 ggaggtgtaa ttaactgtgc caactgctgt tgaaaagtta agatgagatc aggtaaaatg
3361 tggggtcac tgctggcatt agtaagagtt tgggtgatag agatacaagt tggagtgctc
3421 tgaaagggaa tgggagagga ggaactggca acagcaagag ggactgatct tttgaggagt
3481 tttgctttaa gagagagatg aggattaaag caatatttgg aagggcatgt ttggaaaggt
3541 caaagaggt tttaatttta ttttttaaag atgggaggta ctagaggata tttcattgct
3601 gatgggatgt ttcagtagag aggagaccct tgatgaggca ggagaccgaa taatgaattt
3661 ctggagcaat agataccgtg tgggaagcat tcatcaagtg tataatcatc tgtggctttt
3721 aaagtatgat atttttaggc atagttttttg tattaactta agttccactt aagtggttac
3781 agttgctatc gtttccatat aaagtgacta aaatatttt ttaaaattga aatttcttaa
3841 ttataatttg gtttagattt ggtcacacac cagtacaagc aagactcagc tgcctggcca
3901 aggacaactc tatctatgtc ttggcaaatt tggggacaa aaagccatgt aattcccgtg
3961 actccacatg tcctcctaat ggctactttc aatacaatac caatgtggtg tataatacag
4021 aaggaaaact cgtggcacgt taccataagg taagagagag tgacggacgt gtaaaatgga
4081 gcgtgttgtg agtggtcaat gctgggtttg ggagtttgaa tttcattccc tatatgatac
4141 aatattacta gagggttttt ttgttttgtt ttgttttttg tttttttgaaa gtgggcaata
4201 aagaaaatga cactttggc tgggcgtgga ggcttatgcc tgtaagccca gcactttggg
4261 aggctgaggc aggtggatca cttgaggcca ggaatttgag accagtctgg ccaacattgt
4321 gaaacccgt ctctactaaa aaatacaaaa attagcgggg cgtgatggca catgcctgta
4381 gtcccagcta tgtgggagct gaagcaggag acttgcttga cccaggagg tggaggctgc
4441 agtgagccga gattgtgtca ctgcactcca gcctgggtga cagagggaga ctctcaaaaa
4501 aaaaaaaga aaaaaagaa aagaaaaaa gaaaatgaca cgttgtaaaa aactactcag
4561 aaaacatgt aggcagagaa ctgttaaaaa aaaaaaaag tagcatgatg gtccaggatt
4621 gagataaact ttttgcacat ataaacaaa taatttaac ataaaaaag atactaaggt
4681 gactataatc tgggcactgt ttcaataatt ttatatttt ttagagacag ggtctcactg
4741 ttgcccaggc tggagtgcag tggagccatc atggctcact gttaacctca aactcctggg
4801 ctctagtgat cctcctgcct cagcctccca agtagctgag actgtaggca tgtgccacca
4861 tgctaattt taaatatttt tttgaaaca gagtctcact acattgccca ggctgtcttt
4921 gaactcttca cctcaagcag tcctcccacc ttggcctccc aaaatgctga gattagaggc
4981 atgagccact gagcacagcg ataatctaaa tactatttaa tattgaaatg gtagaaagat
5041 gtttcaaaat tgtatgaatc agctttgcat aagttaattt gctatcaaac cacaaaatac
5101 cttattctct acaccagcta atttaattac catcttatag atttaagatc aaaccataaa
5161 atgtttactt taaattctga attgaaaaaa ggaatcaaat aaccctttaag tcataatttt
5221 atactaaact aggtagagaa agaagcctgg ccttttaaat ggatatgtgt gatgtacagg
5281 cagtatgaat gtccttctc cacacccaga tatttgtaa gcatcttaaa ctgtagcctc
5341 agaatctttg gagtggagaa attatctcct ggcagtctca gttaaaatat aaatattaat
5401 taagaggagg gatgttaaac caatggtttt caaatgattt cgatcatgga cccctattgg
5461 aaaaaatcgt taacataagt cctcaatata tgtatttttg tgtgtatt tataaagtgc
5521 aacaatttca aaatgctttc ttcataattt tgtggatttt gacagcttct tttcatatat
5581 atcactgcac ttcacttct tcttaaaatg tgtctcatag taaaaataga aaggtcagtg
5641 cttccatttt cttgcttggg agattgtttg cattatttgt attatctttc aatgcagttt
5701 atttgcagta atcatttgaa gctattctgc cattctgtaa atatgcagga tggcacagtg
5761 cactgaatgt ggacaaacta gcaggaaacc tgcagtcacc ctgtctaagt tgaaaggctc
5821 tcactcttcc ctgagggtac ctcaaggacc gtttgtaacc catgacctct gacatatgtg
5881 aacctaatga gaataccttt gtcgatcaat tccttttttt ttttttttt ttttttttt
5941 aggcagagtc tggctctgtc atcccggctg gagtgcaatg gcacgatctc agctcactgc
6001 aacctctgac tcccaggttc aacccattct cctgcctcag cctcctgagt agctgggatt
6061 acaggtgcat accaccacac ccggctaatt tttggatttt ttagtagaga tggggtttct
6121 ccatgttggc caggctggtc ttgagctcct ggctcaagt tatctgcctg ccttggcctc
6181 ccaaagtgct tggattacag gcatgagcca ccttgcctgg cctgtcaatt cttaaaatag
6241 tagtaaagcc caatttcttt tctatttttt agatattttt tctacactgc agaccatttt
6301 attaactgtt gattccattt attatattag actaagtttt ttttagttt acctagaagg
6361 aatcggggaa ttaaatacat ttctatggta attttgaaag gtgggcaaga gtcactgaga
6421 ttactttgga tgggacacta aagagagaga tgacatctct cacctgactt acaggtattt
6481 attatgcatc tattaatatt acgtttctag gcaccaagga ttcaagaag aataatgcat
6541 gttttttaac ttttaagaag cttataggg caggtgctgt ggttcattcc tgtaatccca
6601 gcactttggg aggccaggt gggtggatca tgaggtcagg agattgagat catcctggct
6661 gacacggtga aaccccgact ctactaaaaa tacgaaaaaa ttagccgggc atagtggcac
```

FIG. 7Q

```
6721 gtgcctgtaa tcccagctac tcgcttgaac tcaggaggtg gagattgcag tgagccgaaa
6781 tcatgccact gcactccagc ctgggtgata gagcgaggct ccgtctcaga aaaataaaat
6841 taaattaaat ttaaaaaaag cttacggact ttggggttta tgggggggggt atttggctct
6901 taactgagag agagggaaag agagagaagg gagagagagg agatgagaga tgctatggac
6961 gtatgttaca tattcctcca cattttcctt agaaatttac ttccaattgc cagatttatc
7021 cgcttcctag gagattccct gcagttgacc atagccaaat ctgttaccaa cttagagggt
7081 ttttatgagt catttcttca acaaataagg ttttactggt tttctcctat ccatttgttg
7141 tagtaccacc tgtactctga gcctcagttt aatgtccctg aaaagccgga gttggtgact
7201 ttcaacaccg catttggaag gtttggcatt ttcacgtgct ttgatatatt cttctatgat
7261 cctggtgtta ccctggtgaa agatttccat gtggacacca tactgtttcc cacagcttgg
7321 atgaacgttt tgccccttttt gacagctatt gaattccatt cagcttgggc aatgggaatg
7381 ggagttaatc ttcttgtggc caacacacat catgtcagcc taaatatgac aggtaattca
7441 tgaccaggtt aggtttcatc ttatatttttt aagtgcagag aaatgaatgc ctcagttatg
7501 acttgtatta atttttttgct tattggaaat tcttactgtg tttgtcatag tttcacaata
7561 gaaaaaaaaa gctagcactt gattataagc tatggttata ctaagacctt tatgtgtatt
7621 attcatttaa ttattacaat aattatatga gatagatagt gtcatcccaa ttttgcagat
7681 gagaaaattg acatacagag agtgcaagta atttgccaaa tgctacccag ctactacttt
7741 cctcagtggc catggaagcc tctatatctt gcccttttgtc tcctcctatg gctgcatggc
7801 atatcctcgt gacatggctg ctgtcttcct ctagagcaat taatgagagg ggacaagaga
7861 gaaaaggaaa gaagccacat tgctatttat gactagttac ccaccatcac ttctgccatg
7921 ttctattcat tggaagtgag tcactaagtc cagcccctct tcaagggaaa aggaattaga
7981 tcctcccacc agaaagaaga attttttaagga attttttggat atatttgaaa accaccacaa
8041 tgaggaatag gggagaattt ttattccctt tcccacctt tcaggaactc ctgactacaa
8101 agatttttgt agttggttta attttccata atgctaataa ataatgctat tatatttaag
8161 gtttaattga aatgagacca aggaatgttt attttaatct cttccattag agaatagaag
8221 tagttaggtg ttcagtgcaa ttagaagcat gtatcctctc tcatcgtgac taatatggtg
8281 gcgtgatcac atgcccaatt ctgatgggga aattggcagt tttggttttt ttgtgtgtgg
8341 tgttgttttt agaagactg tctttcattc acaggaagtg gtatttatgc accaaatggt
8401 cccaaagtgt atcattatga catgaagaca gagttgggaa aacttctcct ttcagaggtg
8461 gattcacatc ccctatcctc gcttgcctac ccaacagctg ttaattggaa tgcctacgcc
8521 accaccatca aaccatttcc agtacagaaa aacactttca ggggatttat ttccagggat
8581 gggttcaact tcacagaact ttttgaaaat gcaggaaacc ttacagtctg tcaaaaggag
8641 ctttgctgtc atttaagcta cagaatgtta caaaagaag agaatgaagt atacgttcta
8701 ggagctttta caggattaca tggccgaagg agaagagagt actggcaggt aatttcagtt
8761 caaatgaaag ggcattcaag tgaaaggtaa attccaggtt aactttttat atttgttcca
8821 gaaaaccagg tgcttttcct tggcttgact ccatgcattg atgccaacac acacacacac
8881 aacacacaca cacacacgtg catttatgca cgtacataca ctgggataaa atatttacaa
8941 tgggaattaa gtataatctt attgcttgct ttaagcatat ttaaaaaatt attaacctaa
9001 ccatgatgag tttcgattg actaataaac cagcctactg tggagaacat caagaagact
9061 tccttaagtg ggtttgccaa catatctaaa ttataaacag tcttattttc acttgcaaaa
9121 ctaacagtaa atagagatac tactttttatt ttagtttctc ttctaatcag atgtcccggg
9181 ttttgtatag ctttcttttt cttttctttt cttttctttt ttttttttt tgagacaatt
9241 tcactctgtc accctggcta gagtgcagta gcatgatctc ggctcactac aacctctgcc
9301 tcccaggttc aagcgattct catgcctcag cctcctgagt agctgggact acaggcatgt
9361 gccaccacac ctgaaaaat atatatatat atatacacat atacaaaata tttttagtag
9421 agacagggt tcaccgtgtt ggccaggctg gtctccaact cctcacctct gctgatccga
9481 ctgcctgcca ctcccaaatt gctgggataa catgtgtgaa ccaccacacc tggccttgta
9541 ttgctttcaa atgacaaatt taaagatga aacttttat agaatgttgg ctctgaattt
9601 gtattttcct attatactcc atgtcccact gccttcttct aaagaaaagg attgggaaga
9661 gaggtgagat taaaggtgg aaaaaatttt aatatccttt cagcttcagt actcttcagt
9721 actattgttg cccaaagatc tccacttcat tgagctcgat gccatcatct gacataccaa
9781 actaatggtt taactctaat tctaaactga cttctttctc ttaatccgct tgttatttag
9841 gaagtgggtt gattctcaag tcactggcca ttttttaataa agcagttaat tataagacac
9901 atgatccaaa tcccttttca gagaaagata atgtttgctt cgctgtagtt aaaaactaag
9961 gcaacatttc tggtatgagt aacttcaatg taaggcattg cgttttatct gcgtttgttc
10021 cacataggtc tgcacaatgc tgaagtgcaa aactactaat ttgacaactt gtggacggcc
10081 agtagaaact gcttctacaa gatttgaaat gttctccctc agtggcacat ttggaacaga
10141 gtatgttttt cctgaagtgc tacttaccga aattcatctg tcacctgaaa aatttgaggt
10201 aagagggactt ttataagt attttcattt tatatgttct ctgaagtcaa gtaaaacaag
10261 ctatagccac tctgccagtt aacttctgct gtgtaacaaa tttcctcaaa accatttctt
10321 tagcccctggt tctgtgggtt ggcaatttga acttggggta ggtaggctgt ttttctggtc
10381 tgagataggc tcagttgacg ttggctgggc tcattgtgtc tgccattggc tagtgggttg
10441 attaggactg accagtttgt gattgccttg tcctggacag ctgggattat taaggccatc
```

FIG. 7R

```
10501 tctcccgtg gtctctcatc tttcagcaaa cctgagcttg ttcacatgtt agctgaatga
10561 gtccaggagc atcaagagaa aaacaaatct ttgcaagttc tttgcaaatc tctgcttgca
10621 ccgtgtttgc aaatgttgca tcaacacagg aagttacatg agcagtggtg attcaaatgg
10681 tagagaaatg aagaactcag acctctcaat gggaagagct ataaaatcac acggcaaaag
10741 gacatgggtc aaggagggga aaatattgtg atcattttt caatttataa caactaatta
10801 taaatgatg atacttcatt ggaagaacat aataaagaac atacctagaa ctgtgagtct
10861 gagataccat tcattgaaga atgtttgttt atagattttt aatttccttt tgtcactagt
10921 gaagacaaac agaaaatcag atgtttatt cacatttttt tttaaacaga gtcttgctct
10981 gtcacccagg ttagagtgca gtggcatgat catagctcac tgaagcctca aactcctggg
11041 ctcagcaat cctcctgcct cagcctcctg agtagctagg atttaaaggc atgtgccact
11101 gcacccagca tttgttcata aattacagtg gctgtagcta attaattcac aaattaagct
11161 ggcttcaaat tagaattatg actctgcagg cttatatctg ctaatataca acacttgcac
11221 acatgcacat acacgcatac atacacatat tccagtggtt tgaatattaa tgtcttctct
11281 gaattgtggc aaacagtgc agggtttcag taactagggt gaaatcattg catattctat
11341 aaaataggt ccaagttaat tcaatcaagg catcaagtaa ggaagtcttt aaaattgcag
11401 attgcttatg gtcatgtatc tgtatctgct gtgttatcag agtggaatat atcatactta
11461 taaaaatgct taattctatg aaaccaacaa tttaacatac agtgtaacct taaggccata
11521 aaatccaaag atcaggaatg ctttgctgcc atagaacctg tttaggcaga atctcatgag
11581 caaattgagg ctggaataaa agctgaagtg ccaactacag aaaatcatga ttaaatctac
11641 agcaaggagt ctggggctaa aatccagtag ctaaaaggtg gctggactga cataaatatc
11701 tatctgagat cacttcaagg aagtgagaga gagaaatcag ggtcaccaag gtaaacttag
11761 gaggacatag ggtctagcca tattgatgca ttatattctg taagcctgaa gatttaaact
11821 gagcacacaa tctaattttc tcgtactact ttgccacttt ttccatgtct tgtactcata
11881 gaaatctatc tctttgagga attgtcccat agtaggactg aacatttacc tgatgaaact
11941 acttcatcca tgggagaagg acaaaaaagt gctagagttt tccaaactag gttaaaggtc
12001 caaagccaga aataccattt cactcttact ctgaaccaca taagtgtttg aaggtggatg
12061 gtgatagtgc atgaagagtt ggagaacgta ataatttat tccattacta cttcctttct
12121 ttgttttaaa aatttcatcc caaatgtctt caggcagtta agaagagtta gagaatgata
12181 caagagaata catgtttaaa tgcttaactc catagtattt gtacatctca actcttaaac
12241 attttttaa attattttta attattatta ttatttgaga tggcgtctcg ctgtgttgcc
12301 cagactggag tgcagtggtg caatctcagc tcactgcaaa ctctgcctct ggggttcaag
12361 cgattctcct gcctcagcct cataagtagc tgggactaca ggtgcatgcc accacgccca
12421 gctactttt gtatttta tggagatggg gtttcaccat attggccagg ctggtctcga
12481 actcctaaca tctagtgatc tgccacctcg acctcccaaa gttctggaat tacaggcatg
12541 agccaccatg cctggccttg ttttaattt ttgtgggtac atagtaggtg tatatattta
12601 tgggttacag gagatattt gatacagaca tgcaatgtgt aataatcaca ttagggtaaa
12661 tatggtatca gtaggtctca acttttaatg attctgtgaa cttgtcatgc tgtatcccat
12721 ctctggttcc ttcttagatg gaaggaagga gggaaggggg catagcacct accgtttaaa
12781 ttgggcacct gtaatcatta tttggatctt gtcttacctg ctccagacca tttgcagaag
12841 aaggaaatga gatatagatt gtattacacc aaaaagata tgaaagagcc atgtgacagc
12901 tggcaggag ggtctttgga attgtagtcc cttggaggga gcatcatgat gagggtgagg
12961 caggtcttta ttttgtaagt gtagattctc tgtggcatga ctttcactga agttcatcag
13021 gttctaagga acagatacta atcaaatttg caagatagat aagcgagaac accaacttgt
13081 tatttaaaa aataggttcc cttagctggg aacaatgaac tgtatgtcaa ggagactctt
13141 cattggcaaa tcctctcaaa agtacaaatg atagatcagt ttgttttgtg agtgcagaat
13201 taaaacaaaa ggagttgggc attcttggaa aagatttcca agaacccacg gaagcctgag
13261 gcaatgtgat tcttctcttt agggctggtg atctgaagac catgtaggat caaggtgccc
13321 actttcctca aaaagagcca aaaaaaagt ccaataaccc attcttggtt tttttagtgc
13381 ttctttctc tagagacctt gcagggcatg gcccttctgt gaatatgttg tttctagaaa
13441 cagcagtcat aatattgaag atgacaaatg ttttacatca gtcatgctca ttatggcttc
13501 ttgagtagct tctcagttct gttgatggat gcacactctc tccatagata tttacacgtt
13561 atcttagagg atcactattg cagagatttc aaacacacttg ttgtgtatcc tcaaccccca
13621 ccaccacttt agtttatgt taaagggtg gtgttactca ccatgcccac aaatgtggaa
13681 acatcttgct ttagcacctt aggcaactct ggtgtattgt cagaagcact ggcagagtct
13741 gttctctgta actaactagt tagataacct tgggaaagtc acttaacctc tgaatttcct
13801 actcatagaa gagaatattt tcctcactga tttggtgagg atcaaatatg ataatgcatg
13861 tgaagaccat ttgtgaatgt tgaagtacaa tcattatctt ctaggatatt tagtcatttt
13921 ctcccccag ttgtaaagca tctgtttcc taattttcaa ttccttcc actccaacta
13981 atttcccaat tttcaatttc ttctccattc caactccatt tccacaacta atgggttcat
14041 tttcttttat tcttgttctg tttattgact gtctatgcat gtttccttct gttcttgttc
14101 aattgctttg tacatattcc tctcttatga aaactccact gtggcttcag gctagatcta
14161 gtcattaatg cctttcacag tctgatctcc accttcctct gatcatattc cttcttctct
14221 tcttcactaa tcttcagcgc tagccagtgg tgtgatgtaa ctttaaacaa ttccttctct
```

FIG. 7S

```
14281 gaggtagaaa acaaaaagcc ctgacttatg gaatttgcca gttttcattg tgtcaatatt
14341 ccgccatga tcccaccagc ttcaagaatg gatctgttgg cagagtttga tagctcacgc
14401 ctgtaatccc agcactttgg gaggctgagt tgggaggacc atttgaggcc aggagttcga
14461 gaacagcctg ggcaacatgt gaagccctg tctctactaa aaatacaaaa attagctggg
14521 cttggtggca cgcccctgta atcccagcta ctggggagct tgaggcagga gaatcacttg
14581 aacccagcag gcggaggttg cagtgagcca agatcatgcc actgcactcc agcctgggtg
14641 acagagcgag actccatctc aaaaaagggg gaaaaaaga atggctgtgt taacagcca
14701 gctgtccaat ttcctggaaa tttaacaatc tgttctcatg agcctgtgca ccactagctc
14761 cagcacacca ctggttttaa ccaatctaga atgagaactc acattgcctt gatctgtcac
14821 acacacttct gtctcagaat gagcctttgc tggttcaatg tccacttccc acaatgtctt
14881 ccaccataca gcccttgaaa gaaattccta acagcttgag ttttttggcag cttgtgtccc
14941 actccgtgaa acagaccagt tcagttttttt ttttctcaga cctcctagca cttacctgtt
15001 ctcttctctg atacactgat aaactgattt ctctctttat gtttagaatc cgctccattt
15061 caccattagc tctttagctt cttgagggaa ggatgtgatg taaactctc tggttcctga
15121 ttgtcttgca cataatcgaa ctcaatgaat tgctgctgct gatttgact ttccattaat
15181 ggttacattt gattgttgaa actaaaatct tgggccctct tgaattgctc tagtcttcat
15241 tatgtagtaa atggctgtcc cctgcctggc ctacttgctg catcctccta aatcagaaat
15301 gatttgacta tacattatat ctaggatggt ttcaaaatga ttaatttgct tttaacttct
15361 atgttaagaa agctgactgt acttttccca cctttttctt aggtgctgaa agatgggcgt
15421 ttggtaaaca agaatggatc atctgggcct atactaacag tgtcactctt tgggaggtgg
15481 tacacaaagg actcacttta cagctcatgt gggaccagca attcagcaat aacttacctg
15541 ctaatattca tattattaat gatcatagct ttgcaaaata ttgtaatgtt ataggcgtc
15601 tctttatcac tcagcttctg catcatatgc ttggctgaat gtgtttatcg gcttcccaag
15661 tttactaaga aactttgaag ggctatttca gtagtataga ccagtgagtc ctaaatattt
15721 tttctcatca ataattattt tttaagtatt angataatgt tgtccatttt tttggctact
15781 ctgaaatgtt gcagtgtgga acaatggaaa gagcctgggt gtttgggtca gataaatgaa
15841 gatcaaactc cagctccagc ctcatttgct tgagactttg tgtgtatggg ggacttgtat
15901 gtatggagt gaggagtttc agggccattg caaacatagc tgtgcccttg aagagaatag
15961 taatgatggg aatttagagg tttatgactg aattcccttt gacattaaag actatttgaa
16021 ttcacctagt tttctgtgct aatgtttatc aggagattta ctttccaatc aaaaggcaat
16081 gtcgacattt atttctacag tgaacgtagt ttgagtgct agaagaattg atggctattc
16141 caagttcata tcaaggaga cctgacccag ggcactcata gccccagctg tcccaccatta
16201 aggctatgc gtaatttaac aggcagaaat ctcataacac aaagaccatg acagttaaaa
16261 gttacactat tttcagcatt tggttgactt ttacaaaat acacatattc catgctactt
16321 gaagtaaact agtatatttg ttattgatca tttaattcag atactcttaa aattaaagaa
16381 ctgatttga atttttcagat ttattttctg atttttatct cccaaagtat ttttaagttc
16441 aatacttta cataaaaaa cacaattgaa gcatttatct tttgttttta catattgtca
16501 taaacctact tatggatttg attttaaaat tctactaaaa tacactagaa aagtaagatt
16561 ccttttataa tctcgtggtt agtattaaga gaagaaatat ggaagttaag ccacactttg
16621 tatttaattt tgagaagagc atacatattc cctatgttca gcattgggac atcaaagatg
16681 gcaattttaa agctcagttc aacgtgcatt tgtgtatata gtccaaatca tataatcatc
16741 aaagttttat gctctttttt ctttttcttt ttctttttt ttttttgaga cagagtctca
16801 ctctgtcacc caagctggag tgcaatggtg ggagttcagc tcattgcaac ctccgcctcc
16861 tgggttcaag tgcttctcct gcctcaacct cccaagtagc tggaattaca ggcacccacc
16921 accatgcccg gctaattttt gtattttag tagagatgga gtttcgccat gttggccagg
16981 ctggtctcga actcctgacc aggtgatcca cccactttgg cctcccgatg tgctgggatt
17041 acaggcatga gccaccatgc ctggcttctt tttccttttc ataagtatg ggacatttaa
17101 aatttgccaa gttttgcttg aggaagttag atgttgtgca gtggttttgc agcatgtatt
17161 ttggctcttg ggcaatgacg tttcatttgc agaagtttag atgttgattg aaaatcaaca
17221 gctgacgtta aacaaactgg tttgagtaag atacaagcaa ggagctcctt tcacagaaag
17281 ggacagttct gattcaagct tggagctctc agtgtacct cagtttgtta aaaataaaaa
17341 caaaaaacga aagcaccaag tgccaaggga attaaagagc acttaatgct ctactgtaaa
17401 attgctgca ccacatttta acccatctcc accgtggttt ctcacataca ttttattttta
17461 tcaaacaacc caagcatagt ttcatttggc ctttatattt ctttgataac tatctttcat
17521 cccatttat tttatttta cttatttatt tatttatttt ttgagataga gtctcgctct
17581 gttgcccagg ccggagtgca gtggtgcgat ctcggctcac ttcaagctcc gcctcccggg
17641 ttcacgccat tctcctgcct cagcctcctg agtagctggg actacaggcg cccgccacca
17701 cgcctggcta atttttttgta tttttagtag agacggggtt tcaccatgtt agccaggatg
17761 gtctcgaact cctgacctca tgatccgccc acctcggcct cccaaagtgc tggaattaca
17821 ggcgtgagcc accgcgcccg gcctcatccc attctaaaat ttcatgttag ttcttgagtc
17881 ccttgtggtt ctggagatag taaacaaagc tcttattttc tcctatttgg ctttcattag
17941 gcttttttcc tgaaatgctc ttttacaact tcctggttac agccccctgt attacaaagt
18001 cacatgctca gcagcagcct tct
```

FIG. 7T

Homo sapiens vanin 3 (VNN3) gene, complete cds (SEQ ID NO:19)
gi|77022115|gb|DQ220706.1|[77022115]
Coding Sequence = join (1814..2026,2123..2253,7573..7765,9494..9781)

```
   1 cgccttatac acctaggaag caaagacatt actaacaaca ttgggtaatc aaatatttaa
  61 ctcaagtttc tattgatttc aacacacaaa aaaagctggt acatttcctg aactagggg
 121 ctgggagaat gaagggaat tcccatatgt ttccttttga ttctattcag aaagtcaggt
 181 gaaccaagaa aagagttaga atttcaactt gaaatatgaa aattattttc ttctcatccc
 241 agatcaatcc atctgtttta catgtttcc ctcttctcct cagaaatttt tttggaaaag
 301 aacttatgtc tgatgtctga tgaaaacaat ttatgtcaga cataaactca gaatttaggg
 361 ctgaatttat gttcatatgt ccttatttcc tgaaatggta tcagggcata aggacatatg
 421 gaaacactgt ggggtatctg ggagcagaaa tatttggata tggaaaagt ttattgaaac
 481 caagggactt tgaattatag aaacaaacca aacccaaaat agacacaaat ctccataact
 541 tacaattttc cttagatctt agaaagaatc tcaagaggga gaagcagtgt taattgttct
 601 agaatcagag atttaaacct taaaaatat tctacatttt aaattaactg atattcaaac
 661 aaggagattc aatccaaaat tgggcgaggg aagtgaattt aactaatcaa aaaacattta
 721 cagagcttag cacagtataa aattctatag aagcagcaga gaattataat gtgaccctgc
 781 ccttaaggga cttataagga tgatatgttt aaaaaataaa agaattaaag gagaacttaa
 841 cacttttga attattgatt agtcttcata tcgaagcggg tttaaactgt agaagacagg
 901 taaagtaaat tgcatctcaa taacaagaat gttcttaaaa ttggcaatgt tcaaaggtgg
 961 aatagactgg cccatcaggt agtagattcc gtcattcaac attcattcat atattgagct
1021 ttcaccatct gtcacacatg tgctggggtg atgaggttca acagtgagca ggacacttcc
1081 cttaccctcc agggccaca tcccaggata catcatctct gtctagatgt ttattggaca
1141 tggatgttct gaaagaaaac agcaagtttc ttttaatct ctttaagaag acaaaaacata
1201 catatataat attaagtatt ggtataatat ttaaattaaa ggtcaagaca acagcaagga
1261 gtgagagaca ttcagcagca cagaaaaaaa tgctatagga gttcagaaat atcacttagg
1321 actggagtgg atttgggagg actctagggg gagctggaac ttagacggat ggagaacaag
1381 ggcttttcaa atagaaatgg ccatacaaat atgtaagtag agtgctcaac aaattgttgc
1441 tatgatgact accttccaat attggcccta ttaatagaaa tgttggctta ccaggaaaat
1501 ttttttttat tagaaaagac ttcaactgcc agtgtgtttt ggactggggt gaattcatct
1561 ggttggctca atcttttagt gttgacttga ctctgaacaa tgtcaacaac tgcactgtac
1621 acttgaatca atccaattac gtcctggctg tcagttttct tgcacaacat cctttctcaa
1681 tgctgtgttg tgtaatatat gtgcaagaaa atataaacag ctgattgcca ggagggattt
1741 aatgtaaagt ttttccagtg aaacaaaacg taagaatctg agtttgtttt tcaaagatca
1801 ctaaatttta gttatgatta tatcacattt tccaaaatgt gtggcagttt ttgccctcct
1861 tgctctgagt gttggtgcac tggacacttt tattgctgca gtatatgagc atgcggtgat
1921 attaccaaac agaacagaaa cacctgtttc aaaagaagaa gctttgctcc tgatgaacaa
1981 gaacatagat gttttggaga aagcagttaa gctggcagcg aagcaggtat taccattta
2041 tacttgtaaa ggagacttgc agtttggtca aagagtattt ggaattcatg acaaacttt
2101 ttgccccact tgtttcgagc agggtgcaca tatcattgtg acccagaag atggaatcta
2161 tggttggatc ttcaccaggg agagcattta ccctatcta aggatatac cagaccctgg
2221 agtgaactgg attccatgta gagaccctg gaggtaatat catatcatta atttctaaac
2281 aaaaagttgt gatttggtaa aacaccaaca gtaaactcac tgaattgac tggtaattgt
2341 gttgataaat agtcaatctg tggcatagga tgtagatgct ttttttccc tgtaatttca
2401 actttagtt tagattgagg gagtacatgt gcaggttgt tacatgggca aattgcatga
2461 cgctgaggat tgggttacaa tgattgcacc acccagcata gtatacaaca ggaaggtttt
2521 cagccttgc cttcctctct ctctctccc tctattagtt cccagtgtct attgctgtca
2581 tctttatggc catgagttcc caatgcttag ctcccactta taagtgagaa catgcagtat
2641 ttggtttgtc gttcctgtgt taacttgctg aggataatgt cctttggtgc tgcaaaagac
2701 atgattttgt tccttcttgt gggcacctag gttaattcca tatctttgct gttgtgaaaa
2761 gtgctgcgat gaacatacaa gtgcacgagt cttttggta gaatgatttc ctttcctttg
2821 ggtatatacc tagtaatggg attgtgagtc gaatggttgc tgtgttttaa gttctctgag
2881 aaatctccaa actgctttcc acaatggctg aactaattta catttccacc aatagtgtgt
2941 aagtgttccc ctttctccat agcatctttt attatttgac ttttttgttaa cagtcattct
3001 gactggtgtg agatgatatc tcattgtggt tttgcttggc atttctctga tgataagtga
3061 tgttgagtgt ttgttcacgt gttttttggc cacttgtatg tcctcttttg agaagtgtct
3121 gttcatgtc tttgcccact tttcaatggg gttattttt ttgttttgc ttattgattt
3181 aagttcctta tggattctag atagtagacc tttgttagat gcctagtttg caaatatttt
3241 ctcccattct gtaggttgtc tatttactct gttgatagtt gcttttgctg tacagagctc
3301 tttagttaaa ttaggtccta catgtcaagt tttgtttttg ttgcaattgc ttttgaggac
3361 ttagtcataa attattttcc aaggttcatg tccagaatgg tgcttcttag attttcttct
3421 aggattctta tagttgaggg tcatacattt aaatctttaa tccatcttga gttaatttt
3481 gtacatggtg aaagatagg gtccagtttc aatcttctgc atatggctag ccagatattc
```

FIG. 7U

```
3541 cagcaccttt tgttgaataa ggagtccttt ccccatactt attttttgtga actttgtttg
3601 agctacagat ggctgtaggt gtgcggcttg gtttctaggc tctctattct gttctattgg
3661 tctatgtgtc tgtttttcta acagtaccat gttgtttga ttactgtagc cttgggtaat
3721 gtgatgcctc aggcttgtt cttttttgttt aggattggtt tggcgattca ggctctttt
3781 tggttccata tgaattttag aaatttttgtt tataaatctg tgaaaaaatg acattggtag
3841 tttgttagaa atagtgttga ggctgggtgc tgtgggtcat gcctataatc ccagcacttt
3901 gggaggccaa ggcaggtgga tcacttgaga ttaggagttt gagaccagcc tggccaacgt
3961 ggtaaaaccc catctctact aaaatacaaa aattagctgg gtgtggtggt gtgtgcctgt
4021 aatcccagct actcgggagg ctaaggcatg agaattgctt gaacgataga gtgagactct
4081 gtctcaaaaa aaaaaaaaaa aaaaaagaa gaaagaaat agtgttgaat ctgcagatac
4141 tgcttatgtt tcatagtgta tatcatctgg catatctcct gtttggtaaa tgacttgaga
4201 tactgatgac tagttggtta tttgttgcaa ttgtcttttca acaatagtag gtgtgaccag
4261 gcgtggtggc tcacacttgt aatcccatca ctgtgggaag ccaaagcagg aggactgctt
4321 gaagccagaa gtttgagacc agcctgcgca gcaaagccag accctattttc ggcaaataaa
4381 aaatttagcc aggtgtggtg gctcacacct ataatcccag ctactcgaga ggctgaagca
4441 ggaggatcac tggggcccag gagtttgagg ctgcagtgag ctatgattgc accactgcac
4501 tccagcctgg gtgacagtaa gaccttgtct taaaaaaata gtaggtatag gccggtgtg
4561 gtggctcacg cctgtaatcc cggaacttta ggaggtggag gtgggcaaat cacctgaggt
4621 caggagttcg agaccagcct ggccaacatg gtgaaacccc atctctacta aaaatacaa
4681 acattagctg ggtgtggttg tgcatgccta taatcccagc tactcgggag actgaggcag
4741 gagaactact tgaacccagg aggcagaggt tgcagtgagc cgagatcacg ccactgcact
4801 ccagactggg caacagagtg agactccatc tcgaaaaaaa aatagtaggt atatacacaa
4861 ttttttatagt aaatgtgttt aattgggttt gaacaaagtg aaaaagttgg aatatctaga
4921 acctgtgtcc caaatacaag taagttggtt catccatgga cacctgcctc cttcacagga
4981 agagtaaaaa gatgaatgag cctgtttcca aagagctttg ctatcactat cattcagaat
5041 gcaatcaata tggccaatgg aaattgtata ggacttgaaa aaggaagccc tacttctggg
5101 accacatttt acgaccacct agctagtgca tgtaagcgta taacctaaat gcttaacatt
5161 tctgtttcat tatctgtaaa acagggataa tagagtccct taattctctt acagatcaga
5221 caagagtaat gaagtaatac acatggaatt tgtacattgt aatgcactct ccaatgctag
5281 ctgtcactat tccttttttt ttttttgttaa cagaagggac tgagtctgaa cttctttgtg
5341 ttcttgtcct ttgagagact ttagtaatta ttagtagatg taatttaggc ataactttct
5401 taaagaaaat atgcataata aatatgatat ctgtgaaata gattatttta gttgtattaa
5461 cttttaaaaa tagtttaaga ttatttcttt aaatggcaaa attgatgggt taagaagtca
5521 tttaacttgc taattttaaa tttacatgca cctgtttaga actacaccta ttgtgcaaaa
5581 agagaaactt ctttgataat tttacctatg tgaaattaag tggaaagtca tgcttaatgg
5641 tacaacattc aggctcagct atgtgagtca aacctcactc tgggattttg cccttttggaa
5701 aaatattctc taaacattgc atggtctgtg tttacagaaa ccatgtcact atgattcaac
5761 atctacttgc ttatgaggcg tttccagaa caggaaggaa tcattatttg ctgcagttga
5821 tgaggcttac acgaaaatgt actgtatttg actgagtca tgaaactgac ttttccaggg
5881 aaaagatatc cataaatttg ataattagct atcgataaat tatttttaagt tgggaaagta
5941 ggtgactgat gaaatgtcaa cattatgaac tcttacacct acttattcaa atgacaacct
6001 ttcagttttg tgttacaaaa aggagaaatc cagtatttaa tataatgata atattggaaa
6061 agaaagtcag ttttctccct ggtgatattt atccctgaag agaatagtag agaggcatgc
6121 ggtcatcctt gtgcatttaa atatttagaa tgctgacatg tcaaacagtt ccatgggctt
6181 ttttcatgag taactagtag gaaatattaa ataactcaaa ttatttagtc aagaaaagaa
6241 aaattaaaca aagtacatga taaagttatt aaggtctta atgaatatga atattaatag
6301 tacttctctg tttttttttag aagaaaataa aagaaaagg tctaaaccag taggccatta
6361 atctgtcctt tttattcaaa ggttagttta acctcaattg cagaggggct gtgagttcat
6421 agagagacat ggaatggcct ctaatcacac aatccataat agcaatttc atttactgag
6481 cacttactttg gtcccaagaa ctgtacctgg tatactatac ccattattac attcaattta
6541 tgtagttggc attactattt gcattacaaa tatgtgaaaa aaggaaggct tatgatctca
6601 tgattgatca ttagattggc tggaattaaa acagtcatgt catttaactg tgctaacgga
6661 atggactcta agggcctaga tgaaccatat tataaataaaa ttttttagtga ctagcaaatc
6721 cacttattta acagagtgag ctggttgcta aacattttttt gtcttatttt ctgctgaaat
6781 ctgcctcact ttaacttcct ttcgtctttt tcctgcattc tatgctatgt tcacacatat
6841 gacccatctc ctataaatta agcctttcaa atatttgaag ccagctatca ccatgctaca
6901 ttctcttctt ataccaagga taaatatctt taatatggat ggacttggta aaacaatttc
6961 atgtctgtac ttatctcagg atttctcatg tggatccact aaggcagaaa ggaagctatt
7021 gttttacatt tgacagatga agaaactgag tcagtacagt gaagtgcttt ttattttta
7081 ttttaatttt taacatttcc actacttaca gctatatttg ttttttata gagacaatct
7141 ggagggtaca aactatttac tgtcacctgg catttctgtt tccaaccaca tctcgtatca
7201 gcaaccttgt acaaattatg gcttggatta tagaaaaggt cctctccatt agcagaatct
7261 gctaaatttc aagtgcttca tatatcttct tgggagcact tcataagaga atgtgctgct
```

FIG. 7V

```
7321  tcttttcatc ctcctcttcc tcttccatct ttcttcct tcagtcttgt actgtaatct
7381  ggagtttggc atagtaaatt aggttagctt tcaggaagat aaacactgta tcacatgaga
7441  gttttaaaat attttctgtt gattcttgac ctagagctgt tgtgttatgg gcaatgggca
7501  aataaagtat cactttggta tttcagaaat cactaaaata tagtaagttt gaggaaatgt
7561  ctattgaatt agattcggca acacaccagt gcaacaaaga ctcagctgcc tggccaagga
7621  caactctatc tatgtcgtgg ctaatattgg ggacaagaag ccatgcaatg ccagtgactc
7681  tcagtgtccc cctgatggcc gttaccaata caacactgat gtggtgtttg attctcaggg
7741  aaaactgttg gcacgctacc ataaggtgag catcacttgt gccttagctc aacttgttac
7801  ttcttctgtg tgcttgtggt atgtatgtgt gtttgtttgt tgaatgttgg ggagagaact
7861  gttatagatg catcttataa ttattacatc atagttgaaa aggagattta attcagttcc
7921  atataaccgt tctgggtttg catttatcat aaaacagaat atggtagagt atttaaatgg
7981  atgtgacaat agccacacaa agcttttaat gttctctgaa aaagaagtaa acattctgtt
8041  tcattcatga tttaatatca ggttcatttt ttagcccaat ttgttagcat ttcatactaa
8101  gctaccatgt attccattag gactttttg attgcaatga aaacaaaacc tcaaatgaaa
8161  atggctttaa aaagatggaa atttccttgc ttatgcacat gtaaaaatgt gtatcataga
8221  aaggacaggt ctcatttcag tgcagtctga cactcagagg ctccaaagtt atcatccacc
8281  cctctagctc tcctagccct ttgttacagc ttcttctca ggggaactct cctttagaa
8341  gccacattgc tggagcaaca cgaaattcac atcttatca acaaaatcta caggaagggt
8401  gtatttctcc ctcctagaac cttgcaaagg cctatcgct ccttgattca attaggtgac
8461  gtgcctttcc tgagctaatc accaaaggat gagggatagg ctgccacatg ggaggagaaa
8521  ggaggagcaa gaggcctcca tggaccacag aggtggggaag tagctctccc cagagcacac
8581  acatgcacac aacaggccaa acaaaaacct gagcaaaaca tatgctgtac tcctgagccc
8641  aggttaagtg gagttttgga aaaagaatca ggctgaaaaa taaaataaaa ttatgaatgg
8701  cttactaatt aataatatgt agcaactgca ttgtctaaat taattttcaa tggacttcac
8761  ttctataaac ctggcagtat cattgggaca catgacaaag tttattttat taacatagta
8821  gtgctgttga aatttaaaga atatagtgga aaacaatctg agaagtgtag gattcaagat
8881  ttcaacctgt gatttttaaga tacacatttt cacatttaa atatcatttg tacatgtggt
8941  ttcattcatt ggttgtaaaa aaataaagt ttttttatta atgtcacagt aagaaaatgt
9001  atagatggtg gtatagtggg gatgatttt acaaatgtat gtgtaacagt tttatttgt
9061  tgttgttgtt gattttggaa atggaatctt gctctgttgc ccaggctgga gtgcagtggc
9121  gcgatctcgg ctcactgcaa cctcggcctc ctgggttcag gggctccc tgcctcagcc
9181  tatgagtagc tgggattaca ggcatatgcc atcatgcctg gctaatttt tttgatattt
9241  gtagtagaga caggggttta ccacattggc caggctggtc tcgaactcct gacctcaagt
9301  gatccaccccg cctcagcctc ctaacatgct gggattacag gcgtaagcca ccacacctgg
9361  cctatgtgta acactttaa acctgcatgt caacatacat gagaggaaag atttaacggg
9421  gaaagactta attgatcaca tctatttggc agttttctta ttaattttct tcttcttgc
9481  tttttattaa cagtacaatc ttttgcacc tgaaattcag tttgatttcc ccaaggattc
9541  agaacttgtg acttttgaca ctccctttgg gaagtttggc attttacttt gctttgacat
9601  tttttctcat gacccagctg tggtggtggt ggatgagttt caattgacag cattctctac
9661  cccacagcat ggtacaacac gctgcccttc ctctcggctg ttccttcca ttcagcatgg
9721  gccaaggcca tgggagtcaa tctacttgct gcaaataccc acaacaccag catgcacatg
9781  acaggtaact cacgcgggcc tgcaccaagt gggagtgaca gtcttaggaa ggcttcattg
9841  attttcaagc cacaaacttt tgtttaataa cttattacc aattttaaca tcacaaaatt
9901  aataatagca tttgttccta cttaaggaac gttcattgtc cttgtgaata aaagagggcaa
9961  acattattat ctcaatttta cttgaaagga aattggagct ggaggaagtc atgtaaaaaa
10021 atcaaagaga gttctaagaa acttcctagc caatgtgcat tagtaatatc gaaataagtc
10081 tggttgttta aagagataac ctacagagca gaagaaaata tttgcaaact atgcatttca
10141 taaaaatcta atatctagaa tccataagga acttaaacaa atcaacaaac aaaaaacaaa
10201 ctatccatt aaaaatgga caaggacat gaacagacac ttctcaaaag aagacataca
10261 tgtggccaac aagcatgtaa aaatgcttaa catcactaat cattacagaa atgcaaatca
10321 aaaccacaat gagataccac ctcgctccag tcagaatggc tatgattaaa aaaataaaaa
10381 caaacagatg ctggcgaggt tgtgaagaaa aaggaaacac ttatacactg ctggtgaaaa
10441 tgtaaattag ttcagccaca gtgaaagca gtttggcgat ttctcagaga acttaaaaca
10501 gaactgccat tcgactcagc aatcccatta ataggtatat accagaagga atataaatca
10561 ttctaccata aagacacatg cacttgtatg ttaattgcag cagttttagc aatagcaata
10621 acgtggaatc aaccaggtg ctcatcaacg gtgaagtgga taagaaaaat gtgatacata
10681 tacaccatag aatactacat agccataaca aagaatgaaa taatgtcctt tgcaacaaga
10741 tggatgcaac tggaggtcat tatcctcagc gaatgaacac aggaacagaa aatcaaatac
10801 ctcgtgttct cacgagttga agttaaacat tgagtacaca tgaacacaaa gagggaaaca
10861 atagacacca gggtttactt gagggggat ggtggggagga ggtgaggat tgaaaaacta
10921 cctattggat actgtgctca ctacctgggt gacaaaatcg tttgcacacc aaacccccagc
10981 aacatgcaat ttacccatgt aacaaacctt cacacgttcc cctctatac ctaaaataac
11041 agttggaaga aaaaaataca aacaaataaa aatatttcaa gcattaaaaa aaaacttgtt
```

FIG. 7W

```
11101 gaagtgataa aaatctcttt tgacttaatc aggtttttag agtttctcct ttatcatatc
11161 catgttcaaa gtaatgcagg cttccttttt aactgttctg ttatttgttg aataacaaat
11221 cccaaacaca aataaactaa atcgtcagtg gagagctaaa attattcttc acgttggggg
11281 attttctagt ttgttgctaa gttagcttaa aactatgcc cccaagtcaa atgataattt
11341 cagtgcaagt agtaccttat ggaggacaca gagtcaaatt ggaacttagg ccaatgtaac
11401 agctatctcc ttaactatct tgaaaatatg ctttaataac tttgtattta acttcacatg
11461 ggatattct attagttggt caccataaca aatctgaaac caatgtttgt atttatgttg
11521 cttgtaggga gtggaatcta cgccccagaa gcagtcaagg tgtaccacta tgacatggaa
11581 acagagagtg gtcagctgtt gctatcagaa ctgaagtctc ggccccgccg tgagcccacc
11641 taccctgcag ctgttgactg gcatgcgtat gccagcagtg tcaagccatt ttcctctgaa
11701 cagtcagatt ttctggggat gattatttt gatgagttta ccttcaccaa gcttaagaga
11761 aatacaggaa attcacacagc ttgccagaaa gatctgtgtt gtcacttaac ttacaagatg
11821 tctgagaagc gaacagacga gatctatgcc ctaggtgctt ttgatggact gcacacagta
11881 gaaggccaat attacttaca ggtagaaatg ctttaatatg ttaaagtggc cttattatca
11941 gtttttcttc taggtcatca ttgcctttct ttgaaaattg ggctggattt agctaatttt
12001 ataattagta atgttatatt tatctctgaa tttgtcccc agaacacatt atttgttcag
12061 tcttagcaag aacagaatta gttcttttag ttgaaaggca aaaacataaa gcaaattgat
12121 tagttctcag caggccaggt tcaggtttca aaagctgcaa tttctgtgta ttctcttttc
12181 ccgtcaggtt actttagagc agtgttttc aaattgtctt caactaaatc cagagaaaga
12241 aggatatttt acctcataac ccagtgtagc caagtggatg tgtgactgaa taaaaaaaaa
12301 gatatttaat tgaaatagtt tatgaaatas tttaaaatcc aattagaaat agctattatt
12361 stgtgcaatg cactctgatt tttaaaatcc tagtctattc tattttgactt cagtataaaa
12421 agtgttaatc ctgacccact atattgattt taggattcat taataagttg ttacctgcag
12481 tttgaaaaat acttcttatg aggcaattta aatatgcatt tatagtttga aattgcatta
12541 tttagctgag aaaatatttg caagtttcct gactcctct ctttcttt cttccatage
12601 tatgtgcatt actgaagtgt caaaccactg acctggaaac gtgtggagaa cctgtggggt
12661 cagcttttac caagtttgaa gacttctcc tcagtggcac atttggaacg cgttatgttt
12721 tcccacagat cattctaagt gggagtcagc ttgccctga aagacattat gaggtaggag
12781 gtgtgcagga tgataaaattc cttgagcag agtagatggg tagagcagca taatgaaaat
12841 ctttgaaata atgagagtat agcaatatcg tggttcacat tctacaagaa acaccttaaa
12901 tatgtggaaa ctatgatatg gaatataaat tgtggtttta gattgccatt aggctgtgat
12961 ggagaatttg gggttcattt ttttaacata aatgtgatgt tgatattcaa ggcaacagga
13021 aattcacaga gaagctaaaa taaaaatgtt gactgctgat aatggcaata atgttgtcat
13081 ttgcatggtg tagaaggtgc aaattaaata cattaaataa tgcatctaca acttattttc
13141 tgggtatact attttgagaa gttgttataa ttatagtaat aactaatatt ttgtatagtg
13201 tttcatgagt ttgaagaaca tatttttata catattattt gaccacctgt gcaacaaatt
13261 tgttggctgc acttttgcac aaagtccctc tactttcaga cttgaaacat gaacctgggt
13321 cttccaacac caaatcctgt gtgattttta ccattcacca ctgcttttaga agggagtgat
13381 cttgcctgag aagggctcta ggttgtaacc taaactctgc actgaagtta accctttgct
13441 ttctttgacc agatttcaag agatggacg ttgaggagcc gaagtggagc ccctttgct
13501 gtcttagtta tggccctgta tggaagagtg tttgagaagg acctccacg cttagggcag
13561 ggatctggga aattccagtg atctccttta gcagagccct tttaggatta gcctggctaa
13621 gaaaggaaga aaaaaaagag atccgttagt gtctgtttag aaaagatgtt ataaacttac
13681 agaaacaaat ataataaact gaagcagatt tgaaaagcaa caagtgtgtg tgcaaatttc
13741 acatttaca tgtttggtat agcacaggtt catttatggg agccgcattc atcctccatg
13801 tatgtgagtt taagtatatg taagtatgta tatgtatagt ggagcgtata tttaaatagg
13861 aggaggtcct agaaaaatcc tttgcagta actgcactaa tgtatgcaag tgttgtttcc
13921 atcatatgat ggttaattt atgtgttgat tgactgggt catgagatgc ccagatagct
13981 ggttaaccat tgtttctggg tgtgtctgtg agggtgttta aaggaagaga acagcatttg
14041 aattggtgga ctgagtaaag cagacggtcc tcccagtgt ggatggtcat cgtccagtcc
14101 cttgagggcc tgcagagaaa aacaagaagg aggaggtttg aattcatttt ctgccagact
14161 acttgagctg gatagagatc ttctcctgcc ttcatgtgct cctggttctc aggccttcag
14221 gcctggactg gaattgacac catcaactct tcagctctca ggccttcgaa tgacccct
14281 ggctttcctg catctccagc ttgcaaatgg cagacccagac tgtgggattt ctcagccttc
14341 ataactgtct gagccaatac cttatcataa atctctttct ctctctctct cctgttggtt
14401 ctctttctct ggagaaccct gactaatgca cttcatttgt aaatacatag gatgaacttt
14461 gaatatgcag aggggtatttg attccagcca attaagatac aggaaattaa agaataagga
14521 catcttttaa agtaactatg aacaacttt tagctagtat tgtccttta gtcatgacta
14581 atttgactcc taagttctat ttatatggaa attgga
```

FIG. 7X

Mus musculus vanin 1 (Vnn1), amino acid sequence (NP_035834.1) (SEQ ID NO:2)
```
  1 mgtswwlaca aafsalcvlk assldtflaa vyehavilpk dtllpvshge alalmnqnld
 61 llegaivsaa kqgahiivtp edgiygvrft rdtiypylee ipdpqvnwip cdnpkrfgst
121 pvqerlscla knnslyvvan mgdkkpcnts dshcppdgrf qyntdvvfds qgklvaryhk
181 qnifmgedqf nvpmepefvt fdtpfgkfgv ftcfdilfhd pavtlvtefq vdtilfptaw
241 mdvlphlaai efhsawamgm gvnflaanlh npsrrmtgsg iyapdsprvf hydrktqegk
301 llfaqlkshp ihspvnwtsy assvestptk tqefqsivff deftfvelkg lkgnytvcqn
361 dlcchlsyqm sekradevya fqafdglhtv egqyylqici llkckttnlr tcgssvdtaf
421 trfemfslsg tfgtryvfpe vlisevklap gefqvssdgr lvslkptsgp vltiglfgrl
481 ygkdwasnas sdfiahslii mlivtpiihy lc
```

Mus musculus vanin 3 (Vnn3), amino acid sequence (NP_036109.2) (SEQ ID NO:4)
```
  1 maslhfpqwa vsfvffaqav gsmdtfiaav yehavilpnk tespvsteea lllinknidi
 61 lesaiklaar qgahiivtpe dgiygwiftr etiypyledi pdpevnwipc rdprrfgytp
121 vqerlsclak ensiyimani gdkkpcnatd phcppdgryq yntnvvfdsk grltaryhky
181 nlfepeiqfd fpkdselvtf dtpfgkfgif tcfdifsydp avvvvkdtqv dsvllptawy
241 ntipllsavp fhsvwaramg vnvlaanthn tsmhmtgsgi yspeavrvyh ydmetesgql
301 llselrsrpr qhatpaevnw sayartvkpf ssgqadfpgk iyfdefsftk ltgsagnytv
361 cqkdlcchlt ykmsesrmde vyvlgafdgl htgegqyylq ictllkcqtt nsrtcgepvg
421 saftkfeefs lsgtfrtkyv fpqivlsgsq laleryyevs rdgrlrsrgg aplpilvmal
481 ygrvferdpp rlgqgpgklq
```

Homo sapiens vanin 1 (VNN1), amino acid sequence (NP_004657.1) (SEQ ID NO:6)
```
  1 mttqlpayva illfyvsras cqdtfiaavy ehaailpnat ltpvsreeal almnrnldil
 61 egaitsaadq gahiivtped aiygwnfnrd slypyledip dpevnwipcn nrnrfgqtpv
121 qerlsciakn nsiyvvanig dkkpcdtsdp qcppdgryqy ntdvvfdsqg klvaryhkqn
181 lfmgenqfnv pkepeivtfn ttfgsfgift cfdilfhdpa vtlvkdfhvd tivfptawmn
241 vlphlsavef hsawamgmrv nflasnihyp skkmtgsgiy apnssrafhy dmkteegkll
301 lsqldshpsh savvnwtsya ssiealssgn kefkgtvffd eftfvkltgv agnytvcqkd
361 lcchlsykms enipnevyal gafdglhtve gryylqicti lkckttnlnt cgdsaetast
421 rfemfsisgt fgtqyvfpev llsenqlapg efqvstdgri fslkptsgpv ltvtlfgrly
481 ekdwasnass gltaqariim liviapivcs lsw
```

Homo sapiens vanin 2 (VNN2), isoform 1, amino acid sequence (NP_004656.2) (SEQ ID NO:8)
```
  1 mvtssfpisv avfalitlqv gtqdsfiaav yehavilpnk tetpvsqeda lnlmnenidi
 61 letaikqaae qgariivtpe dalygwkftr etvfpyledi pdpqvnwipc qdphrfghtp
121 vqarisclak dnsiyvlanl gdkkpcnsrd stcppngyfq yntnvvynte gklvaryhky
181 hlysepqfnv pekpelvtfn tafgrfgift cfdiffydpg vtlvkdfhvd tilfptawmn
241 vipiltaief hsawamgmgiy nlivanthhv slnmtgsgiy apngpkvyhy dmkteigkll
301 lsevdshpls slayptavnw nayattikpf pvqkntfrgf isrdgfnfte lfenagnltv
361 cqkelcchls yrmlqkeene vyvlgaftgl hgrrrreywq vctmlkcktt nlttcgrpve
421 tastrfemfs lsgtfgteyv fpevllteih lspgkfevlk dgrlvnkngs sqpiltvslf
481 grwytkdsly sscqtsnsai tylifillm ialqnivml
```

Homo sapiens vanin 2 (VNN2), isoform 2, amino acid sequence (NP_511043) (SEQ ID NO:10)
```
  1 mnenidilet aikqaaeqga riivtpedal ygwkftretv fpyledipdp qvnwipcqdp
 61 hrfghtpvqa rlsclakdns iyvlanlgdk kpcnsrdstc ppngyfqynt nvvyntegkl
121 varyhkyhly sepqfnvpek pelvtfntaf grfgiftcfd iffydpgvtl vkdfhvdtil
181 fptawmnvlp iltaiefhsa wamgmgvnll vanthhvsln mtgsqiyapn gpkvyhydmk
241 telgkllse vdshplssla yptavnwnay attikpfpvq kntfrgfisr dgfnftelfe
301 nagnltvcqk elcchlsyrm lqkeenevyv lgaftqlhgr rrreywqvct mlkckttnlt
361 tcgrpvetas trfemfslsg tfgteyvfpe vllteihlsp gkfevlkdgr lvnkngssgp
421 iltvslfgrw ytkdslyssc qtsnsaityl lifilimiia lqnivml
```

FIG. 7Y

Homo sapiens vanin 3 (VNN3), isoform 1, amino acid sequence (NP_060869) (SEQ ID NO:12)
```
  1 miishfpkcv avfallalsv galdtfiaav yehavilpnr tetpvskeea lllmnknidv
 61 lekavklaak qgahiivtpe dgiygwiftr esiypyledi pdpgvnwipc rdpwrfgntp
121 vqqrlsclak dnsiyvvani gdkkpcnasd sqcppdqryq yntdvvfdsq gkllaryhky
181 nlfapeiqfd fpkdselvtf dtpfgkfgif tcfdifshdp avvvvdefql tafstpqhgt
241 trcpssrlfp siqhgprpwe siyllqiptt pact
```

Homo sapiens vanin 3 (VNN3), isoform 2, amino acid sequence (NP_ 523239.1) (SEQ ID NO:14)
```
  1 miishfpkcv avfallalsv galdtfiaav yehavilpnr tetpvskeea lllmnknidv
 61 lekavklaak qgahiivtpe dgiygwiftr esiypyledi pdpgvnwipc rdpwrkskkm
121 nepvskelcy hchsecnqyg qwklyrt
```

Homo sapiens vanin 3 (VNN3), isoform 3, amino acid sequence (NP_ 001019631) (SEQ ID NO:16)
```
  1 miishfpkcv avfallalsv galdtfiaav yehavilpnr tetpvskeea lllmnknidv
 61 lekavklaak qgahiivtpe dgiygwiftr esiypyledi pdpgvnwipc rdpwrnh
```

FIG. 7Z

SEQUENCE LISTING

```
<160> NUMBER OF SEQ ID NOS: 19

<210> SEQ ID NO 1
<211> LENGTH: 2255
<212> TYPE: DNA
<213> ORGANISM: Mus musculus
<220> FEATURE:
<221> NAME/KEY: CDS
<222> LOCATION: (22)..(1560)

<400> SEQUENCE: 1
ttgctgtcgt tggacttcag c atg ggc acg tct tgg tgg ctg gcg tgt gct        51
                       Met Gly Thr Ser Trp Trp Leu Ala Cys Ala
                        1               5                   10 gca gcg ttt tct gcc ctc tgt gtc tta aaa gcc agc tcg ctg gat act        99
Ala Ala Phe Ser Ala Leu Cys Val Leu Lys Ala Ser Ser Leu Asp Thr
            15                  20                  25 ttc ctc gcg gct gtt tac gag cat gct gtg atc ctg cct aag gac acc       147
Phe Leu Ala Ala Val Tyr Glu His Ala Val Ile Leu Pro Lys Asp Thr
        30                  35                  40 ctg ttg cca gtg tct cac ggt gag gct ctg gca tta atg aac cag aat       195
Leu Leu Pro Val Ser His Gly Glu Ala Leu Ala Leu Met Asn Gln Asn
    45                  50                  55 ctg gac ctt ctg gaa gga gcg atc gta tct gca gcg aag cag ggt gcg       243
Leu Asp Leu Leu Glu Gly Ala Ile Val Ser Ala Ala Lys Gln Gly Ala
60                  65                  70 cac att att gtg act cca gaa gat ggc ata tac ggt gtg cgt ttc acc       291
His Ile Ile Val Thr Pro Glu Asp Gly Ile Tyr Gly Val Arg Phe Thr
75                  80                  85                  90 agg gat acg atc tac cca tac ctg gag gag atc cca gac cct caa gta       339
Arg Asp Thr Ile Tyr Pro Tyr Leu Glu Glu Ile Pro Asp Pro Gln Val
```

```
                          95                  100                 105
aac tgg ata ccc tgt gat aac cct aaa aga ttt ggc tct acc ccg gtg    387
Asn Trp Ile Pro Cys Asp Asn Pro Lys Arg Phe Gly Ser Thr Pro Val
            110                 115                 120 cag gag aga ctc agc tgc ttg gcc aag aac aac tcc atc tat gtt gtg    435
Gln Glu Arg Leu Ser Cys Leu Ala Lys Asn Asn Ser Ile Tyr Val Val
        125                 130                 135 gcg aac atg gga gac aag aag ccg tgt aac acc agc gac tct cac tgt    483
Ala Asn Met Gly Asp Lys Lys Pro Cys Asn Thr Ser Asp Ser His Cys
    140                 145                 150 cca cct gac ggc aga ttc cag tac aac act gat gtg gtg ttt gat tcc    531
Pro Pro Asp Gly Arg Phe Gln Tyr Asn Thr Asp Val Val Phe Asp Ser
155                 160                 165                 170 cag ggt aaa ctg gtt gcg aga tac cat aag caa aac att ttc atg gga    579
Gln Gly Lys Leu Val Ala Arg Tyr His Lys Gln Asn Ile Phe Met Gly
            175                 180                 185 gaa gat cag ttc aat gtc ccc atg gag cct gag ttt gtg act ttc gac    627
Glu Asp Gln Phe Asn Val Pro Met Glu Pro Glu Phe Val Thr Phe Asp
        190                 195                 200 acc ccc ttt gga aag ttt ggc gtc ttc acc tgt ttc gat att ctc ttc    675
Thr Pro Phe Gly Lys Phe Gly Val Phe Thr Cys Phe Asp Ile Leu Phe
    205                 210                 215 cat gat ccc gct gtc acc ctg gtg aca gaa ttc cag gtg gac acc ata    723
His Asp Pro Ala Val Thr Leu Val Thr Glu Phe Gln Val Asp Thr Ile
220                 225                 230 ctg ttc cca acc gcc tgg atg gac gtc ctt cct cat ttg gca gcc att    771
Leu Phe Pro Thr Ala Trp Met Asp Val Leu Pro His Leu Ala Ala Ile
235                 240                 245                 250 gaa ttc cac tca gct tgg gct atg ggc atg ggg gtc aat ttc cta gca    819
Glu Phe His Ser Ala Trp Ala Met Gly Met Gly Val Asn Phe Leu Ala
            255                 260                 265 gct aat cta cat aat ccc tcg agg aga atg aca gga agt ggt atc tat    867
Ala Asn Leu His Asn Pro Ser Arg Arg Met Thr Gly Ser Gly Ile Tyr
        270                 275                 280 gca ccc gat tct cca agg gtc ttt cac tac gac agg aag acc caa gaa    915
Ala Pro Asp Ser Pro Arg Val Phe His Tyr Asp Arg Lys Thr Gln Glu
    285                 290                 295 gga aaa ctc ctc ttc gct cag ctg aaa tcc cac cca att cac tcc ccg    963
Gly Lys Leu Leu Phe Ala Gln Leu Lys Ser His Pro Ile His Ser Pro
300                 305                 310 gtg aac tgg act tcc tat gct agc agt gta gaa tca acc cca acc aaa   1011
Val Asn Trp Thr Ser Tyr Ala Ser Ser Val Glu Ser Thr Pro Thr Lys
315                 320                 325                 330 acc cag gaa ttt cag agt att gtc ttt ttt gat gag ttt acc ttt gtg   1059
Thr Gln Glu Phe Gln Ser Ile Val Phe Phe Asp Glu Phe Thr Phe Val
            335                 340                 345 gag ctc aaa ggg atc aaa gga aat tac act gtt tgc cag aat gac ctc   1107
Glu Leu Lys Gly Ile Lys Gly Asn Tyr Thr Val Cys Gln Asn Asp Leu
        350                 355                 360 tgc tgt cac cta agc tac cag atg tct gag aag cga gca gat gag gtt   1155
Cys Cys His Leu Ser Tyr Gln Met Ser Glu Lys Arg Ala Asp Glu Val
    365                 370                 375 tat gcc ttt gga gcc ttt gat ggg ctg cac acc gtg gaa ggg cag tac   1203
Tyr Ala Phe Gly Ala Phe Asp Gly Leu His Thr Val Glu Gly Gln Tyr
380                 385                 390 tac cta cag atc tgc atc ctg cta aaa tgt aaa act acc aat tta cgc   1251
Tyr Leu Gln Ile Cys Ile Leu Leu Lys Cys Lys Thr Thr Asn Leu Arg
395                 400                 405                 410 acc tgt ggt agt tca gtg gac acg gct ttt acc agg ttt gaa atg ttc   1299
```

```
              Thr Cys Gly Ser Ser Val Asp Thr Ala Phe Thr Arg Phe Glu Met Phe
                              415                 420                 425 tcg ctc agc ggc act ttt gga acc cgg tat gtc ttc cct gaa gtg ttg         1347
Ser Leu Ser Gly Thr Phe Gly Thr Arg Tyr Val Phe Pro Glu Val Leu
            430                 435                 440 ctg agt gag gtc aag ctc gca cct ggg gag ttt cag gtg tca agt gat         1395
Leu Ser Glu Val Lys Leu Ala Pro Gly Glu Phe Gln Val Ser Ser Asp
                445                 450                 455 ggg cgc ctg gtt agc ctg aag cca acc tcg gga cct gtg tta acc atc         1443
Gly Arg Leu Val Ser Leu Lys Pro Thr Ser Gly Pro Val Leu Thr Ile
        460                 465                 470 ggg ctc ttt ggg agg ttg tat ggg aag gac tgg gca tcc aat gct tcc         1491
Gly Leu Phe Gly Arg Leu Tyr Gly Lys Asp Trp Ala Ser Asn Ala Ser
475                 480                 485                 490 tca gac ttc ata gca cac tcg ctg ata ata atg ctg att gtg acg cct         1539
Ser Asp Phe Ile Ala His Ser Leu Ile Ile Met Leu Ile Val Thr Pro
                495                 500                 505 att ata cat tac ttg tgc tga tggaatttttt acattttta ttttatttag            1590
Ile Ile His Tyr Leu Cys
                510 aaaatttaaa attggtggat gcagaaaaaa taactgtttg tcaacagtgg actcgggtgt       1650 aagcaaataa agtgcctctt ctttagaaaa acatatgtac accagataca tttcaggaaa       1710 attaataaaa ctttgagcat tggaacgaga tggagggcca agtaaaggtc gcatgtgttt       1770 tattcagaag aaataaaaat tacagttaaa aggcacttca aaccatcata agatagattt       1830 acaagaggtg taaatctatt atacatctta ctcagttatg cttagaattt ccaatgtgtt       1890 tgttcatttg ggctattaag tatttatctc aacatttccg ttctctcatg gaccagatcc      1950 tgtagtttta attcttcagt tcaagtccca gttcccacaa cctcagaacg tgactgcctt      2010 ggtgtctttg gcaatgaaga cataagaggc atcattagca tggactttaa ttcaatatga      2070 ctgatctcct cagaagaaat caggacaaag acttgcatca agtgaagccc ttgtgaacac      2130 aggaaaagat ggtcatgtac aacaagaaaa ggggcctcag gagaacgcaa acctgctaac      2190 gtgtcaaact tccaggtctc cagaatcatg aggcaataaa tttctgtttt aaatgaaaaa      2250 aaaaa                                                                  2255

<210> SEQ ID NO 2
<211> LENGTH: 512
<212> TYPE: PRT
<213> ORGANISM: Mus musculus

<400> SEQUENCE: 2

Met Gly Thr Ser Trp Trp Leu Ala Cys Ala Ala Ala Phe Ser Ala Leu
1               5                   10                  15

Cys Val Leu Lys Ala Ser Ser Leu Asp Thr Phe Leu Ala Ala Val Tyr
            20                  25                  30

Glu His Ala Val Ile Leu Pro Lys Asp Thr Leu Leu Pro Val Ser His
        35                  40                  45

Gly Glu Ala Leu Ala Leu Met Asn Gln Asn Leu Asp Leu Leu Glu Gly
    50                  55                  60

Ala Ile Val Ser Ala Ala Lys Gln Gly Ala His Ile Ile Val Thr Pro
65                  70                  75                  80

Glu Asp Gly Ile Tyr Gly Val Arg Phe Thr Arg Asp Thr Ile Tyr Pro
                85                  90                  95

Tyr Leu Glu Glu Ile Pro Asp Pro Gln Val Asn Trp Ile Pro Cys Asp
            100                 105                 110
```

Asn Pro Lys Arg Phe Gly Ser Thr Pro Val Gln Glu Arg Leu Ser Cys
            115                 120                 125

Leu Ala Lys Asn Asn Ser Ile Tyr Val Val Ala Asn Met Gly Asp Lys
        130                 135                 140

Lys Pro Cys Asn Thr Ser Asp Ser His Cys Pro Pro Asp Gly Arg Phe
145                 150                 155                 160

Gln Tyr Asn Thr Asp Val Val Phe Asp Ser Gln Gly Lys Leu Val Ala
                165                 170                 175

Arg Tyr His Lys Gln Asn Ile Phe Met Gly Glu Asp Gln Phe Asn Val
            180                 185                 190

Pro Met Glu Pro Glu Phe Val Thr Phe Asp Thr Pro Phe Gly Lys Phe
        195                 200                 205

Gly Val Phe Thr Cys Phe Asp Ile Leu Phe His Asp Pro Ala Val Thr
    210                 215                 220

Leu Val Thr Glu Phe Gln Val Asp Thr Ile Leu Phe Pro Thr Ala Trp
225                 230                 235                 240

Met Asp Val Leu Pro His Leu Ala Ala Ile Glu Phe His Ser Ala Trp
                245                 250                 255

Ala Met Gly Met Gly Val Asn Phe Leu Ala Ala Asn Leu His Asn Pro
            260                 265                 270

Ser Arg Arg Met Thr Gly Ser Gly Ile Tyr Ala Pro Asp Ser Pro Arg
        275                 280                 285

Val Phe His Tyr Asp Arg Lys Thr Gln Glu Gly Lys Leu Leu Phe Ala
    290                 295                 300

Gln Leu Lys Ser His Pro Ile His Ser Pro Val Asn Trp Thr Ser Tyr
305                 310                 315                 320

Ala Ser Ser Val Glu Ser Thr Pro Thr Lys Thr Gln Glu Phe Gln Ser
                325                 330                 335

Ile Val Phe Phe Asp Glu Phe Thr Phe Val Glu Leu Lys Gly Ile Lys
            340                 345                 350

Gly Asn Tyr Thr Val Cys Gln Asn Asp Leu Cys Cys His Leu Ser Tyr
        355                 360                 365

Gln Met Ser Glu Lys Arg Ala Asp Glu Val Tyr Ala Phe Gly Ala Phe
    370                 375                 380

Asp Gly Leu His Thr Val Glu Gly Gln Tyr Tyr Leu Gln Ile Cys Ile
385                 390                 395                 400

Leu Leu Lys Cys Lys Thr Thr Asn Leu Arg Thr Cys Gly Ser Ser Val
                405                 410                 415

Asp Thr Ala Phe Thr Arg Phe Glu Met Phe Ser Leu Ser Gly Thr Phe
            420                 425                 430

Gly Thr Arg Tyr Val Phe Pro Glu Val Leu Leu Ser Glu Val Lys Leu
        435                 440                 445

Ala Pro Gly Glu Phe Gln Val Ser Ser Asp Gly Arg Leu Val Ser Leu
    450                 455                 460

Lys Pro Thr Ser Gly Pro Val Leu Thr Ile Gly Leu Phe Gly Arg Leu
465                 470                 475                 480

Tyr Gly Lys Asp Trp Ala Ser Asn Ala Ser Ser Asp Phe Ile Ala His
                485                 490                 495

Ser Leu Ile Ile Met Leu Ile Val Thr Pro Ile Ile His Tyr Leu Cys
            500                 505                 510

<210> SEQ ID NO 3
<211> LENGTH: 1819

<212> TYPE: DNA
<213> ORGANISM: Mus musculus
<220> FEATURE:
<221> NAME/KEY: CDS
<222> LOCATION: (113)..(1615)

<400> SEQUENCE: 3

| | | |
|---|---|---|
| atatattcac aggcagctgg ctggcatcac gacttgcgtc tgaatatttt tttttcccac | 60 |
| tgagatacag tagaagaacc ttctgatttt cagagatcac tctattttaa tt atg gct<br>                                                                                                Met Ala<br>                                                                                                 1 | 118 |

```
tca tta cat ttt cct caa tgg gca gtg agt ttt gtc ttc ttt gcc cag    166
Ser Leu His Phe Pro Gln Trp Ala Val Ser Phe Val Phe Phe Ala Gln
      5                  10                  15 gct gtg ggt tca atg gac act ttt att gct gct gtg tat gaa cat gct    214
Ala Val Gly Ser Met Asp Thr Phe Ile Ala Ala Val Tyr Glu His Ala
 20                  25                  30 gtt ata ctg cca aac aaa act gaa agt cct gtt tcc act gaa gag gct    262
Val Ile Leu Pro Asn Lys Thr Glu Ser Pro Val Ser Thr Glu Glu Ala
 35                  40                  45                  50 ttg ctc ctg ata aac aag aac ata gac att ttg gag agt gca atc aag    310
Leu Leu Leu Ile Asn Lys Asn Ile Asp Ile Leu Glu Ser Ala Ile Lys
                 55                  60                  65 ctg gca gcc aga cag ggt gca cat atc att gtg acg cca gaa gat gga    358
Leu Ala Ala Arg Gln Gly Ala His Ile Ile Val Thr Pro Glu Asp Gly
         70                  75                  80 atc tat ggt tgg atc ttc acc agg gag acc att tac ccc tac cta gag    406
Ile Tyr Gly Trp Ile Phe Thr Arg Glu Thr Ile Tyr Pro Tyr Leu Glu
             85                  90                  95 gat ata cca gac cct gaa gtg aac tgg att ccc tgt aga gac cct agg    454
Asp Ile Pro Asp Pro Glu Val Asn Trp Ile Pro Cys Arg Asp Pro Arg
100                 105                 110 agg ttt ggc tac aca cca gta cag gag aga ctg agc tgc ctt gcc aag    502
Arg Phe Gly Tyr Thr Pro Val Gln Glu Arg Leu Ser Cys Leu Ala Lys
115                 120                 125                 130 gag aac tct atc tat att atg gca aat att ggg gac aag aag cca tgc    550
Glu Asn Ser Ile Tyr Ile Met Ala Asn Ile Gly Asp Lys Lys Pro Cys
                135                 140                 145 aat gct act gat cct cat tgt ccc ccg gat ggc cgt tac caa tat aat    598
Asn Ala Thr Asp Pro His Cys Pro Pro Asp Gly Arg Tyr Gln Tyr Asn
            150                 155                 160 acc aat gtg gtc ttc gat tct aag ggt agg cta aca gcc cgc tac cat    646
Thr Asn Val Val Phe Asp Ser Lys Gly Arg Leu Thr Ala Arg Tyr His
                165                 170                 175 aag tac aat ctt ttt gaa cca gag att cag ttt gat ttc ccc aaa gat    694
Lys Tyr Asn Leu Phe Glu Pro Glu Ile Gln Phe Asp Phe Pro Lys Asp
        180                 185                 190 tca gag ctg gtg acc ttt gac acc ccg ttt ggg aag ttt ggc atc ttc    742
Ser Glu Leu Val Thr Phe Asp Thr Pro Phe Gly Lys Phe Gly Ile Phe
195                 200                 205                 210 act tgc ttt gac att ttc tct tat gac cca gct gtg gtg gtt gtg aag    790
Thr Cys Phe Asp Ile Phe Ser Tyr Asp Pro Ala Val Val Val Val Lys
                215                 220                 225 gac acc cag gtc gac agt gtt ctc tta ccc acg gcg tgg tac aac acc    838
Asp Thr Gln Val Asp Ser Val Leu Leu Pro Thr Ala Trp Tyr Asn Thr
            230                 235                 240 ctg ccc ctg ctt tca gca gtt cca ttc cat tcg gtg tgg gcc aga gcc    886
Leu Pro Leu Leu Ser Ala Val Pro Phe His Ser Val Trp Ala Arg Ala
                245                 250                 255 atg ggg gtc aac gtg ctt gct gca aac acc cac aac acc agc atg cat    934
```

```
            Met Gly Val Asn Val Leu Ala Ala Asn Thr His Asn Thr Ser Met His
                260                 265                 270 atg aca ggg agt gga atc tac agc ccg gaa gct gtc cga gtg tac cac              982
Met Thr Gly Ser Gly Ile Tyr Ser Pro Glu Ala Val Arg Val Tyr His
275                 280                 285                 290 tat gac atg gag aca gag agt ggc caa ctg ctg ctt tca gag ctg agg             1030
Tyr Asp Met Glu Thr Glu Ser Gly Gln Leu Leu Leu Ser Glu Leu Arg
                295                 300                 305 tct cgg cct cgc cag cac gcc acc cct gca gag gtt aac tgg agc gct             1078
Ser Arg Pro Arg Gln His Ala Thr Pro Ala Glu Val Asn Trp Ser Ala
            310                 315                 320 tat gcc agg act gtg aag ccg ttc tca tcg ggg cag gca gac ttc cca             1126
Tyr Ala Arg Thr Val Lys Pro Phe Ser Ser Gly Gln Ala Asp Phe Pro
        325                 330                 335 gga aag att tat ttt gac gaa ttt agc ttc acc aag ctt aca gga agt             1174
Gly Lys Ile Tyr Phe Asp Glu Phe Ser Phe Thr Lys Leu Thr Gly Ser
    340                 345                 350 gct gga aat tac aca gtt tgc caa aag gac ctg tgc tgt cac ctg act             1222
Ala Gly Asn Tyr Thr Val Cys Gln Lys Asp Leu Cys Cys His Leu Thr
355                 360                 365                 370 tac aag atg tct gaa agc cga atg gac gag gtg tat gtt ctg ggt gcc             1270
Tyr Lys Met Ser Glu Ser Arg Met Asp Glu Val Tyr Val Leu Gly Ala
                375                 380                 385 ttt gat gga ctc cat aca ggg gaa ggc cag tat tac cta cag ata tgt             1318
Phe Asp Gly Leu His Thr Gly Glu Gly Gln Tyr Tyr Leu Gln Ile Cys
                390                 395                 400 aca ttg ctg aag tgt caa acc acc aac tcg aga act tgt ggg gaa ccc             1366
Thr Leu Leu Lys Cys Gln Thr Thr Asn Ser Arg Thr Cys Gly Glu Pro
            405                 410                 415 gtg ggg tca gct ttt aca aag ttt gaa gaa ttc tct ctc agt ggc acc             1414
Val Gly Ser Ala Phe Thr Lys Phe Glu Glu Phe Ser Leu Ser Gly Thr
        420                 425                 430 ttt cgg aca aaa tat gtt ttc cca cag atc gtg cta agt ggg agt caa             1462
Phe Arg Thr Lys Tyr Val Phe Pro Gln Ile Val Leu Ser Gly Ser Gln
    435                 440                 445                 450 ctt gcc ctg gaa aga tat tat gaa gtc tca aga gat gga cgt ctg agg             1510
Leu Ala Leu Glu Arg Tyr Tyr Glu Val Ser Arg Asp Gly Arg Leu Arg
                455                 460                 465 agt cga ggt gga gcc cct ttg cct atc tta gtg atg gcc ctg tat gga             1558
Ser Arg Gly Gly Ala Pro Leu Pro Ile Leu Val Met Ala Leu Tyr Gly
                470                 475                 480 aga gtg ttt gag aga gac cct ccg cgc tta ggg cag gga cct ggg aag             1606
Arg Val Phe Glu Arg Asp Pro Pro Arg Leu Gly Gln Gly Pro Gly Lys
                485                 490                 495 ctg cag tga tcccttcatt ggggacccca cccgcctgcc ctgacacaag                     1655
Leu Gln
    500 gggcggggtc tgcacaggat tagcctggca gagagcgggg ctctaagagc aagaacaagg           1715 agctgcaggg ttccattagg agatacgatg taagctgctg aaaaggcaaa gcaagtgaga           1775 ggaaacaata aagtaaaaaa gcaaaaaaaa aaaaaaaaaa aaaa                            1819

<210> SEQ ID NO 4
<211> LENGTH: 500
<212> TYPE: PRT
<213> ORGANISM: Mus musculus

<400> SEQUENCE: 4

Met Ala Ser Leu His Phe Pro Gln Trp Ala Val Ser Phe Val Phe Phe
1               5                   10                  15
```

```
Ala Gln Ala Val Gly Ser Met Asp Thr Phe Ile Ala Ala Val Tyr Glu
             20                  25                  30
His Ala Val Ile Leu Pro Asn Lys Thr Glu Ser Pro Val Ser Thr Glu
         35                  40                  45
Glu Ala Leu Leu Leu Ile Asn Lys Asn Ile Asp Ile Leu Glu Ser Ala
 50                  55                  60
Ile Lys Leu Ala Ala Arg Gln Gly Ala His Ile Ile Val Thr Pro Glu
 65                  70                  75                  80
Asp Gly Ile Tyr Gly Trp Ile Phe Thr Arg Glu Thr Ile Tyr Pro Tyr
                 85                  90                  95
Leu Glu Asp Ile Pro Asp Pro Glu Val Asn Trp Ile Pro Cys Arg Asp
             100                 105                 110
Pro Arg Arg Phe Gly Tyr Thr Pro Val Gln Glu Arg Leu Ser Cys Leu
         115                 120                 125
Ala Lys Glu Asn Ser Ile Tyr Ile Met Ala Asn Ile Gly Asp Lys Lys
130                 135                 140
Pro Cys Asn Ala Thr Asp Pro His Cys Pro Pro Asp Gly Arg Tyr Gln
145                 150                 155                 160
Tyr Asn Thr Asn Val Val Phe Asp Ser Lys Gly Arg Leu Thr Ala Arg
                 165                 170                 175
Tyr His Lys Tyr Asn Leu Phe Glu Pro Glu Ile Gln Phe Asp Phe Pro
             180                 185                 190
Lys Asp Ser Glu Leu Val Thr Phe Asp Thr Pro Phe Gly Lys Phe Gly
         195                 200                 205
Ile Phe Thr Cys Phe Asp Ile Phe Ser Tyr Asp Pro Ala Val Val Val
210                 215                 220
Val Lys Asp Thr Gln Val Asp Ser Val Leu Leu Pro Thr Ala Trp Tyr
225                 230                 235                 240
Asn Thr Leu Pro Leu Leu Ser Ala Val Pro Phe His Ser Val Trp Ala
                 245                 250                 255
Arg Ala Met Gly Val Asn Val Leu Ala Ala Asn Thr His Asn Thr Ser
             260                 265                 270
Met His Met Thr Gly Ser Gly Ile Tyr Ser Pro Glu Ala Val Arg Val
         275                 280                 285
Tyr His Tyr Asp Met Glu Thr Glu Ser Gly Gln Leu Leu Leu Ser Glu
290                 295                 300
Leu Arg Ser Arg Pro Arg Gln His Ala Thr Pro Ala Glu Val Asn Trp
305                 310                 315                 320
Ser Ala Tyr Ala Arg Thr Val Lys Pro Phe Ser Ser Gly Gln Ala Asp
                 325                 330                 335
Phe Pro Gly Lys Ile Tyr Phe Asp Glu Phe Ser Phe Thr Lys Leu Thr
             340                 345                 350
Gly Ser Ala Gly Asn Tyr Thr Val Cys Gln Lys Asp Leu Cys Cys His
         355                 360                 365
Leu Thr Tyr Lys Met Ser Glu Ser Arg Met Asp Glu Val Tyr Val Leu
370                 375                 380
Gly Ala Phe Asp Gly Leu His Thr Gly Glu Gly Gln Tyr Tyr Leu Gln
385                 390                 395                 400
Ile Cys Thr Leu Leu Lys Cys Gln Thr Thr Asn Ser Arg Thr Cys Gly
                 405                 410                 415
Glu Pro Val Gly Ser Ala Phe Thr Lys Phe Glu Glu Phe Ser Leu Ser
             420                 425                 430
```

```
Gly Thr Phe Arg Thr Lys Tyr Val Phe Pro Gln Ile Val Leu Ser Gly
            435                 440                 445

Ser Gln Leu Ala Leu Glu Arg Tyr Tyr Glu Val Ser Arg Asp Gly Arg
        450                 455                 460

Leu Arg Ser Arg Gly Gly Ala Pro Leu Pro Ile Leu Val Met Ala Leu
465                 470                 475                 480

Tyr Gly Arg Val Phe Glu Arg Asp Pro Pro Arg Leu Gly Gln Gly Pro
                485                 490                 495

Gly Lys Leu Gln
        500

<210> SEQ ID NO 5
<211> LENGTH: 3109
<212> TYPE: DNA
<213> ORGANISM: Homo sapiens
<220> FEATURE:
<221> NAME/KEY: CDS
<222> LOCATION: (15)..(1556)

<400> SEQUENCE: 5
cattggactt cagc atg act act cag ttg cca gct tac gtg gca att ttg         50
                Met Thr Thr Gln Leu Pro Ala Tyr Val Ala Ile Leu
                 1               5                  10 ctt ttc tat gtc tca aga gcc agc tgc cag gac act ttc att gca gct         98
Leu Phe Tyr Val Ser Arg Ala Ser Cys Gln Asp Thr Phe Ile Ala Ala
         15                  20                  25 gtt tat gag cat gca gcg ata ttg ccc aat gcc acc cta aca cca gtg        146
Val Tyr Glu His Ala Ala Ile Leu Pro Asn Ala Thr Leu Thr Pro Val
 30                  35                  40 tct cgt gag gag gct ttg gca tta atg aat cgg aat ctg gac att ttg        194
Ser Arg Glu Glu Ala Leu Ala Leu Met Asn Arg Asn Leu Asp Ile Leu
45                  50                  55                  60 gaa gga gcg atc aca tca gca gca gat cag ggt gcg cat att att gtg        242
Glu Gly Ala Ile Thr Ser Ala Ala Asp Gln Gly Ala His Ile Ile Val
                 65                  70                  75 act cca gaa gat gct att tat ggc tgg aac ttc aac agg gac tct ctc        290
Thr Pro Glu Asp Ala Ile Tyr Gly Trp Asn Phe Asn Arg Asp Ser Leu
             80                  85                  90 tac cca tat ttg gag gac atc cca gac cct gaa gta aac tgg atc ccc        338
Tyr Pro Tyr Leu Glu Asp Ile Pro Asp Pro Glu Val Asn Trp Ile Pro
         95                 100                 105 tgt aat aat cgt aac aga ttt ggc cag acc cca gta caa gaa aga ctc        386
Cys Asn Asn Arg Asn Arg Phe Gly Gln Thr Pro Val Gln Glu Arg Leu
    110                 115                 120 agc tgc ctg gcc aag aac aac tct atc tat gtt gtg gca aat att ggg        434
Ser Cys Leu Ala Lys Asn Asn Ser Ile Tyr Val Val Ala Asn Ile Gly
125                 130                 135                 140 gac aag aag cca tgc gat acc agt gat cct cag tgt ccc cct gat ggc        482
Asp Lys Lys Pro Cys Asp Thr Ser Asp Pro Gln Cys Pro Pro Asp Gly
                145                 150                 155 cgt tac caa tac aac act gat gtg gta ttt gat tct caa gga aaa ctg        530
Arg Tyr Gln Tyr Asn Thr Asp Val Val Phe Asp Ser Gln Gly Lys Leu
            160                 165                 170 gtg gca cgc tac cat aag caa aac ctt ttc atg ggt gaa aat caa ttc        578
Val Ala Arg Tyr His Lys Gln Asn Leu Phe Met Gly Glu Asn Gln Phe
        175                 180                 185 aat gta ccc aag gag cct gag att gtg act ttc aat acc acc ttt gga        626
Asn Val Pro Lys Glu Pro Glu Ile Val Thr Phe Asn Thr Thr Phe Gly
    190                 195                 200 agt ttt ggc att ttc aca tgc ttt gat ata ctc ttc cat gat cct gct        674
```

```
Ser Phe Gly Ile Phe Thr Cys Phe Asp Ile Leu Phe His Asp Pro Ala
205                 210                 215                 220 gtt acc ttg gtg aaa gat ttc cac gtg gac acc ata gta ttc cca aca       722
Val Thr Leu Val Lys Asp Phe His Val Asp Thr Ile Val Phe Pro Thr
                    225                 230                 235 gct tgg atg aat gtt ttg cca cat ttg tca gct gtt gaa ttc cac tca       770
Ala Trp Met Asn Val Leu Pro His Leu Ser Ala Val Glu Phe His Ser
        240                 245                 250 gct tgg gct atg ggc atg agg gtc aat ttc ctt gca tcc aac ata cat       818
Ala Trp Ala Met Gly Met Arg Val Asn Phe Leu Ala Ser Asn Ile His
            255                 260                 265 tac ccc tca aag aaa atg aca gga agt ggc atc tat gca ccc aat tct       866
Tyr Pro Ser Lys Lys Met Thr Gly Ser Gly Ile Tyr Ala Pro Asn Ser
    270                 275                 280 tca aga gca ttt cat tat gat atg aag aca gaa gag gga aaa ctc ctc       914
Ser Arg Ala Phe His Tyr Asp Met Lys Thr Glu Glu Gly Lys Leu Leu
285                 290                 295                 300 ctc tcg caa ctg gat tcc cac cca tcc cat tct gca gtg gtg aac tgg       962
Leu Ser Gln Leu Asp Ser His Pro Ser His Ser Ala Val Val Asn Trp
                    305                 310                 315 act tcc tat gcc agc agt ata gaa gcg ctc tca tca gga aac aag gaa      1010
Thr Ser Tyr Ala Ser Ser Ile Glu Ala Leu Ser Ser Gly Asn Lys Glu
        320                 325                 330 ttt aaa ggc act gtc ttt ttc gat gaa ttc act ttt gtg aag ctc aca      1058
Phe Lys Gly Thr Val Phe Phe Asp Glu Phe Thr Phe Val Lys Leu Thr
            335                 340                 345 gga gtt gca gga aat tat aca gtt tgt cag aaa gat ctc tgc tgt cat      1106
Gly Val Ala Gly Asn Tyr Thr Val Cys Gln Lys Asp Leu Cys Cys His
    350                 355                 360 tta agc tac aaa atg tct gag aac ata cca aat gaa gtg tac gct cta      1154
Leu Ser Tyr Lys Met Ser Glu Asn Ile Pro Asn Glu Val Tyr Ala Leu
365                 370                 375                 380 ggg gca ttt gac gga ctg cac act gtg gaa ggg cgc tat tat cta cag      1202
Gly Ala Phe Asp Gly Leu His Thr Val Glu Gly Arg Tyr Tyr Leu Gln
                    385                 390                 395 att tgt acc ctg ttg aaa tgt aaa acg act aat tta aac act tgc ggt      1250
Ile Cys Thr Leu Leu Lys Cys Lys Thr Thr Asn Leu Asn Thr Cys Gly
        400                 405                 410 gac tca gct gaa aca gct tct acc agg ttt gaa atg ttc tcc ctc agt      1298
Asp Ser Ala Glu Thr Ala Ser Thr Arg Phe Glu Met Phe Ser Leu Ser
            415                 420                 425 ggc act ttc gga acc cag tat gtc ttt cct gag gtg ttg ctg agt gaa      1346
Gly Thr Phe Gly Thr Gln Tyr Val Phe Pro Glu Val Leu Leu Ser Glu
    430                 435                 440 aat cag ctt gca cct gga gaa ttt cag gtg tca act gac gga cgc ttg      1394
Asn Gln Leu Ala Pro Gly Glu Phe Gln Val Ser Thr Asp Gly Arg Leu
445                 450                 455                 460 ttt agt ctg aag cca aca tcc gga cct gtc tta aca gta act ctg ttt      1442
Phe Ser Leu Lys Pro Thr Ser Gly Pro Val Leu Thr Val Thr Leu Phe
                    465                 470                 475 ggg agg ttg tat gag aag gac tgg gca tca aat gct tca tca ggc ctc      1490
Gly Arg Leu Tyr Glu Lys Asp Trp Ala Ser Asn Ala Ser Ser Gly Leu
        480                 485                 490 aca gca caa gca aga ata ata atg cta ata gtt ata gca cct att gta      1538
Thr Ala Gln Ala Arg Ile Ile Met Leu Ile Val Ile Ala Pro Ile Val
            495                 500                 505 tgc tca tta agt tgg tag aatattgact ttttctcttt tttatttggg             1586
Cys Ser Leu Ser Trp
        510
```

```
ataatttaaa aaatgatgga tgagaaaaga aagattggtc cgggttaata ttatcctcta  1646
gtataagtga attactagtt tctctttatt tagacaaaca cacacacacc agataatata  1706
aacttaataa attatctgtt aatgtagatt ttatttaaaa aactatattt gaacattggt  1766
ctttcttgga cgtgagctaa ttatatcaaa taagtatcac aaatcttta cgcagaagaa  1826
ataaaaacta cgggtagaaa acataagaac tatcataaaa tttacttaca aggaggctgc  1886
tcttgttacc actttttatta tattacgtat cacttattca gctctgctga aaatttccaa  1946
tgactttgtt tgtttgctct tttagttttt tacctaaaca atacatttg attctcttgt  2006
gggttgataa tgtctcccca aaatttacat gttgaagcac ctcagaatgt gactgtattt  2066
ggagacaggg tctttaaaga ggtaaaataa ggtcattagg atagacccta attcaatatg  2126
actgatgatc ataaaagaag aggcgagtag ggcacaacag gcacaaaggg agaccataag  2186
gagacacaga ggaaggacaa ctctttacaa gctaagaaga gagggcctca aagaaaacca  2246
accctgccaa caccttgatc ttggacttcc agcctccaaa actatgagaa ataaatttct  2306
attgtttaag tcacccagtc catggtactt tgttaggcag ccctggcaaa tgaatcaaag  2366
acccattcct gttcctctcc ccaccactac tgttttctac tgtaatctga agcttcaaca  2426
aaaggcttac ctggtaagaa tattcagctg gtctgggtcc tcaagactcc aatagacact  2486
cttaaagaag gattgctgat ggattgatag tgaaaccatt agatcattga attcctctgg  2546
aattagaaaa ccagagagtc ccatttttaag aaattagata tttaatatag cattgtgtgt  2606
tctattttag taacagcaga atctcttgac attacacaac tcagtgaaac aacatcattt  2666
aagccaaaat atctcccaac tgactgatag actctgagca ctaatatcat agtgctgtga  2726
tgatggacaa ttacatagta ccgataacag ccatgcactg tgcaaagcat gcccttctgc  2786
acaggagagc aaggcacttg cagtagtgat ctatgccagc aaaacatcat tttgagacaa  2846
acatttttgt ggcagatgtt tttcctaaaa agtactatat catccaagaa atatttgagt  2906
aaaatccctt gttctttttgg gtgacattaa ctgacatttg cttttttttca agacctaata  2966
gaaaataaga aagcccataa tgtatttaga aacaggaatc ctcagagcaa ttctctgtat  3026
tctcatataa tttcaatgta aaacagaaaa catattgatg tgttggtgat aggcttgaat  3086
tattaaaaac ttcaaaaaca aaa                                          3109
```

<210> SEQ ID NO 6
<211> LENGTH: 513
<212> TYPE: PRT
<213> ORGANISM: Homo sapiens

<400> SEQUENCE: 6

Met Thr Thr Gln Leu Pro Ala Tyr Val Ala Ile Leu Leu Phe Tyr Val
1               5                   10                  15

Ser Arg Ala Ser Cys Gln Asp Thr Phe Ile Ala Ala Val Tyr Glu His
                20                  25                  30

Ala Ala Ile Leu Pro Asn Ala Thr Leu Thr Pro Val Ser Arg Glu Glu
            35                  40                  45

Ala Leu Ala Leu Met Asn Arg Asn Leu Asp Ile Leu Glu Gly Ala Ile
        50                  55                  60

Thr Ser Ala Ala Asp Gln Gly Ala His Ile Ile Val Thr Pro Glu Asp
65                  70                  75                  80

Ala Ile Tyr Gly Trp Asn Phe Asn Arg Asp Ser Leu Tyr Pro Tyr Leu
                85                  90                  95

Glu Asp Ile Pro Asp Pro Glu Val Asn Trp Ile Pro Cys Asn Asn Arg

```
            100                 105                 110
Asn Arg Phe Gly Gln Thr Pro Val Gln Glu Arg Leu Ser Cys Leu Ala
        115                 120                 125

Lys Asn Asn Ser Ile Tyr Val Ala Asn Ile Gly Asp Lys Lys Pro
130                 135                 140

Cys Asp Thr Ser Asp Pro Gln Cys Pro Pro Asp Gly Arg Tyr Gln Tyr
145                 150                 155                 160

Asn Thr Asp Val Val Phe Asp Ser Gln Gly Lys Leu Val Ala Arg Tyr
                165                 170                 175

His Lys Gln Asn Leu Phe Met Gly Glu Asn Gln Phe Asn Val Pro Lys
            180                 185                 190

Glu Pro Glu Ile Val Thr Phe Asn Thr Thr Phe Gly Ser Phe Gly Ile
        195                 200                 205

Phe Thr Cys Phe Asp Ile Leu Phe His Asp Pro Ala Val Thr Leu Val
    210                 215                 220

Lys Asp Phe His Val Asp Thr Ile Val Phe Pro Thr Ala Trp Met Asn
225                 230                 235                 240

Val Leu Pro His Leu Ser Ala Val Glu Phe His Ser Ala Trp Ala Met
                245                 250                 255

Gly Met Arg Val Asn Phe Leu Ala Ser Asn Ile His Tyr Pro Ser Lys
            260                 265                 270

Lys Met Thr Gly Ser Gly Ile Tyr Ala Pro Asn Ser Ser Arg Ala Phe
        275                 280                 285

His Tyr Asp Met Lys Thr Glu Glu Gly Lys Leu Leu Leu Ser Gln Leu
    290                 295                 300

Asp Ser His Pro Ser His Ser Ala Val Val Asn Trp Thr Ser Tyr Ala
305                 310                 315                 320

Ser Ser Ile Glu Ala Leu Ser Ser Gly Asn Lys Glu Phe Lys Gly Thr
                325                 330                 335

Val Phe Phe Asp Glu Phe Thr Phe Val Lys Leu Thr Gly Val Ala Gly
            340                 345                 350

Asn Tyr Thr Val Cys Gln Lys Asp Leu Cys Cys His Leu Ser Tyr Lys
        355                 360                 365

Met Ser Glu Asn Ile Pro Asn Glu Val Tyr Ala Leu Gly Ala Phe Asp
    370                 375                 380

Gly Leu His Thr Val Glu Gly Arg Tyr Tyr Leu Gln Ile Cys Thr Leu
385                 390                 395                 400

Leu Lys Cys Lys Thr Thr Asn Leu Asn Thr Cys Gly Asp Ser Ala Glu
                405                 410                 415

Thr Ala Ser Thr Arg Phe Glu Met Phe Ser Leu Ser Gly Thr Phe Gly
            420                 425                 430

Thr Gln Tyr Val Phe Pro Glu Val Leu Leu Ser Glu Asn Gln Leu Ala
        435                 440                 445

Pro Gly Glu Phe Gln Val Ser Thr Asp Gly Arg Leu Phe Ser Leu Lys
    450                 455                 460

Pro Thr Ser Gly Pro Val Leu Thr Val Thr Leu Phe Gly Arg Leu Tyr
465                 470                 475                 480

Glu Lys Asp Trp Ala Ser Asn Ala Ser Ser Gly Leu Thr Ala Gln Ala
                485                 490                 495

Arg Ile Ile Met Leu Ile Val Ile Ala Pro Ile Val Cys Ser Leu Ser
            500                 505                 510

Trp
```

-continued

```
<210> SEQ ID NO 7
<211> LENGTH: 2034
<212> TYPE: DNA
<213> ORGANISM: Homo sapiens
<220> FEATURE:
<221> NAME/KEY: CDS
<222> LOCATION: (12)..(1574)

<400> SEQUENCE: 7
```

| | | | | | | | | | | | | | | | | |
|---|---|---|---|---|---|---|---|---|---|---|---|---|---|---|---|---|
| aaaccttggc | c | atg | gtc | act | tcc | tct | ttt | cca | atc | tct | gtg | gca | gtt | ttt | | 50 |
| | | Met | Val | Thr | Ser | Ser | Phe | Pro | Ile | Ser | Val | Ala | Val | Phe | | |
| | | 1 | | | 5 | | | | | 10 | | | | | | |

| gcc | cta | ata | acc | ctg | cag | gtt | ggt | act | cag | gac | agt | ttt | ata | gct | gca | 98 |
|---|---|---|---|---|---|---|---|---|---|---|---|---|---|---|---|---|
| Ala | Leu | Ile | Thr | Leu | Gln | Val | Gly | Thr | Gln | Asp | Ser | Phe | Ile | Ala | Ala | |
| 15 | | | | | 20 | | | | | 25 | | | | | | |

| gtg | tat | gaa | cat | gct | gtc | att | ttg | cca | aat | aaa | aca | gaa | aca | cca | gtt | 146 |
|---|---|---|---|---|---|---|---|---|---|---|---|---|---|---|---|---|
| Val | Tyr | Glu | His | Ala | Val | Ile | Leu | Pro | Asn | Lys | Thr | Glu | Thr | Pro | Val | |
| 30 | | | | 35 | | | | | 40 | | | | | 45 | | |

| tct | cag | gag | gat | gcc | ttg | aat | ctc | atg | aac | gag | aat | ata | gac | att | ctg | 194 |
|---|---|---|---|---|---|---|---|---|---|---|---|---|---|---|---|---|
| Ser | Gln | Glu | Asp | Ala | Leu | Asn | Leu | Met | Asn | Glu | Asn | Ile | Asp | Ile | Leu | |
| | | | 50 | | | | | 55 | | | | | 60 | | | |

| gag | aca | gcg | atc | aag | cag | gca | gct | gag | cag | ggt | gct | cga | atc | att | gtg | 242 |
|---|---|---|---|---|---|---|---|---|---|---|---|---|---|---|---|---|
| Glu | Thr | Ala | Ile | Lys | Gln | Ala | Ala | Glu | Gln | Gly | Ala | Arg | Ile | Ile | Val | |
| | | 65 | | | | | 70 | | | | | 75 | | | | |

| act | cca | gaa | gat | gca | ctt | tat | gga | tgg | aaa | ttt | acc | agg | gaa | act | gtt | 290 |
|---|---|---|---|---|---|---|---|---|---|---|---|---|---|---|---|---|
| Thr | Pro | Glu | Asp | Ala | Leu | Tyr | Gly | Trp | Lys | Phe | Thr | Arg | Glu | Thr | Val | |
| | 80 | | | | | 85 | | | | | 90 | | | | | |

| ttc | cct | tat | ctg | gag | gat | atc | cca | gac | cct | cag | gtg | aac | tgg | att | ccg | 338 |
|---|---|---|---|---|---|---|---|---|---|---|---|---|---|---|---|---|
| Phe | Pro | Tyr | Leu | Glu | Asp | Ile | Pro | Asp | Pro | Gln | Val | Asn | Trp | Ile | Pro | |
| 95 | | | | | 100 | | | | | 105 | | | | | | |

| tgt | caa | gac | ccc | cac | aga | ttt | ggt | cac | aca | cca | gta | caa | gca | aga | ctc | 386 |
|---|---|---|---|---|---|---|---|---|---|---|---|---|---|---|---|---|
| Cys | Gln | Asp | Pro | His | Arg | Phe | Gly | His | Thr | Pro | Val | Gln | Ala | Arg | Leu | |
| 110 | | | | 115 | | | | | 120 | | | | | 125 | | |

| agc | tgc | ctg | gcc | aag | gac | aac | tct | atc | tat | gtc | ttg | gca | aat | ttg | ggg | 434 |
|---|---|---|---|---|---|---|---|---|---|---|---|---|---|---|---|---|
| Ser | Cys | Leu | Ala | Lys | Asp | Asn | Ser | Ile | Tyr | Val | Leu | Ala | Asn | Leu | Gly | |
| | | | 130 | | | | | 135 | | | | | 140 | | | |

| gac | aaa | aag | cca | tgt | aat | tcc | cgt | gac | tcc | aca | tgt | cct | cct | aat | ggc | 482 |
|---|---|---|---|---|---|---|---|---|---|---|---|---|---|---|---|---|
| Asp | Lys | Lys | Pro | Cys | Asn | Ser | Arg | Asp | Ser | Thr | Cys | Pro | Pro | Asn | Gly | |
| | | 145 | | | | | 150 | | | | | 155 | | | | |

| tac | ttt | caa | tac | aat | acc | aat | gtg | gtg | tat | aat | aca | gaa | gga | aaa | ctc | 530 |
|---|---|---|---|---|---|---|---|---|---|---|---|---|---|---|---|---|
| Tyr | Phe | Gln | Tyr | Asn | Thr | Asn | Val | Val | Tyr | Asn | Thr | Glu | Gly | Lys | Leu | |
| | 160 | | | | | 165 | | | | | 170 | | | | | |

| gtg | gca | cgt | tac | cat | aag | tac | cac | ctg | tac | tct | gag | cct | cag | ttt | aat | 578 |
|---|---|---|---|---|---|---|---|---|---|---|---|---|---|---|---|---|
| Val | Ala | Arg | Tyr | His | Lys | Tyr | His | Leu | Tyr | Ser | Glu | Pro | Gln | Phe | Asn | |
| 175 | | | | | 180 | | | | | 185 | | | | | | |

| gtc | cct | gaa | aag | ccg | gag | ttg | gtg | act | ttc | aac | acc | gca | ttt | gga | agg | 626 |
|---|---|---|---|---|---|---|---|---|---|---|---|---|---|---|---|---|
| Val | Pro | Glu | Lys | Pro | Glu | Leu | Val | Thr | Phe | Asn | Thr | Ala | Phe | Gly | Arg | |
| 190 | | | | 195 | | | | | 200 | | | | | 205 | | |

| ttt | ggc | att | ttc | acg | tgc | ttt | gat | ata | ttc | ttc | tat | gat | cct | ggt | gtt | 674 |
|---|---|---|---|---|---|---|---|---|---|---|---|---|---|---|---|---|
| Phe | Gly | Ile | Phe | Thr | Cys | Phe | Asp | Ile | Phe | Phe | Tyr | Asp | Pro | Gly | Val | |
| | | | 210 | | | | | 215 | | | | | 220 | | | |

| acc | ctg | gtg | aaa | gat | ttc | cat | gtg | gac | acc | ata | ctg | ttt | ccc | aca | gct | 722 |
|---|---|---|---|---|---|---|---|---|---|---|---|---|---|---|---|---|
| Thr | Leu | Val | Lys | Asp | Phe | His | Val | Asp | Thr | Ile | Leu | Phe | Pro | Thr | Ala | |
| | | 225 | | | | | 230 | | | | | 235 | | | | |

| tgg | atg | aac | gtt | ttg | ccc | ctt | ttg | aca | gct | att | gaa | ttc | cat | tca | gct | 770 |
|---|---|---|---|---|---|---|---|---|---|---|---|---|---|---|---|---|
| Trp | Met | Asn | Val | Leu | Pro | Leu | Leu | Thr | Ala | Ile | Glu | Phe | His | Ser | Ala | |
| | 240 | | | | | 245 | | | | | 250 | | | | | |

| tgg | gca | atg | gga | atg | gga | gtt | aat | ctt | ctt | gtg | gcc | aac | aca | cat | cat | 818 |
|---|---|---|---|---|---|---|---|---|---|---|---|---|---|---|---|---|
| Trp | Ala | Met | Gly | Met | Gly | Val | Asn | Leu | Leu | Val | Ala | Asn | Thr | His | His | |
| 255 | | | | | 260 | | | | | 265 | | | | | | |

```
gtc agc cta aat atg aca gga agt ggt att tat gca cca aat ggt ccc      866
Val Ser Leu Asn Met Thr Gly Ser Gly Ile Tyr Ala Pro Asn Gly Pro
270             275                 280                 285 aaa gtg tat cat tat gac atg aag aca gag ttg gga aaa ctt ctc ctt      914
Lys Val Tyr His Tyr Asp Met Lys Thr Glu Leu Gly Lys Leu Leu Leu
                290                 295                 300 tca gag gtg gat tca cat ccc cta tcc tcg ctt gcc tac cca aca gct      962
Ser Glu Val Asp Ser His Pro Leu Ser Ser Leu Ala Tyr Pro Thr Ala
            305                 310                 315 gtt aat tgg aat gcc tac gcc acc acc atc aaa cca ttt cca gta cag     1010
Val Asn Trp Asn Ala Tyr Ala Thr Thr Ile Lys Pro Phe Pro Val Gln
        320                 325                 330 aaa aac act ttc agg gga ttt att tcc agg gat ggg ttc aac ttc aca     1058
Lys Asn Thr Phe Arg Gly Phe Ile Ser Arg Asp Gly Phe Asn Phe Thr
    335                 340                 345 gaa ctt ttt gaa aat gca gga aac ctt aca gtc tgt caa aag gag ctt     1106
Glu Leu Phe Glu Asn Ala Gly Asn Leu Thr Val Cys Gln Lys Glu Leu
350                 355                 360                 365 tgc tgt cat tta agc tac aga atg tta caa aaa gaa gag aat gaa gta     1154
Cys Cys His Leu Ser Tyr Arg Met Leu Gln Lys Glu Glu Asn Glu Val
                370                 375                 380 tac gtt cta gga gct ttt aca gga tta cat ggc cga agg aga aga gag     1202
Tyr Val Leu Gly Ala Phe Thr Gly Leu His Gly Arg Arg Arg Arg Glu
            385                 390                 395 tac tgg cag gtc tgc aca atg ctg aag tgc aaa act act aat ttg aca     1250
Tyr Trp Gln Val Cys Thr Met Leu Lys Cys Lys Thr Thr Asn Leu Thr
        400                 405                 410 act tgt gga cgg cca gta gaa act gct tct aca aga ttt gaa atg ttc     1298
Thr Cys Gly Arg Pro Val Glu Thr Ala Ser Thr Arg Phe Glu Met Phe
    415                 420                 425 tcc ctc agt ggc aca ttt gga aca gag tat gtt ttt cct gaa gtg cta     1346
Ser Leu Ser Gly Thr Phe Gly Thr Glu Tyr Val Phe Pro Glu Val Leu
430                 435                 440                 445 ctt acc gaa att cat ctg tca cct gga aaa ttt gag gtg ctg aaa gat     1394
Leu Thr Glu Ile His Leu Ser Pro Gly Lys Phe Glu Val Leu Lys Asp
                450                 455                 460 ggg cgt ttg gta aac aag aat gga tca tct ggg cct ata cta aca gtg     1442
Gly Arg Leu Val Asn Lys Asn Gly Ser Ser Gly Pro Ile Leu Thr Val
            465                 470                 475 tca ctc ttt ggg agg tgg tac aca aag gac tca ctt tac agc tca tgt     1490
Ser Leu Phe Gly Arg Trp Tyr Thr Lys Asp Ser Leu Tyr Ser Ser Cys
        480                 485                 490 ggg acc agc aat tca gca ata act tac ctg cta ata ttc ata tta tta     1538
Gly Thr Ser Asn Ser Ala Ile Thr Tyr Leu Leu Ile Phe Ile Leu Leu
    495                 500                 505 atg atc ata gct ttg caa aat att gta atg tta tag ggcgtctctt          1584
Met Ile Ile Ala Leu Gln Asn Ile Val Met Leu
510                 515                 520 tatcactcag cttctgcatc atatgcttgg ctgaatgtgt ttatcggctt cccaagttta   1644
ctaagaaact ttgaagggct atttcagtag tatagaccag tgagtcctaa atatttttc    1704 tcatcaataa ttatttttta agtattatga taatgttgtc cattttttg gctactctga   1764 aatgttgcag tgtggaacaa tggaaagagc ctgggtgttt gggtcagata aatgaagatc   1824
aaactccagc tccagcctca tttgcttgag actttgtgtg tatgggggac ttgtatgtat   1884
gggagtgagg agtttcaggg ccattgcaaa catagctgtg cccttgaaga gaatagtaat   1944
gatgggaatt tagaggttta tgactgaatt cccttttgaca ttaaagacta tttgaattca   2004
aaaaaaaaaa aaaaaaaaa aaaaaaaaa                                      2034
```

```
<210> SEQ ID NO 8
<211> LENGTH: 520
<212> TYPE: PRT
<213> ORGANISM: Homo sapiens

<400> SEQUENCE: 8

Met Val Thr Ser Ser Phe Pro Ile Ser Val Ala Val Phe Ala Leu Ile
1               5                   10                  15

Thr Leu Gln Val Gly Thr Gln Asp Ser Phe Ile Ala Ala Val Tyr Glu
            20                  25                  30

His Ala Val Ile Leu Pro Asn Lys Thr Glu Thr Pro Val Ser Gln Glu
        35                  40                  45

Asp Ala Leu Asn Leu Met Asn Glu Asn Ile Asp Ile Leu Glu Thr Ala
    50                  55                  60

Ile Lys Gln Ala Ala Glu Gln Gly Ala Arg Ile Val Thr Pro Glu
65                  70                  75                  80

Asp Ala Leu Tyr Gly Trp Lys Phe Thr Arg Glu Thr Val Phe Pro Tyr
                85                  90                  95

Leu Glu Asp Ile Pro Asp Pro Gln Val Asn Trp Ile Pro Cys Gln Asp
            100                 105                 110

Pro His Arg Phe Gly His Thr Pro Val Gln Ala Arg Leu Ser Cys Leu
        115                 120                 125

Ala Lys Asp Asn Ser Ile Tyr Val Leu Ala Asn Leu Gly Asp Lys Lys
    130                 135                 140

Pro Cys Asn Ser Arg Asp Ser Thr Cys Pro Pro Asn Gly Tyr Phe Gln
145                 150                 155                 160

Tyr Asn Thr Asn Val Val Tyr Asn Thr Glu Gly Lys Leu Val Ala Arg
                165                 170                 175

Tyr His Lys Tyr His Leu Tyr Ser Glu Pro Gln Phe Asn Val Pro Glu
            180                 185                 190

Lys Pro Glu Leu Val Thr Phe Asn Thr Ala Phe Gly Arg Phe Gly Ile
        195                 200                 205

Phe Thr Cys Phe Asp Ile Phe Phe Tyr Asp Pro Gly Val Thr Leu Val
    210                 215                 220

Lys Asp Phe His Val Asp Thr Ile Leu Phe Pro Thr Ala Trp Met Asn
225                 230                 235                 240

Val Leu Pro Leu Leu Thr Ala Ile Glu Phe His Ser Ala Trp Ala Met
                245                 250                 255

Gly Met Gly Val Asn Leu Leu Val Ala Asn Thr His His Val Ser Leu
            260                 265                 270

Asn Met Thr Gly Ser Gly Ile Tyr Ala Pro Asn Gly Pro Lys Val Tyr
        275                 280                 285

His Tyr Asp Met Lys Thr Glu Leu Gly Lys Leu Leu Leu Ser Glu Val
    290                 295                 300

Asp Ser His Pro Leu Ser Ser Leu Ala Tyr Pro Thr Ala Val Asn Trp
305                 310                 315                 320

Asn Ala Tyr Ala Thr Thr Ile Lys Pro Phe Pro Val Gln Lys Asn Thr
                325                 330                 335

Phe Arg Gly Phe Ile Ser Arg Asp Gly Phe Asn Phe Thr Glu Leu Phe
            340                 345                 350

Glu Asn Ala Gly Asn Leu Thr Val Cys Gln Lys Glu Leu Cys Cys His
        355                 360                 365

Leu Ser Tyr Arg Met Leu Gln Lys Glu Glu Asn Glu Val Tyr Val Leu
```

```
                      370                 375                 380
Gly Ala Phe Thr Gly Leu His Gly Arg Arg Arg Glu Tyr Trp Gln
385                 390                 395                 400

Val Cys Thr Met Leu Lys Cys Lys Thr Thr Asn Leu Thr Thr Cys Gly
                    405                 410                 415

Arg Pro Val Glu Thr Ala Ser Thr Arg Phe Glu Met Phe Ser Leu Ser
                420                 425                 430

Gly Thr Phe Gly Thr Glu Tyr Val Phe Pro Glu Val Leu Leu Thr Glu
            435                 440                 445

Ile His Leu Ser Pro Gly Lys Phe Glu Val Leu Lys Asp Gly Arg Leu
        450                 455                 460

Val Asn Lys Asn Gly Ser Ser Gly Pro Ile Leu Thr Val Ser Leu Phe
465                 470                 475                 480

Gly Arg Trp Tyr Thr Lys Asp Ser Leu Tyr Ser Ser Cys Gly Thr Ser
                    485                 490                 495

Asn Ser Ala Ile Thr Tyr Leu Leu Ile Phe Ile Leu Leu Met Ile Ile
                500                 505                 510

Ala Leu Gln Asn Ile Val Met Leu
            515                 520

<210> SEQ ID NO 9
<211> LENGTH: 1976
<212> TYPE: DNA
<213> ORGANISM: Homo sapiens
<220> FEATURE:
<221> NAME/KEY: CDS
<222> LOCATION: (113)..(1516)

<400> SEQUENCE: 9
gactggagga gcacaggcct tggaaaggaa agcagctgag atccagagga gtggaaggct       60 ccccttgac taaagctaaa caccagtttc tcaggaggat gccttgaatc tc atg aac       118
                                                          Met Asn
                                                            1 gag aat ata gac att ctg gag aca gcg atc aag cag gca gct gag cag       166
Glu Asn Ile Asp Ile Leu Glu Thr Ala Ile Lys Gln Ala Ala Glu Gln
      5                  10                  15 ggt gct cga atc att gtg act cca gaa gat gca ctt tat gga tgg aaa       214
Gly Ala Arg Ile Ile Val Thr Pro Glu Asp Ala Leu Tyr Gly Trp Lys
 20                  25                  30 ttt acc agg gaa act gtt ttc cct tat ctg gag gat atc cca gac cct       262
Phe Thr Arg Glu Thr Val Phe Pro Tyr Leu Glu Asp Ile Pro Asp Pro
35                  40                  45                  50 cag gtg aac tgg att ccg tgt caa gac ccc aca aga ttt ggt cac aca       310
Gln Val Asn Trp Ile Pro Cys Gln Asp Pro His Arg Phe Gly His Thr
                 55                  60                  65 cca gta caa gca aga ctc agc tgc ctg gcc aag gac aac tct atc tat       358
Pro Val Gln Ala Arg Leu Ser Cys Leu Ala Lys Asp Asn Ser Ile Tyr
             70                  75                  80 gtc ttg gca aat ttg ggg gac aaa aag cca tgt aat tcc cgt gac tcc       406
Val Leu Ala Asn Leu Gly Asp Lys Lys Pro Cys Asn Ser Arg Asp Ser
         85                  90                  95 aca tgt cct cct aat ggc tac ttt caa tac aat acc aat gtg gtg tat       454
Thr Cys Pro Pro Asn Gly Tyr Phe Gln Tyr Asn Thr Asn Val Val Tyr
    100                 105                 110 aat aca gaa gga aaa ctc gtg gca cgt tac cat aag tac cac ctg tac       502
Asn Thr Glu Gly Lys Leu Val Ala Arg Tyr His Lys Tyr His Leu Tyr
115                 120                 125                 130 tct gag cct cag ttt aat gtc cct gaa aag ccg gag ttg gtg act ttc       550
```

```
                Ser Glu Pro Gln Phe Asn Val Pro Glu Lys Pro Glu Leu Val Thr Phe
                                135                 140                 145 aac acc gca ttt gga agg ttt ggc att ttc acg tgc ttt gat ata ttc         598
Asn Thr Ala Phe Gly Arg Phe Gly Ile Phe Thr Cys Phe Asp Ile Phe
            150                 155                 160 ttc tat gat cct ggt gtt acc ctg gtg aaa gat ttc cat gtg gac acc         646
Phe Tyr Asp Pro Gly Val Thr Leu Val Lys Asp Phe His Val Asp Thr
            165                 170                 175 ata ctg ttt ccc aca gct tgg atg aac gtt ttg ccc ctt ttg aca gct         694
Ile Leu Phe Pro Thr Ala Trp Met Asn Val Leu Pro Leu Leu Thr Ala
180                 185                 190 att gaa ttc cat tca gct tgg gca atg gga atg gga gtt aat ctt ctt         742
Ile Glu Phe His Ser Ala Trp Ala Met Gly Met Gly Val Asn Leu Leu
195                 200                 205                 210 gtg gcc aac aca cat cat gtc agc cta aat atg aca gga agt ggt att         790
Val Ala Asn Thr His His Val Ser Leu Asn Met Thr Gly Ser Gly Ile
                215                 220                 225 tat gca cca aat ggt ccc aaa gtg tat cat tat gac atg aag aca gag         838
Tyr Ala Pro Asn Gly Pro Lys Val Tyr His Tyr Asp Met Lys Thr Glu
            230                 235                 240 ttg gga aaa ctt ctc ctt tca gag gtg gat tca cat ccc cta tcc tcg         886
Leu Gly Lys Leu Leu Leu Ser Glu Val Asp Ser His Pro Leu Ser Ser
            245                 250                 255 ctt gcc tac cca aca gct gtt aat tgg aat gcc tac gcc acc acc atc         934
Leu Ala Tyr Pro Thr Ala Val Asn Trp Asn Ala Tyr Ala Thr Thr Ile
260                 265                 270 aaa cca ttt cca gta cag aaa aac act ttc agg gga ttt att tcc agg        982
Lys Pro Phe Pro Val Gln Lys Asn Thr Phe Arg Gly Phe Ile Ser Arg
275                 280                 285                 290 gat ggg ttc aac ttc aca gaa ctt ttt gaa aat gca gga aac ctt aca        1030
Asp Gly Phe Asn Phe Thr Glu Leu Phe Glu Asn Ala Gly Asn Leu Thr
                295                 300                 305 gtc tgt caa aag gag ctt tgc tgt cat tta agc tac aga atg tta caa        1078
Val Cys Gln Lys Glu Leu Cys Cys His Leu Ser Tyr Arg Met Leu Gln
            310                 315                 320 aaa gaa gag aat gaa gta tac gtt cta gga gct ttt aca gga tta cat        1126
Lys Glu Glu Asn Glu Val Tyr Val Leu Gly Ala Phe Thr Gly Leu His
            325                 330                 335 ggc cga agg aga aga gag tac tgg cag gtc tgc aca atg ctg aag tgc        1174
Gly Arg Arg Arg Arg Glu Tyr Trp Gln Val Cys Thr Met Leu Lys Cys
340                 345                 350 aaa act act aat ttg aca act tgt gga cgg cca gta gaa act gct tct        1222
Lys Thr Thr Asn Leu Thr Thr Cys Gly Arg Pro Val Glu Thr Ala Ser
355                 360                 365                 370 aca aga ttt gaa atg ttc tcc ctc agt ggc aca ttt gga aca gag tat        1270
Thr Arg Phe Glu Met Phe Ser Leu Ser Gly Thr Phe Gly Thr Glu Tyr
                375                 380                 385 gtt ttt cct gaa gtg cta ctt acc gaa att cat ctg tca cct gga aaa        1318
Val Phe Pro Glu Val Leu Leu Thr Glu Ile His Leu Ser Pro Gly Lys
            390                 395                 400 ttt gag gtg ctg aaa gat ggg cgt ttg gta aac aag aat gga tca tct        1366
Phe Glu Val Leu Lys Asp Gly Arg Leu Val Asn Lys Asn Gly Ser Ser
            405                 410                 415 ggg cct ata cta aca gtg tca ctc ttt ggg agg tgg tac aca aag gac        1414
Gly Pro Ile Leu Thr Val Ser Leu Phe Gly Arg Trp Tyr Thr Lys Asp
420                 425                 430 tca ctt tac agc tca tgt ggg acc agc aat tca gca ata act tac ctg        1462
Ser Leu Tyr Ser Ser Cys Gly Thr Ser Asn Ser Ala Ile Thr Tyr Leu
435                 440                 445                 450
```

```
cta ata ttc ata tta tta atg atc ata gct ttg caa aat att gta atg      1510
Leu Ile Phe Ile Leu Leu Met Ile Ile Ala Leu Gln Asn Ile Val Met
                455                 460                 465 tta tag ggcgtctctt tatcactcag cttctgcatc atatgcttgg ctgaatgtgt       1566
Leu ttatcggctt cccaagttta ctaagaaact ttgaagggct atttcagtag tatagaccag    1626
tgagtcctaa atattttttc tcatcaataa ttatttttta agtattatga taatgttgtc    1686
catttttttg gctactctga aatgttgcag tgtggaacaa tggaaagagc ctgggtgttt    1746
gggtcagata aatgaagatc aaactccagc tccagcctca tttgcttgag actttgtgtg    1806
tatgggggac ttgtatgtat gggagtgagg agtttcaggg ccattgcaaa catagctgtg    1866
cccttgaaga aatagtaat gatgggaatt tagaggttta tgactgaatt cccttttgaca    1926 ttaaagacta tttgaattca aaaaaaaaaa aaaaaaaaa aaaaaaaaa                 1976

<210> SEQ ID NO 10
<211> LENGTH: 467
<212> TYPE: PRT
<213> ORGANISM: Homo sapiens

<400> SEQUENCE: 10

Met Asn Glu Asn Ile Asp Ile Leu Glu Thr Ala Ile Lys Gln Ala Ala
1               5                   10                  15

Glu Gln Gly Ala Arg Ile Ile Val Thr Pro Glu Asp Ala Leu Tyr Gly
            20                  25                  30

Trp Lys Phe Thr Arg Glu Thr Val Phe Pro Tyr Leu Glu Asp Ile Pro
        35                  40                  45

Asp Pro Gln Val Asn Trp Ile Pro Cys Gln Asp Pro His Arg Phe Gly
    50                  55                  60

His Thr Pro Val Gln Ala Arg Leu Ser Cys Leu Ala Lys Asp Asn Ser
65                  70                  75                  80

Ile Tyr Val Leu Ala Asn Leu Gly Asp Lys Lys Pro Cys Asn Ser Arg
                85                  90                  95

Asp Ser Thr Cys Pro Pro Asn Gly Tyr Phe Gln Tyr Asn Thr Asn Val
            100                 105                 110

Val Tyr Asn Thr Glu Gly Lys Leu Val Ala Arg Tyr His Lys Tyr His
        115                 120                 125

Leu Tyr Ser Glu Pro Gln Phe Asn Val Pro Glu Lys Pro Glu Leu Val
    130                 135                 140

Thr Phe Asn Thr Ala Phe Gly Arg Phe Gly Ile Phe Thr Cys Phe Asp
145                 150                 155                 160

Ile Phe Phe Tyr Asp Pro Gly Val Thr Leu Val Lys Asp Phe His Val
                165                 170                 175

Asp Thr Ile Leu Phe Pro Thr Ala Trp Met Asn Val Leu Pro Leu Leu
            180                 185                 190

Thr Ala Ile Glu Phe His Ser Ala Trp Ala Met Gly Met Gly Val Asn
        195                 200                 205

Leu Leu Val Ala Asn Thr His His Val Ser Leu Asn Met Thr Gly Ser
    210                 215                 220

Gly Ile Tyr Ala Pro Asn Gly Pro Lys Val Tyr His Tyr Asp Met Lys
225                 230                 235                 240

Thr Glu Leu Gly Lys Leu Leu Leu Ser Glu Val Asp Ser His Pro Leu
                245                 250                 255

Ser Ser Leu Ala Tyr Pro Thr Ala Val Asn Trp Asn Ala Tyr Ala Thr
            260                 265                 270
```

```
Thr Ile Lys Pro Phe Pro Val Gln Lys Asn Thr Phe Arg Gly Phe Ile
        275                 280                 285

Ser Arg Asp Gly Phe Asn Phe Thr Glu Leu Phe Glu Asn Ala Gly Asn
    290                 295                 300

Leu Thr Val Cys Gln Lys Glu Leu Cys Cys His Leu Ser Tyr Arg Met
305                 310                 315                 320

Leu Gln Lys Glu Glu Asn Glu Val Tyr Val Leu Gly Ala Phe Thr Gly
                325                 330                 335

Leu His Gly Arg Arg Arg Glu Tyr Trp Gln Val Cys Thr Met Leu
                340                 345                 350

Lys Cys Lys Thr Thr Asn Leu Thr Thr Cys Gly Arg Pro Val Glu Thr
                355                 360                 365

Ala Ser Thr Arg Phe Glu Met Phe Ser Leu Ser Gly Thr Phe Gly Thr
370                 375                 380

Glu Tyr Val Phe Pro Glu Val Leu Leu Thr Glu Ile His Leu Ser Pro
385                 390                 395                 400

Gly Lys Phe Glu Val Leu Lys Asp Gly Arg Leu Val Asn Lys Asn Gly
                405                 410                 415

Ser Ser Gly Pro Ile Leu Thr Val Ser Leu Phe Gly Arg Trp Tyr Thr
                420                 425                 430

Lys Asp Ser Leu Tyr Ser Ser Cys Gly Thr Ser Asn Ser Ala Ile Thr
                435                 440                 445

Tyr Leu Leu Ile Phe Ile Leu Leu Met Ile Ile Ala Leu Gln Asn Ile
    450                 455                 460

Val Met Leu
465

<210> SEQ ID NO 11
<211> LENGTH: 1733
<212> TYPE: DNA
<213> ORGANISM: Homo sapiens
<220> FEATURE:
<221> NAME/KEY: CDS
<222> LOCATION: (73)..(897)

<400> SEQUENCE: 11
atgtaaagtt tttccagtga acaaaaacgt aagaatctga gtttgttttt caaagatcac    60
taaattttag tt atg att ata tca cat ttt cca aaa tgt gtg gca gtt ttt   111
             Met Ile Ile Ser His Phe Pro Lys Cys Val Ala Val Phe
               1               5                  10 gcc ctc ctt gct ctg agt gtt ggt gca ctg gac act ttt att gct gca    159
Ala Leu Leu Ala Leu Ser Val Gly Ala Leu Asp Thr Phe Ile Ala Ala
         15                  20                  25 gta tat gag cat gcg gtg ata tta cca aac aga aca gaa aca cct gtt    207
Val Tyr Glu His Ala Val Ile Leu Pro Asn Arg Thr Glu Thr Pro Val
 30                  35                  40                  45 tca aaa gaa gaa gct ttg ctc ctg atg aac aag aac ata gat gtt ttg    255
Ser Lys Glu Glu Ala Leu Leu Leu Met Asn Lys Asn Ile Asp Val Leu
                 50                  55                  60 gag aaa gca gtt aag ctg gca gcg aag cag ggt gca cat atc att gtg    303
Glu Lys Ala Val Lys Leu Ala Ala Lys Gln Gly Ala His Ile Ile Val
             65                  70                  75 acc cca gaa gat gga atc tat ggt tgg atc ttc acc agg gag agc att    351
Thr Pro Glu Asp Gly Ile Tyr Gly Trp Ile Phe Thr Arg Glu Ser Ile
         80                  85                  90 tac ccc tat cta gag gat ata cca gac cct gga gtg aac tgg att cca    399
Tyr Pro Tyr Leu Glu Asp Ile Pro Asp Pro Gly Val Asn Trp Ile Pro
```

-continued

```
              95                  100                 105
tgt aga gac ccc tgg aga ttc ggc aac aca cca gtg caa caa aga ctc      447
Cys Arg Asp Pro Trp Arg Phe Gly Asn Thr Pro Val Gln Gln Arg Leu
110                 115                 120                 125 agc tgc ctg gcc aag gac aac tct atc tat gtc gtg gct aat att ggg      495
Ser Cys Leu Ala Lys Asp Asn Ser Ile Tyr Val Val Ala Asn Ile Gly
                130                 135                 140 gac aag aag cca tgc aat gcc agt gac tct cag tgt ccc cct gat ggc      543
Asp Lys Lys Pro Cys Asn Ala Ser Asp Ser Gln Cys Pro Pro Asp Gly
            145                 150                 155 cgt tac caa tac aac act gat gtg gtg ttt gat tct cag gga aaa ctg      591
Arg Tyr Gln Tyr Asn Thr Asp Val Val Phe Asp Ser Gln Gly Lys Leu
        160                 165                 170 ttg gca cgc tac cat aag tac aat ctt ttt gca cct gaa att cag ttt      639
Leu Ala Arg Tyr His Lys Tyr Asn Leu Phe Ala Pro Glu Ile Gln Phe
    175                 180                 185 gat ttc ccc aag gat tca gaa ctt gtg act ttt gac act ccc ttt ggg      687
Asp Phe Pro Lys Asp Ser Glu Leu Val Thr Phe Asp Thr Pro Phe Gly
190                 195                 200                 205 aag ttt ggc att ttt act tgc ttt gac att ttt tct cat gac cca gct      735
Lys Phe Gly Ile Phe Thr Cys Phe Asp Ile Phe Ser His Asp Pro Ala
                210                 215                 220 gtg gtg gtg gtg gat gag ttt caa ttg aca gca ttc tct acc cca cag      783
Val Val Val Val Asp Glu Phe Gln Leu Thr Ala Phe Ser Thr Pro Gln
            225                 230                 235 cat ggt aca aca cgc tgc ccc tcc tct cgg ctg ttc cct tcc att cag      831
His Gly Thr Thr Arg Cys Pro Ser Ser Arg Leu Phe Pro Ser Ile Gln
        240                 245                 250 cat ggg cca agg cca tgg gag tca atc tac ttg ctg caa ata ccc aca      879
His Gly Pro Arg Pro Trp Glu Ser Ile Tyr Leu Leu Gln Ile Pro Thr
    255                 260                 265 aca cca gca tgc aca tga cagggagtgg aatctacgcc ccagaagcag             927
Thr Pro Ala Cys Thr
270 tcaaggtgta ccactatgac atggaaacag agagtggtca gctgttgcta tcagaactga   987
agtctcggcc ccgccgtgag cccacctacc ctgcagctgt tgactggcat gcgtatgcca  1047
gcagtgtcaa gccatttttcc tctgaacagt cagattttct ggggatgatt tattttgatg  1107
agtttacctt caccaagctt aagagaaata caggaaatta cacagcttgc cagaaagatc  1167
tgtgttgtca cttaacttac aagatgtctg agaagcgaac agacgagatc tatgccctag  1227
gtgcttttga tggactgcac acagtagaag gccaatatta cttacagata tgtgcattac  1287
tgaagtgtca aaccactgac ctggaaacgt gtggagaacc tgtggggtca gcttttacca  1347
agtttgaaga cttctccctc agtggcacat ttggaacgcg ttatgttttc ccacagatca  1407
ttctaagtgg gagtcagctt gcccctgaaa gacattatga gatttcaaga gatggacgct  1467
tgaggagccg aagtggagcc ctttgcctg tcttagttat ggccctgtat ggaagagtgt  1527
ttgagaagga ccctccacgc ttagggcagg atctgggaa attccagtga tctcctttag  1587
cagagccctt ttaggattag cctggctaag aaaggaagaa aaaaagaga tccgttagtg  1647
tctgtttaga aaagatgtta taaacttaca gaaacaaata taataaactg aagcagattt  1707
gaaaagcaaa aaaaaaaaaa aaaaa                                         1733
```

<210> SEQ ID NO 12
<211> LENGTH: 274
<212> TYPE: PRT
<213> ORGANISM: Homo sapiens

<400> SEQUENCE: 12

Met Ile Ile Ser His Phe Pro Lys Cys Val Ala Val Phe Ala Leu Leu
1               5                   10                  15

Ala Leu Ser Val Gly Ala Leu Asp Thr Phe Ile Ala Ala Val Tyr Glu
            20                  25                  30

His Ala Val Ile Leu Pro Asn Arg Thr Glu Thr Pro Val Ser Lys Glu
        35                  40                  45

Glu Ala Leu Leu Leu Met Asn Lys Asn Ile Asp Val Leu Glu Lys Ala
    50                  55                  60

Val Lys Leu Ala Ala Lys Gln Gly Ala His Ile Ile Val Thr Pro Glu
65                  70                  75                  80

Asp Gly Ile Tyr Gly Trp Ile Phe Thr Arg Glu Ser Ile Tyr Pro Tyr
                85                  90                  95

Leu Glu Asp Ile Pro Asp Pro Gly Val Asn Trp Ile Pro Cys Arg Asp
            100                 105                 110

Pro Trp Arg Phe Gly Asn Thr Pro Val Gln Gln Arg Leu Ser Cys Leu
        115                 120                 125

Ala Lys Asp Asn Ser Ile Tyr Val Val Ala Asn Ile Gly Asp Lys Lys
    130                 135                 140

Pro Cys Asn Ala Ser Asp Ser Gln Cys Pro Pro Asp Gly Arg Tyr Gln
145                 150                 155                 160

Tyr Asn Thr Asp Val Val Phe Asp Ser Gln Gly Lys Leu Leu Ala Arg
                165                 170                 175

Tyr His Lys Tyr Asn Leu Phe Ala Pro Glu Ile Gln Phe Asp Phe Pro
            180                 185                 190

Lys Asp Ser Glu Leu Val Thr Phe Asp Thr Pro Phe Gly Lys Phe Gly
        195                 200                 205

Ile Phe Thr Cys Phe Asp Ile Phe Ser His Asp Pro Ala Val Val Val
    210                 215                 220

Val Asp Glu Phe Gln Leu Thr Ala Phe Ser Thr Pro Gln His Gly Thr
225                 230                 235                 240

Thr Arg Cys Pro Ser Ser Arg Leu Phe Pro Ser Ile Gln His Gly Pro
                245                 250                 255

Arg Pro Trp Glu Ser Ile Tyr Leu Leu Gln Ile Pro Thr Thr Pro Ala
            260                 265                 270

Cys Thr

<210> SEQ ID NO 13
<211> LENGTH: 1932
<212> TYPE: DNA
<213> ORGANISM: Homo sapiens
<220> FEATURE:
<221> NAME/KEY: CDS
<222> LOCATION: (73)..(516)

<400> SEQUENCE: 13
atgtaaagtt tttccagtga acaaaacgt aagaatctga gtttgttttt caaagatcac      60
taaattttag tt atg att ata tca cat ttt cca aaa tgt gtg gca gtt ttt   111
            Met Ile Ile Ser His Phe Pro Lys Cys Val Ala Val Phe
            1               5                   10 gcc ctc ctt gct ctg agt gtt ggt gca ctg gac act ttt att gct gca    159
Ala Leu Leu Ala Leu Ser Val Gly Ala Leu Asp Thr Phe Ile Ala Ala
    15                  20                  25 gta tat gag cat gcg gtg ata tta cca aac aga aca gaa aca cct gtt    207
Val Tyr Glu His Ala Val Ile Leu Pro Asn Arg Thr Glu Thr Pro Val

```
              30                  35                  40                  45
tca aaa gaa gaa gct ttg ctc ctg atg aac aag aac ata gat gtt ttg      255
Ser Lys Glu Glu Ala Leu Leu Leu Met Asn Lys Asn Ile Asp Val Leu
             50                  55                  60 gag aaa gca gtt aag ctg gca gcg aag cag ggt gca cat atc att gtg      303
Glu Lys Ala Val Lys Leu Ala Ala Lys Gln Gly Ala His Ile Ile Val
         65                  70                  75 acc cca gaa gat gga atc tat ggt tgg atc ttc acc agg gag agc att      351
Thr Pro Glu Asp Gly Ile Tyr Gly Trp Ile Phe Thr Arg Glu Ser Ile
     80                  85                  90 tac ccc tat cta gag gat ata cca gac cct gga gtg aac tgg att cca      399
Tyr Pro Tyr Leu Glu Asp Ile Pro Asp Pro Gly Val Asn Trp Ile Pro
 95                 100                 105 tgt aga gac ccc tgg agg aag agt aaa aag atg aat gag cct gtt tcc      447
Cys Arg Asp Pro Trp Arg Lys Ser Lys Lys Met Asn Glu Pro Val Ser
110                 115                 120                 125 aaa gag ctt tgc tat cac tgt cat tca gaa tgc aat caa tat ggc caa      495
Lys Glu Leu Cys Tyr His Cys His Ser Glu Cys Asn Gln Tyr Gly Gln
                130                 135                 140 tgg aaa ttg tat agg act tga aaaggaagc cctacttctg ggaccacatt          546
Trp Lys Leu Tyr Arg Thr
            145 ttacgaccac ctagctgagt gataaatcac taaaatatag taagtttgag gaaatgtcta    606
ttgaattaga ttcggcaaca caccagtgca acaaagactc agctgcctgg ccaaggacaa    666
ctctatctat gtcgtggcta atattgggga caagaagcca tgcaatgcca gtgactctca    726
gtgtcccct gatggccgtt accaatacaa cactgatgtg gtgtttgatt ctcagggaaa     786
actgttggca cgctaccata agtacaatct ttttgcacct gaaattcagt ttgatttccc    846
caaggattca gaacttgtga cttttgacac tcccttggg aagttggca tttttacttg      906
ctttgacatt ttttctcatg acccagctgt ggtggtggtg gatgagtttc aattgacagc    966
attctctacc ccacagcatg gtacaacacg ctgcccctcc tctcggctgt tcccttccat   1026
tcagcatggg ccaaggccat gggagtcaat ctacttgctg caaatacca caacaccagc    1086
atgcacatga cagggagtgg aatctacgcc ccagaagcag tcaaggtgta ccactatgac   1146
atggaaacag agagtggtca gctgttgcta tcagaactga agtctcggcc ccgccgtgag   1206
cccacctacc ctgcagctgt tgactggcat gcgtatgcca gcagtgtcaa gccatttcc    1266
tctgaacagt cagattttct ggggatgatt tattttgatg agtttacctt caccaagctt   1326
aagagaaata caggaaatta cacagcttgc cagaaagatc tgtgttgtca cttaacttac   1386
aagatgtctg agaagcgaac agacgagatc tatgccctag gtgcttttga tggactgcac   1446
acagtagaag gccaatatta cttcagata tgtgcattac tgaagtgtca aaccactgac    1506
ctggaaacgt gtggagaacc tgtggggtca gcttttacca gtttgaaga cttctccctc    1566
agtggcacat ttggaacgcg ttatgttttc ccacagatca ttctaagtgg gagtcagctt   1626
gcccctgaaa gacattatga gatttcaaga gatggacgct tgaggagccg aagtggagcc   1686
ccttttgcctg tcttagttat ggccctgtat ggaagagtgt ttgagaagga ccctccacgc   1746
ttagggcagg gatctgggaa attccagtga tctcctttag cagagccctt ttaggattag   1806
cctggctaag aaaggaagaa aaaaagaga tccgttagtg tctgtttaga aaagatgtta    1866
taaacttaca gaaacaaata taataaactg aagcagattt gaaaagcaaa aaaaaaaaa    1926
aaaaaa                                                              1932
```

-continued

<210> SEQ ID NO 14
<211> LENGTH: 147
<212> TYPE: PRT
<213> ORGANISM: Homo sapiens

<400> SEQUENCE: 14

Met Ile Ile Ser His Phe Pro Lys Cys Val Ala Val Phe Ala Leu Leu
1               5                   10                  15

Ala Leu Ser Val Gly Ala Leu Asp Thr Phe Ile Ala Ala Val Tyr Glu
            20                  25                  30

His Ala Val Ile Leu Pro Asn Arg Thr Glu Thr Pro Val Ser Lys Glu
        35                  40                  45

Glu Ala Leu Leu Leu Met Asn Lys Asn Ile Asp Val Leu Glu Lys Ala
    50                  55                  60

Val Lys Leu Ala Ala Lys Gln Gly Ala His Ile Ile Val Thr Pro Glu
65                  70                  75                  80

Asp Gly Ile Tyr Gly Trp Ile Phe Thr Arg Glu Ser Ile Tyr Pro Tyr
                85                  90                  95

Leu Glu Asp Ile Pro Asp Pro Gly Val Asn Trp Ile Pro Cys Arg Asp
            100                 105                 110

Pro Trp Arg Lys Ser Lys Met Asn Glu Pro Val Ser Lys Glu Leu
        115                 120                 125

Cys Tyr His Cys His Ser Glu Cys Asn Gln Tyr Gly Gln Trp Lys Leu
130                 135                 140

Tyr Arg Thr
145

<210> SEQ ID NO 15
<211> LENGTH: 1779
<212> TYPE: DNA
<213> ORGANISM: Homo sapiens
<220> FEATURE:
<221> NAME/KEY: CDS
<222> LOCATION: (73)..(426)

<400> SEQUENCE: 15
atgtaaagtt tttccagtga acaaaacgt aagaatctga gtttgttttt caaagatcac     60
taaattttag tt atg att ata tca cat ttt cca aaa tgt gtg gca gtt ttt    111
            Met Ile Ile Ser His Phe Pro Lys Cys Val Ala Val Phe
            1               5                   10 gcc ctc ctt gct ctg agt gtt ggt gca ctg gac act ttt att gct gca    159
Ala Leu Leu Ala Leu Ser Val Gly Ala Leu Asp Thr Phe Ile Ala Ala
    15                  20                  25 gta tat gag cat gcg gtg ata tta cca aac aga aca gaa aca cct gtt    207
Val Tyr Glu His Ala Val Ile Leu Pro Asn Arg Thr Glu Thr Pro Val
30                  35                  40                  45 tca aaa gaa gaa gct ttg ctc ctg atg aac aag aac ata gat gtt ttg    255
Ser Lys Glu Glu Ala Leu Leu Leu Met Asn Lys Asn Ile Asp Val Leu
                50                  55                  60 gag aaa gca gtt aag ctg gca gcg aag cag ggt gca cat atc att gtg    303
Glu Lys Ala Val Lys Leu Ala Ala Lys Gln Gly Ala His Ile Ile Val
            65                  70                  75 acc cca gaa gat gga atc tat ggt tgg atc ttc acc agg gag agc att    351
Thr Pro Glu Asp Gly Ile Tyr Gly Trp Ile Phe Thr Arg Glu Ser Ile
        80                  85                  90 tac ccc tat cta gag gat ata cca gac cct gga gtg aac tgg att cca    399
Tyr Pro Tyr Leu Glu Asp Ile Pro Asp Pro Gly Val Asn Trp Ile Pro
    95                  100                 105 tgt aga gac ccc tgg aga aat cac taa aatatagtaa gtttgaggaa           446
Cys Arg Asp Pro Trp Arg Asn His

```
Cys Arg Asp Pro Trp Arg Asn His
110                 115 atgtctattg aattagattc ggcaacacac cagtgcaaca aagactcagc tgcctggcca     506
aggacaactc tatctatgtc gtggctaata ttggggacaa gaagccatgc aatgccagtg     566
actctcagtg tccccctgat ggccgttacc aatacaacac tgatgtggtg tttgattctc     626
agggaaaact gttggcacgc taccataagt acaatctttt tgcacctgaa attcagtttg     686
atttccccaa ggattcagaa cttgtgactt ttgacactcc ctttgggaag tttggcattt     746
ttacttgctt tgacattttt tctcatgacc cagctgtggt ggtggtggat gagtttcaat     806
tgacagcatt ctctacccca cagcatggta acacgctg cccctcctct cggctgttcc       866
cttccattca gcatgggcca aggccatggg agtcaatcta cttgctgcaa atacccacaa     926
caccagcatg cacatgacag ggagtggaat ctacgcccca gaagcagtca aggtgtacca     986
ctatgacatg gaaacagaga gtggtcagct gttgctatca gaactgaagt ctcggccccg   1046
ccgtgagccc acctaccctg cagctgttga ctggcatgcg tatgccagca gtgtcaagcc   1106
attttcctct gaacagtcag attttctggg gatgatttat tttgatgagt ttaccttcac   1166
caagcttaag agaaatacag gaaattacac agcttgccag aaagatctgt gttgtcactt   1226
aacttacaag atgtctgaga gcgaacaga cgagatctat gccctaggtg cttttgatgg    1286
actgcacaca gtagaaggcc aatattactt acagatatgt gcattactga agtgtcaaac   1346
cactgacctg gaaacgtgtg agaacctgt ggggtcagct tttaccaagt tgaagactt     1406 ctccctcagt ggcacatttg gaacgcgtta tgttttccca cagatcattc taagtgggag   1466
tcagcttgcc cctgaaagac attatgagat ttcaagagat ggacgcttga ggagccgaag   1526
tggagcccct ttgcctgtct tagttatggc cctgtatgga agagtgtttg agaaggaccc   1586
tccacgctta gggcagggat ctgggaaatt ccagtgatct cctttagcag agccctttta   1646
ggattagcct ggctaagaaa ggaagaaaaa aaagagatcc gttagtgtct gtttagaaaa   1706
gatgttataa acttacagaa acaaatataa taaactgaag cagatttgaa aagcaaaaaa   1766
aaaaaaaaaa aaa                                                     1779
```

<210> SEQ ID NO 16
<211> LENGTH: 117
<212> TYPE: PRT
<213> ORGANISM: Homo sapiens

<400> SEQUENCE: 16

```
Met Ile Ile Ser His Phe Pro Lys Cys Val Ala Val Phe Ala Leu Leu
1               5                   10                  15

Ala Leu Ser Val Gly Ala Leu Asp Thr Phe Ile Ala Ala Val Tyr Glu
            20                  25                  30

His Ala Val Ile Leu Pro Asn Arg Thr Glu Thr Pro Val Ser Lys Glu
        35                  40                  45

Glu Ala Leu Leu Leu Met Asn Lys Asn Ile Asp Val Leu Glu Lys Ala
    50                  55                  60

Val Lys Leu Ala Ala Lys Gln Gly Ala His Ile Ile Val Thr Pro Glu
65                  70                  75                  80

Asp Gly Ile Tyr Gly Trp Ile Phe Thr Arg Glu Ser Ile Tyr Pro Tyr
                85                  90                  95

Leu Glu Asp Ile Pro Asp Pro Gly Val Asn Trp Ile Pro Cys Arg Asp
                100                 105                 110

Pro Trp Arg Asn His
            115
```

<210> SEQ ID NO 17
<211> LENGTH: 36369
<212> TYPE: DNA
<213> ORGANISM: Homo sapiens

<400> SEQUENCE: 17

| | | | | | |
|---|---|---|---|---|---|
| gttaccttgg | caattgcaga | ataaatgcat | tatagttact | aaagtaaaaa | attagatatg | 60 |
| cctgtttgca | gattgaacta | taaaaatacc | attcaaagac | aaatagatct | aaaaataaaa | 120 |
| tggaaaaaca | taaacactaa | ttctgtaaat | attatactta | atgcacaact | gaaacaaaat | 180 |
| ttgccagctt | actcaatatc | aaaatctatg | aacagttttt | ctattttata | taatttccct | 240 |
| ctcctctctc | tggatctcgc | tccccagctc | atttttttctt | tttttttgctc | tgattctttta | 300 |
| tacacctctg | ttgcctctgt | gataagcagc | ttcaaagatg | gttcctaatg | ctttattgga | 360 |
| tagaatacaa | caaaagcgat | gaggtgttgc | ttccccaatt | acattacgaa | gcatccgtgg | 420 |
| cttccatctc | cagtgggttc | acttgctgtc | tggctctaag | ggaatccaga | taccataatg | 480 |
| cgggctgccc | tatggtgagg | tttgcatcac | taggaactca | tgtctctggg | caacaaccaa | 540 |
| tgaggtcttg | atccctgccg | tcagccacat | gagggagctt | ggagctcgga | agtgaatcct | 600 |
| cctggagtca | agccttgata | tagctagccc | tggcagctgc | ttgactgcag | ccttgtgaaa | 660 |
| gagaccttgg | gccagaggca | ccagctaaac | tgccctggga | ttcctgaccc | agagaaagtg | 720 |
| ggagatgatg | tattttttgct | ttttgaagct | gctgaatttg | gggataattt | gttatatagc | 780 |
| aatagaaaat | gagtaactct | tttgtattcc | tctttgtcct | ggcttcccca | ttttgaggaa | 840 |
| aataaagtaa | atcaaagtgt | agagctgaaa | tattcacatg | aaaataataa | taaagtttta | 900 |
| aaattatttg | aatgtcttgt | gttgacattc | caaaatatat | gaattccaaa | aatttatatg | 960 |
| ttgaagtcct | aactgtcagt | atcttagaat | gtaactttt | tggaaaaggg | gtcatttcag | 1020 |
| atctaattag | ttaagatgaa | gttatactgg | agtacagtgg | gcactaaatc | gaattggtcc | 1080 |
| tatgattgag | tctcagtctt | tcagtgagcc | tgtacccctg | ggtttatgac | cttcagttgg | 1140 |
| ctttttttctt | ctgcccttat | ttggcataaa | acaaagcag | gtggatcacc | tgaggtcagc | 1200 |
| aatttgagac | cagcctgccc | aacacggcga | aaccctgtct | ctactaaaaa | tacaaaaaat | 1260 |
| tagcctggcg | tggtggcggg | cgcctgtaat | cccagctact | tgggaggctg | aggcaggaga | 1320 |
| atcacatgaa | cccgagaggc | ggaggttgca | gtgagccaag | atttcgccac | tgcactctag | 1380 |
| cctgggtgac | aagagtgaaa | ctccatctca | aacaacaaca | acaataaaca | aacaacaacg | 1440 |
| atgacaaaaa | aagctagagc | tgggattttc | cctttccctg | tgttaaagat | tagagtggtg | 1500 |
| tcctcacaaa | aagggaaaac | ttggatacag | gcacacacat | ggggagaata | gcatatgaag | 1560 |
| agacacaggg | agaaggcagc | catctatggg | tcaaggagag | aggcctggaa | cacatctttc | 1620 |
| cttcaccgcc | ctcaggagga | accaactctg | ctgacacctt | catctgggac | tcccaccctc | 1680 |
| cagaactgca | aagcaataaa | tttttatttt | tttacaccac | ccagtttatt | gtattttgtt | 1740 |
| aggcagccct | agcgaactaa | tgtacataga | gttcttgagt | taatcttcac | aaattactgc | 1800 |
| aataagggag | ggtcttttgt | tatgtaacaa | tgctatgaaa | tcatagcgtt | ttcttaatta | 1860 |
| acttccgtag | tttaaggtac | taagttctgg | acaccacgtg | tcttctttct | ataaatacca | 1920 |
| ggacatgctc | tgttttttcag | cactcattgg | acttcagcat | gactactcag | ttgccagctt | 1980 |
| acgtggcaat | tttgcttttc | tatgtctcaa | gagccagctg | ccaggacact | ttcattgcag | 2040 |
| ctgtttatga | gcatgcagcg | atattgccca | atgccaccct | aacaccagtg | tctcgtgagg | 2100 |

```
aggctttggc attaatgaat cggaatctgg acattttgga aggagcgatc acatcagcag   2160
cagatcaggt accatctcta ccatctctcc agtgtactgg attctatgag aaaggagggg   2220
gtcctaggag acagggccac tgtcagggtc agttacactt ttagatgata tatgtatcag   2280
agtagccaag aacctttatt ttacagttag aattctactt tcctctcaaa attagagcaa   2340
ggacttccct aaaagtaaga acaaagttaa gaaagaaca atttgctcat tatcaagaag    2400
cagcagacct tgaggaact ggccataaat tcaacatctt tgttcccctt ttctggtaca    2460
gatggaggat ggaggataaa tgggtcaggg actaggtgct attttcagag tattagtggc   2520
cttcatgtac tcatgtgcta ttaaggcttt gcaggttttc aataaatttt ataatctgaa   2580
aacaaattta agttttcaat tccttgccag catgcattat atacttcaca cttcattcta   2640
attacaagat aaaagtatat gtaatgcatt gtgagtcctt aagtttagtg aaggtttcag   2700
tttgaagtta atcatacagt ataaattgtg gtttacacaa atattatttt aaaagctatt   2760
gatcgattag gtgtagacca ggaatacatg aagtgtgata aagtcatgg ataaatgtgt    2820 attacatata tctataaata tatattcttt tgtgttgttg agttaaggtc tcactctgtc   2880
acccaggatg gagtatagtg gtgtgatcac gtctcactgc agccttgact tcccgggctc   2940
aggtgattct cccactacag tctccagagt agctgggacc acagatgcat gccaccgtgc   3000
ccagctaagt tttgtatttt ttgtagagat gggattttgc catgttgccc acgctggact   3060
tgaactcctg acctcaggtg atccacctgc cttgggctcc caaagtgctg ggattacagg   3120
catgagctac cgtgactgcc ctatattctt atatatacta atatttaaaa ggttatcagg   3180
agttctgatg ttcttttca tccttagtcc aactatttcc ttgaaggtca cagagctttt    3240
taaggtgact ctctaattgg aaggtgccca ggttagctca ggcagtactt gtaggcatgg   3300
gacagttcaa gtaaccagtt tgtggctcct cttttctga aagcaggaa tcatgtttgc     3360 aggggaaagc tagggcagag gaggaaataa acagaatatt taagttatta atcagtcttg   3420
acacaggcac agtcatcagc gaaagttcaa ggagaggctt ggttccagga taagctaggt   3480
ttatagttaa cgactgccat aggaaacaac aatggcagga ttagaaaatt aaaatgcttg   3540
actaagccag gtgcggtggc tcatgtctgt aattccaaca ctttgggagg ctgaagcagg   3600
cggatcacct gaggtgggga gttcaagacc atcctgacca atatggagaa accccatctc   3660
tactaaaaat acaaaaatta gccaggcgtg gtggcagatg cctgtgatcc tagctactta   3720
tgaggctgag gcgggagaat cgcttgaacc cgggaggtgg agattgtggt aagccgagat   3780
ctagccattg cactccagcc tgggcagcag agcgaaactc catctgaaaa aaaaaaaaa    3840 gagagaaaaa aaaatgcttg actagaagcc caaacctcac cattatgtaa catatccatg   3900
caacaaacct gcatttgtac cctttgaatc taaaattaga aataaagaaa agaaaagaaa   3960
aagaaaaaga agtgacagtg cactgaaaaa aaggaaatt aaaatgcttt ggaaaagaaa    4020
ataaattata aaatataga aacaaaata agatttaagg ggtgtggggg aagcccaaat     4080
agttgttact cagccactca gctcctcagc tcctcttgca ggcccccctt tggattaagt   4140
tgcattttta acagggtgcg catattattg tgactccaga agatgctatt tatggctgga   4200
acttcaacag ggactctctc tacccatatt tggaggacat cccagaccct gaagtaaact   4260
ggatcccctg taataatcgt aacaggtaaa gaaacaactt gtgaaaatt cactagtaaa    4320 catcaacttg atttacctgg gaaaactttg ttgatgatca ttgcatagat ccacgatcaa   4380
ttcttaagtt tcagtatagc ttatttttca tctactatgg gtatatttac tgggagagca   4440
```

-continued

```
aatatgaatt atgaagtcac agaaatcaga gctagaaagt agcttagaaa tcatcacatt    4500
cagtgtgaac atctctggtc tctgactcct caccagtgaa cagaaaaata tttccctgtg    4560
taggtctgtg atttgaaaac tatatgagta aatggcaaaa gagagtcaca tcagtttaag    4620
attaatagtt ttccttctc attgctaaga tagctgatga ggttaatgta gtaaaagtcc     4680
ttaaagtgta agctgattgt aatctaagag gtgatatggc aggattttaa gtggtttaag    4740
tcaggtctcg gctacagaga tattaagtgt ggtgaaagca gcactattaa ttttaatgta    4800
aggaaaccaa tatcttatac acctaagaaa atcatgtcga ttcacatact tctttctgaa    4860
tacacatggc taaaattatt ttaggaattc ctcttttgga actattctca aaaccgcaca    4920
acgccagtta gaatggtgat cattaaaaag tcaggaaaca acagatgctg gagaggatgt    4980
ggagaaaggg gaactctttt acactgttgg tgggagtata aattagttca accattgtgg    5040
aagacagtgt ggtgattcct caaggatcta gaaccagaaa taccatttga cccaccaatc    5100
ccattactgg gtatatacca aaggatcata aatcatttta ctataaagac acatgcatgc    5160
atatgtttat tgcagcactg ttcacaatag caaagacttg gaaccaaccc aaataccat     5220 caatggtaga ctggataaag aaaatgtggc acatatatac cacagaacac tacacagctg    5280
taaaaaagga taagttcatg tcctttgcag ggacatggat aaagctggaa accatcattc    5340
tcagcaaact aacacaggaa cagaaaacaa aacactgcat gttctcgctc ataagtggga    5400
gttgaacaac gagaatacat ggacacaagg aggggaacat cacacaccgg ggcctgtcgg    5460
ggagtcgggg gctaagggag ggatggcatt aggagaaata cctaatgtag atgatgggtt    5520
ggtgggtgca gcaaaccacc atggcacgtg tatacctatg taacaagcct gcatgttctg    5580
cacatgtatc tcagaactta agtataata ataataatac taaaattaaa aatcccacag     5640
aaactggctg ggtgtggtga ctcatgcctg taattccaac actttgggag gccgaggcag    5700
gaggatcacc tgaggtcagg agtttgagac cagcctggcc aatttggcaa acccccatct    5760
ctactaaaaa tacaaaaatt agtggggcgt ggtggtgggc acctataatc ccagctactt    5820
ggaaggctga ggcagggaga actgcttgaa cctgggaggc agaggttgca gtgagccaag    5880
atagtgcacc tgcactccag cctgggtaac agagctagac tctgtctcaa aaacaaacaa    5940
acaaacaaac ccacaaaaac tacttacaga gacaccttga ttttgacaag gtggattttg    6000
ataaattcca gtgttattta tcgtaatcat ttactctatt cttatttaat tgtaccataa    6060
ttatttctta tttaatcatg tcatatgtca gtgcttcagt ttctaaaagg caagcactct    6120
attatcactt ccactatgaa ttgaattgac ttatttctga atggcctttc cctagaacct    6180
catctccaag ggcctcctga acatccccac aaggatgtcc cattcacttc atttcaagga    6240
acacggttgc ccatttatgt tttccatcaa ctaatgatgt ctgaatgtct tgccttaatt    6300
ctctctgtct ctctctctct ttttttttt tttgagagag agactctgtg tcgcccaagc     6360
tggagtgcag tggcgtgatc tcagctcact gcaacctcta cccccaggt ccaagcaatt     6420 cttgtgcctc agcctcccga agatgacaag tgtgagccac aacacccagc tagttttttg    6480
tattttcagt agagatgggt ttcaccatgt tggccaggct ggtcttgaac tcctggcctc    6540
aagtgatcca cctgctcggc ctcccaaagt gctgggatta caggtatgag tcatcacgcc    6600
cagctgcctt aatttattaa ctctgcaaat ttttttgag tacctattat gtctaaacat     6660
tgttctgggc aatgaagtga acaaaacaga ttaaaaattc ctgtccccctt gaaatttata   6720 ttctagtgtg gggaggtaat aaatgttta aaaagataat tatctatcta tctatcatct     6780
atctatcatc tatctattat ctatctacct atctttatat aggtatcttt catctgtcta    6840
```

```
cctatctatg atatgaggtg gaagtaaatg ttatggaaaa aataaagtgg ggaaggtgaa   6900
tagggtggca agcgtggggc tgaaatttta aaaggtcgtc tgagggcatc acagtgagat   6960
ttcagcaaag acctgaaaga aatgaggcaa tagatcatgt gagtatctga aaaaagtgca   7020
ttccaggctg aaggaattct aaattccaag atcctgtggt cagagtatgt gtctaaccta   7080
tggaacagaa aaagggttag tgtggttaca gtgatgtgac agaagaggag aaaagtagga   7140
aatggaggca gaagggcagg aggagcgcaa tgttgagaat agactccagg gtataggtca   7200
ccaaagaagc agagggcagt tcaaaagctg ttgtgatcat tatggcatag agatgatggg   7260
tctgagacca agaaatggta gaagtttagg tattgagaag tggacagatt ccgaataaag   7320
tttgaaagta gcactggcag gttttgttga agactggat gtaggatgtg agagaaaagg    7380
aggactcaat atccttccct gctctcatag aatcagatct catcttattg agtatgtttg   7440
aagtatgcac atagttgatt gctttctctt ctcatattca ccaaactttt gggacctaca   7500
tcacctctta gactgagcgt taaaggaaca ggctctcatc actttctttt tttatttaat   7560
ttatttagca tttatatgtc atatcgttcc agaaggattt gaagtttcta attatatcta   7620
atataattaa aaataggata ctttagttct aacaacaaac tagaacccat atgaatagag   7680
gaagcagttg ttatgaggca tcatggtaaa gagctgctca ttacaactgg atgttaagta   7740
tagttctaag agtttctgag cagctaagag aagtacaatt ttgttcagac actttgattg   7800
catcatagaa gaaagcttgc atatttcttc agagacaaac tatgtctaat aacctaactt   7860
aaagatgaat ttacttattc aactgttttt gttaattatt ttattttaa ctttcatggg    7920 tacatagtag atgtatatat ttatagggta catgagatgt tttgatgttt gtacacaagc   7980
atgcaatggt aacaatcaca tcatgaagaa tggggtttcc atcccctcaa gcatttatcc   8040
tttgtattac aaaccattca attatgctct tttaggtatt taaaaatgta caattaagtt   8100
attattgatt atagtcaccc tgttgtgcta ttgaatacta gaccttattc attcattcta   8160
actatttttt tgtacccatt aatctcctca ctttctcccc actcctcccc taactaccct   8220
tcccagcctc tggtaaccat cttttctattc tctatctcta tctccatgag ttcaattgtt   8280
ttgattttca gatcccacaa ataagtgaga acatgtgatg tttgcctttc tgtgcctaac   8340
ttacgttatt tcacataacc taatgatctc cagttccatt catattgttg caaatgactg   8400
gatctcattc tttttgtagc tgaatagtac tttattgtgt acatgtacca cacgttgtt    8460 tccaaatttt ggctattgtg aacagagttg caataaacat gaaagtgcag atatcttttc   8520
tatatactga ttttctttt gaggagtata tacccagcag tgggattgct ggatcgtatg    8580
gtggctctat ttttagtttt ttgagaaacc ttcaaactgt tctctacagt gactgtacta   8640
atttgcattc ccactaacag tgtatgaggg ttccctttc tccacatcct caccagcatt    8700
tgttataagt cattttaaca ggtgtgagat gatataattg tacttttgat ttgctttttt   8760
ttttttttga cagagcct ccctcttgtt gcccaggctg aagtgcaatg gtgccatctt      8820
ggctcactgc aacctctgcc tcctgggttc aagcaattct cctgcctcag cctcacgagt   8880
agctgggatt acaggtgcct gccactacac ccagctattt ttgtattttt ggtagagacg   8940
gggttccacc atgttgtcca ggctgatctc aaactcctga cctcaggtga tcctcttgcc   9000
tcagcctcca gaaatgctgg gattacaggt gtgaatcacc atgcccggtt gatttgcagt   9060
tttctgatga tcagtgatgt tgagcaactt ttcacatgcc tgtttgccat ttgtataact   9120
tcttttgaga aatgtctgtt caaatctttt gcccatttttt ggattggatt attagatttt   9180
```

```
ttttcctata gagttgtttg gacttcttac atattccggt tatgaatccc ttataagatg    9240
gatagtttgc acatatttta tcccaatctg tgggttgtct cttcactttc ttgatagttt    9300
cccctgctgt gcagaagctt tttaccttca tgtgattcca tttgtccatt tttgctttgg    9360
ttgcctgtgc ctgtggggta ttactcaaga aatctttgtc cagaccaatg tcctggagag    9420
tttccccaaa gttttctttt agtagtttca tagtttgagg tcaaatattt aagtatataa    9480
ttcattttta tttgatttt gtatatggtg agagataggg gtctactttc attcttccgc     9540
atatgggtat ctggttttcc cagcaccatt tattgaaaaa actgtccttt ccccaatata    9600
tgctcttggc atctttgttg aagacgagtt cactgtagat atttgggttt atttctgggt    9660
tctctcttct gtttcattgg tctatgtgtc tgtttttatg ccagtaccat gcagttttgg    9720
ttactagagc tctgtagtat aatttaaagt caggtaatgt gatttctcca gttttttttc    9780
tttttgctta ggagggcttc tggatcttct gtgtttccac gtaaatttca gaattttttt    9840
ttctatgtct gtgaagaatg acattggtat tttgatggag attgcattga atctgtagaa    9900
tgctttggat agtatgggca ttttaacaat attgattctt ccaatctatg aacatggaat    9960
atctttccat gttttgtgtc ctcttcaatt tcttacatca atgttttaca gacttcattg   10020
tagagagctt tctcttcttt ggataaatta attcctaggt attgtatttt atttatagct   10080
ataacaaatg ctattccttt cttgatttct ttttcagatt gcttgctgtt ggcacagaaa   10140
tgctactgat ttttttatgtt gattttgtat cctgcaactt tactgaattt gtttgtcagt   10200
tctattagtt ttttggtgga gtctttaggg ttttccaagt ataagataat aacatctgca   10260
aacaaaaata atttcctcc tttccaattt ggatgcattt tatttctttc tcttgtctga    10320
ttactttagt gagaacctcc actactatgt tgaataatag tggtgaaaat ggacattctt   10380
gtcttttcta gatcttagag aaaagctttc agttttccct cattcagtat gataccagcc   10440
atgggtctgt cataaatggc tattattgtg ttgaggtatg ttccttctat atccagtcat   10500
tgagggtttt tattatgaag gaatgttgaa ttttaccaaa tatttttttca gtgtcaattg   10560
aaatgaccat ttggttttg ttcttcattc tgttgatatg atgtgccaca tcaattgatt   10620
tgtgcatgtt gaaccatcct tgcacccttg ggataaatcc gacttggtca tgatgaataa   10680
ttttttaatg tgtcgttgca tttggtttgc tagtattttg ttgaggttt tttgcatcaa    10740
tgttcatcag ggatgttggg ctgtagtttt cttttttatg tgtctttgcc tggttttggt   10800
atagtataat actagcctca ttgaatgagt ttggaagcat tcctttctct attttttgga   10860
atagtttgaa taggatttgt attagttctt taattgtttg gtaaaattca gcactgaagc   10920
ctttaagtcc tgggcttttt tttgctggga gatctttat tacagcttca atcttattat    10980
ttgttatctg tctattcagg ttttggattt ctttgtggtt caatcttggt aggctgtatg   11040
tgtctaggaa tttattcatg tcttttaggt tttccaattt atcggcatgt agttgctcat   11100
agtaatctct aatgatcttt tgaatttctg cagtattggt tataatgtct catttttcat   11160
ctctgagttt attttcttc tatctttttt tcttagtctc actaaaagtc aatttatct    11220
tttcaaaaag aaacttttta gttttttttg gatgtttttt atttcaattt catttatttc   11280
tgttcagatg tttattattt ttcttctact aatttcaggt ttggtttgct cttccttttc   11340
tagtttaaaa aaatatatca ttaggctgtt tacttgaagg ttttcttctt tgttagtgta   11400
ggcacttata gctataaact ttcctcttag aacgattttg ctgtatccca taagttttga   11460
tatgttgcat atccatttc atttgtttca ataaaaattt taaatttctt cttaatttct    11520
tcattaaccct gctggtaatt caggagcaca ttgtttaaat tctgtatgtt tgtatagttt   11580
```

-continued

```
tcaaaattcc ctttgctatt gatttctagt actattccac tgtggtcaga gaagatactt    11640
gatatgatct caattttttt taatgtttta agatttgttt tgtgacctaa catatggtct    11700
ctccttgaga atgatccatg tgctggggag aagaatgttt attctgtagc cattggatga    11760
aattttctgt aactatctat taagcccact tggtctgtaa tgcagattaa gtccaatgtt    11820
tctttatttt ttttttcctt ctggatgatc tgtccaatgc tgaaagtagg atgttgaaat    11880
ctccagctat tattgcattg ggatctatct ctctctttag ctctagtaat atgtcctta    11940 tatatctgtg tgctcaagtg ttagcacact tgtgtgctca attgttatat cctctgacag    12000
aattgacctc tttatcatta tataattaat ttctttgtct cctttttatgg ttttttgtcct    12060 gaaatctatt ctgtctgata aaaatatagc taccccctgct cctttttgttt tccatttgca    12120 tggaaatctt tgctatcccct ttattttctg tctgtgtgtg tctttataag tgaagtgtgt    12180
ttcttgtaca caatcgacca ttgccattga ttttttttct tttttatcca tttagccact    12240
ctatgtcttt tgattggaga gtttagacca tttacattca atgttttatt gttaagtaag    12300
gacatactcc tgccattttg ttttttttgtt ttctggttgt tttgtggtgt tgtcttcctt    12360
tcttcctgtc ttcctttttg tgaaggtgtt tttctctgat ggtatgtttt aattttttgct    12420 tttcattttt tgtgtatctg ttgtaggttt tttgatttga tgttatgcag cttgtaaata    12480
acaacttata gttcattatt ttaaagtgat gacaacttaa cattgattgt ataaactaac    12540
aagcaaagag aaagctaata aaagcttcat actttaactt catcccccat acttttaatt    12600
tttaatactt tctatttata tcttatactg tctatgtctt aaaaagctttt tataattatt    12660 attttttgatt ggttcatctt ttagttttttc tactcaagat atgagaagtt tacaccacaa    12720
ttacagagtt ataacactcc atgtttgtct gtgtacttac tagtgagttt tgtaccttaa    12780
gatgctttct tattggttat tgatgtcttt ttctttcaga ttgaagaaat ttctttagca    12840
tttcttataa gagaaggcag tgggttcttt tctggctcag ggtgggtcta gaaatgccat    12900
ccaggagcta agtcctggaa ttgaggactt taggagtctg cttggtgctt catgttactg    12960
tggctaagtt ggtacccaat ttgtaagaca aagtcctttt actcttcct ctcctttcct    13020 ccccatgcct ccccatggct acaacagctg ggaatgtgct gggtcacacc tgaaaccagc    13080
atggtactgg gtcccaccca agcctcgtgg tgagtactgc ctggctatca ctgatgttta    13140
ttcaaagccc aagggctctt tagttagcag gtgatgattc ttgccaggac tgggtccttc    13200
catttaaggc aagaagttcc cttatagcct agtgtatgtc tagaaatatc atcagggagc    13260
tagggcctgg gttgggggat tcagtactct acttggtgct ttatttttact gtggttgagc    13320 tgttatccaa gttgcaagac aaagtcctct ttatgctcct gtctcctttc ttaaggcaga    13380
gggacggagt ctctcaaagc tgtgagctgt gctgcctgga gttggaggag ggttgatgca    13440
accactcctt tgactactcc agctggtgtc tcactaggtt atgtgcgctc caaggctact    13500
ggttctgagc tcagtacagc actaggactt gcctaggaat tgtagtcctt gtggcctaaa    13560
tcagctgtcc ccaacgtttt tggcaccagg gactggtttt gtggaagaca attttttaat    13620
ggacagggtg gagtatgctt tctggataaa actgttccac cttagatcat caggcattag    13680
ttaaattctc ataaggaaca tgcaacctag attcctcaga tgcacagttc acaacaggct    13740
tccattccta tgagaatcta atgctgcaac tgatctgaca ggaggcagag ctcaggcagt    13800
aatgtcactc atctcctact gtgcagccag tttctaacag gccatggact ggtactgccg    13860
tgcagcccaa ttcctaacag gccacagtcc atggcatagg gattgggaac ccctggccta    13920
```

```
gactgccttt caagtttatt tagaacccca gagaacttta tcccacattg gtgatccttg    13980
gtagaactca ggttctgact gctgggtagg acaattcctc tctgacaaga gctgttctaa    14040
atgtgccctc tgtgggcact ggctgaattc tgtgccatgt tgctttctgc tgttacatgg    14100
caacactgac ttccaatgta aagtcccaca atcactgtac tttccttccc ccaagggcac    14160 aaatttctc tccacaccat gtggtaacct ggaggatggg ggagagtggt attggcaatt     14220
aaagactttc tttcttacct ccttcagtgc ctctttcctt gatatgattt taaaacaagg    14280
tactgtgatt actcttctga ttttggttc ttatgaaggt tcattcttgt tgtggatggt     14340
tgttcagttt ggtgatcctg caggaagaca attgctggaa ggttctattt ggccatcttc    14400
ctctgcttcc tcctcatctt ttatttcttc ctcttgcctg attgctctgg ctaggacttc    14460
cagtatgatg ttgaatagaa gtggtgaagg tgggcttcct tgtcttgtta cagttcttag    14520
aacaaaggct ttcagctttt ccccattcca taggatgtta gctgtaggtg ctgacatata    14580
cgccatctat agcctttatt atgttgaggt atattccttc tgtataataa agtgcacatg    14640
tctgaattat atattacttg ccttgagggt gccaagaaac tatttatact gcctagaata    14700
ttaaccttta ttatgcctaa agagttcatt agtcaaatgt tggttttgat gtagacctca    14760
tagtttaaaa tttaacattt aaattaaatg ggttataatt tttaatacca cctaaataca    14820
atatattgat ccaatataga aagttagatc aatgttagaa ataaagagtc acagtgtacc    14880
tttccagact tgtcattagc atttcatatt tatagttta gctttgattt gaatgtctca     14940
cagatgaact taaatcaaca cataattcca ccatagcata atagtaatta ggcagtttcc    15000
ctaaatttga gaacattgcc ttaatgtagt tgtgatgttt tgaggcttca tagcttaaat    15060
ccattatacc attatggaat ctatagagca gggctatgga gaaaggcttc agagaagttt    15120
tttttgctac tataacctta tttaaagaaa caaacagaaa aaaacccaaa cgtatttgaa    15180
gtctgcttaa atattactgt taaatgtgaa gtgtttatat ctaacattca taatcatatg    15240
aatgtcaaca tttagtttcg agtagaaaaa gataaatcat tactgtgagt taagaaattt    15300
aaatggagat gtgtgaggga gcatgtccat ttcatccttc ccatctccac cctccccaga    15360
gtttcatccc cagggtgccc ttcttggttt ccagcctctg gtgttctgct tggggtcttg    15420
acttcttccc atgccactca ggctcagccc cagactagaa cagggtttgg gaagcagtgg    15480
ggatagccaa gatgggtgtc agtggtggc ccagcagttt ctgtcccagg agtggccaca     15540 ggccagggt agtggtggct gtgcatgtgg ccagcctgct gccattgtcc catccttgtc     15600
agggccctct ctttcacctt acagcatctg aggggcagag ctctagagtg tttgggcaga    15660
caatgcctct gaaaattttt ttttaaataa aatttagatg acaagtatat atcatatatg    15720
cagtgaccaa gcataaact actttacagt catctaactg ctgtagcaat gatatgtaac     15780
tacagtgtca aaacaccctg acagttttca gaaacccaat gtggagacca tctgccatat    15840 cttactttt ctttaggtac aatattcaaa ttcatattga ttttgcttac atatgaatag     15900
tttcaaattt gttcacatat ggtttaaact ttttgtccct attgtcttac tcaggcttgt    15960
gtaacttaaa atgagcctga gcatgggtct acacacagca agatgtgtaa taaaaacaca    16020
attttagtgc tactttcaaa attcatgcta ttaagaaaga tgctgttttc aaagctgaaa    16080
agatcatgaa atggctaact tacatatcag aggttggata attccttact attgaggtgt    16140
tatattttct gtgtagtaaa tgccttcaaa tattaactga aagatcagtg aagtcatttt    16200 ccccttttgtg attccaactt catttgtttt attttgaaga taattaatat tttaattgca    16260 aagaaaatt atagcattgg aaaattttct gtatatggag aataacaatg aaccaaattt     16320
```

```
accaattagg gaaccatttc aggaattgtt ggatggtgaa tttttcttca gtaactatgc   16380
tttagttgca atgcagtatg cccagaaaca atccatttca acttctgaat gtttgatttg   16440
gaacatttgt ttgatgagta ttcagttaaa cacttggata caaactcttt ccagaaggtc   16500
acatctctac catttatctt ggaatgtttc tgaagacatt ctactcattt tattaactgt   16560
atacacttct gttttttggat ctccaatatg attatagaca atatcaacat agaaggcttt   16620
gatttagact ccaaagttta gagcatttga tcttgacatg ccttaaattg ggcttccagt   16680
caaaattgag gccacttctc ctttcaaatg gcaagttctc ttgaatgagt gaatagtgga   16740
gttgtagaaa ttgaaaggca gtagtagctt tcactttaca ttacaacttc tccaatgcaa   16800
tcttttccat tctcatcaag tctgaaaccg tgaacctata ttcacctatt tggaacacat   16860
cagttgccaa tgggacatcc ctttcctctt ctattgattt tacagccgaa tagaagaagc   16920
tcagttcaac acatccaagg tgcttgggct gcaccttcat ttaacacagg aatctgtcca   16980
gtaaattcac agagaaaatg cctttgtgtt aaagccaaag aactgaatta gactaacatc   17040
ttgtacttca aagtcctgta gccttgcagt cattctgagg ctattgtcta tcatgtgcaa   17100
actcaattag tctcaaacca cagatcttta actgacatct agacttcagt tccaacaagg   17160
cattcagctg gtgtagcagt ttctgacagt caggtttcag tacctctatc atcttgatag   17220
tgattgagcc tcagtggtaa ccacccttct tgggcctgca ctcacctcac cccacgaaat   17280
ccaatctcag aggcctagga acaaagcaa acagagaggc ccagggaggg gaagccttcc   17340
tgggtggatg tctctgcaga gccaccaaga tcatattgcc ctcatcaggg tcagcttgga   17400
gctgaagggc tgaaaaggca ttttgatatt tgattgcata ttatttcata ctgttatttc   17460
agagttttgt gtgcacacat tgtttcttca gtaagcctaa tgctttataa gcatagcaac   17520
cacatctgac atttctatgt ctctcacatt gtatgcttgg acagctctgc ctggaatatt   17580
cttcccccag ttgcccacat gtccaatata gtgctttgtg ttgtgtcaaa acctaatgca   17640
tatttgttga atatttaaca tgtgctgatt ttagattagt aaatatcttt ccgataattg   17700
atgatttttg ttatacctaa agattgaaca ctttgaaagc agccttagaa aatgcatttc   17760
aattattctc tttcacctcc tccttctgtg cccagggcaa aactctgcat ggattaagga   17820
ctcagcaaat atcatggatg aagcaacagg cagatttcag gcaccataag caaactgaat   17880
ttttaaaccc taaattagga catgtggtct aattttggag catttatgt gtacgccaaa   17940
cagcctgaga aatgtagctt gaattgaaat atattagaat acatgaagac taatagagtc   18000
agtaggaaaa tatgtttgtc atcagaactg tttcagaaat ccaaaacacc aacctactta   18060
ttccaccact taaggtgatc caaaagact gggggtaaac atgtttcaag tggttcaatg   18120
tgttgtaatt tatatctatg catttcagat atcaattgaa gcaaaggtgg gttaaactat   18180
tgaacggttg ttcttctta caacacatt gaaataataa ttttctatat gtattattat   18240
atccttttcc aatcttttc aaggatatgt tttatagatg attgctatgg ctttccttat   18300
attcattata caaatttgtt tgtagatcta gtagccaata tttgatgtca ccaaatttttt   18360
attcatacaa cagttatctc agccttctca gctattcttc ataaccatt tatcatttca   18420
gagttgtgca atagaggata aatatagcaa tatgttaaat attattttca aaattgtatt   18480
ttaattgctt tactgggaca attattggta actttgtaaa agaataaaaa aatcaggcat   18540
taacaaatgc tccaggattt ccattgtttc atactagctg gtactgccct agccaatcct   18600
tgttacctct tatttgaaca atggcaacag cttcctaatg aatcccctgc atttagtctc   18660
```

```
tcactgttcc agtacattct acactccgtg ttctatttat ctttatgaag aaaattttga    18720
ccaggttgct tctgtcttca aaggctttaa tagtacctat ttattactaa atttggaaca    18780
aatcttagcc tcttgtgcaa agctcaatat ccatccttcc ttccttcctt cctccctgcc    18840
tcccttcttt ctttcttttt ttaaaatatt tttaaacttt ttatttttt gagacagagt     18900
ctcactctgt cacccaggct ggagtgcagg ggcgcaatct cagctcactg caagctccac    18960
ctcccgagtt cacgccattc tgctgcctca gcctcctgag tagctggaac tacaggcacc    19020
tgccaccacg cctggctaat ttttgtatt tttagtggag acggggtttc accgtgttag     19080
ccaggatggt ctcgatctcc tgacctcagg tgttccactg gcctcagtct tgcaaagtgc    19140
taggattaca ggcgtgagcc actgtgccct ctcctctcct ctcctcccct ccctcctct     19200
cccctcccct cccttctctc tttcctttct tctcaaatct gagaatgtct tcatttctcc    19260
ctcccttttg aagggcagtt ctgatggata tagaattctt ggttgtcaga tttttttttc    19320
tttcagtact ttaaatatat cagctcaatg ctttgtggtc tccaaagtta ttgatgagaa    19380
atctgccgat aatcttattg gggatccctt gtatgtatga gtcacttctg tcttgctgct    19440
ttcaagattc tcattttgtc tttggctctc tacaatttga ttatagtgtg tcttagtgtg    19500
agtctctttg aattcattct cttggagttt gttgagcttc ttggatcttt atattcatat    19560
cttctcttcaa gtttgggaag ttttcagcca ttatttcttc aaataatctc tcttctcctt   19620
ctgagactcc cacagtgcat gtgttggaca ctcaatggtg ttcctaaggc tctgttcaat    19680
tttctttaat attttttgtt gttgttctgc agactcaata atttcaatgg tcctgtcttc    19740
cagttcactg tttctttttt ctacatgcct gaattggtct tcgaatcctc ctataaaata    19800
ttcatttcag ttattgtaat tttcagctcc agattctttt taggttttct atcttttat     19860
tgatatttct actttgtttt gttttttgat tttctccaca tcttccttta ttttcttaag    19920
cttctgtaaa accattgttt taaagtctgt gtttagtagg tctgtcatgt ggtcctttt    19980
agggatgatt ttcgttggtt tattttttcct ttcttttgag tgagtcatac tttcctgttt   20040
ctttgtatga tttgtgattt ttttggttga taactagaca tttgaatctt atcacatggt    20100
tactctggga atcagattct ctgggttttgc tatgttttgt tgtttgtttg ttttgttgtt   20160
gtaggatgtt tgtgttgagg atcagcttga gatgtaaatt taaggtcttc ttagacctt    20220
tatgagtctg tacctttccc tgggcatgta tggcgacttt ctaaatttcc ctgtatattt    20280
aattgcttat tccttaaatg tctcactatc caaaggagaa aaagagaaaa taaataaata    20340
aataagacac tggttcttta aatctcctgg aagccacttc agccagaaag agggcctgca    20400
aaaatggtgt gtctgtatgt atacacaaca atagctgctt gcctttgcat ttgtacctcc    20460
atgatcagaa gcaacaatta gtgatcagaa tgcagatctc gtatatttga aagacaaggt    20520
cattattgtc caccctgctc ccataagctg cctgcaagct gctttaggaa cacagacatg    20580
gcagcctgtc acagggacag gggatgagga attggtaacc actattgagc taagagctaa    20640
aatggactga aattaactgt aagttacctt ccaagcattc ttctggaagt tgcaagcact    20700
agagctccaa aatagtaata ttagacagat tccaacagtg caattgttat ctaggtgggg    20760
agaaaaattc cctgctctgc tatcttccca gcatccctct acctctaaat ttttgttaac    20820
tcattcaaaa aaattttttt ttgagatgga gtctcactct tgttgcctag gatggagtgc    20880
aatggcatga tctcagctca ccacaacctc tgcctcccaa gatcaagcaa ttctcccacc    20940
tcagcctctt gagtagctgg gattataggc gcacgccacc aggcccagct aattttgtat    21000
ttttagtaga gacggggttt cttcatgttg gtctggctgg tctcgaactc ctgacctcag    21060
```

```
ctgatccacc cacctcggcc tcccaaaatg ttgggattac aggcatgagc taccacacct   21120
ggccccccaa aatttgtttt ttgagacagg gttttgctct gttgcccagg ttggaatgca   21180
gtggaactca ctgtagcctc aaaatcccaa gttcaagcaa tcatcccacc tcagtctccc   21240
aaatatctga gactacaggc acacaccact atgcctggct attttttttt tttttcattt   21300
tttgtagaga gacagtcttg ctttgttgcc caggctggtc tcaaactcct gggctcaagc   21360
aatccttcct ccttggactc ccaaagtgct ggaattacag gcatgagcaa ccacacccac   21420
cccaagatat tttttaatgc ctctcttctg ttagacataa ttttagtaaa cgggatatgt   21480
aagtcattga tctatgatat ccacaggatg ctgcagacat tataagacaa acacgtaagt   21540
gaaaatatga ctatagatta cgataaatgc tatgaagaaa aaatacgtgg tctggaatct   21600
tatcctacag taggttccta caaccaattt tactcaagca tgggcttcct ctgaactcct   21660
ttcttgtctt aatacttctc ttctaattat tgttatttag aatttacttt tgcatatatc   21720
aaataatagg tttaggcaac tatcattcag gattttgttg agagttaaga ttgatttaca   21780
aagatttttt tcctccaata aacatgtatc agatttggcc agaccccagt acaagaaaga   21840
ctcagctgcc tggccaagaa caactctatc tatgttgtgg caaatattgg ggacaagaag   21900
ccatgcgata ccagtgatcc tcagtgtccc cctgatggcc gttaccaata caacactgat   21960
gtggtatttg attctcaagg aaaactggtg gcacgctacc ataaggtaaa attaatttgc   22020
aaataatcca attagttaat gcctaatgaa ataaagtggg caaggagaaa aatatgttat   22080
tgataatgat aagcacactt tagaaatcga gtaggggcaa agcatagaaa gtaatgataa   22140
agtgtggaaa gctcctataa agaggcttaa ggggttccgt gtacatataa gaacacagga   22200
gtgtgttttc aggagtgtgt agcagtcaga aagtgccgca tgcattatgt tgcctaatgt   22260
tgccttttgg actttgtcct tttaaaggca taccctggca atgggtcaag gctagaatga   22320
aaaactgctt accacataga ctctgtcttg aggagaatgg aacaaacaaa gttccttgcc   22380
aaggaaaaca gttaagtcta cttggcaaac agaagtaatc tattttatgt cttataagat   22440
tccagtgggt ctttatagat aaagataccc atgtacatat ttgtaatgtg gagactgaac   22500
taaaggccca atttagctag aatggcctct gattctctaa agcaaactca tttcccatga   22560
aaacactgat catagatgaa attggcacta agatgtgagc ttgtactttt tcccacactg   22620
tgatgtccag atcaacttcc taaaataatt ttttctctt tatcttctgt ttattgcagc   22680
aaaaccttt catgggtgaa aatcaattca atgtacccaa ggagcctgag attgtgactt   22740
tcaataccac ctttggaagt tttggcattt tcacatgctt tgatatactc ttccatgatc   22800
ctgctgttac cttggtgaaa gatttccacg tggacaccat agtattccca acagcttgga   22860
tgaatgtttt gccacatttg tcagctgttg aattccactc agcttgggct atgggcatga   22920
gggtcaattt ccttgcatcc aacatacatt accctcaaa gaaaatgaca ggtaatgtgt   22980
gatcttaaag atatgcaggc tgatgtaatc agaaagaaa agaaaaaaa aacatgtttt   23040
tctagctaac gcatactcct taatacaatg ttttccagct cttaattttt gaacatctag   23100
ctgttaatat gctatagaat caatctcagt ctaaattgtt ttgtagattt atttggtttt   23160
atttaacttg atttttttt caaaatatat gacttcttac atacaactct cccttcttgg   23220
cttcttggtt tcatacttta attgatttcc tctcacttct ctgtctttat cagcatgttt   23280
tactgaaatt aataaaacat ataacttaga gagagtaaaa tgtgaatatg aggttaaaat   23340
agtaataaca attatgaaat ccctttttac tttccaattt caaatgatgt tttcaactta   23400
```

```
ttacttccag gaagtggcat ctatgcaccc aattcttcaa gagcatttca ttatgatatg   23460
aagacagaag agggaaaact cctcctctcg caactggatt cccacccatc ccattctgca   23520
gtggtgaact ggacttccta tgccagcagt atagaagcgc tctcatcagg aaacaaggaa   23580
tttaaaggca ctgtcttttt cgatgaattc acttttgtga agctcacagg agttgcagga   23640
aattatacag tttgtcagaa agatctctgc tgtcatttaa gctacaaaat gtctgagaac   23700
ataccaaatg aagtgtacgc tctaggggca tttgacggac tgcacactgt ggaagggcgc   23760
tattatctac aggtaatatt ttgatgtcag aagagttact ggataaaata aagacactca   23820
gttaaatata cagtttagat aaataatgaa tgattttta gtataagcat atcacacttt   23880
tggggattta tgtatgctaa aaattttgtt gtttatttga aattcaactt tagctgggaa   23940
gcctacaaat acaggctaaa tttatttgct aaatctttt ttttttttt tgagacagag   24000 tctcactctg tagcccaagc tggagtgcag tggtgcatca gctcactgca agctctgcct   24060
cctcggccaa gcaattctca cgcctcagcc tcccaagtag ctgggactac aggcgagtgc   24120
caccacgcct ggctaatttt tttgttgttg ttgtatttta gtagagacag agtttcacca   24180
tattggccag ggtggtctca aactccccga gctcaggtga tccgcccacc tcagcctccc   24240
aaagtgttga gattataggc atgagccacc gtgcctgcc tatttgctaa accttgaaac   24300
cttagatgtc agttcaattt taagctgatt gggaaaaggc aggacattta cttgcagtag   24360
cagtattaaa aataaatatt caaattacag atcattataa caggagttca ttgaaaaccc   24420 atttattc ctgcctgaac aaattaagcc attttcctta tatgttcaca aatgcctatc   24480
ttgctttata aagagtttga cactaagtat atcctggata tgaatggggt tgaccaccaa   24540
gatagttcaa tggaatggtt tattgctgca aagatccaat ctctcattgc tcgcaagtgg   24600
cctccatggt cctctcattc ttctcttctc ttccttggtc tggcccccat cttatctcac   24660
ttaacagggc ttcctattga cagtctgaca atctcagctc catccagtca gttctccata   24720
ttgtagttac agaaatcaca aaaagctgtt tttgattata atactgtctg gcttaaaatt   24780
cttcactgac ttctaattga caaatcaaat ttcttaacat gaaagacaca caaagtctag   24840
atgtgtggtc ccttcctatt ctctatcctc taatctcact tctacttaca aatatcctgg   24900
gcttctgcaa tattgaaata ttttcccatc tcctatttgc tagcatatgc agaacctcaa   24960
ggtgtttgca cagattgttt ggtccttta ccgtggcgag ccccacctac taatctttca   25020
tagcactttt ctggtgttat cgtcaccaag aggggttcct ggatatttcc cacagagcta   25080
ctcctacctc tccagatgag ttaagtacat cctttatgtg ctcccaggac acccatgct   25140 tagctttatc aaagacatat tatgtcatag tattcactta cttatttgag actgagaacc   25200
ccttgagtgc tgaaattatg ccaactgcac agtattttgt ttgctctatg ataactaccc   25260
taacaatact ttttcgtttt agcaaatgaa ggcctactat atgccaggta tttatttagt   25320
gttaatgata tgaagataaa taagcataga tcctcctctt gaagaattca gtctttagta   25380
atggagaaag acatttgaac agataatttc agcataggtt ggcatgtgat tgtccgtaga   25440
atgcacattt tgctggagga gtactaaaga gctctactta gattaatttg ggaatgcagg   25500
gaagtttctg gagctgatgc tattatccag gtgaaaaaga gtaggagggg attctttgtg   25560
gtgtgaagag catgaacaag ggtgtggatg caggcaggag cagggtctgc agggaacagc   25620
aacaggtcag tgctactaag gcaactgagg catggcttgc gaagctgggt ttggtgggaa   25680
ataagcctgg aagcaacatc ctgtcctgca ggatcttacc tagcacactt aagattcagc   25740
ctttattctg tgggtgatgg tcagctggtg gaagtggtcc agtgaaggaa tgatgtggtc   25800
```

```
agatctacct ttgaatatat catttttact actctgtaga tgatggagca aagacccaaa    25860
agactagatt attaaaatag tcttattaag ggtctggacc aagactgtgt tgttggaat    25920 aaaagcaggg catggagtct agacatattt agaaatgga actcagtggc caatttgatg    25980
tggaacagga aaacggaatg gagagtccag aatgtggcag atttctggca agaatggctg    26040
ggtgggtgag atgcatctga cagatcagga ggcaagagag gagcagactc actgacagtg    26100
ggtagaggct gagttcagtt atagatgtgc tggttttgaa gtagttatga gacattcagc    26160
tggacccagc cagttgtctg ttgaatactt tggtctgatg cttaagggag atactagaat    26220
tagaaatatt gtttcaaaaa tcagcaagat acaaggggca attaagcaaa caacagtgaa    26280
tgatacgaca aaggagactg tactgacagt aaagaactat tgacaaagta gaacctttgg    26340
gagcttcggt atttggggca ggaaaggaca gaggacaaga aacctgcaaa tacaattaag    26400
aaataaagga aaatttaaaa agagaacatc tggtagatgc caaggaagta gagactcttg    26460
gaggaaagaa atcatgaggt gtattaacac aatacgttga ccattattag catttttgag    26520
tataattttg gcagaatttt ctgagctcat aatgatagga tgatgggcag attatattgg    26580
gttgaaaagt caaagggaag tgaatgcact ttttcccca agaaatctta tctgagacaa    26640
gaagaagaga agcaagacaa tggtttaaca gagactcatg gtcaggagaa atgtgtgtgt    26700
atgtgtgtat gtgtgtgtgt gtgtttctca acaaacgaga gagccttgat tgcctttgta    26760
ggtctaagag aaagagctac aaaaggaaaa aatacataaa atatgagagg aatcaggtcc    26820
agtgcagtgg cctgtaatcc cagcactttg ggaggtcaag gcgggcagat catctgagat    26880
caggagtttg tgaccctgt ccaacatggt gaaacctgtc tctactaaaa atacaaaaat    26940
tagccaggca tggtggcagg cgcctgcaat cccagctact tggaaggctg agacaggaga    27000
attgcttgat cctgggagat agaggttgca gtgagctgaa attgtgccac tgcactccag    27060
cctaggcaac agagtgagac tctgtctcaa aataaaataa aatatacaag gaatcattac    27120
tcctactcag tgttccaagg tgctggagga aagagggaaa aatagtatca tgaacacagg    27180
tacaaaatgt ccaacaactg gaaattaaat gaatcatatt gtagaagaac atttattgcc    27240
ataaaattat taccatatac catatgttat attaacatat atagcctat atatgtgaca    27300 ttcatatggt attatattgc tatataaatt tttaaaatta aaatataaat tgtgatgtat    27360
tatttttaag ttaaaaaag ttggtcacaa acaagagag taatctctta gctcttcttc    27420
cctccttttc cttcctgcct cctcaatctt ttcctacctt tttacctcct ccagagtctt    27480
ggctctacct aaagagagtt gtgggaagtt ctttcttagt gttgtgaggt aggttagctt    27540
tgtcaagtaa aaccaagctt tctgtttatc ttgctagacg gtgatattc atctaaacga    27600 ttggtaccag atatgttttg gaatcttcct atttaaagat aataatacat attacttgat    27660
attaccagca gagtctggga aaataccccag aatcaaacat attaatatat ctattggaaa    27720
acatgggatt attcaccctta aatagcttga ataaaaatgt tatagcctta tgttaattca    27780
agttaggtct taatgccaat gtgccagtgg gttacaaaaa tcctttattt tcagaagatt    27840 ttggatttt gtattgaaga taaggaattt tggtataata ttatattat aattttcat    27900 agtctaactg tgatgatata ttatgcttga aaatctcga ttatccaccaa agctacctc    27960 caaaccaagg gaagagacac aaagagaggt aaaagtgaaa taaaccccta tcttgccaca    28020
cagattttcc aagcattta tagcaaatat gcataatttt gttatatca gtatgtcatt    28080 gcaaacatca ctcagagttt tgcttttata gttttctt gttttttcta aagttattaa    28140
```

```
ttgccttatt tttttaaatt tcgttaattt tctttgactt tttgttaaaa ccccatatct   28200
tccaacagca tctcagaata atttttccac aatatcattt tcataagttt atcttgagct   28260
aaaaataata acctttctct gcactggttt ccctctagtc attctgcaca gttgtcatat   28320
tgagatttcc tttactgtca tcctaggaat gctctcttag ctatttcctt gttttaggtt   28380
ctctgttttt ctccttctac ctttatttgc tcctttgttc tgttgtagtc aacgctgtct   28440
agtcacattg ctctaatctg aactggctgc tctccatgcc ttgtatacga taggagtcat   28500
cctggaatct ccctttatcc tcatggtgaa gattttctt taccacttcc ctgtgtggat   28560 ttcctgttt ctgttcccg tcttccttgt tttgggcttg tgccctcttt cttgttgtta   28620
acagtttccg gaaagagagt gatcgggatg caagattttt gagactcact ggtctgaaac   28680
tgcctttcct cttaaattta gttaagtatt tccctgggca tggaattcaa aggtggttat   28740
gacttttctt caggattgtg aatgtattta tatcctccca tcttacgttg ctattgagaa   28800
ttctgaagtt cttctgattc ctgattcttt gtatgtgtat tcctcattcc acaccttccc   28860
cagaatgcat gcagaatttc ttcctttcta tttttctttt tctttttctg aaactcttat   28920
tattgggatc ttctgcctct tggattaggg ctctaatttt ccgacatttt ctctgctatt   28980
ttttactact ttatttttct cctctacttt ctgagagatt tcctcctctt gatcttccaa   29040
atcttgtact gaatctttta ttttttgttaa catgttctta atttccaaga actcttttt   29100 cttgtcttcg gagtttcaac acttattgtt gttttgtgca tgtattattt tttcttctct   29160
ctctgaggct atttaggaaa ttttttattg aagctcctcc cccctgcttc cttcaagttg   29220
cttttatctg cttttttatt tgcttttca tgcaataagt ttttctcaca tgtctggtaa   29280
ctcttgggga ttaccaaaaa ctcatagaaa attctgacca tgtgagtaac acttgccaat   29340
tttgagcttc atgatagaat gatctagctg gaccttttgc tgcggggaaa tcggaggtaa   29400
gtgtctttgg agacttcctc ttgggatggt caggtctccc aggtttcaag attcttctaa   29460
tttccttctt gaatcagttg cctaatttag gaaataaaaa tacaggatct ccaggtaaat   29520
ttgaagttca gataaacttt gttttttttg agagagtctc tttctgttgc caaggctgga   29580
gtgcagtggc atgatttccg ctcactgcaa cctctgcctc ccgggttcaa gcaattctcc   29640
tgcctcagcc tcccgagtag ctgggattac aggttcatgc caccactccc agctaatttt   29700
ttatattttt ggtacagatg gggtttcccc atgttggcca ggctggtctc gaactcctga   29760
cctcaagtga tccgcctgcc tcggcctccc aaagtgctgg gattacaggt gggagccact   29820
gctcccagcc cagataaaca tttttttaa aaagtgtaag tatgtcccat tcaatattta   29880
agacatactt atactaaaaa attatttgtt gtgtatctga acttcacatt taactgggag   29940
tcttgtcctg tgttttacct ggcaacccta ttcctgaaag ataaatcctt gctgacagca   30000
ttagggatcc aagtgaggaa aatggccttg caaggtgtgg gtggggtgg aggggaacg   30060 ttttcaacat tcagtgttat ttattcaggt aatcccttc aactatgtct cttaaacttt   30120
catctaaaga ccatccactt taccctctct ggaaacattc tccgttattt actgagtag   30180 gggaggatca gttatctggt tttttggagg acttagtatc caaggcatcc ttcacaactt   30240
tctgctcatt tattttcctt tgactgccac aactttactc ctagctctag gtatagagca   30300
gtcccagtga ttaatttgag tgctttgcag tgtagatagg gattcttggc tctttctact   30360
gctagtttag gacctggttt tcttgggtct gctgaatcaa ttactacttt ttgtatcaac   30420
atcctagttt ttaaaactgt gttgtggtct atcctcctat tttcctacct tgtgggtta   30480 aaaaaaatag tgttctttg aaggattgta ggaaataaaa ttgaagcata tgttcattct   30540
```

```
acctttacct gaaagttact tctatcccat cttaatacac ttgcactgaa gtgattactt   30600
tccacctgca aagtggaaac aataagacca gttagcggct gctgctttag tcaagcaaga   30660
gatgaaggtg acttggaata tgctgtacag atggcattaa atgaatatgg atctccttt     30720 ggaaactttt catctgcatg gtgagatgac tcacatactt agattttata ttcaaatagc   30780
tacgtactat agtggaagaa aaacttaatg gagaagtgtt tcagttcttg cgcagtatag   30840
aggatatgac ttttccagat tacagggggtt gcctctaggt caactctagg gctcattaca  30900
actctgaagc tcttttattg tgtgaaacag gcaataagat atgatttaca caggtgccta   30960
aattaaacct ttaaacacat tttaaattct tgataattaa aatcattagt aacttgagaa   31020
caatgaagat atagctgttc atggctatag gccaaggatc tgattgcttt tacagggcta   31080 atcttttga cagtgaattg caggaggcac tggggcttaa agcccttat ttttattatt     31140 agttgtatta attattcagt gataaactgg atgactctaa tgaagaagta acattatttt   31200
accaaataaa gtggcatagg cattttctta gatcaagaga gtatttcagt tgactttctc   31260 atgtttttt tttaagagca tctagcagtt tatttaatta ttttattcta tttttatct     31320 ttaaaattta tcctagcttt attgtcatta acaaatgaaa attgtatatc tttacagtgt   31380
atgatgtgac gttttgatat gtgtacacac cgtgaaatga ttaaatcaag caaattcaca   31440
tatcccacat gactttctta tgacttactg gttttcatga cttccctaga tttgtacct    31500 gttgaaatgt aaaacgacta atttaaacac ttgcggtgac tcagctgaaa cagcttctac   31560 caggttttgaa atgttctccc tcagtggcac tttcggaacc cagtatgtct ttcctgaggt  31620
gttgctgagt gaaaatcagc ttgcacctgg agaatttcag gtaagaatct tcgaatattg   31680
ccaattagtt tcatgtaaga ggaagcactt tttgatataa aaatctgctc aagtgcttac   31740
aaatatcata aaatttccat ttagaaaggt taagattatc cttggggatc atgaaggaca   31800
ttgagcaggc tgcatttctt gtctggaaat tcttaacata taattactg tgtccttcag    31860 aataaaaaaa tatatatctt attttgggga ttataggagg ttaaagtct tccaagtaga    31920 aagaagattc aacgagagta gtttcagaac cagtgccatt ggagccccctt aggaccactg  31980 gggagtgatg gcctagggaa gttgaaagga gtccctctcg tcgagtgagt caaggctctg   32040
tgtgatggta gaaggaaaag agacaaggaa aagctgaaga agagagaatt tgacagtggc   32100
ggatgttagc aaaaaagcaa aaacttttta agttcagaa ataatccctt gcttcacatg    32160
tgctctgccc agccacattc tttcgctgac ttcctgcaag ttctcctccc actcccgtt    32220 cctggtagaa accactgctg gggtgtggga ggacaatgga atggtgagga ggttgtggtg   32280
agcaagagac aggagatgac agatgctcag ttcaaatccc tgttagtcaa ttgcttcggg   32340
ccattgtggg gagtctttat cttgtctgag aggactaggt ttctcttctg tatactgcca   32400
aatccactgg tttgtgttta ttaactctta cggcgcttcc acaggtaagt aaattagaag   32460
acattgatta cgggcatctc actaataaat gaatcagtgc cagtttcata gctccaattt   32520
ttcttgtact tggcaacatt tcaaatttttt ctgatagaat ggaatttggc cagtattttt  32580
gtttcttcat tctgttatag taaatttaa aagtgattta tgggattgta aaacttgaag    32640
gtagcctttg cctacttttt tgttttaatc aggtgtcaac tgacggacgc ttgttagtc    32700 tgaagccaac atccggacct gtcttaacag taactctgtt tgggaggttg tatgagaagg   32760
actgggcatc aaatgcttca tcaggcctca cagcacaagc aagaataata atgctaatag   32820
ttatagcacc tattgtatgc tcattaagtt ggtagaatat tgacttttc tcttttttat    32880
```

```
ttgggataat ttaaaaaatg atggatgaga aaagaaagat tggtccgggt taatattatc   32940
ctctagtata agtgaattac tagtttctct ttatttagac aaacacacac acaccagata   33000
atataaactt aataaattat ctgttaatgt agattttatt taaaaaacta tatttgaaca   33060
ttggtctttc ttggacgtga gctaattata tcaaataagt atcacaaatc ttttacgcag   33120
aagaaataaa aactacgggt agaaaacata agaactatca taaaatttac ttacaaggag   33180
gctgctcttg ttaccacttt tattatatta cgtatcactt attcagctct gctgaaaatt   33240
tccaatgact ttgtttgttt gctctttttg ttttttacct aaacaataca ttttgattct   33300
cttgtgggtt gataatgtct ccccaaaatt tacatgttga agcacctcag aatgtgactg   33360
tatttggaga cagggtcttt aaagaggtaa aataaggtca ttaggataga ccctaattca   33420
atatgactga tgatcataaa agaagaggcg agtagggcac aacaggcaca aagggagacc   33480
ataaggagac acagaggaag gacaactctt tacaagctaa gaagagaggg cctcagaaga   33540
aaccaaccct gccaacacct tgatcttgga cttccagcct ccaaaactat gagaaataaa   33600
tttctattgt ttaagtcacc cagtccatgg tactttgtta ggcagccctg gcaaatgaat   33660
caaagaccca ttcctgttcc tctccccacc actactgttt tctactgtaa tctgaagctt   33720
caacaaaagg cttacctggt aagaatattc agctggtctg ggtcctcaag actccaaatag   33780 acactcttag agaaggattg ctgatggatt gatagtgaaa ccattagatc attgaattcc   33840
tctggaatta gaaaaccaga gagtcccatt ttaagaaatt agatatttaa tatagcattg   33900
tgtgttctat tttagtaaca gcagaatctc ttgacattac acaactcagt gaaacaacat   33960
catttaagcc aaaatatctc ccaactgact gatagactct gagcactaat atcatagtgc   34020
tgtgatgatg gacaattaca tagtaccgat aacagccatg cactgtgcaa agcatgccct   34080
tctgcacagg agagcaaggc acttgcagta gtgatctatg ccagcaaaac atcattttga   34140
gacaaacatt tttgtggcag atgttttttcc taaaaagtac tatatcatcc aagaaatatt   34200
tgagtaaaat cccttgttct tttgggtgac attaactgac atttgctttt tttcaagacc   34260
taatagaaaa taagaaagcc cataatgtat ttagaaacag gaatcctcag agcaattctc   34320
tgtattctca tataatttca atgtaaaaca gaaaacatat tgatgtgttg gtgataggct   34380
tgaattatta aaaacttcaa aaacatccta agtgtttctt ttttgctcaa cgttgtcaac   34440
tatagtaggt ctcccttgtg gtgtaatgaa ttgcccccaa actattatct taaaacaaca   34500
aacatttatt atcttatagc atttctgagg gtcaggatct gggactggct tagtggagtt   34560
gttctggatc agggcctttg gaaagttgta gttaacttgt ccccagggct gccatcatct   34620
caaggctcgg gtggggctgg agaaaatctg cttctcagct cactcacggc ggttgccagg   34680
cctccattct ttaggatgct agaaaaactt tcataaaatg tcatctggct tctcctagag   34740
caatgatact gagagagaaa gcacatgaga gaaagagcga gggaacttgg atgtaagcca   34800
cagtctttga aaacctaatc acagaagtga catctcttct tccacatgat gttggtcaca   34860
tggaccaaca atggcacaac gtggacagaa tcaaacagag ttgagaatat caggaggtgg   34920
ggcttcatgg gggccatttt ggatgctatc atagtgaata tatgtattta tatttatatc   34980
tgtatatatt gcaatgtaat ttaaaaaata ggattgtttt ccttttcttt ttgctatatg   35040
tgatatgtat ttcaaaatac actcccaata gttacgtctg aaaagcacta cactaaaaaa   35100
ctttctatac attgaataat taaattaaat aatctaataa tctctacttt tggtccatag   35160
taaatttaag ttaactgttt gccttaacta cagtttgtgg caaaaccatc tcctttttaat  35220 atacacaagg gactttttttt tttttttttg agacggagtt ttgctcttgt tgcccaggct   35280
```

```
ggaatgcgat ggtgtgatct cagctcactg caacctctgt ctcctgggtt taagcgattc    35340
tcctgccaga gcctcctgtg tagctgggat tacaggctgg gattacaggc atgcgccacc    35400
atgcctgcct aattttgtat ttttagtaga gatggggttt ctccatgttg gtcaggttgg    35460
tctcgaaacc cgagctcagg tgatccaccc gtctaggcct cccaaagtgc tgggattaca    35520
ggcgtgagcc accatgcccg gcccgtggga cttttgcatt cattttcag aagcttactt     35580 tgtagggaa catacattaa aaggtaacaa ataaacagc ataagttcca gaattattaa      35640
ttcatgaagt gcaaccacta ggaaaagggg tcttaaaaac atcaccctct ttactggatt    35700 cttgaagaa accaagattt ttttcctaat aatctgtttt atacacaata tataccaaaa     35760
atatataaat ataaagtat ataacaaaag tgaaagaaac tgactcttaa tcacaatgtt     35820
ctgaatagca agaggaatac taaaaaagtc aactagaaag tcatgtcaac gtcaaaatct    35880
gttctgaaac acatcacttt gatttatac tgaaagccga tacctcgaat ttcctctgct     35940
tcgctgtcct gtggttgtac tgggcatgtt ccaaatgtat cacttttatt tttatttcaa    36000
taatttcaag tgttatttta gattcaggag gcccatgtgc aggtttgtta catgggtata    36060
ttcagtaatg ctgaggtttg gggtacaaat gatcctgtca cccaggtgat aagcataata    36120 cccaaaggt agttttcagc ccttttcccc tccctgtttc ccagctgtag tagccgctag     36180
tgtctgttgt taccatcttt atatctatgt gtaccaaatg tttagcttcc atttaaaagt    36240
gagaatatgc agtatttggt tttctgttcc tgccttaact tgcttaggat aatggcctcc    36300
agctgcatcc atgttgctgc aaaagacatg attttgttct ttttttatggc tctgtggtat   36360 tctatggtg                                                            36369

<210> SEQ ID NO 18
<211> LENGTH: 18023
<212> TYPE: DNA
<213> ORGANISM: Homo sapiens

<400> SEQUENCE: 18
atactaacag tctattatac aatctgctaa aaattcataa aaatatctat ccctttacat       60
tttccacaaa agggcttgac catttttcct gaattatttt tagttttctg ctctatagag      120
ataagaaaag ttattccttt aatagaaact tctattcaaa gcagaaaata tgagcagatc      180
ttatttatag cccctaggcc ccattcttaa caaaacattt atctcagtaa gaaggaaagc      240
acagaataaa ctttgtttaa tcgtacctac tcttctatgc tgtctaaaag catttccgtg      300
acttttacca aagggctgga taaaaataaa acaaatcctt tatttggcag gattgggcct      360
ggggaaggga gaatatgaat gtcctaagaa ggcatctgag atcacatcct gtatttgttg      420
ttattattgt tttttttttt tttttttttt ttgagacgga gtttcgctct gtcgcccagc      480
ctggagcgca atggtgtgat ctcagctcac tgcagcctct gcctcctggg ttccagcgat      540
tctcctgcct cagcctcccg agtagctggg attacaggcg cccaccacca cgaccagcta      600 cttttttgtgt ttttggtaga gatgggggt tccactatgt tggccaggct ggtcttgaac      660
tcctgacctc aggtgatctg cctgcctcgg cctcccaaag tgctaggatt acaggcatga      720
gccactgcac ctggcctgtt agcattgttt ttaaactcat tgttgttatt tgctgctaac      780
aaaaatgtaa gttacatctt ctccttatta caacacagat gatctttatc accaatcctg      840
gactcttccc cttccctggc atcttcctcc aaagcagggg gtggggaggg aggaaaaaga      900
aggaggagaa ggagtaggag gagaaggaga agtaggggga ggatgggag ggaagggtga      960
```

```
aagagagaaa gaaggaaaga agcggagtat cctgaggcct ggggccccct gagctgagat    1020
tcctcctctg gcctaggtgc ctcggggtat tgttgctgta ggcactaact atacagcagt    1080
gaacaaacca gacacaaaat cctgcttttc tggagcacat gttttcagtc cttaatagca    1140
ataagtaagt cagagtgtag atttgggtaa attttgttat caatattgtc ctgtgttaca    1200
ttttcttagt agtaagtatt taatattttc cccccgtct aaaataaac acaatgtaag       1260 tgactcaaca gaaccaaaaa aattgttgtc aattttaaa tttaataaat gagatatttg      1320
ttgggatgtg attttttac acgagagtta gttatgagtt tctattaaca aaagctggaa     1380
ttgttctata tttgaattcg ggtgtctttt ggaaattcaa tattaaatct tagtactaat    1440
agtacatgct gttcaatccc tgtaatactt tctgattgtc ttaaatggac tgcaacttttt   1500 ctttctttaa aagtggtcag atatattgcg ttcttaagat tataaagtag gccaagtgca    1560
gtggctcacg cctgtaatcc cagcactttg agaggctgag gtggatggat cacaagatca    1620
ggagtttgag accagcctgg ccaatattgt gaaacccat ctctactaaa aatacaaaaa     1680
ttagctggac gtggtggcgc gcacctgtag tcctagctgt ttcagaggct gaagaaggac    1740
aatcgcttga acctgggagg tggaagttgt agtgagctga gcttgcgcca ctgcattcca    1800
gcctgggtga cagagcaaac tccgcctcaa aaaaaaaaa aaaaaaaaa aagaagaaga       1860 agaagaagaa gaagaagaag aagaagaaga aaagatgaa taaagtaaaa ggccagtaac     1920
tggcagccac atgttatgca acattctcc cctctgtaaa tactcatga atgttatttt      1980 tgctttcaga aatcactaaa ccttggccat ggtcacttcc tcttttccaa tctctgtggc    2040 agttttgcc ctaataaccc tgcaggttgg tactcaggac agttttatag ctgcagtgta     2100
tgaacatgct gtcattttgc caaataaaac agaaacacca gtttctcagg aggatgcctt    2160
gaatctcatg aacgagaata tagacattct ggagacagcg atcaagcagg cagctgagca    2220
ggtattctct tatttctgtt aatcataatg tacacgaggg gcatgggagc tggtggaaga    2280
cgagagagct gaattgtctg tgttgtacat ggaaaaatca ttttttatttt gcttgttttg   2340 aacagggtgc tcgaatcatt gtgactccag aagatgcact ttatggatgg aaatttacca    2400
gggaaactgt tttcccttat ctggaggata tcccagaccc tcaggtgaac tggattccgt    2460
gtcaagaccc ccacaggtat tttaactatc ttagtctttt gtgcaaaagt aactctctaa    2520
aatgcgcacg ttcaccaaag caaaatgatt gctcttgaat taccatatat gtggtatatg    2580
ttatggttat atttatctca acatttgtca gattttaaaa aattgtactt agatactatt    2640
taacaatctt ttgtgattga aaatctttat taaattttga gaaatgtgt aaataggta      2700 ttcctgcaag aaaaactaag ggaagagatc tcatagatac aagtagtaac ttaatttctg    2760
aagtagacag tggattgtgt taggaataca ttccaaagcc tctgctgaag ggacacctt     2820 tcaatgttat agagtctctc cattccagag ttgcttctta ggcagaaaga cttcaccatg    2880
tattttcaag tgaatcataa gaccttatgc tttgaaactg catttcccta ggctcacaaa    2940
tctaattttc ctgggaaaag gttatctaga aaccttctaa tatatattaa aaatctgggt    3000
cctactgtca tcctggaggt gtcaacgtgg cagttgcatg gacaagtctg gcatgaaaag    3060
acaaaattat atctggagat agaaaatcaa atgtcagcat atagatggtg ttaaacacca    3120
tgatgagttc acctgtggag tgagttagag aagagtttag gtataaggct tgagcactag    3180
gaaattctag tgtttagact cggaagaaaa cgaggaatca gcagaagagt cgaagaagag    3240
caaccaataa ataggaaaat gagagggtgg gtccaataga gaagtgaggt gtttccagaa    3300
ggaggtgtaa ttaactgtgc caactgctgt tgaaaagtta agatgagatc aggtaaaatg    3360
```

```
tgggggtcac tgctggcatt agtaagagtt tgggtgatag agatacaagt tggagtgctc    3420
tgaaagggaa tgggagagga ggaactggca acagcaagag ggactgatct tttgaggagt    3480
tttgctttaa gagagagatg aggattaaag caatatttgg aagggcatgt ttggaaaggt    3540
caaaagaggt tttaatttta ttttttaaag atggggaggta ctagaggata tttcattgct    3600
gatgggatgt ttcagtagag aggagaccct tgatgaggca ggagaccgaa taatgaattt    3660
ctggagcaat agataccgtg tgggaagcat tcatcaagtg tataatcatc tgtggctttt    3720
aaagtatgat attttttaggc atagtttttg tattaactta agttccactt aagtggttac    3780
agttgctatc gtttccatat aaagtgacta aaatatttt ttaaaattga aatttcttaa    3840
ttataatttg gtttagattt ggtcacacac cagtacaagc aagactcagc tgcctggcca    3900
aggacaactc tatctatgtc ttggcaaatt tgggggacaa aaagccatgt aattcccgtg    3960
actccacatg tcctcctaat ggctactttc aatacaatac caatgtggtg tataatacag    4020
aaggaaaact cgtggcacgt taccataagg taagagagag tgacggacgt gtaaaatgga    4080
gcgtgttgtg agtggtcaat gctgggttta ggagtttgaa tttcattccc tatatgatac    4140
aatattacta gagggtttt ttgttttgtt ttgttttttg tttttgaaa gtgggcaata    4200 aagaaaatga cacttttggc tgggcgtgga ggcttatgcc tgtaagccca gcactttggg    4260
aggctgaggc aggtggatca cttgaggcca ggaatttgag accagtctgg ccaacattgt    4320 gaaacccgt ctctactaaa aaatacaaaa attagcgggg cgtgatggca catgcctgta    4380
gtcccagcta tgtgggagct gaagcaggag acttgcttga acccaggagg tggaggctgc    4440
agtgagccga gattgtgtca ctgcactcca gcctgggtga cagagggaga ctctcaaaaa    4500
aaaaaaaaga aaaaaagaa aaagaaaaaa gaaaatgaca cgttgtaaaa aactactcag    4560
aaaaacatgt aggcagagaa ctgttaaaaa aaaaaaaaag tagcatgatg gtccaggatt    4620
gagataaact ttttgcacat ataaaacaaa taattttaac ataaaaaaag atactaaggt    4680
gactataatc tgggcactgt ttcaataatt ttatattttt ttagagacag ggtctcactg    4740
ttgcccaggc tggagtgcag tggagccatc atggctcact gttaacctca aactcctggg    4800
ctctagtgat cctcctgcct cagcctccca agtagctgag actgtaggca tgtgccacca    4860
tgctaatttt taaatatttt tttgaaaaca gagtctcact acattgccca ggctgtcttt    4920
gaactcttca cctcaagcag tcctcccacc ttggcctccc aaaatgctga gattagaggc    4980
atgagccact gagcacagcc ataatctaaa tactatttaa tattgaaatg gtagaaagat    5040
gtttcaaaat tgtatgaatc agctttgcat aagttaattt gctatcaaac cacaaaatac    5100 cttatttct acaccagcta atttaattac catcttatag atttaagatc aaaccataaa    5160
atgtttactt taaattctga attgaaaaaa ggaatcaaat aacctttaag tcataatttt    5220
atactaaact aggtagagaa agaagcctgg ccttttaaat ggatatgtgt gatgtacagg    5280
cagtatgaat gtcccttctc cacacccaga tattttgtaa gcatcttaaa ctgtagcctc    5340
agaatctttg gagtggagaa attatctcct ggcagtctca gttaaaatat aaatattaat    5400
taagaggagg gatgttaaac caatggtttt caaatgattt cgatcatgga cccctattgg    5460
aaaaaatcgt taacataagt cctcaatata tgtatttttg tgtgtgtatt tataaagtgc    5520
aacaatttca aaatgctttc ttcataattt tgtggatttt gacagcttct tttcatatat    5580
atcactgcac ttcactttct tcttaaaatg tgtctcatag taaaaataga aaggtcagtg    5640
cttccatttt cttgcttggg agattgtttg cattatttgt attatctttc aatgcagttt    5700
```

```
atttgcagta atcatttgaa gctattctgc cattctgtaa atatgcagga tggcacagtg    5760
cactgaatgt ggacaaacta gcaaggaacc tgcagtcacc ctgtctaagt tgaaaggctc    5820
tcactcttcc ctgagggtac ctcagggacc gtttgtaacc catgacctct gacatatgtg    5880
aacctaatga gaatacccttt gtcgatcaat tcctttttttt tttttttttt tttttttttt    5940
aggcagagtc tggctctgtc atcccggctg gagtgcaatg gcacgatctc agctcactgc    6000
aacctctgac tcccaggttc aacccattct cctgcctcag cctcctgagt agctgggatt    6060
acaggtgcat accaccacac ccggctaatt tttggatttt ttagtagaga tggggtttct    6120
ccatgttggc caggctggtc ttgagctcct ggcctcaagt tatctgcctg ccttggcctc    6180
ccaaagtgct tggattacag gcatgagcca ccttgcctgg cctgtcaatt cttaaaatag    6240
tagtaaagcc caatttcttt tctatttttt agatatttt tctacactgc agaccatttt    6300
attaactgtt gattccattt attatattag actaagtttt tttttagttt acctagaagg    6360
aatcggggaa ttaaatacat ttctatggta attttgaaag gtgggcaaga gtcactgaga    6420
ttactttgga tgggacacta aagagagaga tgacatctct cacctgactt acaggtattt    6480
attatgcatc tattaatatt acgtttctag gcaccaagga ttcaaagaag aataatgcat    6540
gttttttaac ttttaagaag cttatagggc caggtgctgt ggttcattcc tgtaatccca    6600
gcactttggg aggcccaggt gggtggatca tgaggtcagg agattgagat catcctggct    6660
gacacggtga aaccccgact ctactaaaaa tacgaaaaaa ttagccgggc atagtggcac    6720
gtgcctgtaa tcccagctac tcgcttgaac tcaggaggtg gagattgcag tgagccgaaa    6780
tcatgccact gcactccagc ctgggtgata gagcgaggct ccgtctcaga aaataaaat    6840 taaattaaat ttaaaaaaag cttacggact tggggttta tggggggggt atttggctct    6900
taactgagag agagggaaag agagagaagg gagagagagg agatgagaga tgctatggac    6960
gtatgttaca tattcctcca cattttcctt agaaatttac ttccaattgc cagatttatc    7020
cgcttcctag gagattccct gcagttgacc atagccaaat ctgttaccaa cttagagggt    7080
ttttatgagt catttcttca acaaataagg ttttactggt tttctcctat ccatttgttg    7140
tagtaccacc tgtactctga gcctcagttt aatgtccctg aaaagccgga gttggtgact    7200
ttcaacaccg catttggaag gtttggcatt ttcacgtgct ttgatatatt cttctatgat    7260
cctggtgtta ccctggtgaa agatttccat gtggacacca tactgtttcc cacagcttgg    7320
atgaacgttt tgcccctttt gacagctatt gaattccatt cagcttgggc aatgggaatg    7380
ggagttaatc ttcttgtggc caacacacat catgtcagcc taaatatgac aggtaattca    7440
tgaccaggtt aggtttcatc ttatattttt aagtgcagag aaatgaatgc ctcagttatg    7500
acttgtatta attttttgct tattggaaat tcttactgtg tttgtcatag tttcacaata    7560
gaaaaaaaaa gctagcactt gattataagc tatggttata ctaagacctt tatgtgtatt    7620
attcatttaa ttattacaat aattatatga gatagatagt gtcatcccaa ttttgcagat    7680
gagaaaattg acatacagag agtgcaagta atttgccaaa tgctacccag ctactacttt    7740
cctcagtggc catggaagcc tctatatctt gccctttgtc tcctcctatg gctgcatggc    7800
atatcctcgt gacatggctg ctgtcttcct ctagagcaat taatgagagg ggacaagaga    7860 gaaaggaaa gaagccacat tgctatttat gactagttac ccaccatcac ttctgccatg    7920
ttctattcat tggaagtgag tcactaagtc cagcccctct tcaagggaa aggaattaga    7980 tcctcccacc agaaagaaga atttttaagga attttggat atatttgaaa accaccacaa    8040
tgaggaatag gggagaattt ttattcccctt tccccacctt tcaggaactc ctgactacaa    8100
```

```
agatttttgt agttggttta attttccata atgctaataa ataatgctat tatatttaag    8160
gtttaattga aatgagacca aggaatgttt attttaatct cttccattag agaatagaag    8220
tagttaggtg ttcagtgcaa ttagaagcat gtatcctctc tcatcgtgac taatatggtg    8280
gcgtgatcac atgcccaatt ctgatgggga aattggcagt tttggttttt ttgtgtgtgg    8340
tgttgttttt agaagacttg tctttcattc acaggaagtg gtatttatgc accaaatggt    8400
cccaaagtgt atcattatga catgaagaca gagttgggaa aacttctcct ttcagaggtg    8460
gattcacatc ccctatcctc gcttgcctac ccaacagctg ttaattggaa tgcctacgcc    8520
accaccatca aaccatttcc agtacagaaa aacactttca ggggattat ttccagggat     8580
gggttcaact tcacagaact ttttgaaaat gcaggaaacc ttacagtctg tcaaaaggag    8640
ctttgctgtc atttaagcta cagaatgtta caaaagaag agaatgaagt atacgttcta     8700
ggagcttta caggattaca tggccgaagg agaagagagt actggcaggt aatttcagtt     8760
caaatgaaag ggcattcaag tgaaaggtaa attccaggtt aacttttat atttgttcca     8820
gaaaaccagg tgcttttcct tggcttgact ccatgcattg atggcaacac acacacacac    8880
aacacacaca cacacacgtg catttatgca cgtacataca ctgggataaa atatttacaa    8940
tgggaattaa gtataatctt attgcttgct ttaagcatat ttaaaaaatt attaacctaa    9000
ccatgatgag tttcgatttg actaataaac cagcctactg tggagaacat caagaagact    9060
tccttaagtg ggtttgccaa catatctaaa ttataaacag tcttattttc acttgcaaaa    9120
ctaacagtaa atagagatac tactttttat ttagtttctc ttctaatcag atgtcccggg    9180
ttttgtatag cttttcttt cttttcttt ctttttcttt tttttttttt tgagacaatt      9240
tcactctgtc accctggcta gagtgcagta gcatgatctc ggctcactac aacctctgcc    9300
tcccaggttc aagcgattct catgcctcag cctcctgagt agctgggact acaggcatgt    9360
gccaccacac ctggaaaaat atatatat atatacacat atacaaaata tttttagtag       9420
agacagggtt tcaccatgtt ggccaggctg gtctccaact cctcacctct gctgatccga    9480
ctgcctcggc ctcccaaatt gctgggataa catgtgtgaa ccaccacacc tggccttgta    9540
ttgctttcaa atgacaaatt ttaaagatga aacttttat agaatgttgg ctctgaattt     9600
gtatttccct attatactcc atgtcccact gccttcttct aaagaaaagg attgggaaga    9660
gaggtgagat taaagggtgg aaaaaatttt aatatccttt cagcttcagt actcttcagt    9720
actattgttg cccaaagatc tccacttcat tgagctcgat gccatcatct gacataccaa    9780
actaatggtt taactctaat tctaaactga cttctttctc ttaatccgct tgttatttag    9840
gaagtgggtt gattctcaag tcactggcca ttttaataa agcagttaat tataagacac       9900
atgatccaaa tcccttttca gagaaagata atgtttgctt cgctgtagtt aaaaactaag    9960
gcaacatttc tggtatgagt aacttcaatg taaggcattg cgttttatct gcgtttgttc   10020
cacataggtc tgcacaatgc tgaagtgcaa aactactaat ttgacaactt gtggacggcc   10080
agtagaaact gcttctacaa gatttgaaat gttctccctc agtggcacat ttggaacaga   10140
gtatgttttt cctgaagtgc tacttaccga aattcatctg tcacctggaa aatttgaggt   10200
aagaggactt ttataagagt attttcattt tatatgttct ctgaagtcaa gtaaacaag    10260
ctatagccac tctgccagtt aacttctgct gtgtaacaaa tttcctcaaa accatttctt   10320
tagccctggt tctgtgggtt ggcaattga acttggggta ggtaggctgt ttttctggtc    10380
tgagataggc tcagttgacg ttggctgggc tcattgtgtc tgccattggc tagtgggttg   10440
```

```
attaggactg accagtttgt gattgccttg tcctggacag ctgggattat taaggccatc    10500
tctccccgtg gtctctcatc tttcagcaaa cctgagcttg ttcacatgtt agctgaatga    10560
gtccaggagc atcaagagaa aaacaaatct ttgcaagttc tttgcaaatc tctgcttgca    10620
ccgtgtttgc aaatgttgca tcaacacagg aagttacatg agcagtggtg attcaaatgg    10680
tagagaaatg aagaactcag acctctcaat gggaagagct ataaaatcac acggcaaaag    10740
gacatgggtc aaggaggggga aaatattgtg atcatttttt caatttataa aactaatta    10800
taaaatgatg atacttcatt ggaagaacat aataaagaac atacctagaa ctgtgagtct    10860
gagataccat tcattgaaga atgtttgttt atagatttttt aatttccttt tgtcactagt    10920
gaagacaaac agaaaatcag atgtttattt cacattttttt tttaaacaga gtcttgctct    10980
gtcacccagg ttagagtgca gtggcatgat catagctcac tgaagcctca aactcctggg    11040
ctcaagcaat cctcctgcct cagcctcctg agtagctagg atttaaaggc atgtgccact    11100
gcacccagca tttgttcata aattacagtg gctgtagcta attaattcac aaattaagct    11160
ggcttcaaat tagaattatg actctgcagg cttatatctg ctaatataca acacttgcac    11220
acatgcacat acacgcatac atacacatat tccagtggtt tgaatattaa tgtcttctct    11280
gaattgtggc aaacagtggc agggtttcag taactagggt gaaatcattg catattctat    11340
aaaatagggt ccaagttaat tcaatcaagg catcaagtaa ggaagtcttt aaaattgcag    11400
attgcttatg gtcatgtatc tgtatctgct gtgttatcag agtggaatat atcatactta    11460
taaaaatgct taattctatg aaaccaacaa tttaacatac agtgtaacct taaggccata    11520
aaatccaaag atcaggaatg ctttgctgcc atagaacctg tttaggcaga atctcatgag    11580
caaattgagg ctggaataaa agctgaagtg ccaactacag aaaatcatga ttaaatctac    11640
agcaaggagt ctggggctaa aatccagtag ctaaaaggtg gctggactga cataaatatc    11700
tatctgagat cacttcaagg aagtgagaga gagaaatcag ggtcaccaag gtaaacttag    11760
gaggacatag ggtctagcca tattgatgca ttatattctg taagcctgaa gatttaaact    11820
gagcacacaa tctaattttc tcgtactact ttgccacttt ttccatgtct tgtactcata    11880
gaaatctatc tctttgagga attgtcccat agtaggactg aacatttacc tgatgaaact    11940
acttcatcca tgggagaagg acaaaaaaat gctagagttt tccaaactag gttaaaggtc    12000
caaagccaga ataccatttt cactcttact ctgaaccaca taagtgtttg aaggtggatg    12060
gtgatagtgc atgaagagtt ggagaacgta aataatttat tccattacta cttcctttct    12120
ttgttttaaa aatttcatcc caaatgtctt caggcagtta agaagagtta gagaatgata    12180
caagagaata catgtttaaa tgcttaactc catagtattt gtacatctca actcttaaac    12240
attttttttaa attattttta attattatta ttatttgaga tggcgtctcg ctgtgttgcc    12300
cagactggag tgcagtggtg caatctcagc tcactgcaaa ctctgcctct tgggttcaag    12360
cgattctcct gcctcagcct cataagtagc tgggactaca ggtgcatgcc accacgccca    12420
gctactttttt gtatttttag tggagatggg gtttcaccat attggccagg ctggtctcga    12480
actcctaaca tctagtgatc tgccacctcg acctcccaaa gttctggaat acaggcatg    12540
agccaccatg cctggccttg ttttaattt ttgtgggtac atagtaggtg tatatattta    12600
tgggttacag gagatatttt gatacagaca tgcaatgtgt aataatcaca ttagggtaaa    12660
tatggtatca gtaggtctca acttttaatg attctgtgaa cttgtcatgc tgtatcccat    12720
ctctggttcc ttcttagatg gaaggaagga gggaaggggg catagcacct accgtttaaa    12780
ttgggcacct gtaatcatta tttggatctt gtcttacctg ctccagacca tttgcagaag    12840
```

```
aaggaaatga gatatagatt gtattacacc aaaaaagata tgaaagagcc atgtgacagc   12900
tggcagggag ggtctttgga attgtagtcc cttggaggga gcatcatgat gagggtgagg   12960
caggtcttta ttttgtaagt gtagattctc tgtggcatga ctttcactga agttcatcag   13020
gttctaagga acagatacta atcaaatttg caagatagat aagcgagaac accaacttgt   13080
tattttaaaa aataggttcc cttagctggg aacaatgaac tgtatgtcaa ggagactctt   13140
cattggcaaa tcctctcaaa agtacaaatg atagatcagt ttgttttgtg agtgcagaat   13200
taaaacaaaa ggagttgggc attcttggaa aagatttcca agaacccacg gaagcctgag   13260
gcaatgtgat tcttctcttt agggctggtg atctgaagac catgtaggat caaggtgccc   13320
actttcctca aaaagagcca aaaaaaaagt ccaataaccc attcttggtt ttttagtgc   13380 ttcttttctc tagagacctt gcagggcatg gcccttctgt gaatatgttg tttctagaaa   13440
cagcagtcat aatattgaag atgacaaatg ttttacatca gtcatgctca ttatggcttc   13500
ttgagtagct tctcagttct gttgatggat gcacactctc tccatagata tttacacgtt   13560
atcttagagg atcactattg cagagatttc aacacacttg ttgtgtatcc tcaaccccca   13620
ccaccacttt agttttatgt taaagggtg gtgttactca ccatgcccac aaatgtggaa   13680
acatcttgct ttagcacctt aggcaactct ggtgtattgt cagaagcact ggcagagtct   13740
gttctctgta actaactagt tagataacct tgggaaagtc acttaacctc tgaatttcct   13800
actcatagaa gagaatattt tcctcactga tttggtgagg atcaaatatg ataatgcatg   13860
tgaagacact ttgtgaatgg tgaagtacaa tcattatctt ctaggatatt tagtcatttt   13920
ctcctcccag ttgtaaagca tctgtttttcc taattttcaa ttcttctcc actccaacta   13980 atttcccaat tttcaatttc ttctccattc caactccatt tccacaacta atgggttcat   14040
tttcttttat tcttgttctg tttattgact gtctatgcat gtttccttct gttcttgttc   14100
aattgctttg tacatattcc tctcttatga aaactccact gtggcttcag gctagatcta   14160
gtcattaatg cctttcacag tctgatctcc accttcctct gatcatattc cttcttctct   14220
tcttcactaa tcttcagcgc tagccagtgg tgtgatgtaa cttaaacaa ttccttctct   14280 gaggtagaaa acaaaaagcc ctgacttatg gaatttgcca gttttcattg tgtcaatatt   14340
cccgccatga tcccaccagc ttcaagaatg gatctgttgg cagagtttga tagctcacgc   14400
ctgtaatccc agcactttgg gaggctgagt tgggaggacc atttgaggcc aggagttcga   14460
gaacagcctg ggcaacatgg tgaagccctg tctctactaa aaatacaaaa attagctggg   14520
cttggtggca cgcccctgta atcccagcta ctggggagct tgaggcagga gaatcacttg   14580
aacccagcag gcggaggttg cagtgagcca agatcatgcc actgcactcc agcctgggtg   14640
acagagcgag actccatctc aaaaaagggg gaaaaaaaga atggctgtgt ttaacagcca   14700
gctgtccaat ttcctggaaa tttaacaatc tgttctcatg agcctgtgca ccactagctc   14760
cagcacacca ctggttttaa ccaatctaga atgagaactc acattgcctt gatctgtcac   14820
acacacttct gtctcagaat gagcctttgc tggttcaatg tccacttccc acaatgtctt   14880
ccaccataca gcccttgaaa gaaattccta acagcttgag ttttttggcag cttgtgtccc   14940 actccgtgaa acagaccagt tcagttttt ttttctcaga cctcctagca cttacctgtt   15000
ctcttctctg atacactgat aaactgattt ctctctttat gtttagaatc cgctccattt   15060
caccattagc tctttagctt cttgagggaa ggatgtgatg tataactctc tggttcctga   15120
ttgtcttgca cataatcgaa ctcaatgaat tgctgctgct gattttgact ttccattaat   15180
```

```
ggttacattt gattgttgaa actaaaatct tgggccctct tgaattgctc tagtcttcat    15240
tatgtagtaa atggctgtcc cctgcctggc ctacttgctg catcctccta aatcagaaat    15300
gatttgacta tacattatat ctaggatggt ttcaaaatga ttaatttgct tttaacttct    15360
atgttaagaa agctgactgt acttttccca ccttttcttt aggtgctgaa agatgggcgt    15420
ttggtaaaca agaatggatc atctgggcct atactaacag tgtcactctt tgggaggtgg    15480
tacacaaagg actcacttta cagctcatgt gggaccagca attcagcaat aacttacctg    15540
ctaatattca tattattaat gatcatagct ttgcaaaata ttgtaatgtt atagggcgtc    15600
tctttatcac tcagcttctg catcatatgc ttggctgaat gtgtttatcg gcttcccaag    15660
tttactaaga aactttgaag ggctatttca gtagtataga ccagtgagtc ctaaatattt    15720
tttctcatca ataattattt tttaagtatt atgataatgt tgtccatttt tttggctact    15780
ctgaaatgtt gcagtgtgga acaatggaaa gagcctgggt gtttgggtca gataaatgaa    15840
gatcaaactc cagctccagc ctcatttgct tgagactttg tgtgtatggg ggacttgtat    15900
gtatgggagt gaggagtttc agggccattg caaacatagc tgtgcccttg aagagaatag    15960
taatgatggg aatttagagg tttatgactg aattcccttt gacattaaag actatttgaa    16020
ttcacctagt tttctgtgct aatgtttatc aggagattta cttccaatc aaaaggcaat     16080 gtcgacattt atttctacag tgaacgtagt tttgagtgct agaagaattg atggctattc    16140
caagttcata tcaaaggaga cctgacccag ggcactcata gccccagctg tcccacctta    16200
aggctatggc gtaatttaac aggcagaaat ctcataacac aaagaccatg acagttaaaa    16260
gttacactat tttcagcatt tggttgactt tttacaaaat acacatattc catgctactt    16320
gaagtaaact agtatatttg ttattgatca tttaattcag atactcttaa aattaaagaa    16380
ctgattttga attttcagat ttattttctg atttttatct cccaaagtat ttttaagttc    16440
aatactttta cataaaaaaa cacaattgaa gcatttatct tttgttttta catattgtca    16500
taaacctact tatggatttg attttaaaat tctactaaaa tacactagaa aagtaagatt    16560 cctttataa tctcgtggtt agtattaaga gaagaaatat ggaagttaag ccacactttg     16620
tatttaattt tgagaagagc atacatattc cctatgttca gcattgggac atcaaagatg    16680
gcaattttaa agctgtaatg aacgtgcatt tgtgtatata gtccaaatca tataatcatc    16740
aaagttttat gctctttttt cttttctttt tctttttttt ttttttgaga cagagtctca    16800
ctctgtcacc caagctggag tgcaatggtg ggagttcagc tcattgcaac ctccgcctcc    16860
tgggttcaag tgcttctcct gcctcaacct cccaagtagc tggaattaca ggcacccacc    16920
accatgcccg gctaattttt gtattttttag tagagatgga gtttcgccat gttggccagg    16980
ctggtctcga actcctgacc aggtgatcca cccactttgg cctcccgatg tgctgggatt    17040
acaggcatga gccaccatgc ctggcttctt tttcctttc ataaagtatg ggacatttaa    17100
aatttgccaa gttttgcttg aggaagttag atgttgtgca gtggttttgc agcatgtatt    17160
ttggctcttg ggcaatgacg tttcatttgc agaagtttag atgttgattg aaaatcaaca    17220
gctgacgtta acaaactgg tttgagtaag atacaagcaa ggagctcctt tcacagaaag    17280
ggacagttct gattcaagct tggagctctc agctgtacct cagtttgtta aaataaaaaa    17340
caaaaaacga aagcaccaag tgccaaggaa attaagagc acttaatgct ctactgtaaa    17400
attgcctgca ccacatttta acccatctcc accgtggttt ctcacataca ttttatttta    17460
tcaaacaacc caagcatagt ttcatttggc ctttatattt ctttgataac tatctttcat    17520 cccatttttat tttattttta cttatttatt tatttatttt ttgagataga gtctcgctct    17580
```

```
gttgcccagg ccggagtgca gtggtgcgat ctcggctcac ttcaagctcc gcctcccggg    17640
ttcacgccat tctcctgcct cagcctcctg agtagctggg actacaggcg cccgccacca    17700
cgcctggcta attttttgta ttttagtag agacggggtt tcaccatgtt agccaggatg     17760
gtctcgaact cctgacctca tgatccgccc acctcggcct cccaaagtgc tggaattaca    17820
ggcgtgagcc accgcgcccg gcctcatccc attctaaaat ttcatgttag ttcttgagtc    17880
ccttgtggtt ctggagatag taaacaaagc tcttattttc tcctatttgg ctttcattag    17940
gcttttttcc tgaaatgctc ttttacaact tcctggttac agcccctgt attacaaagt     18000 cacatgctca gcagcagcct tct                                            18023

<210> SEQ ID NO 19
<211> LENGTH: 14616
<212> TYPE: DNA
<213> ORGANISM: Homo sapiens

<400> SEQUENCE: 19
cgccttatac acctaggaag caaagacatt actaacaaca ttgggtaatc aaatatttaa      60
ctcaagtttc tattgatttc aacacacaaa aaaagctggt acatttcctg gaactagggg     120
ctgggagaat gaaggggaat tcccatatgt ttccttttga ttctattcag aaagtcaggt     180
gaaccaagaa aagagttaga atttcaactt gaaatatgaa aattattttc ttctcatccc     240
agatcaatcc atctgtttta catagtttcc ctcttctcct cagaaatttt tttggaaaag     300
aacttatgtc tgatgtctga tgaaaacaat ttatgtcaga cataaactca gaatttaggg     360
ctgaatttat gttcatatgt ccttatttcc tgaaatggta tcagggcata aggacatatg     420
gaaacactgt ggggtatctg ggagcagaaa tatttggata atggaaaagt ttattgaaac     480
caagggactt tgaattatag aaacaaacca aacccaaaat agacacaaat ctccataact     540
tacaattttc cttagatctt agaaagaatc tcaagaggga gaagcagtgt taattgttct     600
agaatcagag atttaaacct taaaaaatat tctacatttt aaattaactg atattcaaac     660
aaggagattc aatccaaaat tgggcgaggg aagtgaattt aactaatcaa aaaacattta     720
cagagcttag cacagtataa aattctatag aagcagcaga gaattataat gtgaccctgc     780
ccttaaggga cttataagga tgatatgttt aaaaaataaa agaattaaag gagaacttaa     840 cacttttga attattgatt agtcttcata tggaagcggg tttaaactgt agaagacagg     900
taaagtaaat tgcatctcaa taacaagaat gttcttaaaa ttggcaatgt tcaaaggtgg     960
aatagactgg cccatcaggt agtagattcc gtcattcaac attcattcat atattgagct    1020
ttcaccatct gtcacacatg tgctggggtg atgaggttca acagtgagca ggacacttcc    1080
cttaccctcc aggggccaca tcccaggata catcatctct gtctagatgt ttattggaca    1140
tggatgttct gaaagaaaac agcaagtttc tttttaatct cttttaagaag acaaaacata   1200 catatataat attaagtatt ggtataatat ttaaattaaa ggtcaagaca acagcaagga    1260
gtgagagaca ttcagcagca cagaaaaaaa tgctatagga gttcagaaat atcacttagg    1320
actggagtgg atttgggagg actctagggg gagctggaac ttagacggat ggagaacaag    1380
ggcttttcaa atagaaatgg ccatacaaat atgtaagtag agtgctcaac aaattgttgc    1440
tatgatgact accttccaat attggcccta ttaatagaaa tgttggctta ccaggaaaat    1500
ttttttttat tagaaaagac ttcaactgcc agtgtgtttt ggactggggt gaattcatct    1560
ggttggctca atcttttagt gttgacttga ctctgaacaa tgtcaacaac tgcactgtac    1620
```

```
acttgaatca atccaattac gtcctggctg tcagttttct tgcacaacat ccttctcaa    1680
tgctgtgttg tgtaatatat gtgcaagaaa atataaacag ctgattgcca ggagggattt    1740
aatgtaaagt ttttccagtg aaacaaaacg taagaatctg agtttgtttt tcaaagatca    1800
ctaaatttta gttatgatta tatcacattt tccaaaatgt gtggcagttt ttgccctcct    1860
tgctctgagt gttggtgcac tggacacttt tattgctgca gtatatgagc atgcggtgat    1920
attaccaaac agaacagaaa cacctgtttc aaaagaagaa gctttgctcc tgatgaacaa    1980
gaacatagat gttttggaga agcagttaa gctggcagcg aagcaggtat taccatttta     2040
tacttgtaaa ggagacttgc agtttggtca aagagtattt ggaattcatg acaaactttt    2100
ttgccccact tgtttcgagc agggtgcaca tatcattgtg accccagaag atggaatcta    2160
tggttggatc ttcaccaggg agagcattta ccctatcta gaggatatac cagaccctgg     2220
agtgaactgg attccatgta gagacccctg gaggtaatat catatcatta atttctaaac    2280
aaaaagttgt gatttggtaa acaccaaca gtaaactcac tgaatttgac tggtaattgt     2340
gttgataaat agtcaatctg tggcatagga tgtagatgct tttttttccc tgtaatttca    2400
acttttagtt tagattgagg gagtacatgt gcaggtttgt tacatgggca aattgcatga    2460
cgctgaggat tgggttacaa tgattgcacc acccagcata gtatacaaca ggaaggtttt    2520
cagcccttgc cttcctctct ctctctcccc tctattagtt cccagtgtct attgctgtca    2580
tctttatggc catgagttcc caatgctag ctcccactta taagtgagaa catgcagtat     2640
ttggttttct gttcctgtgt taacttgctg aggataatgt cctttggtgc tgcaaaagac    2700
atgatttgt tccttcttgt gggcacctag gttaattcca tatctttgct gttgtgaaaa     2760
gtgctgcgat gaacatacaa gtgcacgagt cttttggta gaatgatttc cttcctttg      2820
ggtatatacc tagtaatggg attgtgagtc gaatggttgc tgtgttttaa gttctctgag    2880
aaatctccaa actgctttcc acaatggctg aactaattta catttccacc aatagtgtgt    2940
aagtgttccc ctttctccat agcatctttt attatttgac ttttttgttaa cagtcattct   3000
gactggtgtg agatgatatc tcattgtggt tttgcttggc atttctctga tgataagtga    3060
tgttgagtgt ttgttcacgt gttttttggc cacttgtatg tcctcttttg agaagtgtct    3120
gttcatgtct tttgcccact tttcaatggg gttattgtt ttgttttgc ttattgattt      3180
aagttcctta tggattctag atagtagacc tttgttagat gcctagtttg caaatatttt    3240
ctcccattct gtaggttgtc tatttactct gttgatagtt gcttttgctg tacagagctc    3300
tttagttaaa ttaggtccta catgtcaagt tttgtttttg ttgcaattgc ttttgaggac    3360
ttagtcataa attattttcc aaggttcatg tccagaatgg tgcttcttag attttcttct    3420
aggattctta tagtttgagg tcatacattt aaatctttaa tccatcttga gttaattttt    3480
gtacatggtg aaagataggg gtccagtttc aatcttctgc atatggctag ccagatattc    3540
cagcaccttt tgttgaataa ggagtccttt ccccatactt attttgtga actttgtttg     3600
agctacagat ggctgtaggt gtgcggcttt gtttctaggc tctctattct gttctattgg    3660
tctatgtgtc tgttttctta acagtaccat gttgtttga ttactgtagc cttgggtaat     3720
gtgatgcctc aggctttgtt cttttgtttt aggattggtt tggcgattca ggctcttttt    3780
tggttccata tgaattttag aaattttgtt tataaatctg tgaaaaatg acattggtag     3840
tttgttagaa atagtgttga ggctgggtgc tgtgggtcat gcctataatc ccagcacttt    3900
gggaggccaa ggcaggtgga ttacttgaga ttaggagttt gagaccagcc tggccaacgt    3960
ggtaaaaccc catctctact aaaatacaaa aattagctgg gtgtggtggt gtgtgcctgt    4020
```

```
aatcccagct actcgggagg ctaaggcatg agaattgctt gaacgataga gtgagactct    4080
gtctcaaaaa aaaaaaaaaa aaaaaagaa gaaagaaat agtgttgaat ctgcagatac     4140
tgcttatgtt tcatagtgta tatcatctgg catatctcct gtttggtaaa tgacttgaga    4200
tactgatgac tagttggtta tttgttgcaa ttgtctttca acaatagtag gtgtgaccag    4260
gcgtggtggc tcacacttgt aatcccatca ctgtgggaag ccaaagcagg aggactgctt    4320
gaagccagaa gtttgagacc agcctgcgca gcaaagccag accctatttc ggcaaataaa    4380
aaatttagcc aggtgtggtg gctcacacct ataatcccag ctactcgaga ggctgaagca    4440
ggaggatcac tggggcccag gagtttgagg ctgcagtgag ctatgattgc accactgcac    4500
tccagcctgg gtgacagtaa gaccttgtct taaaaaaata gtaggtatag gccgggtgtg    4560
gtggctcacg cctgtaatcc cggaacttta ggaggtggag gtgggcaaat cacctgaggt    4620
caggagttcg agaccagcct ggccaacatg gtgaaacccc atctctacta aaaatacaa    4680 acattagctg ggtgtggttg tgcatgccta atcccagc tactcgggag actgaggcag    4740
gagaactact tgaacccagg aggcagaggt tgcagtgagc cgagatcacg ccactgcact    4800
ccagactggg caacagagtg agactccatc tcgaaaaaaa aatagtaggt atatacacaa    4860
tttttatagt aaatgtgttt aattgggttt gaacaaagtg aaaaagttgg aatatctaga    4920
acctgtgtcc caaatacaag taagttggtt catccatgga cacctgcctc cttcacagga    4980
agagtaaaaa gatgaatgag cctgtttcca aagagctttg ctatcactat cattcagaat    5040
gcaatcaata tggccaatgg aaattgtata ggacttgaaa aaggaagccc tacttctggg    5100
accacatttt acgaccacct agctgagtga tgtaagcgta taacctaaat gcttaacatt    5160
tctgtttcat tatctgtaaa acagggataa tagagtccct taattctctt acagatcaga    5220
caagagtaat gaagtaatac acatggaatt tgtacattgt aatgcactct ccaatgctag    5280
ctgtcactat tcctttttt ttttttgttaa cagaagggac tgagtctgaa cttcttgtg    5340 ttcttgtcct ttgagagact ttagtaatta ttagtagatg taatttaggc ataactttct    5400
taaagaaaat atgcataata aatatgatat ctgtgaaata gattatttta gttgtattaa    5460
cttttaaaaa tagtttaaga ttatttcttt aaatggcaaa attgatgggt taagaagtca    5520
tttaacttgc taattttaaa tttacatgca cctgtttaga actacaccta ttgtgcaaaa    5580
agagaaactt ctttgataat tttacctatg tgaaattaag tggaaagtca tgcttaatgg    5640
tacaacattc aggctcagct atgtgagtca aacctcactc tgggattttg ccctttggaa    5700
aaatattctc taaacattgc atggtctgtg tttacagaaa ccatgtcact atgattcaac    5760
atctacttgc ttatgaggcg tttcccagaa caggaaggaa tcattatttg ctgcagttga    5820
tgaggcttac acgaaaatgt actgtatttg actgggctaa tgaaactgac ttttccaggg    5880 aaagatatc cataaatttg ataattagct atcgataaat tattttaagt tgggaaagta    5940
ggtgactgat gaaatgtcaa cattatgaac tcttacacct acttattcaa atgacaacct    6000
ttcagttttg tgttacaaaa aggagaaatc cagtatttaa tataatgata atattggaaa    6060
agaaagtcag ttttctccct ggtgatattt atccctgaag agaatagtag agaggcatgc    6120
ggtcatcctt gtgcatttaa atatttagaa tgctgacatg tcaaacagtt ccatgggctt    6180
ttttcatgag taactagtag gaaatattaa ataactcaaa ttatttagtc aagaaaagaa    6240
aaattaaaca aagtacatga taagttatt aaggtctta atgaatatga atattaatag    6300
tacttctctg ttttttttag aagaaaataa aaagaaaagg tctaaaccag taggccatta    6360
```

```
atctgtcctt tttattcaaa ggttagttta acctcaattg cagagggct gtgagttcat    6420
agagagacat ggaatggcct ctaatcacac aatccataat agcaattttc atttactgag    6480
cacttacttg gtcccaagaa ctgtacctgg tatactatac ccattattac attcaattta    6540
tgtagttggc attactattt gcattacaaa tatgtgaaaa aaggaaggct tatgatctca    6600
tgattgatca ttagattggc tggaattaaa acagctatgt catttaactg tgctaacgga    6660
atggactcta agggcctaga tgaaccatat tataataaaa ttttagtga ctagcaaatc    6720
cacttattta acagagtgag ctggttgcta acattttt gtcttatttt ctgctgaaat    6780
ctgcctcact ttaacttcct ttcgtctttt tcctgcattc tatgctatgt tcacacatat    6840
gacccatctc ctataaatta agcctttcaa atatttgaag ccagctatca ccatgctaca    6900
ttctcttctt ataccaagga taaatatctt taatatggat ggacttggta aaacaatttc    6960
atgtctgtac ttatctcagg atttctcatg tggatccact aaggcagaaa ggaagctatt    7020
gttttacatt tgacagatga agaaactgag tcagtacagt gaagtgcttt ttattttta    7080
ttttaatttt taacatttcc actacttaca gctatatttg ttttttata gagacaatct    7140
ggagggtaca aactatttac tgtcacctgg catttctgtt tccaaccaca tctcgtatca    7200
gcaaccttgt acaaattatg gcttggatta tagaaaaggt cctctccatt agcagaatct    7260
gctaaatttc aagtgcttca tatatcttcc tgggagcact tcataagaga atgtgctgct    7320
tcttttcatc ctcctcttcc tcttccatct tttctttcct tcagtcttgt actgtaatct    7380
ggagtttggc atagtaaatt aggttagctt tcaggaagat aaacactgta tcacatgaga    7440
gttttaaaat atttctgtt gattcttgac ctagagctgt tgtgttatgg gcaatgggca    7500
aataaagtat cactttggta tttcagaaat cactaaaata tagtaagttt gaggaaatgt    7560
ctattgaatt agattcggca acacaccagt gcaacaaaga ctcagctgcc tggccaagga    7620
caactctatc tatgtcgtgg ctaatattgg ggacaagaag ccatgcaatg ccagtgactc    7680
tcagtgtccc cctgatggcc gttaccaata caacactgat gtggtgtttg attctcaggg    7740
aaaactgttg gcacgctacc ataaggtgag catcacttgt gccttagctc aacttgttac    7800
ttcttctgtg tgcttgtggt atgtatgtgt gtttgtttgt tgaatgttgg ggagagaact    7860
gttatagatg catcttataa ttattacatc atagttgaaa aggagattta attcagttcc    7920
atataaccgt tctgggtttg catttatcat aaaacagaat atggtagagt atttaaatgg    7980
atgtgacaat agccacacaa agcttttaat gttctctgaa aaagaagtaa acattctgtt    8040
tcattcatga tttaatatca ggttcatttt ttagcccaat ttgttagcat ttcatactaa    8100
gctaccatgt attccattag gactttttg attgcaatga aaacaaaacc tcaaatgaaa    8160
atggctttaa aaagatggaa atttccttgc ttatgcacat gtaaaaatgt gtatcataga    8220
aaggacaggt ctcatttcag tgcagtctga cactcagagg ctccaaagtt atcatccacc    8280
cctctagctc tcctagccct ttgttacagc ttctttctca ggggaactct ccttttagaa    8340
gccacattgc tggagcaaca cgaaattcac atctttatca acaaaatcta caggaagggt    8400
gtatttctcc ctcctagaac cttgcaaagg cctatcgct ccttgattca attaggtgac    8460
gtgcctttcc tgagctaatc accaaaggat gagggatagg ctgccacatg ggaggagaaa    8520
ggaggagcaa gaggcctcca tggaccacag aggtgggaag tagctctccc cagagcacac    8580
acatgcacac aacaggccaa acaaaaacct gagcaaaaca tatgctgtac tcctgagccc    8640
aggttaagtg gagttttgga aaagaatca ggctgaaaaa taaataaaa ttatgaatgg    8700
cttactaatt aataatatgt agcaactgca ttgtctaaat taattttcaa tggacttcac    8760
```

```
ttctataaac ctggcagtat cattgggaca catgacaaag tttattttat taacatagta    8820
gtgctgttga aatttaaaga atatagtgga aaacaatctg agaagtgtag gattcaagat    8880
ttcaacctgt gattttaaga tacacatttt cacattttaa atatcatttg tacatgtggt    8940
ttcattcatt ggttgtaaaa aaaataaagt tttttattaa atgtcacagt aagaaaatgt    9000
atagatggtg gtatagtggg gatgattttt acaaatgtat gtgtaacagt tttattttgt    9060
tgttgttgtt gattttggaa atggaatctt gctctgttgc ccaggctgga gtgcagtggc    9120
gcgatctcgg ctcactgcaa cctcggcctc ctgggttcag gggctccccc tgcctcagcc    9180
tatgagtagc tgggattaca ggcatatgcc atcatgcctg gctaattttt tttgatattt    9240
gtagtagaga cagggtttta ccacattggc caggctggtc tcgaactcct gacctcaagt    9300
gatccacccg cctcagcctc ctaacatgct gggattacag gcgtaagcca ccacacctgg    9360
cctatgtgta acacttttaa acctgcatgt caacatacat gagaggaaag atttaacggg    9420
gaaagactta attgatcaca tctatttggc agttttctta ttaattttct tcttctttgc    9480
tttttattaa cagtacaatc tttttgcacc tgaaattcag tttgatttcc ccaaggattc    9540
agaacttgtg acttttgaca ctcccttttgg gaagtttggc attttttactt gctttgacat    9600 tttttctcat gacccagctg tggtggtggt ggatgagttt caattgacag cattctctac    9660
cccacagcat ggtacaacac gctgcccctc ctctcggctg ttcccttcca ttcagcatgg    9720
gccaaggcca tgggagtcaa tctacttgct gcaaataccc acaaccaccag catgcacatg    9780 acaggtaact cacgcgggcc tgcaccaagt gggagtgaca gtcttaggaa ggcttcattg    9840
attttcaagc cacaaacttt tgtttaataa ctttattacc aattttaaca tcacaaaatt    9900
aataatagca tttgttccta cttaaggaac gttcattgtc cttgtgaata aaagaggcaa    9960
acattattat ctcaattttta cttgaaagga aattggagct ggaggaagtc atgtaaaaaa   10020
atcaaagaga gttctaagaa acttcctagc caatgtgcat tagtaatatc gaaataagtc   10080
tggttgttta aagagataac ctacagagca gaagaaaata tttgcaaact atgcatttca   10140
taaaaatcta atatctagaa tccataagga acttaaacaa atcaacaaac aaaaaacaaa   10200
ctatcccatt aaaaaatgga caaggacat gaacagacac ttctcaaaag aagacataca   10260
tgtggccaac aagcatgtaa aaatgcttaa catcactaat cattacagaa atgcaaatca   10320
aaaccacaat gagataccac ctcgctccag tcagaatggc tatgattaaa aataaaaaa    10380 caaacagatg ctggcgaggt tgtgaagaaa aaggaaacac ttatacactg ctggtgaaaa   10440
tgtaaattag ttcagccaca gtggaaagca gtttggcgat ttctcagaga acttaaaaca   10500
gaactgccat tcgactcagc aatcccatta ataggtatat accagaagga atataaatca   10560
ttctaccata aagacacatg cacttgtatg ttaattgcag cagttttagc aatagcaata   10620
acgtggaatc aacccaggtg ctcatcaacg gtgaagtgga taagaaaat gtgatacata   10680 tacaccatag aatactacat agccataaca aagaatgaaa taatgtcctt tgcaacaaga   10740
tggatgcaac tggaggtcat tatcctcagc gaatgaacac aggaacagaa aatcaaatac   10800
ctcgtgttct cacgagttga agttaaacat tgagtacaca tgaacacaaa gaggggaaca   10860
atagacacca gggtttactt gaggggggat ggtgggagga gggtgaggat tgaaaaacta   10920
cctattggat actgtgctca ctacctgggt gacaaaatcg tttgcacacc aaaccccagc   10980
aacatgcaat ttacccatgt aacaaacctt cacacgttcc ccttctatac ctaaaataac   11040
agttggaaga aaaaaataca aacaaataaa aatatttcaa gcattaaaaa aaaacttgtt   11100
```

```
gaagtgataa aaatctcttt tgacttaatc aggttttag agttctcct ttatcatatc    11160
catgttcaaa gtaatgcagg cttccttttt aactgttctg ttatttgttg aataacaaat    11220
cccaaacaca aataaactaa atcgtcagtg gagagctaaa attattcttc acgttggggg    11280
attttctagt ttgttgctaa gttagcttaa aactatgccc cccaagtcaa atgataattt    11340
cagtgcaagt agtaccttat ggaggacaca gagtcaaatt ggaacttagg ccaatgtaac    11400
agctatctcc ttaactatct tgaaaatatg ctttaataac tttgtattta acttcacatg    11460
ggaatattct attagttggt caccataaca aatctgaaac caatgtttgt atttatgttg    11520
cttgtaggga gtggaatcta cgccccagaa gcagtcaagg tgtaccacta tgacatggaa    11580
acagagagtg gtcagctgtt gctatcagaa ctgaagtctc ggccccgccg tgagcccacc    11640
taccctgcag ctgttgactg gcatgcgtat gccagcagtg tcaagccatt ttcctctgaa    11700
cagtcagatt ttctggggat gatttatttt gatgagttta ccttcaccaa gcttaagaga    11760
aatacaggaa attacacagc ttgccagaaa gatctgtgtt gtcacttaac ttacaagatg    11820
tctgagaagc gaacagacga gatctatgcc ctaggtgctt ttgatggact gcacacagta    11880
gaaggccaat attacttaca ggtagaaatg ctttaatatg ttaaagtggc cttattatca    11940
gttttcttc taggtcatca ttgccttct ttgaaaattg ggctggattt agctaattt    12000
ataattagta atgttatatt tatctctgaa ttttgtcccc agaacacatt atttgttcag    12060
tcttagcaag aacagaatta gttcttttag ttgaaaggca aaaacataaa gcaaattgat    12120
tagttctcag caggccaggt tcaggtttca aaagctgcaa tttctgtgta ttctcttttc    12180
ccgtcaggtt actttagagc agtgtttttc aaattgtctt caactaaatc cagagaaaga    12240
aggatatttt acctcataac ccagtgtagc caagtggatg tgtgactgaa taaaaaaaaa    12300
gatatttaat tgaaatagtt tatgaaataa tttaaaatag aattagaaat agctattatt    12360
atgtgcaatg cactctgatt tttaaaatcc tagtctattc tatttgactt cagtataaaa    12420
agtgttaatc ctgacccact atattgattt taggattcat taataagttg ttacctgcag    12480
tttgaaaaat acttcttatg aggcaattta aatatgcatt tatagtttga aattgcatta    12540
tttagctgag aaaatatttg caagttttct gactccttct cttttctttt cttccataga    12600
tatgtgcatt actgaagtgt caaaccactg acctggaaac gtgtggagaa cctgtggggt    12660
cagcttttac caagtttgaa gacttctccc tcagtggcac atttggaacg cgttatgttt    12720
tcccacagat cattctaagt gggagtcagc ttgcccctga aagacattat gaggtaggag    12780
gtgtgcagga tgataaaattc ctttgagcag agtagatggg tagagcagca taatgaaaat    12840
ctttgaaata atgagagtat agcaatatcg tggttcacat tctacaagaa acaccttaaa    12900
tatgtggaaa ctatgatatg gaatataaat tgtggtttta gattgccatt aggctgtgat    12960
ggagaatttg gggttcattt ttttaacata aatgtgatgt tgatattcaa ggcaacagga    13020
aattcacaga gaagctaaaa taaaatgtt gactgctgat aatggcaata atgttgtcat    13080
ttgcatggtg tagaaggtgc aaattaaata cattaaataa tgcatctaca acttattttc    13140
tgggtatact attttgagaa gttgttataa ttatagtaat aactaatatt ttgtatagtg    13200
tttcatgagt ttgaagaaca tatttttata catattattt gaccacctgt gcaacaaatt    13260
tgttggctgc actttcgcac aaagtccctc tactttcaga cttgaaacat gaacctgggt    13320
cttccaacac caaatcctgt gtgatttta ccattctaca ctgctttagg agggagtgat    13380
cttgcctgag aagggctcta ggttgtaacc taaactctgc actgaagtta acccttgct    13440
ttctttgacc agatttcaag agatggacgc ttgaggagcc gaagtggagc ccctttgcct    13500
```

```
gtcttagtta tggccctgta tggaagagtg tttgagaagg accctccacg cttagggcag  13560
ggatctggga aattccagtg atctccttta gcagagccct tttaggatta gcctggctaa  13620
gaaaggaaga aaaaaaagag atccgttagt gtctgtttag aaaagatgtt ataaacttac  13680
agaaacaaat ataataaact gaagcagatt tgaaaagcaa caagtgtgtg tgcaaatttc  13740
acattttaca tgtttggtat agcacaggtt catttatggg agccgcattc atcctccatg  13800
tatgtgagtt taagtatatg taagtatgta tatgtatagt ggagcgtata tttaaatagg  13860
aggaggtcct agaaaaatcc ttttgcagta actgcactaa tgtatgcaag tgttgtttcc  13920
atcatatgat ggttaatttt atgtgttgat ttgactgggt catgagatgc ccagatagct  13980
ggttaaccat tgtttctggg tgtgtctgtg agggtgtttc aaggaagaga acagcatttg  14040
aattggtgga ctgagtaaag cagacggtcc tccccagtgt ggatggtcat cgtccagtcc  14100
cttgagggcc tgcagagaaa aacaagaagg aggaggtttg aattcatttt ctgccagact  14160
acttgagctg gatagagatc ttctcctgcc ttcatgtgct cctggttctc aggccttcag  14220
gcctggactg gaattgacac catcaactct tcagctctca ggccttcgaa tgacacccct  14280
ggctttcctg catctccagc ttgcaaatgg cagaccagac tgtgggattt ctcagccttc  14340
ataactgtct gagccaatac cttatcataa atctctttct ctctctctct cctgttggtt  14400
ctctttctct ggagaaccct gactaatgca cttcatttgt aaatacatag gatgaacttt  14460
gaatatgcag agggtatttg attccagcca attaagatac aggaaattaa agaataagga  14520
catcttttaa agtaactatg aacaacttt tagctagtat tgtccctta gtcatgacta  14580 atttgactcc taagttctat ttatatggaa attgga                            14616
```

COMBINATION THERAPY AND USES THEREOF FOR TREATMENT AND PREVENTION OF PARASITIC INFECTION AND DISEASE

CROSS REFERENCE TO RELATED APPLICATIONS

This application claims priority to co-pending U.S. application Ser. No. 13/277,942, filed Oct. 20, 2011, and the benefit of U.S. provisional application Ser. No. 61/394,958, filed on Oct. 20, 2010; both of these prior applications are incorporated herein by reference in their entirety.

FIELD OF THE INVENTION

The present invention relates to the prevention and/or treatment of infectious diseases, and more particularly parasitic infection and disease, such as *Plasmodium* infection and associated disease such as malaria.

INCORPORATION-BY-REFERENCE OF MATERIAL SUBMITTED AS AN ASCII TEXT FILE

A Sequence Listing is submitted herewith as an ASCII compliant text file named "Sequence_Listing.txt", created on Jul. 14, 2014, and having a size of ~176 kilobytes, as permitted under 37 CFR 1.821(c). The material in the aforementioned file is hereby incorporated by reference in its entirety.

BACKGROUND OF THE INVENTION

Parasites are organisms that live on or within another organism (the host) and harm the host. Diseases caused by parasites such as protozoa and helminths are among the leading causes of death and disease in tropical and subtropical regions of the world.

Malaria is an infectious disease that causes severe morbidity and mortality with an estimated 300-500 million cases worldwide and more than 1 million deaths annually in sub-Saharan Africa alone. The disease is caused by protozoan parasites of the genus *Plasmodium*, transmitted by mosquitoes. The most serious forms of malaria are caused by *Plasmodium falciparum* and *Plasmodium vivax*, but other species (e.g., *Plasmodium ovale*, *Plasmodium malariae*, and *Plasmodium knowlesi*) can also infect humans.

Among the murine malarial parasites, *Plasmodium chabaudi* (*P. chabaudi*) AS provides a unique experimental model to study the erythroid stage of the disease (Li, C. et al., 2001. *Med. Microbiol. Immunol.* (Berl) 189:115-126). *P. chabaudi* AS produces an infection in mice that shares many similarities with *P. falciparum* malaria in humans, including anemia, splenomegaly, hepatomegaly, renal alterations, hypoglycemia, and parasite sequestration (Cox, J. et al., 1987. *Parasite Immunol.* 9:543-561; Landau, I. and Gautret, P. 1998. Animal models: rodents. In *Malaria, Parasite Biology, Pathogenesis, and Protection*. I. W. Sherman, editor ASM Press, Washington D.C., pages 401-417). Among the murine malarial parasites, *Plasmodium berghei* (*P. berghei*) ANKA provides a unique model to study the cerebral stage of the disease (Hunt, N. H. et al., 2006 *Int. J. Parasitol* 36: 569-582). *P. berghei* ANKA produces an infection in mice that shares many similarities with cerebral malaria in humans, including sequestration of infected erythrocytes at the blood brain barrier, and appearance of cerebral symptoms such as fever, tremors, paralysis, coma and death.

In humans, malaria provides a clear example of host genetic factors influencing onset, progression, type of disease developed and ultimate outcome of infection (Hill, A. V. 1998. *Annu. Rev. Immunol.* 16: 593-617). Epidemiological data, together with linkage and association studies have shown that selection pressure from the parasite has caused retention of disease-associated but malaria-protective alleles in the human population, suggesting co-evolution of the host and parasite. Such otherwise deleterious alleles include those causing sickle cell anemia (Allison, A. C. 1954. *Br. Med. J.* 1(4857): 290-294; Willcox, M. A. et al., 1983. *Ann. Trop. Med. Parasitol.* 77: 239-246), thalassemias (Weatherall, D. J. 2001. *Nat. Rev. Genet.* 2: 245-255), and glucose-6-phosphate dehydrogenase deficiency (Ruwende, C. et al., 1995. *Nature* 376: 246-249). Polymorphisms in other erythroid proteins, including common variants of the Duffy antigen (Miller, L. H. et al., 1976. *N. Engl. J. Med.* 295: 302-304), the erythrocyte band 3 (anion exchanger) (Allen, S. J. et al., 1999. *Am. J. Trop. Med. Hyg.* 60: 1056-1060), and glycophorin C (Patel, S. S., et al., 2001. *Blood* 98:3489-3491), as well as variants in the TNF-α cytokine (McGuire, W. et al., 1994. *Nature* 371: 508-510) and the CD36 scavenger receptor (Aitman, T. J. et al., 2000. *Nature* 405: 1015-1016) are also associated with protection against malaria. Additional linkage studies in Burkina Faso have suggested a complex genetic component of susceptibility showing blood parasitemia levels linked to the 5q31-q33 region (Rihet, P. et al., 1998. *Am. J. Hum. Genet.* 63: 498-505). The genetic component of malaria susceptibility is further modified by environmental factors (Kwiatkowski, D. 2000. *Curr. Opin. Genet. Dev.* 10: 320-324).

No efficacious vaccines are currently available to prevent or control the spread of parasitic diseases such as malaria, and most existing therapeutics are either not completely effective or toxic to the human host. Also, drugs often fail as a result of the selection and spread of drug resistant variants of the parasites. Notably, control of malaria has been hampered by the spread of drug resistance in both the *Plasmodium* parasites and the *Anopheles* insect vector, and by the lack of an efficacious vaccine (Moorthy, V. S. et al., 2004. *Lancet* 363: 150-156).

Therefore, there is a need to develop new approaches for the prevention and/or treatment of parasitic diseases such as malaria.

The present description refers to a number of documents, the content of which is herein incorporated by reference in their entirety.

SUMMARY OF THE INVENTION

The present invention relates to decreasing susceptibility to parasite infection or disease or to preventing or treating parasite infection or disease.

Accordingly, in a first aspect, the present invention provides a method for decreasing susceptibility to parasite infection or disease or for preventing or treating parasite infection or disease, in a subject, said method comprising administering to said subject an effective amount of (i) (a) cystamine; (b) cysteamine; (c) an agent capable of inducing the production of (a) or (b); (d) a functional derivative, analog, conjugate, metabolite, prodrug or precursor of any of (a) to (c); (e) a pharmaceutically acceptable salt of any of (a) to (d); or (f) any combination of (a) to (e); and (ii) an artemisinin-related compound.

In another aspect, the present invention provides a method for decreasing susceptibility to parasite infection or disease or for preventing or treating parasite infection or disease, in a subject, said method comprising administering to said subject an effective amount of (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) an artemisinin-related compound.

In an embodiment, the above-mentioned method comprises administering to said subject an effective amount of (i) (a) cystamine; (b) cysteamine; (c) a pharmaceutically acceptable salt of (a) or (b); or (d) any combination of (a) to (c); and (ii) an artemisinin-related compound.

In an embodiment, the above-mentioned method comprises administering to said subject an effective amount of (i) cysteamine or a pharmaceutically acceptable salt thereof and (ii) (a) an artemisinin-related compound.

In various embodiments, the method results in reduced levels of parisitemia, delay in peak levels of parasitemia, or reduced severity of infection compared to treatment with cystamine, cysteamine, a derivative or pharmaceutically acceptable salt thereof or an artemisinin-related compound alone.

In another aspect, the present invention provides a use of (i) (a) cystamine; (b) cysteamine; (c) an agent capable of inducing the production of (a) or (b); (d) a functional derivative, analog, conjugate, metabolite, prodrug or precursor of any of (a) to (c); (e) a pharmaceutically acceptable salt of any of (a) to (d); or (f) any combination of (a) to (e); and (ii) an artemisinin-related compound, for decreasing susceptibility to parasite infection or disease or for preventing or treating parasite infection or disease.

In another aspect, the present invention provides a use of (i) (a) cystamine; (b) cysteamine; (c) an agent capable of inducing the production of (a) or (b); (d) a functional derivative, analog, conjugate, metabolite, prodrug or precursor of any of (a) to (c); (e) a salt of any of (a) to (d); or (f) any combination of (a) to (e); and (ii) an artemisinin-related compound, for the preparation of a medicament for decreasing susceptibility to parasite infection or disease or for preventing or treating parasite infection or disease.

In another aspect, the present invention provides a use of (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) an artemisinin-related compound, for decreasing susceptibility to parasite infection or disease or for preventing or treating parasite infection or disease.

In another aspect, the present invention provides a use of (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) an artemisinin-related compound, for the preparation of a medicament for decreasing susceptibility to parasite infection or disease or for preventing or treating parasite infection or disease.

In an embodiment, the above-mentioned use is of (i) (a) cystamine; (b) cysteamine; (c) a pharmaceutically acceptable salt of any of (a) or (b); or (d) any combination of (a) to (c); and (ii) (a) artemisinin, (b) a functional derivative, analog, conjugate, metabolite, prodrug or precursor of artemisinin, (c) a pharmaceutically acceptable salt of (a) or (b), or (d) any combination of (a) to (c).

In another embodiment, the above-mentioned use is of (i) cysteamine or a pharmaceutically acceptable salt thereof; and (ii) an artemisinin-related compound.

In another aspect, the present invention provides a package for decreasing susceptibility to parasite infection or disease or for preventing or treating parasite infection or disease, said package comprising (i) (a) cystamine; (b) cysteamine; (c) an agent capable of inducing the production of (a) or (b); (d) a functional derivative, analog, conjugate, metabolite, prodrug or precursor of any of (a) to (c); (e) a salt of any of (a) to (d); or (f) any combination of (a) to (e); and (ii) an artemisinin-related compound.

In another aspect, the present invention provides a package for decreasing susceptibility to parasite infection or disease or for preventing or treating parasite infection or disease, said package comprising (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) an artemisinin-related compound.

In another aspect, the present invention provides a package comprising (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and (ii) an artemisinin-related compound, for decreasing susceptibility to parasite infection or disease or for preventing or treating parasite infection or disease in a subject.

In an embodiment, the above-mentioned i) and ii) are packaged separately.

In another embodiment, the above-mentioned i) and ii) are packaged in the same formulation.

In an embodiment, the above-mentioned compound i) is present in a delayed release composition.

In another embodiment, the above-mentioned package further comprises labels and instructions for use.

In another aspect, the present invention provides a package comprising (i) a plurality of doses of a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and (ii) a plurality of doses of an artemisinin-related compound, for decreasing susceptibility to parasite infection or disease or for preventing or treating parasite infection or disease in a subject.

In an embodiment, the above-mentioned (i) and (ii) are packaged separately.

In another embodiment, the above-mentioned (i) and (ii) are packaged together.

In an embodiment, the above-mentioned package comprises (i) (a) cystamine; (b) cysteamine; (c) a pharmaceutically acceptable salt of (a) or (b); or (d) any combination of (a) to (c) and (ii) an artemisinin-related compound.

In a further embodiment, the above-mentioned package comprises (i) cysteamine or a pharmaceutically acceptable salt thereof; and (ii) an artemisinin-related compound.

In another embodiment, the above-mentioned package further comprises instructions for decreasing susceptibility to parasite infection or disease or for preventing or treating parasite infection or disease.

In another aspect, the present invention provides a package for decreasing susceptibility to parasite infection or disease or for preventing or treating parasite infection or disease, said package comprising (i) (a) cystamine; (b) cysteamine; (c) an agent capable of inducing the production of (a) or (b); (d) a functional derivative, analog, conjugate, metabolite, prodrug or precursor of any of (a) to (c); (e) a salt of any of (a) to (d); or (f) any combination of (a) to (e); and (ii) instructions for using (i) in combination with an artemisinin-related compound, for decreasing susceptibility to parasite infection or disease or for preventing or treating parasite infection or disease.

In another aspect, the present invention provides a package for decreasing susceptibility to parasite infection or disease or for preventing or treating parasite infection or disease, said package comprising (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) instructions for using (i) in combination with an artemisinin-related compound, for decreasing susceptibility to parasite infection or disease or for preventing or treating parasite infection or disease.

In another aspect, the present invention provides a package for decreasing susceptibility to parasite infection or disease or for preventing or treating parasite infection or disease, said package comprising (i) an artemisinin-related compound; and (ii) instructions for using (i) in combination with (a) cystamine; (b) cysteamine; (c) an agent capable of inducing the production of (a) or (b); (d) a functional derivative, analog, conjugate, metabolite, prodrug or precursor of any of (a) to (c); (e) a salt of any of (a) to (d); or (f) any combination of (a) to (e); for decreasing susceptibility to parasite infection or disease or for preventing or treating parasite infection or disease.

In another aspect, the present invention provides a package for decreasing susceptibility to parasite infection or disease or for preventing or treating parasite infection or disease, said package comprising (i) an artemisinin-related compound; and (ii) instructions for using (i) in combination with (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); for decreasing susceptibility to parasite infection or disease or for preventing or treating parasite infection or disease.

In another aspect, the present invention provides a composition for decreasing susceptibility to parasite infection or disease or for preventing or treating parasite infection or disease, said composition comprising: (i) (a) cystamine; (b) cysteamine; (c) an agent capable of inducing the production of cysteamine; (d) a functional derivative, analog, conjugate, metabolite, prodrug or precursor of any of (a) to (c); (e) a pharmaceutically acceptable salt of any of (a) to (d); or (f) any combination of (a) to (e); and (ii) an artemisinin-related compound.

In another aspect, the present invention provides a composition for decreasing susceptibility to parasite infection or disease or for preventing or treating parasite infection or disease, in a subject, said composition comprising (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) an artemisinin-related compound.

In an embodiment, the above-mentioned composition comprises (i) (a) cystamine; (b) cysteamine; (c) a pharmaceutically acceptable salt of (a) or (b); or (d) any combination of (a) to (c); and (ii) an artemisinin-related compound.

In a further embodiment, the above-mentioned composition comprises (i) cysteamine or a pharmaceutically acceptable salt thereof; and (ii) an artemisinin-related compound.

In an embodiment, the above-mentioned composition further comprises a pharmaceutically acceptable carrier or excipient.

In another aspect, the present invention provides a combination comprising: (i) (a) cystamine; (b) cysteamine; (c) an agent capable of inducing the production of cysteamine; (d) a functional derivative, analog, conjugate, metabolite, prodrug or precursor of any of (a) to (c); (e) a pharmaceutically acceptable salt of any of (a) to (d); or (f) any combination of (a) to (e); and (ii) (a) an artemisinin-related compound; for decreasing susceptibility to parasite infection or disease or for preventing or treating parasite infection or disease.

In another aspect, the present invention provides a combination comprising (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); and (ii) an artemisinin-related compound; for decreasing susceptibility to parasite infection or disease or for preventing or treating parasite infection or disease.

In another aspect, the present invention provides (i) (a) cystamine; (b) cysteamine; (c) an agent capable of inducing the production of cysteamine; (d) a functional derivative, analog, conjugate, metabolite, prodrug or precursor of any of (a) to (c); (e) a pharmaceutically acceptable salt of any of (a) to (d); or (f) any combination of (a) to (e); or (ii) a composition comprising (i) and a pharmaceutically acceptable carrier; for use in combination with (iii) an artemisinin-related compound; or (iv) a composition comprising (iii) and a pharmaceutically acceptable carrier; for decreasing susceptibility to parasite infection or disease or for preventing or treating parasite infection or disease.

In another aspect, the present invention provides (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); or (ii) a composition comprising (i) and a pharmaceutically acceptable carrier; for use in combination with (iii) an artemisinin-related compound; or (iv) a composition comprising (iii) and a pharmaceutically acceptable carrier; for decreasing susceptibility to parasite infection or disease or for preventing or treating parasite infection or disease.

In another aspect, the present invention provides (i) an artemisinin-related compound; or (ii) a composition comprising (i) and a pharmaceutically acceptable carrier; for use in combination with (iii) (a) cystamine; (b) cysteamine; (c) an agent capable of inducing the production of cysteamine; (d) a functional derivative, analog, conjugate, metabolite, prodrug or precursor of any of (a) to (c); (e) a pharmaceutically acceptable salt of any of (a) to (d); or (f) any combination of (a) to (e) or (iv) a composition comprising (iii) and a pharmaceutically acceptable carrier; for decreasing susceptibility to parasite infection or disease or for preventing or treating parasite infection or disease.

In another aspect, the present invention provides (i) an artemisinin-related compound; or (ii) a composition comprising (i) and a pharmaceutically acceptable carrier; for use in combination with (iii) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d); or (iv) a composition comprising (iii) and a pharmaceutically acceptable carrier; for decreasing susceptibility to parasite infection or disease or for preventing or treating parasite infection or disease.

The present invention further provides a combination for decreasing susceptibility to parasite infection or disease or for preventing or treating parasite infection or disease, said combination comprising: (i) (a) cystamine; (b) cysteamine; (c) an agent capable of inducing the production of cysteamine; (d) a functional derivative, analog, conjugate, prodrug or precursor of any of (i) to (iii); (e) a pharmaceutically acceptable salt of any of (a) to (d); or (f) any combination of (a) to (e); and (ii) an artemisinin-related compound.

The present invention further provides a combination for decreasing susceptibility to parasite infection or disease or for preventing or treating parasite infection or disease, in a subject, said combination comprising (i) (a) a compound of formula I: $NH_2$—$CH_2$—$CH_2$—S—R (I), wherein R is H or S—$CH_2$—$CH_2$—$NH_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and (ii) (a) an artemisinin-related compound.

In embodiments, the above-mentioned combination comprises: (i) (a) cystamine; (b) cysteamine; (c) a pharmaceutically acceptable salt of (a) or (b); or (d) any combination of (a) to (c); and (ii) an artemisinin-related compound.

In embodiments, the above-mentioned combination comprises: (a) cysteamine or a pharmaceutically acceptable salt thereof; and (b) an artemisinin-related compound.

In an embodiment, the above-mentioned artemisinin-related compound is (a) artemisinin, (b) a functional derivative, analog, conjugate, metabolite, prodrug or precursor of artemisinin, (c) a pharmaceutically acceptable salt of (a) or (b), or (d) any combination of (a) to (c).

In an embodiment, the above-mentioned artemisinin derivative is artesunate. In another embodiment, the above-mentioned artemisinin metabolite is dihydroartemisinin.

In another embodiment, the above-mentioned agent capable of inducing the production of cystamine or cysteamine is (a) a pantetheinase polypeptide, (b) a fragment or variant of (a) having pantetheinase activity; (c) a nucleic acid encoding the polypeptide of (a) or (b), (d) an agent capable of increasing pantetheinase activity or expression, or (e) any combination of (a) to (d).

In an embodiment, the above-mentioned polypeptide comprises the amino acid sequence of SEQ ID NO: 6, 8, 10, 12, 14 or 16.

In another embodiment, the above-mentioned nucleic acid comprises a nucleotide sequence which encodes a polypeptide comprising the amino acid sequence of SEQ ID NO: 6, 8, 10, 12, 14 or 16. In a further embodiment, the above-mentioned nucleic acid comprises the coding sequence of SEQ ID NO: 5, 7, 9, 11, 13, 15, 17, 18 or 19.

In an embodiment, the above-mentioned (i) and (ii) are packaged separately.

In another embodiment, the above-mentioned (i) and (ii) are packaged together.

In an embodiment, the above-mentioned compounds i) and ii) act synergistically.

In an embodiment, the above-mentioned synergy results in use of effective doses of compound i) and/or ii) that are lower than doses administered when the compounds are administered in the absence of the other composition.

In an embodiment, the above-mentioned effective dose of compound (i) is lower than a dose of (i) administered in the absence of compound (ii).

In an embodiment, the above-mentioned effective dose of compound (ii) is lower than a dose of (ii) administered in the absence of compound (i).

In an embodiment, the above-mentioned effective dose of (i) and (ii) are lower than a dose of compound (i) or compound (ii) administered in the absence of the other composition.

In an embodiment, the dose of compound (i) and/or (ii) is suboptimal.

In an embodiment, the above-mentioned effective dose of compound (i) is in the range of 1 to 500 mg/kg.

In an embodiment, the above-mentioned compound (i) is present in a delayed release composition.

In an embodiment, the peak level of parisitemia is reduced.

In an embodiment, the above-mentioned administering prevents parisitemia.

In an embodiment, the above-mentioned compound (i) is administered less than four times a day.

In an embodiment, the above-mentioned compound (i) is administered twice daily.

In an embodiment, the above-mentioned compounds (i) and (ii) are administered coextensively.

In an embodiment, the above-mentioned parasite is of the genus *Plasmodium*. In a further embodiment, the above-mentioned parasite is *Plasmodium falciparum, Plasmodium vivax, Plasmodium ovale, Plasmodium malariae,* or *Plasmodium knowlesi*.

In another embodiment, the above-mentioned disease is malaria. In a further embodiment, the above-mentioned malaria is blood-stage malaria or cerebral malaria.

In an embodiment, the above-mentioned subject is a mammal. In a further embodiment, the above-mentioned mammal is a human.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 1A: plasma levels of cysteamine-free base (measured by HPLC) following either intraperitoneal (i.p.) or subcutaneous (s.c.) injections (120 mg/kg) were measured in 3 mice and used to calculate $C_{max}$ and AUC pharmacokinetic parameters (see text). Error bars indicate standard deviation from the mean.

FIG. 1B: A/J female mice were infected with P. chabaudi ($10^5$ pRBC i.v.) and treated daily (either s.c. or i.p.) with cysteamine (120 mg/kg) starting at day 1 to day 10. Blood parasitemia was monitored on days 5, 6, and 7 and is plotted. The % inhibition of parasite replication was calculated by comparison to the blood parasitemia measured in PBS-treated controls and is indicated below the graphs. Each dot represents a mouse. Levels of statistical significance are represented by asterisks; *, P<0.01; , P<0.05 (compared to PBS control group);

FIG. 2A: the plasma levels of cysteamine-free base (measured by HPLC) following subcutaneous (s.c.) injection (50 mg/kg) were measured in 3 mice and used to calculate $C_{max}$ and AUC pharmacokinetic parameters (see text). Error bars indicate standard deviation from the mean. FIG. 2B: A/J female mice were infected with P. chabaudi ($10^5$ pRBC i.v.) and treated daily with cysteamine (s.c.) from day 1 to day 10, with the indicated dosing: 1×150 mg/kg, 3×50 mg/kg, or 4×50 mg/kg, given at 1 or 2 h intervals. Blood parasitemia was monitored on days 5, 6, and 7 and is plotted. The % inhibition of parasite replication was calculated by comparison to the blood parasitemia measured in PBS-treated controls and is indicated below the graphs. Each dot represents a mouse. Levels of statistical significance are represented by asterisks; ***, P<0.01 (compared to PBS control group);

FIG. 5C: Kaplan-Meier survival plot for experimental treatment groups for which lethality was observed. Depiction of artesunate doses and dashed versus solid lines are as described for FIG. 5B. FIG. 5D: Parasitemia levels at day 6 post-infection for all experimental groups are shown, with each dot representing a mouse. Mean levels are shown as bars;

FIG. 6B: Parasitemia levels at day 6 post-infection for all experimental groups are shown, with each dot representing a mouse. Mean levels are shown as bars;

FIGS. 7A to 7Z show the nucleotide and amino acid sequences of murine and human pantetheinase (Vanin, Vnn) genes and polypeptides;

DISCLOSURE OF THE INVENTION

Described herein are studies using the mouse model system of *Plasmodium* infection which show that treatment of mice with a combination of cysteamine and artemisinin-related compounds (e.g., the artemisinin derivative artesunate and the artemisinin metabolite dihydroartemisinin) leads to a synergistic reduction in parasitemia in these mice and to an increase in survival.

Cysteamine ($C_2H_7NS$, CAS#60-23-1) has the following chemical formula: $NH_2$—$CH_2$—$CH_2$—SH It is often used as a salt, such as the hydrochloride salt, $C_2H_8ClNS$ (CAS#156-57-0), which has the following formula: $^-Cl^+NH_3$—$CH_2$—$CH_2$—SH Cystamine ($C_4H_{12}N_2S_2$) is the oxidized form of cysteamine (i.e., a dimer of cysteamine) and has the following chemical formula: $NH_2$—$CH_2$—$CH_2$—S—S—$CH_2$—$CH_2$—$NH_2$ Cystamine may also be in the form of a salt, such as a dihydrochloride salt (CAS #56-17-7) or phosphate salt (CAS#3724-89-8).

As such, a compound of formula I: $NH_2$—$CH_2$—$CH_2$—S—R (I) wherein R is H or S—$CH_2$—$CH_2$—$NH_2$; an agent capable of inducing the production of the compound of formula I; a functional derivative, analog, conjugate, prodrug or precursor of the compound of formula I; or salts (e.g., pharmaceutically acceptable salts) thereof, are also useful in the methods, uses, and compositions of the present invention.

Cysteamine, and more particularly the bitartrate salt thereof (commercialized under the trade name Cystagon™) has been approved for the pharmacological management of cystinosis, an autosomal recessive disorder caused by mutations in the lysosomal cystine carrier cystinosin (encoded by the CTNS gene), whose absence leads to intracellular cystine crystals, widespread cellular destruction, renal Fanconi syndrome in infancy, renal glomerular failure in later childhood and other systemic complications (Kleta R. and Gahl W. A., 2004. *Expert Opin. Pharmacother.* 5(11): 2255-2262).

Figure 3A:
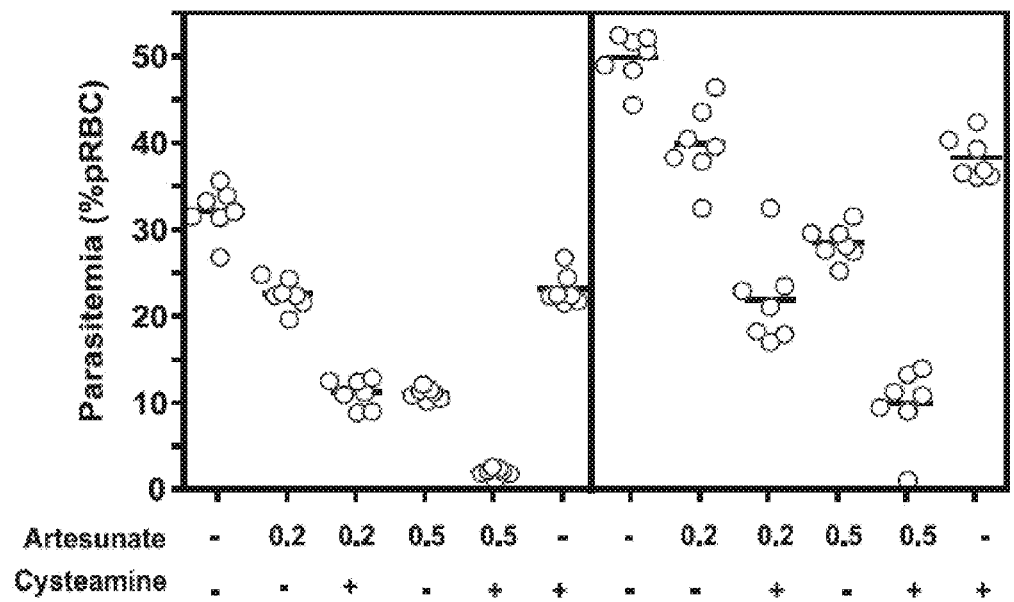
FIGS. 3A to 3C show the synergistic effect of cysteamine on artemisinin efficacy against replication of *Plasmodium chabaudi* in vivo. Groups (n=6) of female A/J (FIGS. 3A and B) or C57BL/6 (FIG. 3C) mice were infected with P. chabaudi ($10^7$ pRBC, i.v.) and treated for 4 days (days 0, 1, 2, and 3) with indicated doses (in mg/kg) of artesunate (FIGS. 3A and C) or dihydroartemisinin (DHA) (FIG. 3B) and/or cysteamine (170 mg/kg, i.p.), and blood parasitemia (expressed as percentage of parasitized erythrocytes) was determined at days 4 (left) and 5 (right) post infection. In all experiments, control groups were treated with PBS. The presence or absence of cysteamine is indicated by a plus or a minus, respectively, and doses of artemisinin derivatives in mg/kg are indicated below the plots. Each dot represents a mouse and bars indicate the mean of the group.
Figure 3B:
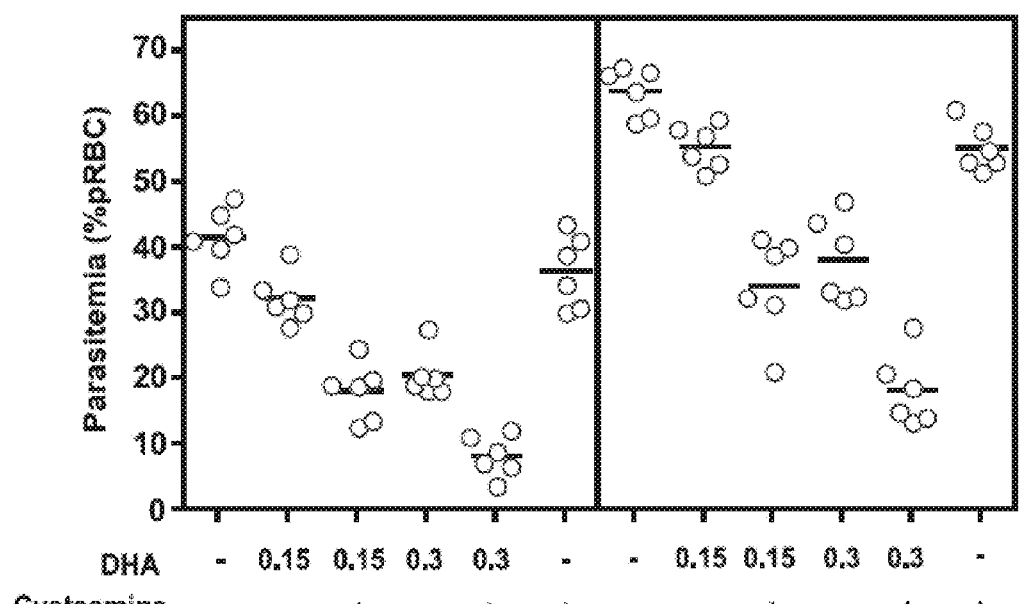

Cysteamine is a metabolite (product) generated by pantetheinase enzymatic activity. Pantetheinase (EC 3.5.1.92) is a ubiquitous enzyme encoded by the Vanin genes (FIG. 3, SEQ ID NOs:1, 3, 5, 7, 9, 11, 13, 15, and 17-19); 2 genes in mice (Vanin-1 and -3) and 3 genes in human (Vanin-1, -2 and -3). It is an amidohydrolase that hydrolyzes pantetheine (which is a metabolic product of Coenzyme A (CoA) degradation) to pantothenic acid (also called pantothenate or vitamin B5) and cysteamine.

Artemisinin (CAS#63968-64-9) is a sesquiterpene lactone which was first isolated from the plant *Artemisia annua*, and has the following formula:

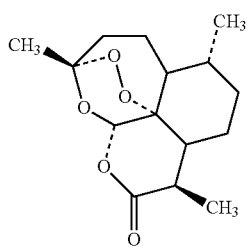

An active metabolite of artemisinin and artemisinin-related compounds is dihydroartemisinin (CAS#71939-50-9), which has the following formula:

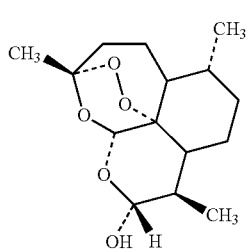

Accordingly, in an aspect, the present invention provides a method for decreasing susceptibility to parasite infection or disease or for preventing or treating parasite infection or disease, in a subject, said method comprising administering to said subject an effective amount of (i) (a) cysteamine; (b) cysteamine; (c) an agent capable of inducing the production of (a) or (b); (d) a functional derivative, analog, conjugate, metabolite, prodrug or precursor of any of (a) to (c); (e) a salt of any of (a) to (d); or (f) any combination of (a) to (e); and (ii) an artemisinin-related compound.

The present invention further provides a method for decreasing susceptibility to parasite infection or disease or for preventing or treating parasite infection or disease in a subject (an animal such as a mammal, in a further embodiment a human), said method comprising administering to said subject an effective amount of (i) (a) a compound of formula I:$NH_2$—$CH_2$—$CH_2$—S—R (I) wherein R is H or S—$CH_2$—$CH_2$—$NH_2$; (b) an agent capable of inducing the production of the compound of formula I; (c) a functional derivative, analog, conjugate, metabolite, prodrug or precursor of (a) or (b); (d) a pharmaceutically acceptable salt of any of (a) to (c); or (e) any combination of (a) to (d) and (ii) an artemisinin-related compound.

In another aspect, the invention provides a use of (i) (a) cysteamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and (ii) an artemisinin-related compound, for decreasing susceptibility to parasite infection or disease or for preventing or treating parasite infection or disease; or for the preparation of a medicament for decreasing susceptibility to parasitic infection or disease or for preventing or treating parasite infection or disease.

In another aspect, the invention provides a combination of (i) (a) cysteamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and (ii) an artemisinin-related compound, for use in decreasing susceptibility to parasite infection or disease or for use in preventing or treating parasite infection or disease; or for use in the preparation of a medicament for decreasing susceptibility to parasitic infection or disease or for use in preventing or treating parasite infection or disease.

In an embodiment, the above-mentioned parasite infection is an infection of a parasite of the genus *Plasmodium*. In an embodiment, the above-mentioned *Plasmodium* parasite is an artemisinin-resistant human *Plasmodium* parasite.

In an embodiment, the above-mentioned disease is malaria. In a further embodiment, the above-mentioned malaria is blood-stage malaria. In another embodiment, the above-mentioned malaria is cerebral malaria.

Accordingly, the invention further provides a method for treating or preventing malaria in an animal, comprising administering to the animal (i) a cysteamine-related compound and (ii) an artemisinin-related compound.

As used herein, the term "cysteamine-related compound" refers to cysteamine and functional derivatives, analogs, conjugates, prodrugs or precursors of cysteamine and various cysteamine salts (such as cysteamine hydrochloride, cysteamine salicylate, cysteamine phosphate and cysteamine bitartrate [Cystagon™]). Also included within the scope of the subject invention are analogs, derivatives, conjugates, metabolites, prodrugs and precursors of cysteamine (such as cystamine, the oxidized form of cysteamine, cysteine, and the like), which have the ability, as described herein, to prevent and/or treat and/or decrease the susceptibility to parasite infections, such as infection by a *Plasmodium* parasite (e.g., *P. falciparum* infection) and/or to prevent and/or treat associated disease (e.g., malaria), and more particularly to act synergistically with artemisinin and artemisinin-related compounds. Various analogs, derivatives, conjugates, prodrugs and metabolites of cysteamine are known and include, for example, compounds, compositions, formulations and methods of delivery as set forth in U.S. Pat. Nos. 6,521,266; 6,468,522; 6,340,746; 5,714,519 and 5,554,655 and PCT publication No. WO 2007/089670.

As used herein, the term "artemisinin-related compound" refers to artemisinin and to functional derivatives, analogs, conjugates, metabolites, prodrugs or precursors of artemisinin, as well as salts thereof, and includes the artemisinin derivatives/analogs artesunate, artemether, arteether, artelinic acid, artenimol and artemotil, the artemisinin precursor artemisinic acid (Ro D K, et al., *Nature* 440:940-943), as well as the artemisinin metabolite dihydroartemisinin. Also included within the scope of the subject invention are analogs, derivatives, conjugates, metabolites, prodrugs and precursors of artemisinin which have the ability, as described herein, to prevent and/or treat and/or decrease the susceptibility to parasite infections, such as infection by a *Plasmodium* parasite (e.g., *P. falciparum* infection) and/or to prevent and/or treat associated disease (e.g., malaria), and more particularly to act synergistically with cysteamine and cysteamine-related compounds. Also included within the scope of the subject invention are analogs, derivatives, conjugates, metabolites, prodrugs and precursors of artemisinin which have the ability which may be metabolized into a biologically active metabolite of artemisinin (e.g., dihydroartemisinin), as well as synthetic trioxolanes (mimicking the trioxolane structure of artemisinin) such as those described in Vennerstrom et al., 2004, *Nature* 430, 900-904 (Arterolane) and O'Neill et al., *Angewandte Chemie International Edition*, 2010, 49(33): 5693-97. Various functional analogs, derivatives, conjugates, prodrugs and metabolites of artemisinin, as well as methods to produce them, are described, for example, in Posner et al., 1999, *J. Med. Chem.* 42(2): 300-304, Li et al., 2000, *J. Med. Chem.* 43(8): 1635-1640, Li et al., 2003, *Bioorganic & Medicinal Chemistry* 11(20): 4363-4368, Ploypradith P, 2004. *Acta Trop* 89:329-342, PCT publications No. WO/2008/127381, WO/2008/046109, WO/2007/116135, WO/2007/009388, WO/2003/076446, WO/2000/042046, WO/2000/004025, WO/2000/004024, WO/1999/065914 and WO/1991/014689. Artemisinin-related compounds have been shown to be active against a variety of parasites including *Plasmodium* parasites, *Toxoplasma* parasites, *Schistosoma* parasites and helminths and (Dunay I R, et al., 2009, *Antimicrob Agents Chemother* 53:4450-4456; Keiser J, Utzinger J (2007) *Curr Opin Infect Dis* 20:605-612; Sissoko M S et al., (2009) *PLoS One* 4:e6732).

Methods to isolate and/or produce artemisinin and/or artemisinin-related compounds are well known in the art. Methods to produce/isolate artemisinin from tissue culture or whole plant of *Artemisia annua* are described, for example, in Liu et al., 2006, *Appl Microbiol Biotechnol.* 72(1):11-20, Epub 2006 Jun. 3. The synthesis of artemisinin may also be performed using basic organic reagents, for example using the methods described in Schmid and Hofheinz, *J. Am. Chem. Soc.* (1983) 105(3): 624-625. The precursor of artemisinin, artemisinic acid, may for example be produced at high levels in an engineered *Saccharomyces cerevisiae* system (Ro D K et al., 2006, *Nature* 440(7086): 940-943). Methods to produce/synthesize various functional analogs, derivatives, conjugates, prodrugs and metabolites of artemisinin, are described, for example, in Posner et al., 1999, *J. Med. Chem.* 42(2): 300-304, Li et al., 2000, *J. Med. Chem.* 43(8): 1635-1640, Li et al., 2003, *Bioorganic & Medicinal Chemistry* 11(20): 4363-4368, PCT publications No. WO/2008/127381, WO/2008/046109, WO/2007/116135, WO/2007/009388, WO/2003/076446, WO/2000/042046, WO/2000/004025, WO/2000/004024, WO/1999/065914 and WO/1991/014689.

In an embodiment, the above-mentioned agent capable of inducing the production of cystamine, cysteamine, or a compound of formula I is (a) a pantetheinase polypeptide, (b) a fragment or variant of (a) having pantetheinase activity; (c) a nucleic acid encoding the polypeptide of (a) or (b), (d) an agent capable of increasing pantetheinase activity or expression, or (e) any combination of (a) to (d).

In an embodiment, the above-mentioned pantetheinase polypeptide comprises the amino acid sequence of SEQ ID NO: 2, 4, 6, 8, 10, 12, 14 or 16 (FIG. 7), or a variant/fragment thereof having pantetheinase activity.

In an embodiment, the above-mentioned pantetheinase nucleic acid comprises (a) the coding sequence of SEQ ID NO: 1, 3, 5, 7, 9, 11, 13, 15, 17, 18 or 19 (FIG. 7); (b) a nucleotide sequence which encodes a polypeptide comprising the amino acid sequence of SEQ ID NO: 2, 4, 6, 8, 10, 12, 14 or 16; or (c) a fragment, variant or complement of (a) or (b) encoding a pantotheinase polypeptide.

The above-mentioned coding sequences correspond to: (a) nucleotides 22 to 1560 for SEQ ID NO: 1, (b) nucleotides 113-1615 for SEQ ID NO: 3, (c) nucleotides 15-1556 for SEQ ID NO: 5, (d) nucleotides 12-1574 for SEQ ID NO: 7, (e) nucleotides 113-1516 for SEQ ID NO: 9, (f) nucleotides 73-897 for SEQ ID NO: 11, (g) nucleotides 73-516 for SEQ ID NO: 13, (h) nucleotides 73-426 for SEQ ID NO: 15, (i) the junction of nucleotides 1959-2168, 4155-4278, 21806-22005, 22680-22971, 23411-23772, 31490-31660 and 32673-32855 for SEQ ID NO: 17, (j) the junction of nucleotides 2009-2221, 2346-2476, 3857-4049, 7144-7432, 8375-8748, 10028-10198 and 15403-15594 for SEQ ID NO: 18, and (k) the junction of nucleotides 1814-2026, 2123-2253, 7573-7765 and 9494-9781 for SEQ ID NO: 19 (FIGS. 7A to Z).

In another embodiment, the above-mentioned nucleic acid fragment or variant encodes a polypeptide having pantetheinase activity.

In an embodiment, the above-mentioned pantetheinase nucleic acid comprises the nucleotide sequence of SEQ ID NO: 1, 3, 5, 7, 9, 11, 13, 15, 17, 18 or 19 (FIGS. 7A to Z).

The increase of expression of a pantetheinase nucleic acid or encoded polypeptide or pantetheinase activity in cell or tissue of said subject may be achieved, for example, by administrating to a subject: (a) a polypeptide comprising the amino acid sequence of SEQ ID NO: 2, 4, 6, 8, 10, 12, 14 or 16, or a variant or fragment thereof having pantetheinase activity; (b) a nucleic acid molecule encoding pantetheinase or a functional variant thereof (e.g., a nucleic acid which encodes the polypeptide of SEQ ID NO: 2, 4, 6, 8, 10, 12, 14 or 16, or a variant or fragment thereof having pantetheinase activity) or (c) a composition (e.g., a pharmaceutical composition) comprising the above-mentioned polypeptide or nucleic acid and, for example, a pharmaceutically acceptable carrier/excipient.

A variant and/or fragment of pantetheinase which retains activity (e.g., having a domain conferring pantetheinase activity) may also be used in the uses and methods of the invention. Variants or homologs include protein sequences, which are substantially identical to the amino acid sequence of a pantetheinase (e.g., SEQ ID NO: 2, 4, 6, 8, 10, 12, 14 or 16), sharing significant structural and functional homology with a pantetheinase (e.g., SEQ ID NO: 2, 4, 6, 8, 10, 12, 14 or 16). Variants include, but are not limited to, proteins or peptides, which differ from a pantetheinase (e.g., SEQ ID NO: 2, 4, 6, 8, 10, 12, 14 or 16) by any modifications, and/or amino acid substitutions, deletions or additions. Modifications can occur anywhere including the polypeptide backbone, (i.e. the amino acid sequence), the amino acid side chains and the amino or carboxy termini. Such substitutions, deletions or additions may involve one or more amino acids. Fragments include a fragment or a portion of a pantetheinase or a fragment or a portion of a homolog or variant of a pantetheinase which retains pantetheinase activity. The pantetheinase polypeptide (or a variant or fragment thereof having pantetheinase activity) may also be fused with another polypeptide or conjugated to one or more molecules.

"Homology", "homologous" and "homolog" refer to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to or is a "homolog" of another sequence if the two sequences are substantially identical and the functional activity of the sequences is conserved (as used herein, the term 'homologous' does not infer evolutionary relatedness). Two nucleic acids or amino acid sequences are considered "substantially identical" if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90%, 95%, 96%, 97%, 98% or 99%, e.g., with any of SEQ ID NOs: 1-19. As used herein, a given percentage of homology between sequences denotes the degree of sequence identity in optimally aligned sequences. An "unrelated" or "non-homologous" sequence shares less than 40% identity, though preferably less than about 25% identity, with any of SEQ ID NOs: 1-19.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, at least 95%, at least 96%, at least 97%, at least 98% or at least 99%, e.g., with any of SEQ ID NOs: 1-19. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, more preferably highly stringent conditions. Hybridization to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

The above-mentioned nucleic acid may be delivered to cells in vivo using methods well known in the art such as direct injection of DNA, receptor-mediated DNA uptake, viral-mediated transfection or non-viral transfection and lipid based transfection, all of which may involve the use of gene therapy vectors. Direct injection has been used to introduce naked DNA into cells in vivo (see e.g., Acsadi et al. (1991) *Nature* 332: 815-818; Wolff et al. (1990) *Science* 247: 1465-1468). A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor (see for example Wu, G. and Wu, C. H. (1988) *J. Biol. Chem.* 263: 14621; Wilson et al. (1992) *J. Biol. Chem.* 267: 963-967; and U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel et al. (1991) *Proc. Natl. Acad. Sci. USA* 88: 8850; Cristiano et al. (1993) *Proc. Natl. Acad. Sci. USA* 90: 2122-2126).

Defective retroviruses are well characterized for use as gene therapy vectors (for a review see Miller, A. D. (1990) *Blood* 76: 271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include psiCrip, psiCre, psi2 and psiAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85: 6460-6464; Wilson et al. (1988) *Proc. Natl. Acad. Sci. USA* 85: 3014-3018; Armentano et al. (1990) *Proc. Natl. Acad. Sci. USA* 87: 6141-6145; Huber et al. (1991) *Proc. Natl. Acad. Sci. USA* 88: 8039-8043; Ferry et al. (1991) *Proc. Natl. Acad. Sci. USA* 88: 8377-8381; Chowdhury et al. (1991) *Science* 254: 1802-1805; van Beusechem et al. (1992) *Proc. Natl. Acad. Sci. USA* 89: 7640-7644; Kay et al. (1992) *Human Gene Therapy* 3: 641-647; Dai et al. (1992) *Proc. Natl. Acad. Sci. USA* 89: 10892-10895; Hwu et al. (1993) *J. Immunol.* 150: 4104-4115; U.S. Pat. No. 4,868,116; U.S. Pat. No. 4,980,286; U.S. Pat. No. 4,980,286; PCT Application WO 89/07136; PCT Application WO 89/02468; PCT Application WO 89/05345; and PCT Application WO 92/07573).

For use as a gene therapy vector, the genome of an adenovirus may be manipulated so that it encodes and expresses a nucleic acid compound of the invention (e.g., a pantetheinase nucleic acid), but is inactivated in terms of its ability to replicate in a normal lytic viral life cycle. See for example Berkner et al. (1988) *BioTechniques* 6: 616; Rosenfeld et al. (1991) *Science* 252: 431-434; and Rosenfeld et al. (1992) *Cell* 68: 143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89: 6482-6486), hepatocytes (Herz and Gerard (1993) *Proc. Natl. Acad. Sci. USA* 90: 2812-2816) and muscle cells (Quantin et al. (1992) *Proc. Natl. Acad. Sci. USA* 89: 2581-2584).

Adeno-associated virus (AAV) may be used as a gene therapy vector for delivery of DNA for gene therapy purposes. AAV is a naturally occurring defective virus that requires another virus, such as an adenovirus or a herpes virus, as a helper virus for efficient replication and a productive life cycle (Muzyczka et al. *Curr. Topics in Micro. and Immunol.* (1992) 158:97-129). AAV may be used to integrate DNA into non-dividing cells (see for example Flotte et al. (1992) *Am. J. Respir. Cell. Mol. Biol.* 7: 349-356; Samulski et al. (1989) *J. Virol.* 63: 3822-3828; and McLaughlin et al. (1989) *J. Virol.* 62: 1963-1973). An AAV vector such as that described in Tratschin et al. (1985) *Mol. Cell. Biol.* 5: 3251-3260 may be used to introduce DNA into cells (see for example Hermonat et al. (1984) *Proc. Natl. Acad. Sci. USA* 81: 6466-6470; Tratschin et al. (1985) *Mol. Cell. Biol.* 4: 2072-2081; Wondisford et al. (1988) *Mol. Endocrinol.* 2: 32-39; Tratschin et al. (1984) *J. Virol.* 51: 611-619; and Flotte et al. (1993) *J. Biol. Chem.* 268: 3781-3790). Lentiviral gene therapy vectors may also be adapted for use in the invention.

General methods for gene therapy are known in the art. See for example, U.S. Pat. No. 5,399,346 by Anderson et al. A biocompatible capsule for delivering genetic material is described in PCT Publication WO 95/05452 by Baetge et al. Methods of gene transfer into hematopoietic cells have also previously been reported (see Clapp, D. W., et al., *Blood* 78: 1132-1139 (1991); Anderson, *Science* 288: 627-9 (2000); and Cavazzana-Calvo et al., *Science* 288: 669-72 (2000)).

The present invention relates to the administration of (i) (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and (ii) an artemisinin-related compound, to elicit any of the effects discussed above. The (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and the artemisinin-related compound may be administered alone or in combination with at least one other agent, such as stabilizing compound, which may be administered in any sterile, biocompatible pharmaceutical carrier, including, but not limited to, saline, buffered saline, dextrose, and water. The (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and the artemisinin-related compound may be administered alone or in combination with other agents, drugs or hormones. The (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and the artemisinin-related compound utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual or rectal means. The (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e); and artemisinin-related compound may be administered separately or together (e.g., together in a composition). The combination of therapeutic agents and compositions of the present invention may be administered or co-administered in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, the (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e) may be administered to a patient before, concomitantly, before and after, or after the artemisinin-related compound is administered.

As such, in embodiments, the invention further provides:

(1) a composition (e.g., a pharmaceutical composition or medicament) comprising (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e)) and a pharmaceutically acceptable diluent or carrier;

(2) a composition comprising (a) an artemisinin-related compound and a pharmaceutically acceptable diluent or carrier;

(3) a composition comprising (i) (a) cystamine; (b) cysteamine; (c) an agent capable of inducing the production of cysteamine and/or cystamine; (d) a functional derivative, analog, conjugate, prodrug or precursor of (a) to (c); (e) a pharmaceutically acceptable salt of any of (a) to (d); or (f) any combination of (a) to (e); and (ii) an artemisinin-related compound; or (4) a composition comprising (i) (a) cystamine; (b) cysteamine; (c) an agent capable of inducing the production of cysteamine and/or cystamine; (d) a functional derivative, analog, conjugate, prodrug or precursor of (a) to (c); (e) a pharmaceutically acceptable salt of any of (a) to (d); or (f) any combination of (a) to (e); and (ii) an artemisinin-related compound; and (iii) a pharmaceutically acceptable diluent or carrier.

As such, in an embodiment, the present invention further provides a combination of compositions (1) and (2) mentioned above for decreasing susceptibility to parasite infection or disease or for preventing or treating parasite infection or disease (e.g., malaria). The present invention further provides composition (3) or composition (4) mentioned above for decreasing susceptibility to parasite infection or disease or for preventing or treating parasite infection or disease (e.g., malaria). In an embodiment, components (i) and (ii) of the composition of (3) are formulated together. In an embodiment, components (i) and (ii) of the composition of (3) are formulated separately.

As used herein "pharmaceutically acceptable carrier" or "excipient" includes any and all solvents, buffers, dispersion media, coatings, antibacterial and antifungal agents, isotonic and absorption delaying agents, and the like that are physiologically compatible. The carrier can be suitable, for example, for intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration. Formulations may be in the form of liquid solutions or suspension; for oral administration, formulations may be in the form of tablets or capsules; and for intranasal formulations, in the form of powders, nasal drops, or aerosols.

Formulations suitable for oral administration can consist of (a) liquid solutions, such as an effective amount of active agent(s)/composition(s) suspended in diluents, such as water, saline or PEG 400; (b) capsules, sachets or tablets, each containing a predetermined amount of the active ingredient, as liquids, solids, granules or gelatin (e.g., unit dose); (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art. The oral formulation may further contain one or more coatings, such as an enteric coating. Enterically coated formulations of cystamine, cysteamine and derivatives thereof are described, for example, in PCT publication No. WO 2007/089670.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds/compositions of the invention include ethylenevinyl acetate copolymer particles, osmotic pumps, implantable infusion systems, and liposomes. Formulations for inhalation may contain excipients, (e.g., lactose) or may be aqueous solutions containing, for example, polyoxyethylene-9-lauryl ether, glycocholate and deoxycholate, or may be oily solutions for administration in the form of nasal drops, or as a gel.

For preparing pharmaceutical compositions from the compound(s)/composition(s) of the present invention, pharmaceutically acceptable carriers are either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired. The powders and tablets may typically contain from 5% or 10% to 70% of the active compound/composition. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use are prepared by dissolving the active compound(s)/composition(s) in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Pharmaceutically acceptable carriers include sterile aqueous solutions or dispersions and sterile powders for the extemporaneous preparation of sterile injectable solutions or dispersion. The use of such media and agents for pharmaceutically active substances is well known in the art (Rowe et al., *Handbook of pharmaceutical excipients*, 2003, 4$^{th}$ edition, Pharmaceutical Press, London UK). Except insofar as any conventional media or agent is incompatible with the active compound, use thereof in the pharmaceutical compositions of the invention is contemplated.

It is further contemplated that the cystamine, cysteamine, a derivative or pharmaceutically acceptable salt thereof can be administered orally in a delayed release formulation. Exemplary delayed release formulations are disclosed in U.S. Pat. No. 8,026,284.

The composition may also contain a combination of active compounds for the particular indication being treated, preferably those with complementary activities that do not adversely affect each other. It may be desirable to use the above-mentioned composition in addition to one or more agents currently used to prevent or treat the disorder in question (e.g., an antimalarial such as sulfadoxine-pyrimethamine [Fansidar®], mefloquine [Lariam®], atovaquone, proguanil, atovaquone-proguanil [Malarone®], quinine, doxycycline, primaquine), Lumefantrine (or benflumetol). The above-mentioned agents may be formulated in a single composition or in several individual compositions which may be co-administered in the course of the treatment.

Formulations to be used for in vivo administration are preferably sterile. This is readily accomplished, for example, by filtration through sterile filtration membranes.

The amount of the pharmaceutical composition which is effective in the prevention and/or treatment of a particular disease, disorder or condition (e.g., parasite infection and/or parasite-related disease) will depend on the nature and severity of the disease, the chosen prophylactic/therapeutic regimen, the target site of action, the patient's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 1000 mg/kg of body weight/day will be administered to the subject. In an embodiment, a daily dose range of about 0.01 mg/kg to about 500 mg/kg, in a further embodiment of about 0.1 mg/kg to about 200 mg/kg, in a further embodiment of about 1 mg/kg to about 100 mg/kg, in a further embodiment of about 10 mg/kg to about 50 mg/kg, may be used. The dose administered to a patient, in the context of the present invention should be sufficient to effect a beneficial prophylactic and/or therapeutic response in the patient over time. The size of the dose also will be determined by the existence, nature, and extent of any adverse side-effects that accompany the administration. Effective doses may be extrapolated from dose response curves derived from in vitro or animal model test systems. For example, in order to obtain an effective mg/kg dose for humans based on data generated from rat studies, the effective mg/kg dosage in rat may be divided by six.

The cystamine, cysteamine, a derivative or pharmaceutically acceptable salt thereof or any combination thereof may be administered one, two or three or four times per day. In various embodiments, an effective dosage of cystamine, cysteamine, or derivative of a pharmaceutically acceptable salt thereof may be within the range of 0.01 mg to 1000 mg per kg (mg/kg) of body weight per day. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg, or may range between any two of the foregoing values. In some embodiments, the cystamine, cysteamine, a derivative or pharmaceutically acceptable salt thereof is administered at a total daily dose of from approximately 0.25 g/m$^2$ to 4.0 g/m$^2$ body surface area, e.g., at least about 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 g/m$^2$. In some embodiments, the cystamine, cysteamine, a derivative or pharmaceutically acceptable salt thereof may be administered at a total daily dose of about 1-1.5 g/m$^2$ body surface area, or 0.5-1 g/m2 body surface area, or about 0.7-0.8 g/m$^2$ body surface area, or about 1.35 g/m$^2$ body surface area.

Examples of treatment regimens for artemisinin, artesunate and artemether recommended by the World Health Organization (WHO) (The use of Artemisinin and its derivatives as anti-malarial drugs, Report of a Joint CTD/DMP/TDR Informal Consultation, Geneva, 10-12 Jun. 1998) for the treatment of parasitic disease (malaria) are provided below:

Artemisinin may be administered at 20 mg/kg in a divided dose (loading dose) on the first day, followed by 10 mg/kg once a day for 6 days. Artesunate may be administered at 4 mg/kg in a divided dose on the first day, followed by 2 mg/kg once a day for 6 days. Artemether may be administered at 4 mg/kg in a divided dose on the first day, followed by 2 mg/kg once a day for 6 days.

In an embodiment, the dose of (a) cystamine; (b) cysteamine; (c) an agent capable of inducing the production of cysteamine and/or cystamine; (d) a functional derivative, analog, conjugate, metabolite, prodrug or precursor of (a) to (c); (e) a pharmaceutically acceptable salt of any of (a) to (d); or (f) any combination of (a) to (e) and/or (a) an artemisinin-related compound that is used/administered in the methods, uses, compositions, packages and combinations of the invention is a suboptimal dose. "Suboptimal dose" as used herein refers to a dose of one of the compounds of the combination described herein, which, when used in the absence of another compound of the combination, results in a biological effect of 50% or less (e.g., inhibition of parasitemia of 50% or less), in an embodiment of 40% or less, in a further embodiment of 30% or less, in a further embodiment of 20% or less, in a further embodiment of 10% or less. As such, use of a combination of the compounds described herein, where one or more compounds in the combination is used at a suboptimal dose, may achieve increased efficacy/biological effect (e.g., inhibition of parasitemia) relative to using the compound(s) in the absence of the other(s), at a comparable suboptimal dose.

The terms "treat/treating/treatment" and "prevent/preventing/prevention" as used herein, refers to eliciting the desired biological response, i.e., a therapeutic and prophylactic effect, respectively. In accordance with the subject invention, the therapeutic effect comprises one or more of a decrease/reduction in parasite load (parasitemia), an amelioration of symptoms and parasite-related effects, and increased survival time of the affected host animal, following administration of (a) cysteamine, cystamine, a compound of formula I, an agent capable of increasing expression of pantetheinase or pantetheinase activity, an agent capable of inducing the production of cysteamine, a functional derivative, analog, metabolite, prodrug or precursor thereof, or salts thereof, and (b) an artemisinin-related compound. In embodiments, the decrease in parasite load or parasitemia induced by the treatment may be, for example, a 10%, 20%, 30%, 40%, 50%, 60%, 70%, 80%, 90%, 95%, 98%, 99% or 100% (i.e., complete elimination of the parasite) decrease in parasitemia. In accordance with the invention, a prophylactic effect may comprise a decrease in the onset of or of the severity of one or more of parasite load or parasitemia, symptoms and parasite-related effects, and increased survival time of the affected host animal, following administration of (a) cysteamine, cystamine, a compound of formula I, an agent capable of increasing expression of pantetheinase or pantetheinase activity, an agent capable of inducing the production of cysteamine, a functional derivative, analog, prodrug or precursor thereof, or salts thereof and (b) an artemisinin-related compound.

As such, a "therapeutically effective" or "prophylactically effective" amount of (a) cysteamine, cystamine, a compound of formula I, an agent capable of inducing expression of pantetheinase, an agent capable of inducing the production of cysteamine, a functional derivative, analog or precursor thereof, or salts thereof, or any combinations thereof, and (b) an artemisinin-related compound, may be administered to an animal, in the context of the methods of treatment and prevention, respectively, described herein.

In an embodiment, the above-mentioned subject is a mammal. A mammal, including for purposes of treatment and prevention, refers to any animal classified as a mammal, including humans, domestic and farm animals, and zoo, sports or pet animals such as dogs, horses, cats, cows etc. In an embodiment, the mammal is human.

Parasitic or parasite infection refers to an infection by an organism that lives on or inside another organism (host) and typically causes harm to the host. Parasite disease or parasitic disease refers to a disease or condition associated with parasite infection of a host. In an embodiment, the above-mentioned parasite is a protozoa. In an embodiment, the above-mentioned parasite is of the *Plasmodium* genus. In a further embodiment, the parasite is *Plasmodium falciparum, Plasmodium vivax, Plasmodium ovale,* or *Plasmodium malariae.*

The invention further provides kits or packages (e.g., commercial packages) comprising the above-mentioned compositions or agents together with instructions for their use for decreasing susceptibility to parasite infection or disease or for preventing or treating parasite infection or disease such as malaria (e.g., blood-stage malaria or cerebral malaria).

The arrangement and construction of such kits is conventionally known to one of skill in the art. Such kits may include, for example, container(s) (e.g., syringe and/or vial and/or ampoule) for containing the agent or combination of agents or compositions, other apparatus for administering the therapeutic agent(s) and/or composition(s) and/or diluent(s). The kit may optionally further include instructions. The instructions may describe how the agent(s) and the diluent should be mixed to form a pharmaceutical formulation. The instructions may also describe how to administer the resulting pharmaceutical formulation to a subject.

As used herein, a synergistic effect (e.g., reduction in parasitemia, increase in survival time) is achieved when the effect of the combined drugs is greater than the theoretical sum of the effect of each agent in the absence of the other. One potential advantage of combination therapy with a synergistic effect is that lower dosages (e.g., a suboptimal dose) of one or both of the drugs or therapies may be used in order to achieve high therapeutic activity with low toxicity. In an embodiment, the combination therapy results in at least a 5% increase in the effect as compared to the predicted theoretical additive effect of the agents. In a further embodiment, the combination therapy results in at least a 10% increase in the effect as compared to the predicted theoretical additive effect of the agents. In a further embodiment, the combination therapy results in at least a 20% increase in the effect as compared to the predicted theoretical additive effect of the agents. In a further embodiment, the combination therapy results in at least a 30% increase in the effect as compared to the predicted theoretical additive effect of the agents. In a further embodiment, the combination therapy results in at least a 50% increase in the effect as compared to the predicted theoretical additive effect of the agents.

A further advantage of using the drugs in combination is that efficacy may be achieved in situations where either drug alone would not have an effect. For example, in a case where the parasite is resistant to a drug when used alone but is affected by the drugs when used in combination.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The articles "a" and "an" are used herein to refer to one or to more than one (i.e., to at least one) of the grammatical object of the article. The term "such as" is used herein to mean, and is used interchangeably, with the phrase "such as but not limited to". The following examples are illustrative of various aspects of the invention, and do not limit the broad aspects of the invention as disclosed herein.

MODE(S) FOR CARRYING OUT THE INVENTION

The present invention is illustrated in further details by the following non-limiting examples.

Example 1

Materials and Methods

Mice.

A/J and C57BL/6 (B6) mice were purchased from the Jackson Laboratories (Bar Harbor, Me.) and were housed at McGill University according to the guidelines of the Canadian Council on Animal Care. An LDH virus-free isolate of *P. chabaudi* AS was maintained by weekly passage in A/J mice. Mice were infected intravenously into the tail vein (i.v.) with $10^6$ or $10^7$ pRBC suspended in pyrogen-free saline. Following infection, the percentage of pRBC was determined daily on thin blood smears stained with Dif-Quik™ (Dade Behring, Newark, Del.), as described (Fortin A, et al. (2001) *Proc Natl Acad Sci USA* 98: 10793-10798).

Pharmacokinetic Studies of Cysteamine Hydrochloride In Vivo.

Cysteamine was detected in plasma by high performance liquid chromatography analysis with ultraviolet detection (Dias V C, et al. (1998) *Clin Chem* 44: 2199-2201). Briefly, blood was collected in EDTA/heparin-containing tubes, and plasma was obtained by centrifugation. Plasma thiols were reduced by treatment with Tris(2-carboxyethyl)phosphine (0.05M final concentration, 20 min. at 20° C.), and proteins were precipitated with tri-chloroacetic acid (TCA, 10% final concentration). Free thiols from the protein-free supernatant were derivatized using SBD-F (7-benzo-2-oxa-1,3-diazole-4-sulfonic acid), used at a final concentration of 0.2 mg/ml (1 hr at 60° C.) in 0.05 M borate buffer (pH 9.5). The mixture was then analyzed by HPLC: the mobile phase consisted of an aqueous solvent (0.1M acetic acid, 0.1 sodium acetate, pH 4.3) running on a Supelco™ LC-8 column, and elution of plasma analytes was with a 0-10% acetonitrile gradient. Detection of SBD-F derivatized analytes was by reading fluorescence at 515 nm (excitation at 385 nm). Cysteamine elution peaks were quantified (surface area), and plasma concentrations were calculated using a set of internal cysteamine standards processed at the same time. Area under the curve ($AUC_{t0\text{-}tlast}$) was calculated using the trapezoid approximation method.

Cysteamine, Chloroquine, Artesunate and Dihydroartemisinin Administration In Vivo.

Cysteamine hydrochloride (Sigma, Burlington ON) was prepared in PBS. Chloroquine hydrochloride, artesunate and dihydroartemisinin were provided by Dafra Pharmaceuticals; chloroquine was prepared in PBS, artesunate and DHA were prepared in 5% sodium bicarbonate and diluted in water to appropriate concentrations. All solutions were prepared fresh daily, filter sterilized and injections were performed intraperitoneally (i.p) or subcutaneously (s.c.) for 4 days or according to treatment regimen. Mice were weighed prior to treatment to determine appropriate doses and injection volumes ranged from 100-400 μL per mouse. In the case of animals treated with two drugs, artemisinin derivatives were administered first (due to the short half life of cysteamine), followed by cysteamine 5-10 minutes later on alternate sides. Untreated control animals were injected with PBS alone.

Statistical Tests.

Groups with normally distributed data points were compared using parametric unpaired t-tests, while groups with non-Gaussian distributions were compared using non-parametric Mann-Whitney tests. Survival differences were analyzed using the Log-Rank test. Synergistic effects were defined as: the percent inhibition of the combination therapy was >10% greater than the sum of the percent inhibition of the individual mice. Standard error of percent inhibition was calculated from individual mice compared to the mean parasitemia level of the control group.

Example 2

Figure 1A:
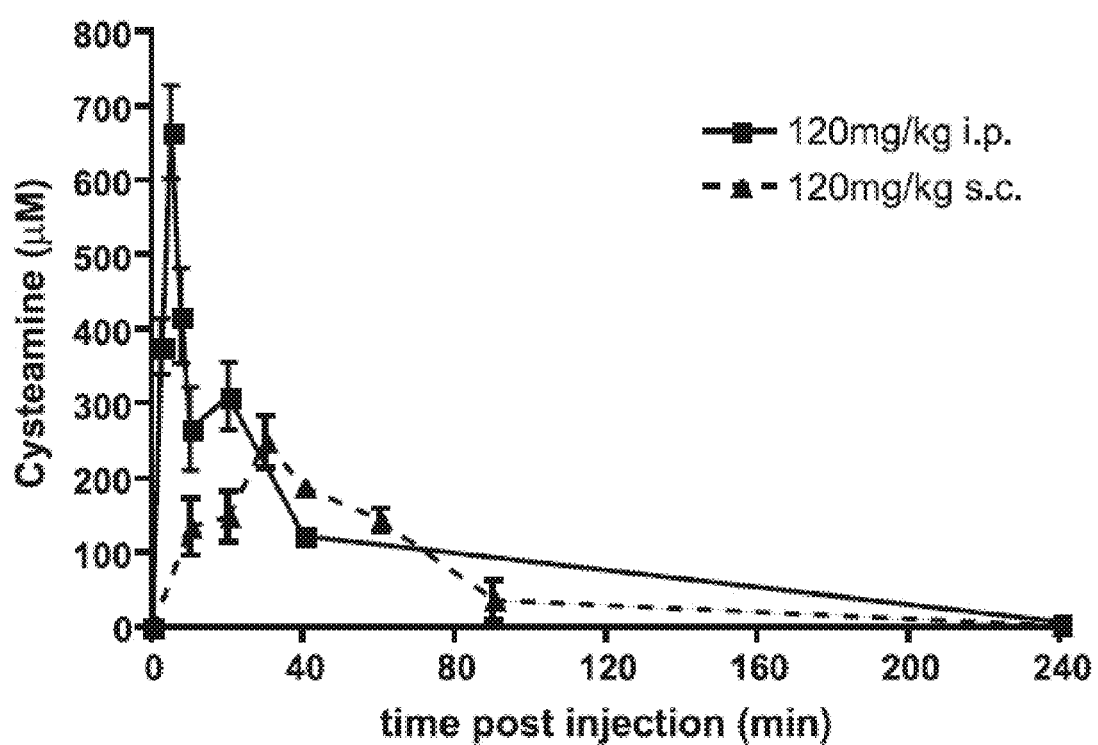
FIGS. 1A and 1B show the effect of cysteamine on replication of *Plasmodium chabaudi* in vivo.
Figure 1B:
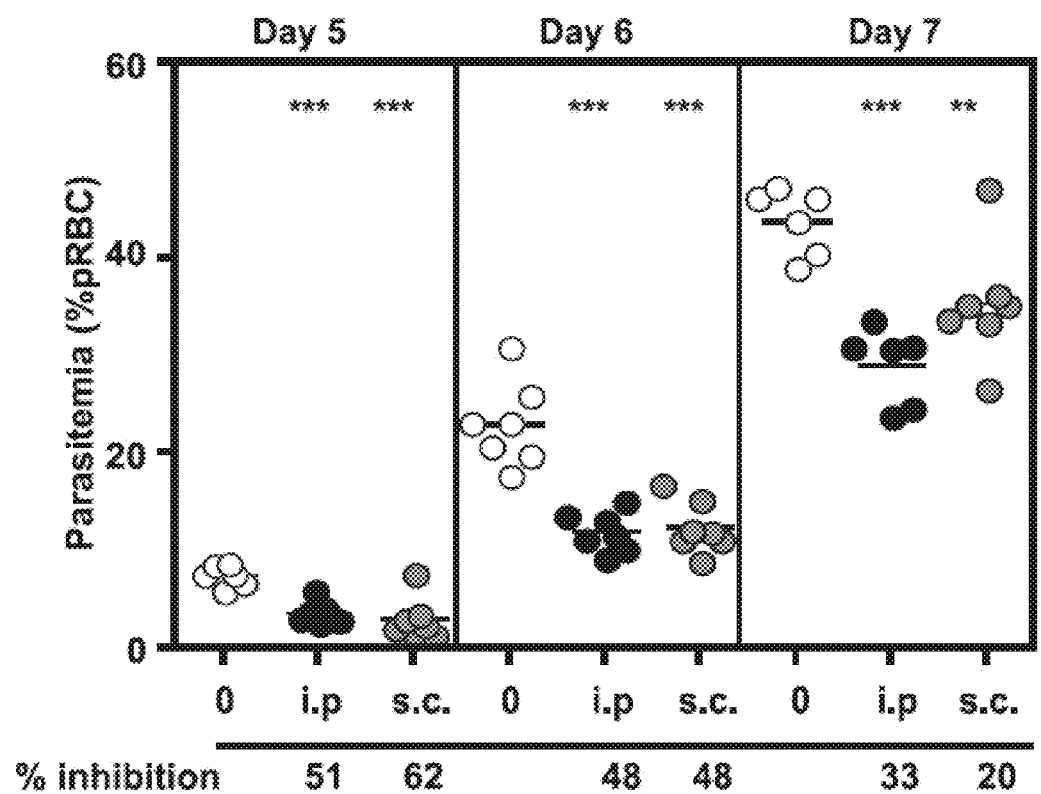

Characteristics of Cysteamine Activity Against *Plasmodium chabaudi* Infection In Vivo To gain more insight into the anti-malarial effect of cysteamine (Cys) in vivo, the pharmacokinetic characteristics (plasma level) of Cys administered through the sub-cutaneous (s.c.) and intra-peritoneal (i.p) routes was compared. Peak plasma concentration ($C_{max}$) and total bioavailability (area under the curve, AUC) after administration of a single dose of 120 mg/kg of Cys hydrochloride (FIG. 1A) was measured. The $C_{max}$ was higher (665 μM) and reached more rapidly ($T_{max}$<5 min) following i.p injection, compared to the s.c. route, where a $C_{max}$ of 250 μM was attained with a $T_{max}$ of 30 min. On the other hand, total Cys bioavailability ($AUC_{T0\text{-}Tlast}$) was comparable for both routes (24282 vs 15277 min×μM for i.p. and s.c., respectively). To determine which pharmacokinetic parameter (AUC vs. $C_{max}$) is important for efficacy against *Plasmodium*, the i.p. and s.c. routes of injection were compared in a continuous treatment regimen, starting one day prior to infection ($10^5$ pRBC of *P. chabaudi*, i.v.) and continuing daily for 7 days. Parasitemia was monitored on thin blood smears at days 5, 6 and 7 following infection (FIG. 1B). Treatment of infected animals with 120 mg/kg of Cys administered either s.c. or i.p. caused a highly significant (p<0.01) 50% reduction in parasitemia at day 5 and 6, relative to saline injected controls. These results suggest that total Cys exposure ($AUC_{T0\text{-}Tlast}$) is a pharmacokinetic parameter influencing the anti-malarial effect of Cys.

Example 3

Figure 2A:
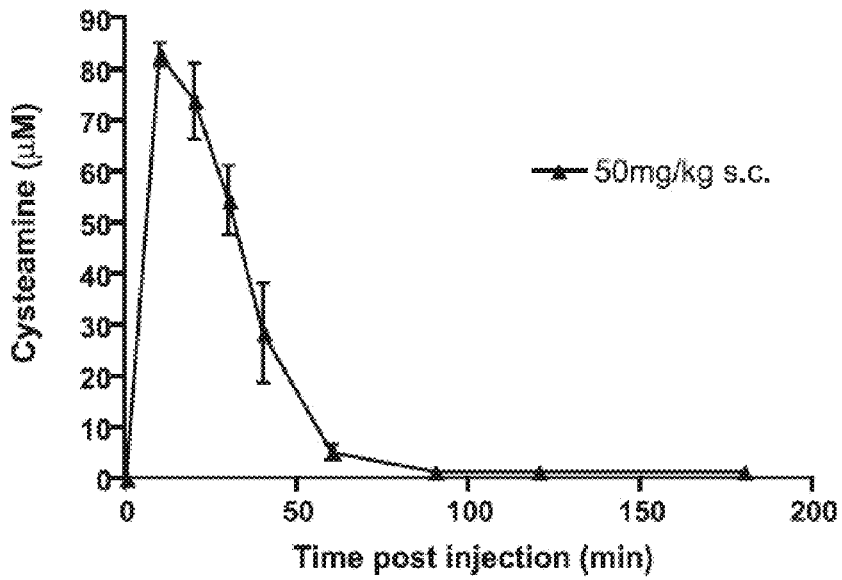
FIGS. 2A and 2B show the effect of cysteamine dosing used for treatment of cystinosis on replication of *Plasmodium chabaudi* in vivo.
Figure 2B:
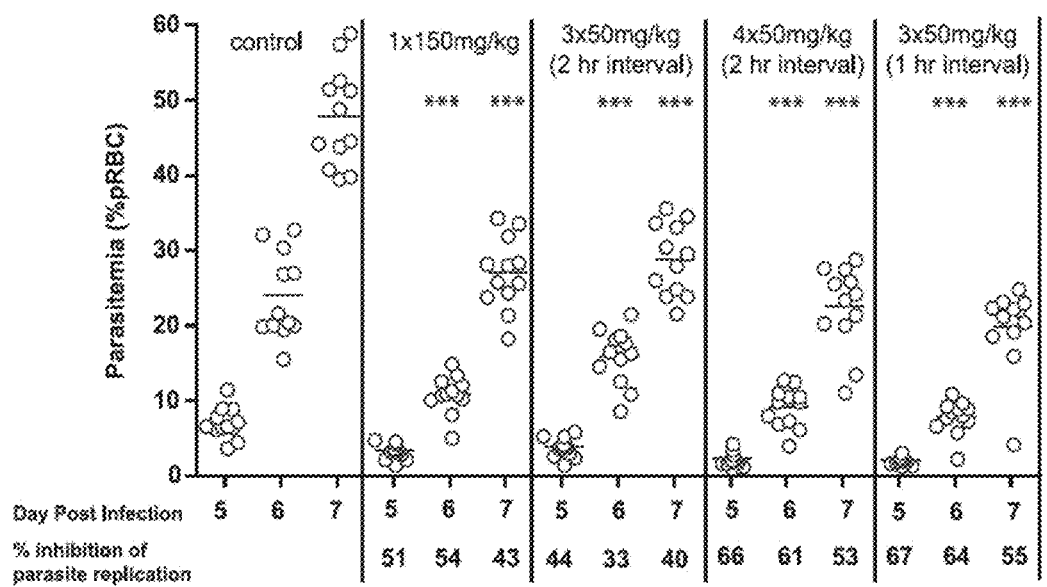

Cysteamine Dosing Used in the Treatment of Cystinosis Reduces Parasitemia During *P. chabaudi* Infection In Vivo It was next determined whether Cys at equivalent dosing to that used in the clinical treatment of nephropathic cystinosis in humans has an effect on the course and severity of *P. chabaudi* infection in mice. In cystinosis patients, Cys is given orally as Cys bitartrate (Cystagon®). The PK profile of an oral dose of 1475 mg of Cys bitartrate (500 mg cysteamine base), includes a peak plasma concentration of 39 μM ($C_{max}$) with a concomitant AUCT0-Tlast of 3613 min×(Fidler M C, et al. (2007) *Br J Clin Pharmacol* 63: 36-40). Results depicted in FIG. 2A show that a single s.c. injection of 50 mg/kg Cys hydrochloride in mice has a PK profile comparable to that of one oral dose of Cystagon® in humans, including a $C_{max}$ of ~80 μM and an AUC of 2845 min×μM. The efficacy of different regimens of 50 mg/kg Cys s.c. (number of injections, interval between injections) on replication of *P. chabaudi* in vivo was evaluated. *P. chabaudi*-infected mice were treated daily, starting at day −1 and continuing to day 10, with either 1×150 mg/kg, 3×50 mg/kg given at 2 hr intervals, 4×50 mg/kg given at 2 hr intervals or 3×50 mg/kg given at 1 hr intervals of Cys, and blood parasitemia was monitored at days 5, 6 and 7 (FIG. 2B). Significant reduction (40-67%) of blood parasitemia was seen for all treatment regimens, with the strongest effect achieved with 3×50 mg/kg given at 1 hr intervals. All 50 mg/kg repeated dosing regimens (s.c.) showed inhibitory effects on parasitemia that were similar to that produced by a single s.c. injection of 150 mg/kg Cys, in agreement with data from FIGS. 1A and 1B showing that is a pharmacokinetic parameter influencing the anti-malarial effect of Cys. These results suggest that multiple Cys treatments at doses similar to those used in humans for cystinosis, can significantly reduce blood-stage replication of *Plasmodium* parasites in mice.

Example 4

Figure 3C:
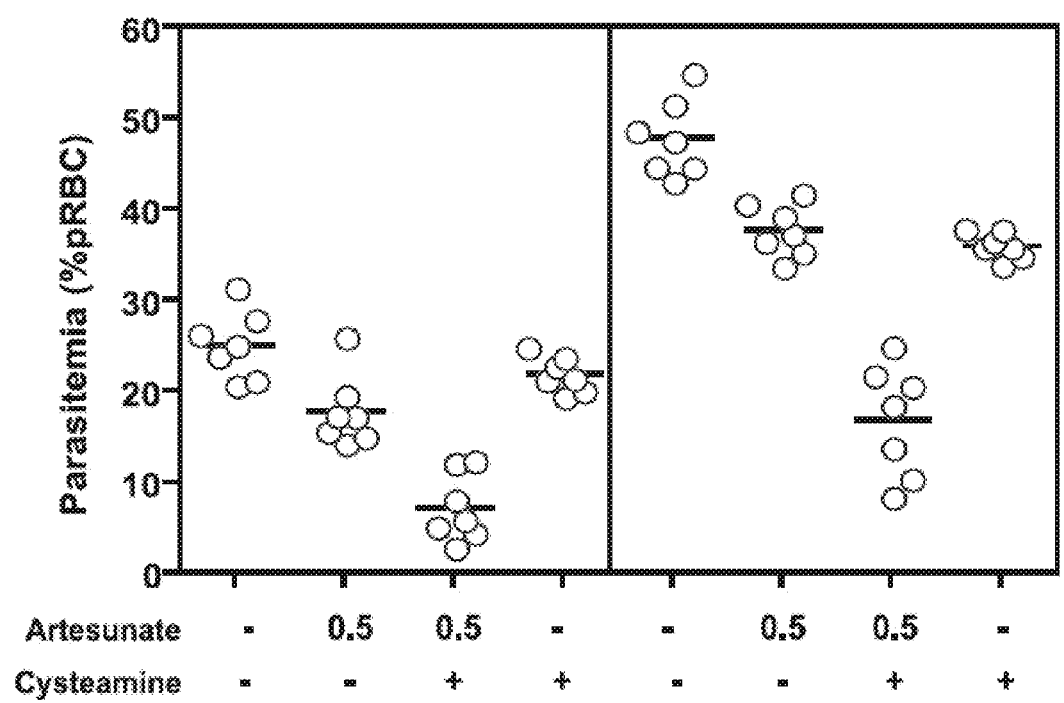

Cysteamine and Artemisinin Derivatives Show Synergistic Effects Against *Plasmodium* In Vivo The effect of Cys on the potency and efficacy of the anti-malarial artemisinin derivatives was tested. In these studies, artemisinin derivatives were given at sub-optimal concentrations to distinguish between the lack of an effect and additive or synergistic effects of Cys addition. Synergy (Tallarida R J (2001) *J Pharmacol Exp Ther* 298: 865-872) is defined as a total anti-malarial activity (reduction in blood parasitemia compared to untreated controls in a standard 4-day test) of the two compounds administered together being greater than the sum of the independent activities of the two compounds given alone. We tested combinations of Cys and either artesunate (ART) or dihydroartemisinin (DHA), the bioactive form of artemisinin. Pantetheinase-deficient mice were infected with *P. chabaudi* ($10^7$ pRBC, i.v.) and treated with Cys (170 mg/kg) and/or sub-optimal doses of ART (0.2 or 0.5 mg/kg) (FIG. 3A) or DHA (0.15 or 0.3 mg/kg) (FIG. 3B) from day 0-3 and parasitemia was monitored on days 4 and 5. Sub-optimal doses of the artemisinin derivatives alone resulted in parasitemia inhibition ranging from 20-30%, while higher doses of these drugs could inhibit parasitemia 40-60%, compared to controls (FIG. 3A/B; TABLE 1). However, addition of Cys to either ART or DHA resulted in stronger inhibition of parasitemia than the additive effect of the two compounds, indicating a synergistic effect (TABLE 1; stars). Synergy was observed at all concentrations of ART and DHA tested. Mice receiving both Cys and ART/DHA also showed fewer symptoms of disease (ruffled fur, lethargy), compared to mice receiving either PBS or only one compound. To assess whether the synergistic effect between Cys and ART was restricted to A/J mice deficient in pantetheinase, the experiment were repeated in pantetheinase sufficient and malaria-resistant C57BL/6 mice (FIG. 3C). Potentiation of the antimalarial activity of ART (0.5 mg/kg) by Cys was also clearly evident in these C57BL/6 mice at both days 4 and 5 post-infection, with combined treatment causing a 65-71% reduction in parasitemia compared to PBS controls, greater than either compound tested alone (13-29%) (TABLE 1).

TABLE 1

Effect of cysteamine and artemisinin derivative combinations on blood-stage replication of *Plasmodium chabaudi* in vivo

| Mouse type and drug | Dose (mg/kg) | Cysteamine (170 mg/kg) | Inhibition of parasitemia (% PBS control)[a] Day 4 | Day 5 |
|---|---|---|---|---|
| Pantetheinase-deficient A/J | | | | |
| Artesunate | 0.2 | − | 30 | 20 |
| Artesunate | 0.2 | + | 65* | 56* |
| Artesunate | 0.5 | − | 65 | 43 |
| Artesunate | 0.5 | + | 93 | 80* |
| DHA | 0.15 | − | 22 | 13 |
| DHA | 0.15 | + | 56* | 46* |
| DHA | 0.3 | − | 50 | 40 |
| DHA | 0.3 | + | 80 | 71* |
| NA[b] | 0 | + | 28 | 23 |
| Pantetheinase-sufficient C57BL/6 | | | | |
| Artesunate | 0.5 | − | 29 | 21 |
| Artesunate | 0.5 | + | 71* | 65* |
| NA | 0 | + | 13 | 25 |

[a]* indicates synergy between the compounds.
[b]NA, no drug administered.

Example 5

Figure 4A:
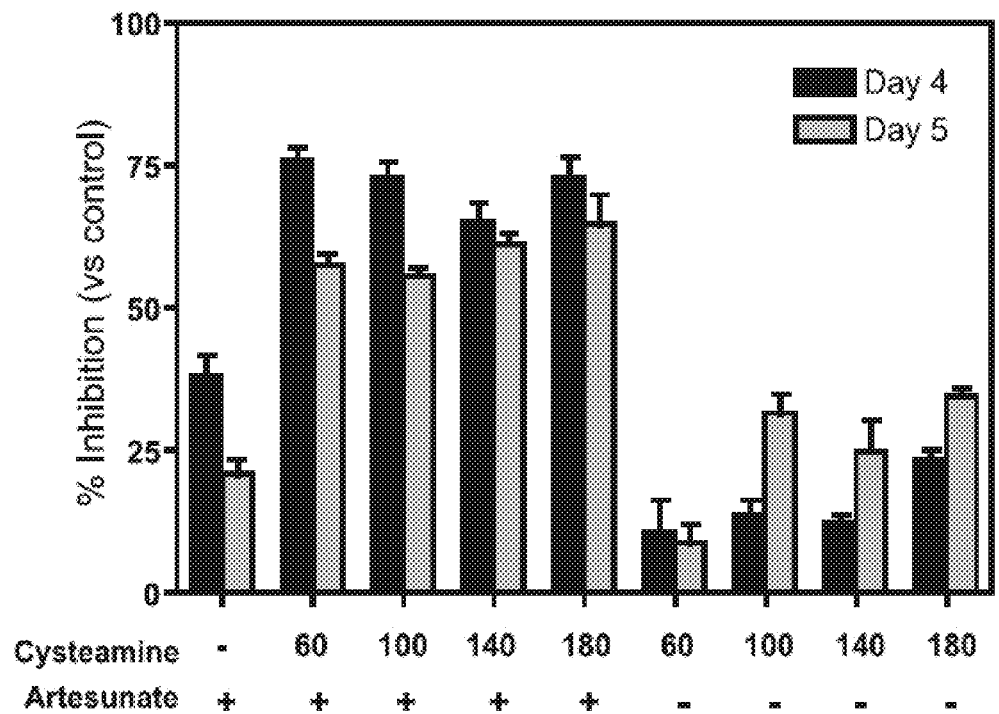
FIGS. 4A to 4C show the dose-dependent synergistic effect of cysteamine on artemisinin efficacy against replication of *Plasmodium chabaudi* in vivo. Groups (n=6) of female A/J mice were infected with P. chabaudi ($10^7$ pRBC, i.v.) and treated for 4 days (days 0, 1, 2, and 3) with increasing doses (indicated) of artesunate (FIG. 4C) and/or cysteamine (FIGS. 4A and B) given i.p. Blood parasitemia was determined at days 4 and 5 post-infection, and the inhibitory effects of the different drug treatments on blood-stage P. chabaudi replication were calculated for each animal compared to the mean of PBS-treated controls (expressed as a percentage). The presence or absence of drug is indicated by a plus or minus, respectively, and all doses are in mg/kg. Error bars represent standard error of the mean.
Figure 4B:
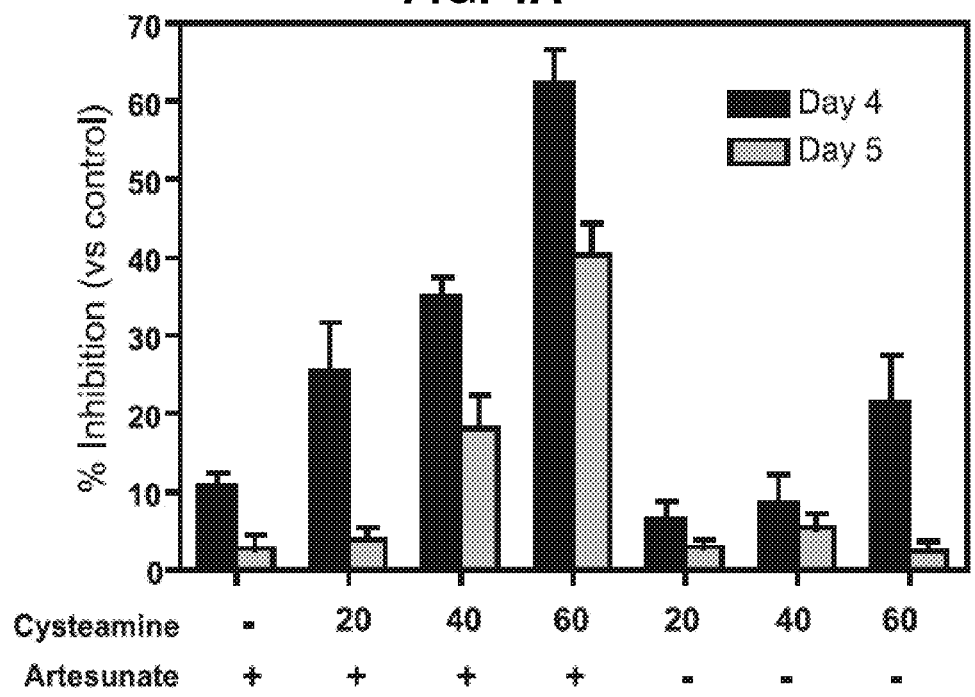
Figure 4C:
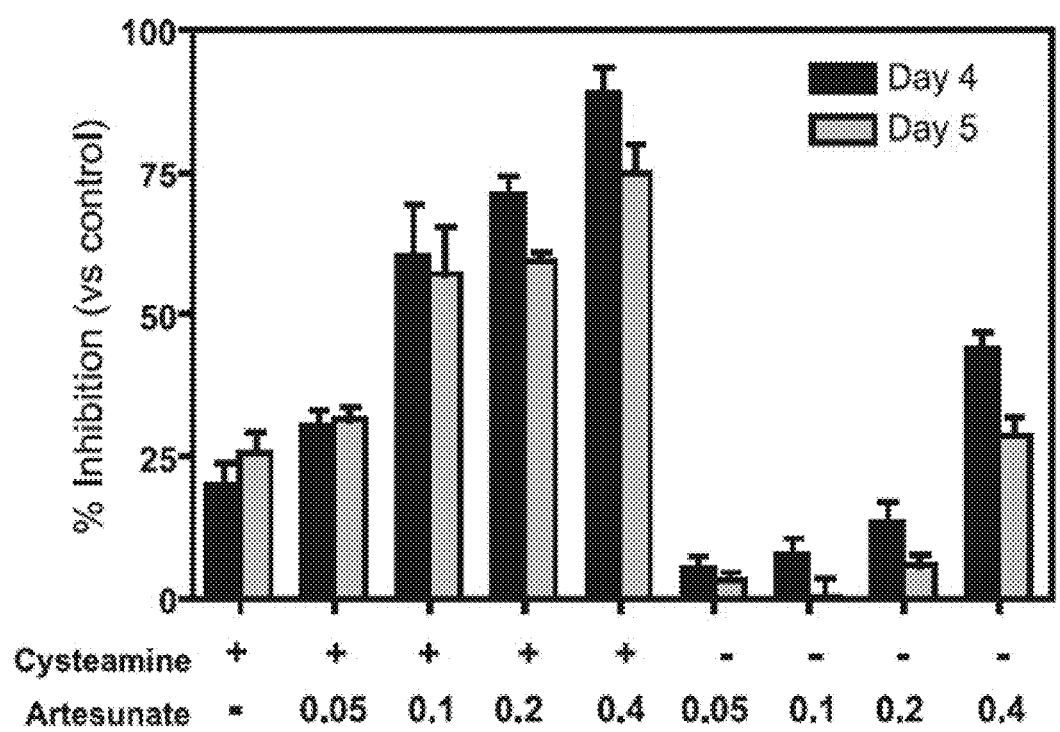

Synergistic Inhibition of *Plasmodium* Replication by Artesunate and Cysteamine is Dose-Dependent It was subsequently examined whether Cys potentiation of ART was dose dependent. Initially, Cys doses of 60, 100, 140 and 180 mg/kg were tested with a sub-optimal ART dose of 0.2 mg/kg. The drugs were administered from day 0-3 post infection, parasitemia was counted at day 4 and day 5 and the percent inhibition was calculated compared to PBS-treated controls (FIG. 4A). At 0.2 mg/kg, ART alone inhibits parasitemia by ~20% (day 4) and 40% (day 5) while inhibition by Cys alone was partially dose dependent (varying between 10% and 25%). Synergy was observed for all Cys doses tested (varying between 50% and 75% reduction in parasitemia), although without a clear dose-dependent effect in this Cys dosing range. Testing a lower Cys dose range (20, 40 and 60 mg/kg) revealed a clear dose-dependent effect on synergistic inhibition of parasitemia, with doses as low as 20-40 mg/kg showing potentiation of the ART effect (FIG. 4B). It was also assessed whether Cys could potentiate low doses of artesunate which, given alone, have no significant effect on parasitemia. In this experiment, Cys (170 mg/kg) was administered in combination, or not, with increasing doses of ART (0.05, 0.1, 0.2, 0.4 mg/kg) in the same 4-day experimental protocol. In these experiments, a strong potentiation (minimum of 3-fold) of low-dose artesunate by Cys was detected, with 60-75% inhibition of parasitemia replication for combinations containing low dose ART at 0.1 and 0.2 mg/kg, compared to <10% for these doses of ART used alone (FIG. 4C).

Example 6

Figure 5A:
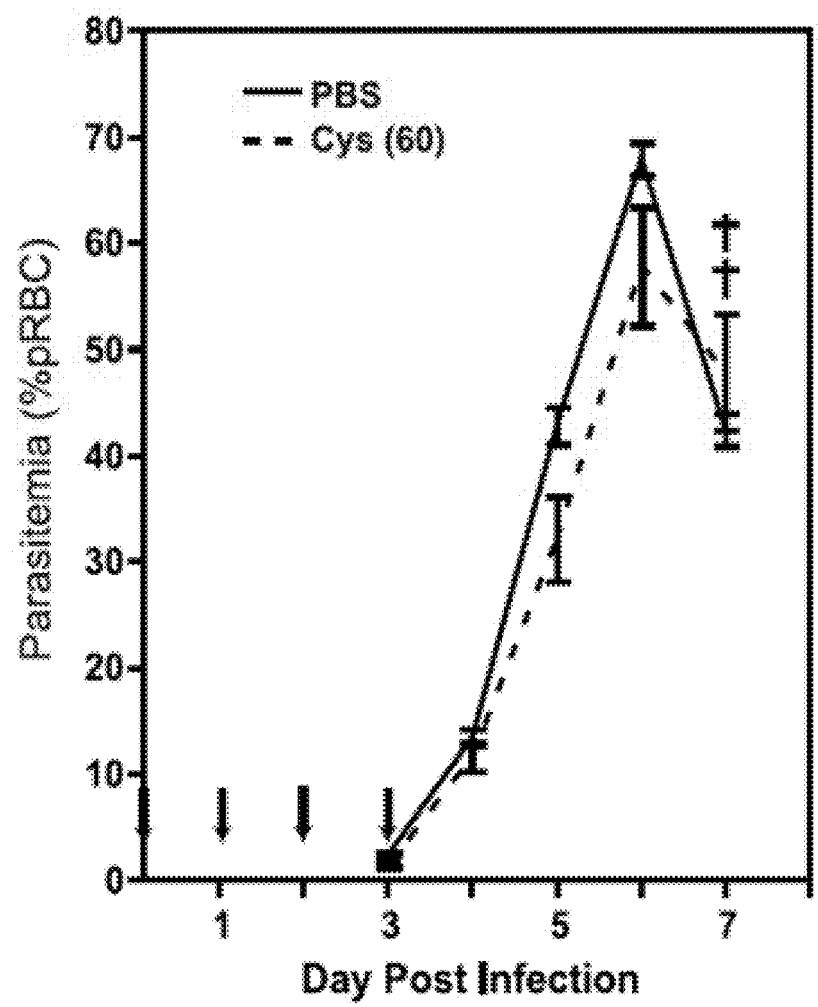
FIGS. 5A to 5D show the effect of cysteamine and artesunate combinations on progression and resolution of P. chabaudi infection in vivo. Groups (n=6) of female A/J mice were infected with P. chabaudi ($10^6$ pRBC, i.v.) and treated for 4 days (days 0, 1, 2, and 3) with PBS (FIG. 5A), cysteamine (60 mg/kg, FIG. 5A), or cysteamine (60 mg/kg) combined with increasing doses of artesunate (0.5, 1.0, 5, or 10 mg/kg, FIG. 5B), all given i.p. Blood parasitemia was measured daily up to day 20 (expressed as percentage of pRBC), and death was recorded (indicated by a cross). Solid and dashed lines represent mice receiving artesunate doses alone or in combination with cysteamine, respectively; artesunate doses are depicted by the abbreviations "Art0.5", "Art1", "Art5", and "Art10", as indicated. Error bars represent standard deviation of the mean, and arrows represent drug treatment days.
Figure 5B:
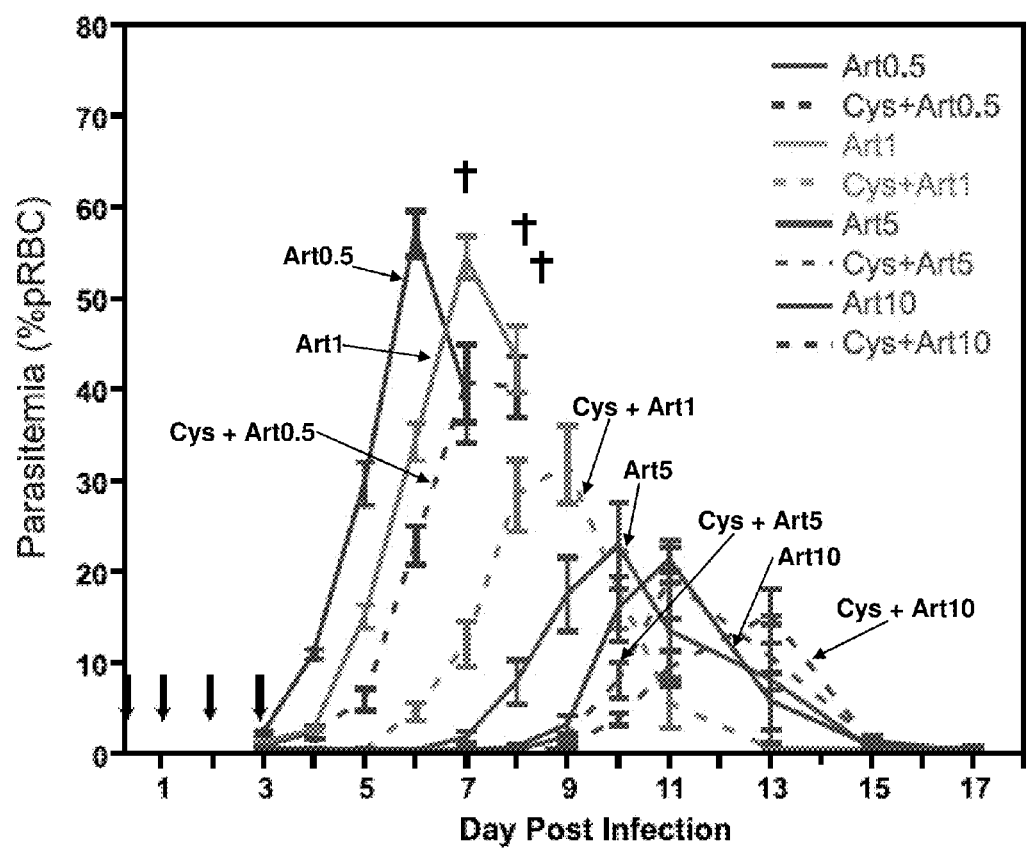
Figure 5C:
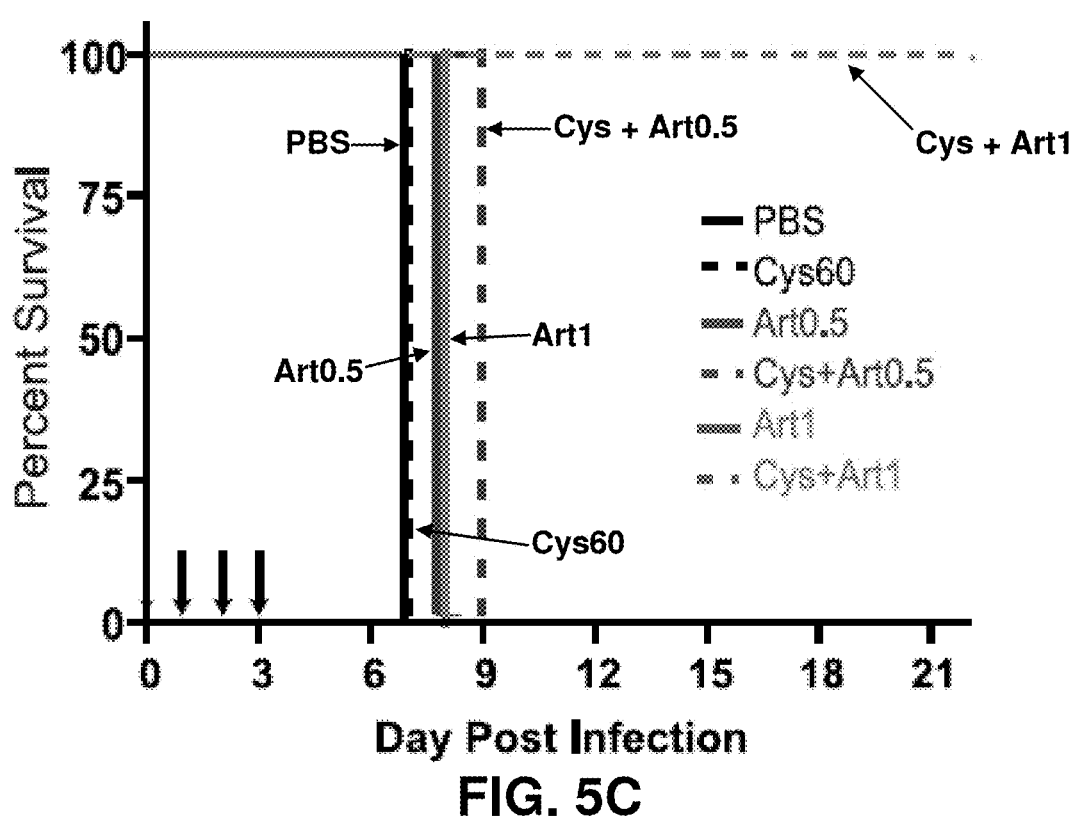
Figure 5D:
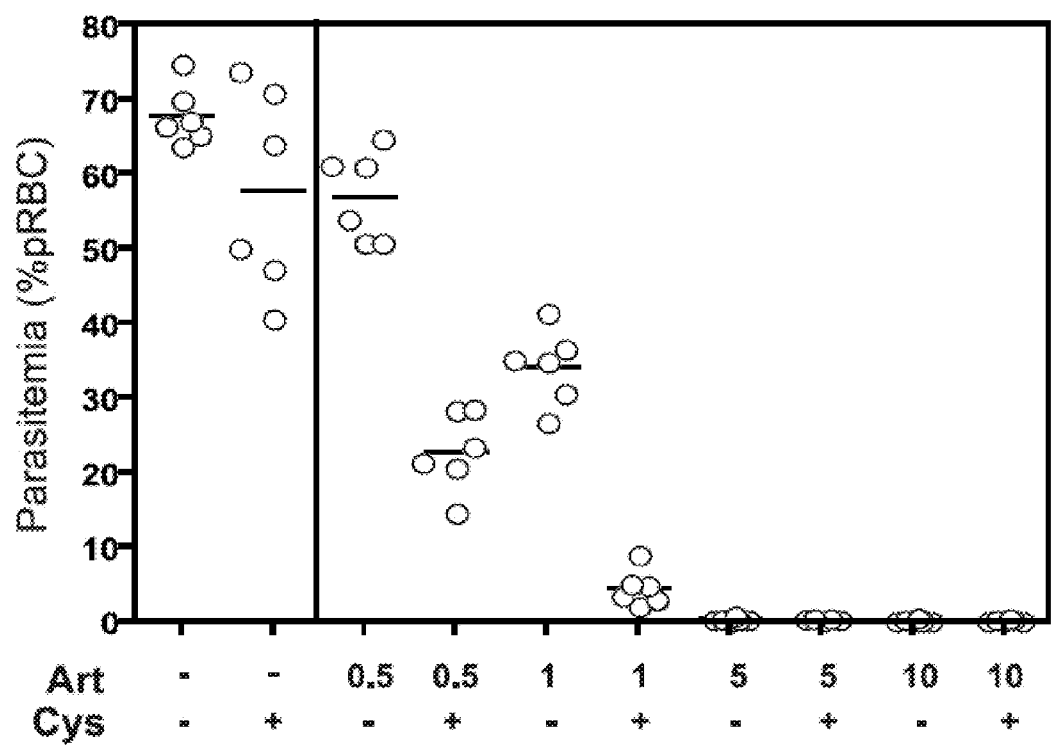

The Impact of Cysteamine and Artesunate in Combination on the Resolution of *P. chabaudi* Infection It was investigated if low dose Cys could potentiate standard doses of ART that show therapeutic activity in vivo and concurrently determined possible long-term effects on patent parasitemia, resolution of infection and survival in a lethal infection model. In this protocol, mice were infected with $10^6$ pRBC *P. chabaudi* (i.v.) and treated with Cys (60 mg/kg) and/or ART (0.5, 1, 2, 5 and 10 mg/kg) for 4 days (days 0-3), while blood parasitemia and survival were followed for 22 days. Control animals treated with either PBS or Cys alone (60 mg/kg) developed high parasite burdens, which peaked at day 6, and all mice succumbed to the infection by day 7 (FIGS. 5A and 5C). In animals receiving ART alone, there was a dose-dependent effect on infection, which manifested as a delay in the onset of parasitemia and a reduction of peak parasitemia. Strikingly, the addition of Cys (60 mg/kg) to all ART doses tested had a beneficial effect on infection kinetics, causing both a further delay in onset (by 2 to 3 days), and a reduction of peak levels of parasitemia relative to mice receiving only the corresponding dose of ART (FIG. 5B). Notably, the addition of Cys to 0.5 mg/kg or 1 mg/kg of ART caused a strong potentiation of the ART effect, with a further 60-70% reduction in parasitemia at day 6 (FIG. 5D). Likewise, although all mice treated with 0.5 mg/kg ART succumbed to the infection early (day 8), mice additionally receiving Cys survived until day 9; moreover, addition of Cys to 1.0 mg/kg ART completely rescued animals from lethality of infection, with 100% survival in this group (FIGS. 5B, 5C). These results indicate that the synergistic effect of low doses of Cys on artemisinin derivatives not only impacts early parasite burdens, but also significantly improves ultimate outcome to infection.

Example 7

Figure 6A:
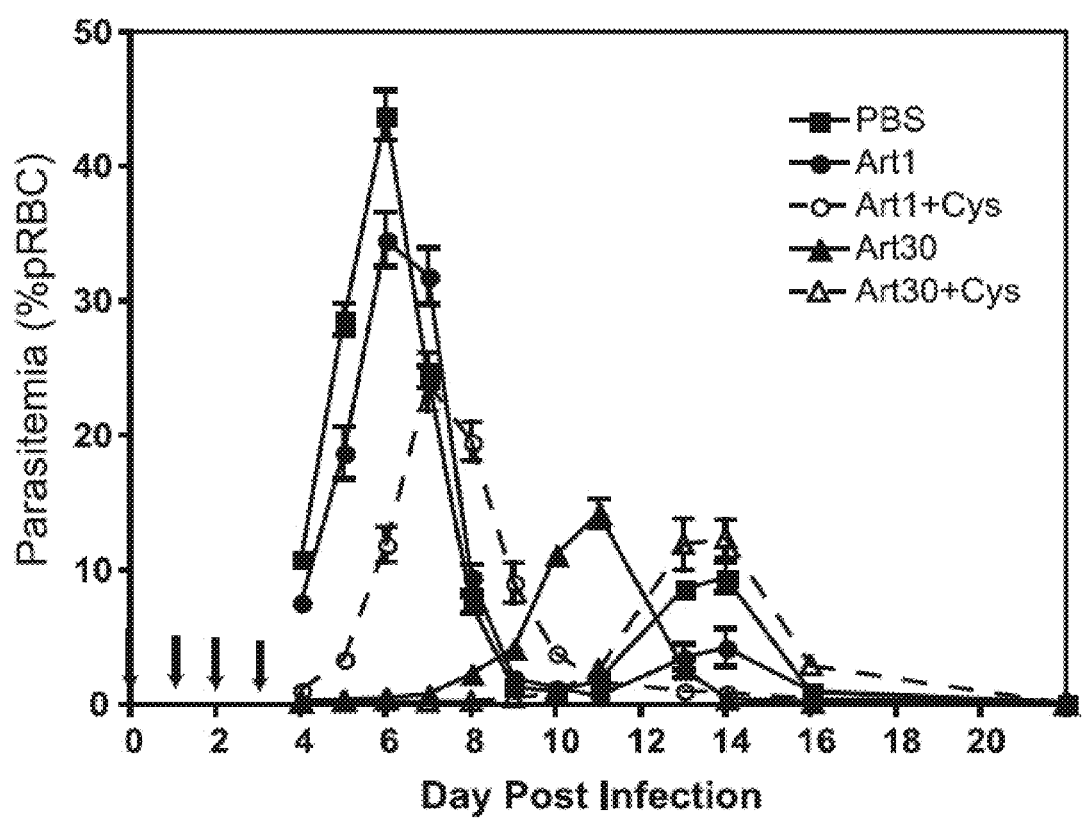
FIGS. 6A and 6B show the effect of cysteamine and artesunate combinations on progression of P. chabaudi in pantetheinase-sufficient B6 mice. Groups (n=6) of female B6 mice were infected with P. chabaudi ($10^6$ pRBC, i.v.) and treated for 4 days (days 0, 1, 2, and 3) with either PBS or artesunate (1.0 or 30 mg/kg) combined with, or without, cysteamine (60 mg/kg, FIG. 6A), all given i.p. Blood parasitemia was measured daily up to day 22 (expressed as percentage of pRBC). Solid and dashed lines represent mice receiving artesunate doses alone or in combination with cysteamine, respectively. Error bars represent standard deviation of the mean, and arrows represent drug treatment days.
Figure 6B:
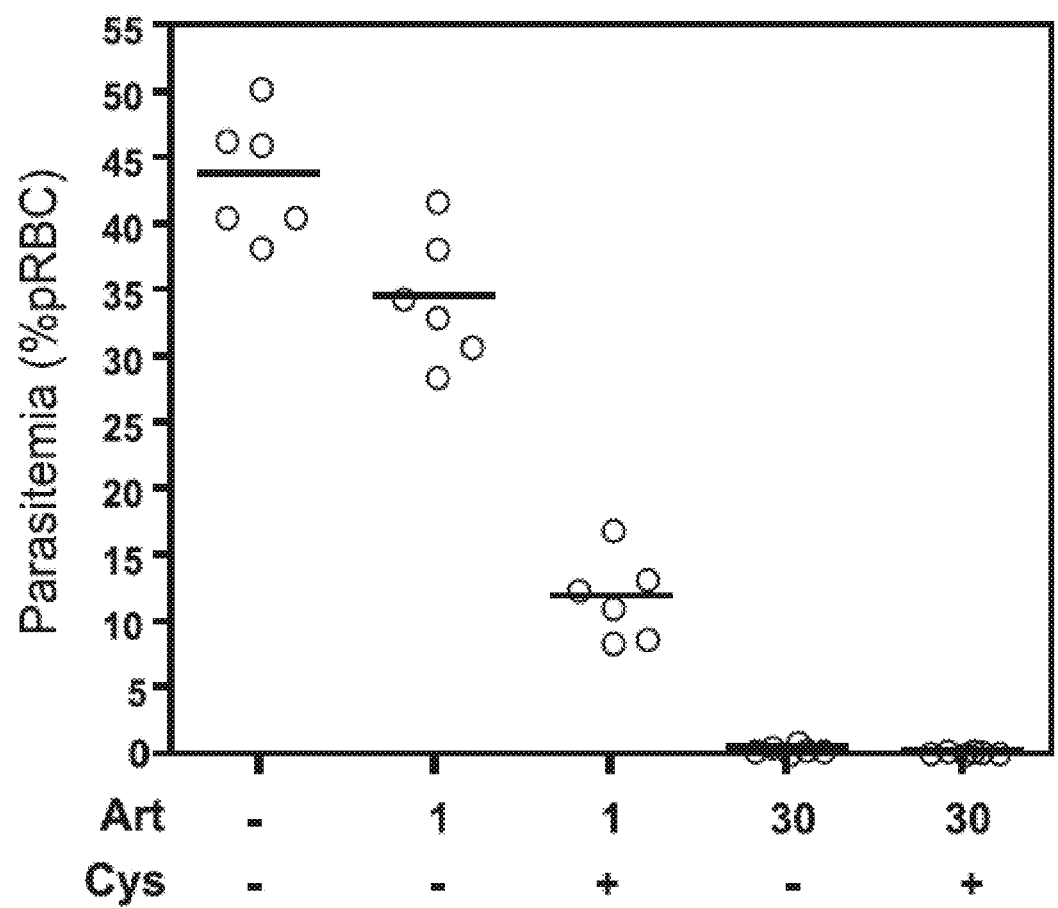

Effect of Cysteamine and Artesunate Combinations on Progression of *P. chabaudi* in Pantetheinase-Sufficient B6 Mice To investigate whether the effects on parasite burden over the course of infection would also be observed with a pantetheinase-sufficient mouse strain, a similar experiment was performed using female B6 mice. Groups of mice were infected with $10^6$ P. chabaudi pRBC i.v. and treated with PBS, 1 mg/kg or 30 mg/kg of Art, or 1 mg/kg or 30 mg/kg of Art plus 60 mg/kg of Cys for 4 days. A reduction in parasite levels and a delay in the peak were observed when Cys and Art are given in combination, compared to results with Art administered alone, at both high and low doses (FIG. 6A). As in A/J mice, the effect of Cys addition to 1 mg/kg of Art has a clear effect on early parasite replication at day 6 (FIG. 6B). Although a "curative" dose combination was not achieved with a 4-day treatment regimen, parasite levels remained under 12% pRBC in the 30 mg/kg Art-plus-Cys group, and mice did not display any outward symptoms of disease such as lethargy or ruffled fur. B6 mice were able to completely clear parasite burdens and survive the infection, even in the control PBS-treated group. However, the addition of Cys eliminated the appearance of recrudescent parasitemia around day 14, as seen with the control group (FIG. 6A). These results indicate that the synergistic effect of low doses of Cys on artemisinin derivatives not only impacts early parasite burdens but can also significantly improve ultimate outcome to infection.

Example 8

Effect of Cysteamine and Artesunate Combinations on Progression of *Plasmodium berghei* ANKA Infection Intravenous infection with *Plasmodium berghei* ANKA is an accepted mouse model of cerebral malaria (CM) (Hunt, N. H. et al. 2006, *Int. J. Parasitol.* 36: 569-582). The infection causes the following pathology. First, there is appearance of blood parasitemia, starting at days 3 or 4, which can go up to 10% by day 7-8. Starting at day 5-6, there is emergence of cerebral symptoms caused by permeability of the blood brain barrier, concomitant to trapping of parasitized red cells in the microvasculature and acute pathological host inflammatory response in situ. This cerebral phase quickly progresses from tremors, to paralysis, to coma, and is uniformly lethal in mice by days 8-10. In this model, progress of infection and possibly drug effects may be monitored by a) appearance and intensity of blood parasitemia (between days 5-8), b) appearance of cerebral symptoms, and c) lethality.

Figure 8A:
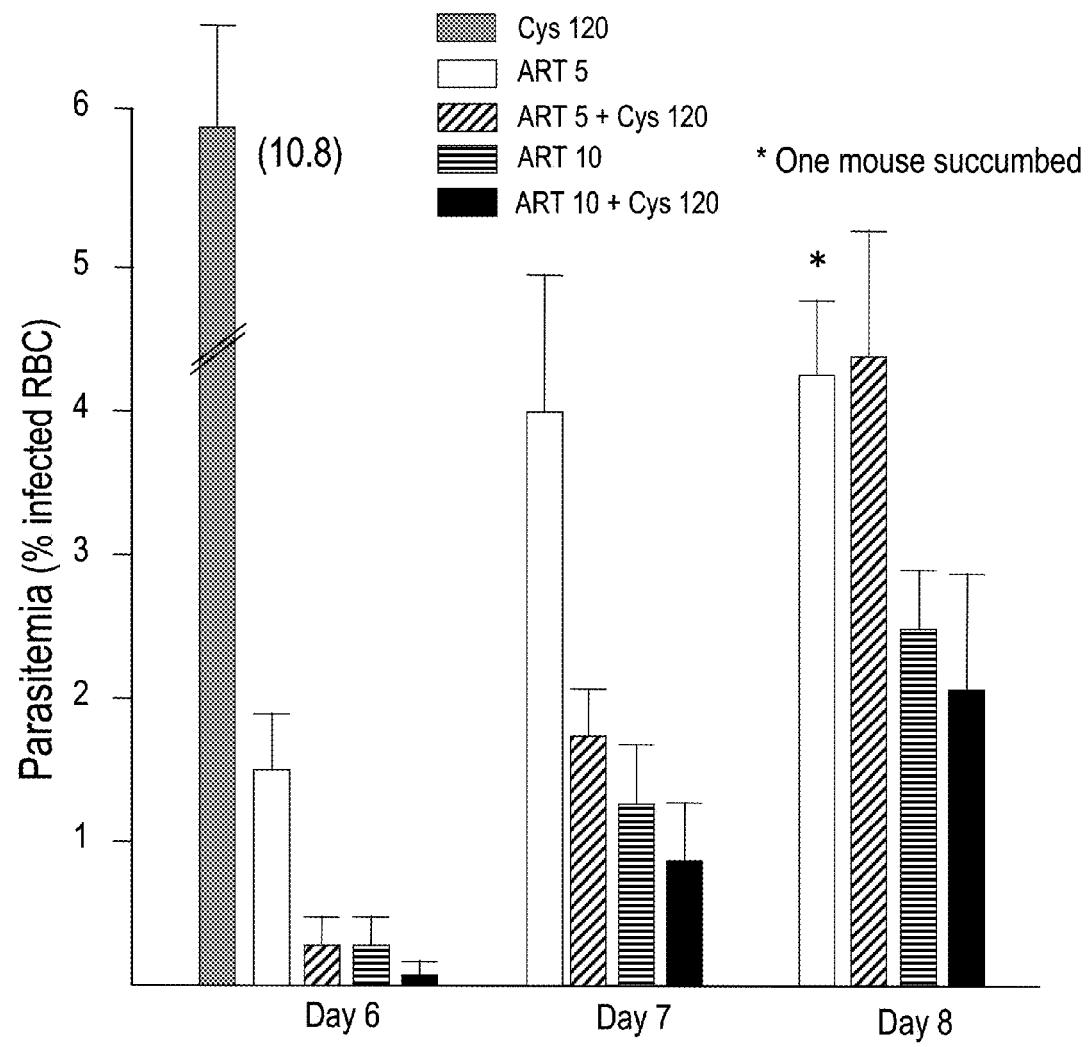
FIGS. 8A and 8B show the results of two independent experiments on the effect of cysteamine and artesunate combinations on the progression of *Plasmodium berghei* ANKA infection (parasitemia). Groups of 5 adult 18-20 g C57BL/6J males and females were infected intravenously with 1×$10^6$ erythrocytes parasitized with P. berghei ANKA at time "0". Two hours later, mice were injected i.p with either Artemisinin alone or with Artemisinin/Cysteamine combinations (at the indicated concentrations in mg/kg body weight). In the case of the latter, Artemisinin was injected first in one quadrant, and cysteamine was injected second, 10-15 minutes later in another quadrant. The drug treatment was further repeated at days 1, 2 and 3 post-infection to emulate the standard 4-day test used in anti-malarial drug discovery. Starting at day 5, blood was collected, thin blood smears were prepared, and parasitemia was determined (400 erythrocytes counted, expressed as percentage parasitized erythrocytes). Error bars show standard deviations on the mean.
Figure 8B:
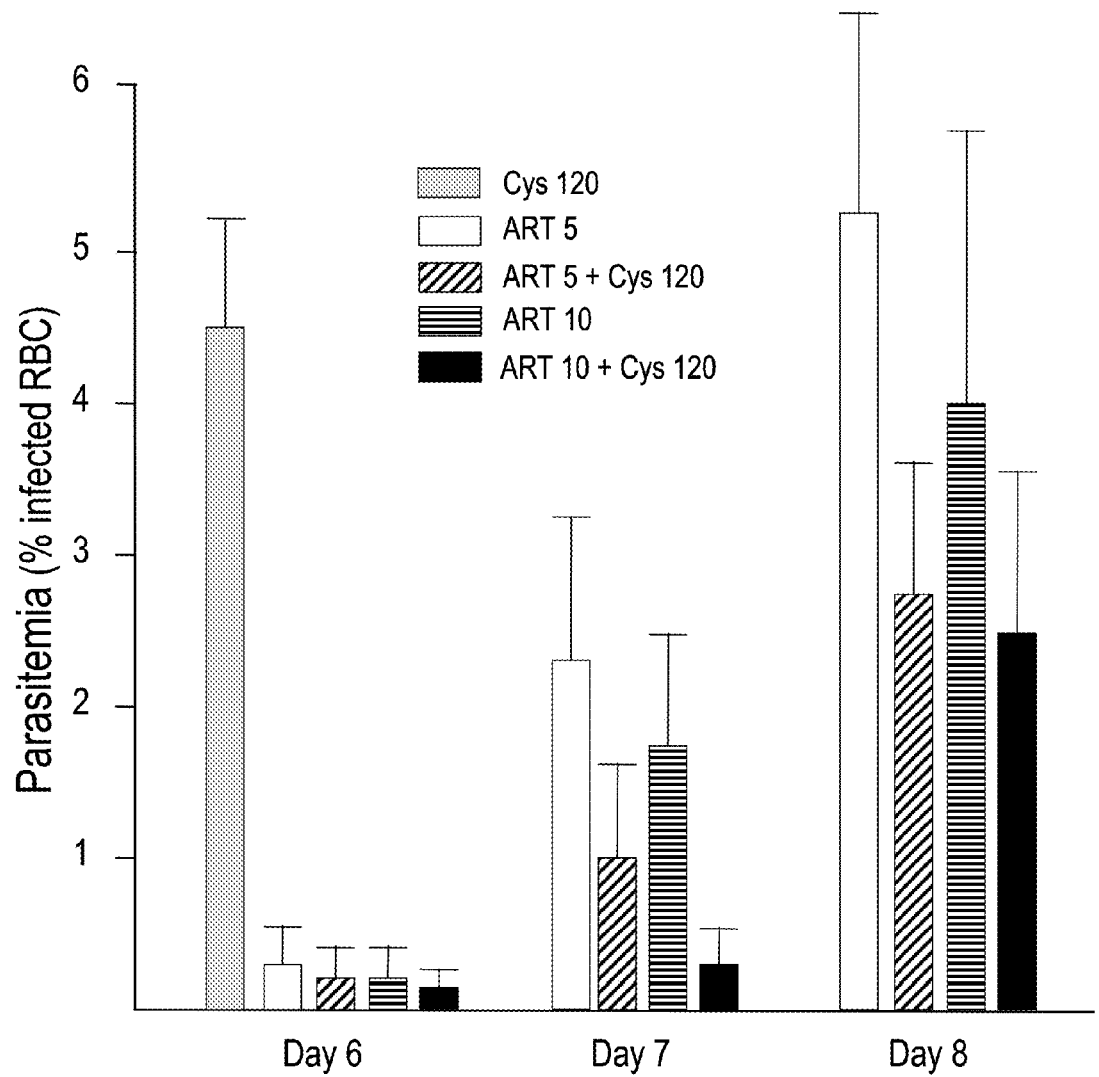

The results depicted in FIGS. 8A and 8B show that addition of Cysteamine to either of the two Artemisinin dosings (5 or 10 mg/kg) causes a delay in the rise of parasitemia and seems to cause a reduction in absolute levels measured at days 6-8 over what is detected in animals treated with Artemisinin alone. Second, the addition of cysteamine to Artemisinin causes an effect which is comparable (FIG. 8A) or superior (FIG. 8B) to that of doubling the dose of Artemisinin.

Figure 9A:
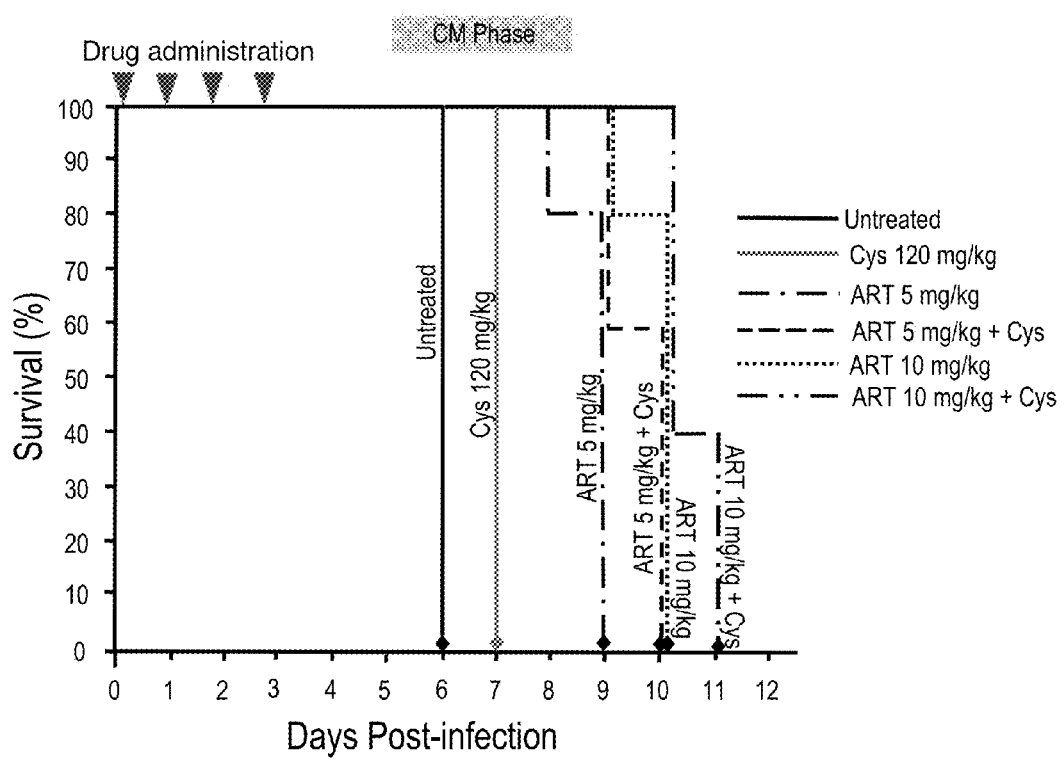
FIGS. 9A and 9B show the results of two independent experiments on the effect of cysteamine and artesunate combinations on the survival of *Plasmodium berghei* ANKA-infected mice. Infection and drug administration were performed as described above for FIGS. 8A and 8B. Animals were monitored for the appearance and severity of cerebral symptoms (CM phase, shown as rectangle in graph), and moribund animals were euthanized, and time of death was recorded.
Figure 9B:
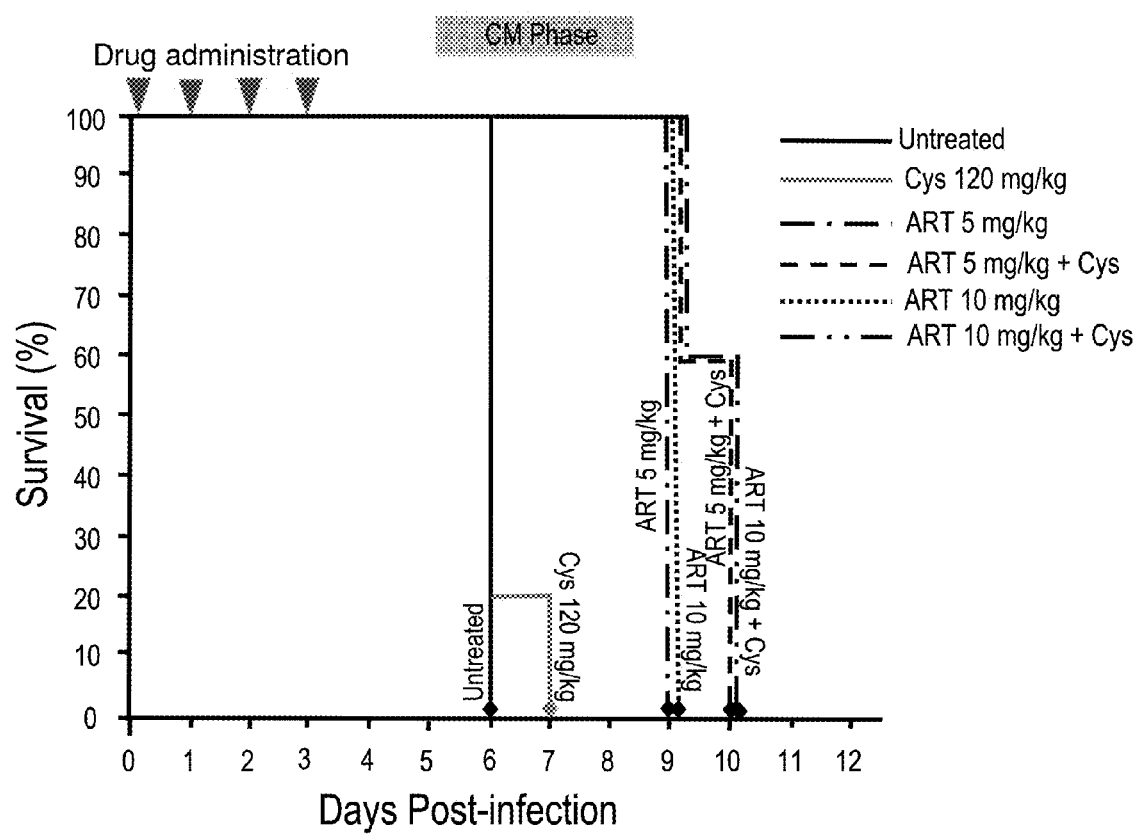

With respect to survival (FIGS. 9A and 9B), Cysteamine alone had a minor positive effect on survival of *P. berghei*-infected animals. Adding cysteamine to Artemisinin prolonged survival of *P. berghei*-infected animals over that measured in animals treated with Artemisinin alone, and this by a factor of 1-2 days.

Although the present invention has been described herein above by way of specific embodiments thereof, it can be modified, without departing from the spirit and nature of the subject invention as defined in the appended claims.

What is claimed is:

1. A method for decreasing susceptibility to parasite infection or disease or for preventing or treating parasite infection or disease, in a subject in need thereof, said method comprising administering to said subject an effective amount of
(i) (a) a compound of formula I:

$$NH_2-CH_2-CH_2-S-R \qquad (I)$$

wherein R is H or S—CH$_2$—CH$_2$—NH$_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and
(ii) an artemisinin-related compound selected from the group consisting of artemether, arteether, artelinic acid, artenimol, artemotil, and artemisinic acid.

2. The method of claim 1, wherein said method comprises administering to said subject an effective amount of
(i) (a) cystamine; (b) cysteamine; (c) a pharmaceutically acceptable salt of (a) or (b); or (d) any combination of (a) to (c); and
(ii) an artemisinin-related compound selected from the group consisting of artemether, arteether, artelinic acid, artenimol, artemotil, and artemisinic acid.

3. The method of claim 2, wherein said method comprises administering to said subject an effective amount of
(i) cysteamine or a pharmaceutically acceptable salt thereof; and
(ii) an artemisinin-related compound selected from the group consisting of artemether, arteether, artelinic acid, artenimol, artemotil, and artemisinic acid.

4. The method according to claim 1, wherein said parasite is of the genus *Plasmodium*.

5. The method according to claim 1, wherein said disease is malaria.

6. The method according to claim 5, wherein said malaria is blood-stage malaria.

7. The method according to claim 5, wherein said malaria is cerebral malaria.

8. The method according to claim 1, wherein said subject is a human.

9. The method according to claim 1 wherein compounds (i) and (ii) act synergistically.

10. The method of claim 9, wherein the synergy results in use of effective doses of compound (i) and/or (ii) that are lower than doses administered when the compounds are administered in the absence of the other compound.

11. The method of claim 10, wherein the dose of compound (i) and/or (ii) is suboptimal.

12. The method of claim 1, wherein the effective dose of compound (i) is in the range of 1 to 500 mg/kg.

13. The method of claim 1, wherein compound (i) is present in a delayed release composition.

14. The method according to claim 1, wherein the peak level of parisitemia is reduced.

15. The method according to claim 1, wherein the administering prevents parisitemia.

16. The method according to claim 1, wherein compound (i) is administered less than four times a day.

17. The method according to claim 1, wherein compound (i) is administered twice daily.

18. The method of claim 1, wherein compounds (i) and (ii) are administered coextensively.

19. A composition for decreasing susceptibility to parasite infection or disease or for preventing or treating parasite infection or disease, in a subject, said composition comprising
(i) (a) a compound of formula I:

$$NH_2-CH_2-CH_2-S-R \quad (I)$$

wherein R is H or S—CH$_2$—CH$_2$—NH$_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and
(ii) an artemisinin-related compound selected from the group consisting of artemether, arteether, artelinic acid, artenimol, artemotil, and artemisinic acid, (b) a functional derivative, analog, conjugate, metabolite, prodrug or precursor of artemisinin, (c) a pharmaceutically acceptable salt of (a) or (b), or (d) any combination of (a) to (c).

20. The composition according to claim 19, wherein said composition comprises
(i) (a) cystamine; (b) cysteamine; (c) a pharmaceutically acceptable salt of (a) or (b); or (d) any combination of (a) to (c); and
(ii) an artemisinin-related compound selected from the group consisting of artemether, arteether, artelinic acid, artenimol, artemotil, and artemisinic acid.

21. The composition according to claim 20, wherein said composition comprises
(a) cysteamine or a pharmaceutically acceptable salt thereof; and
(b) an artemisinin-related compound selected from the group consisting of artemether, arteether, artelinic acid, artenimol, artemotil, and artemisinic acid.

22. The composition according to claim 19, further comprising a pharmaceutically acceptable carrier or excipient.

23. A package comprising
(i) (a) a compound of formula I:

$$NH_2-CH_2-CH_2-S-R \quad (I)$$

wherein R is H or S—CH$_2$—CH$_2$—NH$_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and
(ii) an artemisinin-related compound selected from the group consisting of artemether, arteether, artelinic acid, artenimol, artemotil, and artemisinic acid;
for decreasing susceptibility to parasite infection or disease or for preventing or treating parasite infection or disease in a subject.

24. The package of claim 23, wherein (i) and (ii) are packaged separately.

25. The package of claim 23, wherein (i) and (ii) are packaged in the same formulation.

26. The package of claim 23 wherein compound M is present in a delayed release composition.

27. The package of claim 23, further comprising labels and instructions for use.

28. The method according to claim 4, wherein the *Plasmodium* is an artemisinin-resistant human *Plasmodium* parasite.

29. A method for decreasing susceptibility to parasite infection or disease or treating parasite infection or disease wherein the parasite is an artemisinin-resistant human *Plasmodium* parasite, in a subject in need thereof, said method comprising administering to said subject an effective amount of
(i) (a) a compound of formula I:

$$NH_2-CH_2-CH_2-S-R \quad (I)$$

wherein R is H or S—CH$_2$—CH$_2$—NH$_2$; (b) an agent capable of inducing the production of the compound of formula I; (c) a functional derivative, analog, conjugate, prodrug or precursor of (a) or (b); (d) a pharmaceutically acceptable salt of any of (a) to (c); or (e) any combination of (a) to (d); and
(ii) an artemisinin-related compound.

30. The method of claim 29, wherein said method comprises administering to said subject an effective amount of
(i) (a) cystamine; (b) cysteamine; (c) a pharmaceutically acceptable salt of (a) or (b); or (d) any combination of (a) to (c); and
(ii) an artemisinin-related compound.

31. The method according to claim 29, wherein said disease is malaria.

32. The method according to claim 29, wherein said malaria is blood-stage malaria.

33. The method according to claim 29, wherein said malaria is cerebral malaria.

34. The method according to claim 29, wherein compounds (i) and (ii) act synergistically.

35. The method of claim 34, wherein the synergy results in use of effective doses of compound i) and/or ii) that are lower than doses administered when the compounds are administered in the absence of the other composition.

36. The method of claim 35, wherein the dose of compound (i) and/or (ii) is suboptimal.

37. The method of claim 29, wherein the effective dose of compound (i) is in the range of 1 to 500 mg/kg.

38. The method of claim 29, wherein compound (i) is present in a delayed release composition.

39. The method according to claim 29, wherein the peak level of parisitemia is reduced.

40. The method according to claim 29, wherein the administering prevents parisitemia.

41. The method according to claim 29, wherein compound (i) is administered less than four times a day.

42. The method according to claim 29, wherein compound (i) is administered twice daily.

43. The method of claim 29, wherein compounds (i) and (ii) are administered coextensively.

* * * * *